(12) United States Patent
Berdini et al.

(10) Patent No.: US 7,385,059 B2
(45) Date of Patent: Jun. 10, 2008

(54) 3,4-DISUBSTITUTED 1H-PYRAZOLE COMPOUNDS AND THEIR USE AS CYCLIN DEPENDENT KINASE AND GLYCOGEN SYNTHASE KINASE-3 MODULATORS

(75) Inventors: Valerio Berdini, Cambridge (GB); Michael Alistair O'Brien, Herts (GB); Maria Grazia Carr, Luton (GB); Theresa Rachel Early, Macclesfield (GB); Adrian Liam Gill, Caldecote (GB); Gary Trewartha, Herts (GB); Alison Jo-Anne Woolford, Cambridge (GB); Andrew James Woodhead, Cambridge (GB); Paul Graham Wyatt, Dundee (GB)

(73) Assignee: Astex Therapeutics Limited, Cambridge (GB)

( * ) Notice: Subject to any disclaimer, the term of this patent is extended or adjusted under 35 U.S.C. 154(b) by 0 days.

(21) Appl. No.: 11/336,599

(22) Filed: Jan. 20, 2006

(65) Prior Publication Data

US 2006/0194843 A1  Aug. 31, 2006

Related U.S. Application Data

(63) Continuation of application No. PCT/GB2004/003179, filed on Jul. 22, 2004.

(60) Provisional application No. 60/569,763, filed on May 10, 2004, provisional application No. 60/489,046, filed on Jul. 22, 2003.

(30) Foreign Application Priority Data

Jul. 22, 2004 (GB) ................... 0317127.9

(51) Int. Cl.
C07D 211/00 (2006.01)
A01N 43/40 (2006.01)

(52) U.S. Cl. ........................ 546/188; 514/317

(58) Field of Classification Search ................ 546/188
See application file for complete search history.

(56) References Cited

U.S. PATENT DOCUMENTS

| 4,282,361 | A | 8/1981 | Hecht et al. |
| 6,066,738 | A | 5/2000 | Dinsmore et al. |
| 2002/0091116 | A1 | 7/2002 | Zhu et al. |
| 2004/0087798 | A1 | 5/2004 | Yamada |
| 2004/0116399 | A1 | 6/2004 | Zhu et al. |
| 2004/0214870 | A1 | 10/2004 | Xin et al. |
| 2005/0119305 | A1 | 6/2005 | Naka et al. |

FOREIGN PATENT DOCUMENTS

| EP | 0947500 | 10/1999 |
| EP | 1348707 | 10/2003 |
| EP | 1642594 | 4/2006 |
| WO | 9849166 | 11/1998 |
| WO | 9852941 | 11/1998 |
| WO | 9932477 | 7/1999 |
| WO | 00/62778 | 10/2000 |
| WO | 01/02385 | 1/2001 |
| WO | 01/19798 | 3/2001 |
| WO | 0119788 | 3/2001 |
| WO | 01/58869 A2 | 8/2001 |
| WO | 01/64642 | 9/2001 |
| WO | 0164643 | 9/2001 |
| WO | 01/98290 | 12/2001 |
| WO | 02/00651 | 1/2002 |
| WO | 02/18346 | 3/2002 |
| WO | 02/22601 | 3/2002 |
| WO | 02/051810 | 7/2002 |
| WO | 02/062804 | 8/2002 |

(Continued)

Primary Examiner—Kamal A. Saeed
Assistant Examiner—Robert Havlin
(74) Attorney, Agent, or Firm—Heslin Rothenberg Farley Mesiti P.C.; Philip E. Hansen

(57) ABSTRACT

The invention provides compounds of the formula (0) or salts or tautomers or N-oxides or solvates thereof for use in the prophylaxis or treatment of disease states and conditions such as cancers mediated by cyclin-dependent kinase and glycogen synthase kinase-3.

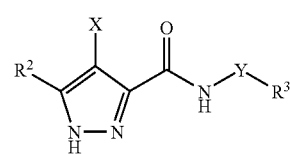

(0)

In formula (0):
X is a group $R^1$-A-$NR^4$— or a 5- or 6-membered carbocyclic or heterocyclic ring;
A is a bond, $SO_2$, C=O, $NR^g$(C=O) or O(C=O) wherein $R^g$ is hydrogen or $C_{1-4}$ hydrocarbyl optionally substituted by hydroxy or $C_{1-4}$ alkoxy;
Y is a bond or an alkylene chain of 1, 2 or 3 carbon atoms in length;
$R^1$ is hydrogen; a carbocyclic or heterocyclic group having from 3 to 12 ring members; or a $C_{1-8}$ hydrocarbyl group optionally substituted by one or more substituents selected from halogen (e.g. fluorine), hydroxy, $C_{1-4}$ hydrocarbyloxy, amino, mono- or di-$C_{1-4}$ hydrocarbylamino, and carbocyclic or heterocyclic groups having from 3 to 12 ring members, and wherein 1 or 2 of the carbon atoms of the hydrocarbyl group may optionally be replaced by an atom or group selected from O, S, NH, SO, $SO_2$;
$R^2$ is hydrogen; halogen; $C_{1-4}$ alkoxy (e.g. methoxy); or a $C_{1-4}$ hydrocarbyl group optionally substituted by halogen (e.g. fluorine), hydroxyl or $C_{1-4}$ alkoxy (e.g. methoxy);
$R^3$ is selected from hydrogen and carbocyclic and heterocyclic groups having from 3 to 12 ring members; and
$R^4$ is hydrogen or a $C_{1-4}$ hydrocarbyl group optionally substituted by halogen (e.g. fluorine), hydroxyl or $C_{1-4}$ alkoxy (e.g. methoxy).

20 Claims, No Drawings

FOREIGN PATENT DOCUMENTS

| | | |
|---|---|---|
| WO | 02/064586 | 8/2002 |
| WO | 02/070483 | 9/2002 |
| WO | 02074312 | 9/2002 |
| WO | 02074774 | 9/2002 |
| WO | 02101007 | 12/2002 |
| WO | 03/011287 | 2/2003 |
| WO | 03/020217 | 3/2003 |
| WO | 03018536 | 3/2003 |
| WO | 03024448 | 3/2003 |
| WO | 2003/048081 | 6/2003 |
| WO | 2003/48158 | 6/2003 |
| WO | 03082872 | 10/2003 |
| WO | 2004/085385 | 10/2004 |
| WO | 2004/099127 | 11/2004 |
| WO | 2005058881 | 6/2005 |

3,4-DISUBSTITUTED 1H-PYRAZOLE COMPOUNDS AND THEIR USE AS CYCLIN DEPENDENT KINASE AND GLYCOGEN SYNTHASE KINASE-3 MODULATORS

CROSS REFERENCE TO RELATED APPLICATIONS

This application is a continuation of copending PCT International Application PCT/GB2004/003179, filed Jul. 22, 2004, and published under PCT Article 21(2) in English as WO 2005/012256 on Feb. 10, 2005. PCT/GB2004/003179 claimed benefit from U.S. Provisional Applications 60/489,046, filed Jul. 22, 2003, and 60/569,763, filed May 10, 2004. PCT/GB2004/003179 also claimed priority from British application 0317127.9, filed Jul. 22, 2003. The entire contents of each of the prior applications are incorporated herein by reference.

FIELD OF THE INVENTION

This invention relates to pyrazole compounds that inhibit or modulate the activity of cyclin dependent kinases (CDK) and glycogen synthase kinase-3 (GSK-3), to the use of the compounds in the treatment or prophylaxis of disease states or conditions mediated by cyclin dependent kinases and glycogen synthase kinase-3, and to novel compounds having cyclin dependent kinase or glycogen synthase kinase-3 inhibitory or modulating activity. Also provided are pharmaceutical compositions containing the compounds and novel chemical intermediates.

BACKGROUND OF THE INVENTION

Protein kinases constitute a large family of structurally related enzymes that are responsible for the control of a wide variety of signal transduction processes within the cell (Hardie, G. and Hanks, S. (1995) *The Protein Kinase Facts Book. I and II*, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., *FASEB J.*, 9:576-596 (1995); Knighton, et al., *Science*, 253:407-414 (1991); Hiles, et al., *Cell*, 70:419-429 (1992); Kunz, et al., *Cell*, 73:585-596 (1993); Garcia-Bustos, et al., *EMBO J.*, 13:2352-2361 (1994)).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, disease and conditions of the immune system, disease and conditions of the central nervous system, and angiogenesis.

The process of eukaryotic cell division may be broadly divided into a series of sequential phases termed G1, S, G2 and M. Correct progression through the various phases of the cell cycle has been shown to be critically dependent upon the spatial and temporal regulation of a family of proteins known as cyclin dependent kinases (CDKs) and a diverse set of their cognate protein partners termed cyclins. CDKs are cdc2 (also known as CDK1) homologous serine-threonine kinase proteins that are able to utilise ATP as a substrate in the phosphorylation of diverse polypeptides in a sequence dependent context. Cyclins are a family of proteins characterised by a homology region, containing approximately 100 amino acids, termed the "cyclin box" which is used in binding to, and defining selectivity for, specific CDK partner proteins.

Modulation of the expression levels, degradation rates, and activation levels of various CDKs and cyclins throughout the cell cycle leads to the cyclical formation of a series of CDK/cyclin complexes, in which the CDKs are enzymatically active. The formation of these complexes controls passage through discrete cell cycle checkpoints and thereby enables the process of cell division to continue. Failure to satisfy the pre-requisite biochemical criteria at a given cell cycle checkpoint, i.e. failure to form a required CDK/cyclin complex, can lead to cell cycle arrest and/or cellular apoptosis. Aberrant cellular proliferation, as manifested in cancer, can often be attributed to loss of correct cell cycle control. Inhibition of CDK enzymatic activity therefore provides a means by which abnormally dividing cells can have their division arrested and/or be killed. The diversity of CDKs, and CDK complexes, and their critical roles in mediating the cell cycle, provides a broad spectrum of potential therapeutic targets selected on the basis of a defined biochemical rationale.

Progression from the G1 phase to the S phase of the cell cycle is primarily regulated by CDK2, CDK3, CDK4 and CDK6 via association with members of the D and E type cyclins. The D-type cyclins appear instrumental in enabling passage beyond the G1 restriction point, where as the CDK2/cyclin E complex is key to the transition from the G1 to S phase. Subsequent progression through S phase and entry into G2 is thought to require the CDK2/cyclin A complex. Both mitosis, and the G2 to M phase transition which triggers it, are regulated by complexes of CDK1 and the A and B type cyclins.

During G1 phase Retinoblastoma protein (Rb), and related pocket proteins such as p130, are substrates for CDK(2, 4, & 6)/cyclin complexes. Progression through G1 is in part facilitated by hyperphosphorylation, and thus inactivation, of Rb and p130 by the CDK(4/6)/cyclin-D complexes. Hyperphosphorylation of Rb and p130 causes the release of transcription factors, such as E2F, and thus the expression of genes necessary for progression through G1 and for entry into S-phase, such as the gene for cyclin E. Expression of cyclin E facilitates formation of the CDK2/cyclin E complex which amplifies, or maintains, E2F levels via further phosphorylation of Rb. The CDK2/cyclin E complex also phosphorylates other proteins necessary for DNA replication, such as NPAT, which has been implicated in histone biosynthesis. G1 progression and the G1/S transition are also regulated via the mitogen stimulated Myc pathway, which feeds into the CDK2/cyclin E pathway. CDK2 is also connected to the p53 mediated DNA damage response pathway via p53 regulation of p21 levels. p21 is a protein inhibitor of CDK2/cyclin E and is thus capable of blocking, or delaying, the G1/S transition. The CDK2/cyclin E complex may thus represent a point at which biochemical stimuli from the Rb, Myc and p53 pathways are to some degree integrated. CDK2 and/or the CDK2/cyclin E complex therefore represent good targets for therapeutics designed at arresting, or recovering control of, the cell cycle in aberrantly dividing cells.

The exact role of CDK3 in the cell cycle is not clear. As yet no cognate cyclin partner has been identified, but a dominant negative form of CDK3 delayed cells in G1, thereby suggesting that CDK3 has a role in regulating the G1/S transition.

Although most CDKs have been implicated in regulation of the cell cycle there is evidence that certain members of the CDK family are involved in other biochemical processes. This is exemplified by CDK5 which is necessary for correct neuronal development and which has also been implicated in the phosphorylation of several neuronal proteins such as Tau, NUDE-1, synapsin1, DARPP32 and the Munc18/Syntaxin1A complex. Neuronal CDK5 is conventionally activated by binding to the p35/p39 proteins. CDK5 activity can, however, be deregulated by the binding of p25, a truncated version of p35. Conversion of p35 to p25, and subsequent deregulation of CDK5 activity, can be induced by ischemia, excitotoxicity, and β-amyloid peptide. Consequently p25 has been implicated in the pathogenesis of neurodegenerative diseases, such as Alzheimer's, and is therefore of interest as a target for therapeutics directed against these diseases.

CDK7 is a nuclear protein that has cdc2 CAK activity and binds to cyclin H. CDK7 has been identified as component of the TFIIH transcriptional complex which has RNA polymerase II C-terminal domain (CTD) activity. This has been associated with the regulation of HIV-1 transcription via a Tat-mediated biochemical pathway. CDK8 binds cyclin C and has been implicated in the phosphorylation of the CTD of RNA polymerase II. Similarly the CDK9/cyclin-T1 complex (P-TEFb complex) has been implicated in elongation control of RNA polymerase II. PTEF-b is also required for activation of transcription of the HIV-1 genome by the viral transactivator Tat through its interaction with cyclin T1. CDK7, CDK8, CDK9 and the P-TEFb complex are therefore potential targets for anti-viral therapeutics.

At a molecular level mediation of CDK/cyclin complex activity requires a series of stimulatory and inhibitory phosphorylation, or dephosphorylation, events. CDK phosphorylation is performed by a group of CDK activating kinases (CAKs) and/or kinases such as wee1, Myt1 and Mik1. Dephosphorylation is performed by phosphatases such as cdc25(a & c), pp2a, or KAP.

CDK/cyclin complex activity may be further regulated by two families of endogenous cellular proteinaceous inhibitors: the Kip/Cip family, or the INK family. The INK proteins specifically bind CDK4 and CDK6. p16$^{ink4}$ (also known as MTS1) is a potential tumour suppressor gene that is mutated, or deleted, in a large number of primary cancers. The Kip/Cip family contains proteins such as p21$^{Cip1,Waf1}$, p27$^{Kip1}$ and p57$^{Kip2}$. As discussed previously p21 is induced by p53 and is able to inactivate the CDK2/cyclin(E/A) and CDK4/cyclin (D1/D2/D3) complexes. Atypically low levels of p27 expression have been observed in breast, colon and prostate cancers.

Conversely over expression of cyclin E in solid tumours has been shown to correlate with poor patient prognosis. Over expression of cyclin D1 has been associated with oesophageal, breast, squamous, and non-small cell lung carcinomas.

The pivotal roles of CDKs, and their associated proteins, in co-ordinating and driving the cell cycle in proliferating cells have been outlined above. Some of the biochemical pathways in which CDKs play a key role have also been described. The development of monotherapies for the treatment of proliferative disorders, such as cancers, using therapeutics targeted generically at CDKs, or at specific CDKs, is therefore potentially highly desirable. CDK inhibitors could conceivably also be used to treat other conditions such as viral infections, autoimmune diseases and neuro-degenerative diseases, amongst others. CDK targeted therapeutics may also provide clinical benefits in the treatment of the previously described diseases when used in combination therapy with either existing, or new, therapeutic agents. CDK targeted anticancer therapies could potentially have advantages over many current antitumour agents as they would not directly interact with DNA and should therefore reduce the risk of secondary tumour development.

Glycogen Synthase Kinase-3 (GSK3) is a serine-threonine kinase that occurs as two ubiquitously expressed isoforms in humans (GSK3α & beta GSK3β). GSK3 has been implicated as having roles in embryonic development, protein synthesis, cell proliferation, cell differentiation, microtubule dynamics, cell motility and cellular apoptosis. As such GSK3 has been implicated in the progression of disease states such as diabetes, cancer, Alzheimer's disease, stroke, epilepsy, motor neuron disease and/or head trauma. Phylogenetically GSK3 is most closely related to the cyclin dependent kinases (CDKs).

The consensus peptide substrate sequence recognised by GSK3 is (Ser/Thr)-X-X-X-(pSer/pThr), where X is any amino acid (at positions (n+1), (n+2), (n+3)) and pSer and pThr are phospho-serine and phospho-threonine respectively (n+4). GSK3 phosphorylates the first serine, or threonine, at position (n). Phospho-serine, or phospho-threonine, at the (n+4) position appear necessary for priming GSK3 to give maximal substrate turnover. Phosphorylation of GSK3α at Ser21, or GSK3β at Ser9, leads to inhibition of GSK3. Mutagenesis and peptide competition studies have led to the model that the phosphorylated N-terminus of GSK3 is able to compete with phospho-peptide substrate (S/TXXXpS/pT) via an autoinhibitory mechanism. There are also data suggesting that GSK3α and GSKβ may be subtly regulated by phosphorylation of tyrosines 279 and 216 respectively. Mutation of these residues to a Phe caused a reduction in in vivo kinase activity. The X-ray crystallographic structure of GSK3β has helped to shed light on all aspects of GSK3 activation and regulation.

GSK3 forms part of the mammalian insulin response pathway and is able to phosphorylate, and thereby inactivate, glycogen synthase. Upregulation of glycogen synthase activity, and thereby glycogen synthesis, through inhibition of GSK3, has thus been considered a potential means of combating type II, or non-insulin-dependent diabetes mellitus (NIDDM): a condition in which body tissues become resistant to insulin stimulation. The cellular insulin response in liver, adipose, or muscle tissues, is triggered by insulin binding to an extracellular insulin receptor. This causes the phosphorylation, and subsequent recruitment to the plasma membrane, of the insulin receptor substrate (IRS) proteins. Further phosphorylation of the IRS proteins initiates recruitment of phosphoinositide-3 kinase (PI3K) to the plasma membrane where it is able to liberate the second messenger phosphatidylinosityl 3,4,5-trisphosphate (PIP3). This facilitates co-localisation of 3-phosphoinositide-dedependent protein kinase 1 (PDK1) and protein kinase B (PKB or Akt) to the membrane, where PDK1 activates PKB. PKB is able to phosphorylate, and thereby inhibit, GSK3α and/or GSKβ through phosphorylation of Ser9, or ser21, respectively. The inhibition of GSK3 then triggers upregulation of glycogen synthase activity. Therapeutic agents able to inhibit GSK3 may thus be able to induce cellular responses akin to those seen on insulin stimulation. A further in vivo substrate of GSK3 is the eukaryotic protein synthesis initiation factor 2B (eIF2B). eIF2B is inactivated via phosphorylation and is thus able to suppress protein biosynthesis. Inhibition of GSK3, e.g. by inactivation of the "mammalian target of rapamycin" protein (mTOR), can thus upregulate protein biosynthesis. Finally there is some evidence for regulation of GSK3 activity via the mitogen activated protein kinase (MAPK) pathway through phosphorylation of GSK3 by kinases such as mitogen activated protein kinase activated protein kinase 1 (MAPKAP-K1 or RSK). These data suggest that GSK3 activity may be modulated by mitogenic, insulin and/or amino acid stimulii.

It has also been shown that GSK3β is a key component in the vertebrate Wnt signalling pathway. This biochemical pathway has been shown to be critical for normal embryonic development and regulates cell proliferation in normal tissues. GSK3 becomes inhibited in response to Wnt stimulii. This can lead to the de-phosphorylation of GSK3 substrates such as Axin, the adenomatous polyposis coli (APC) gene product and β-catenin. Aberrant regulation of the Wnt pathway has been associated with many cancers. Mutations in APC, and/or β-catenin, are common in colorectal cancer and other tumours. β-catenin has also been shown to be of importance in cell adhesion. Thus GSK3 may also modulate cellular adhesion processes to some degree. Apart from the biochemical pathways already described there are also data implicating GSK3 in the regulation of cell division via phosphorylation of cyclin-D1, in the phosphorylation of transcription factors such as c-Jun, CCAAT/enhancer binding protein α (C/EBPα), c-Myc and/or other substrates such as Nuclear Factor of Activated T-cells (NFATc), Heat Shock Factor-1 (HSF-1) and the c-AMP response element binding protein (CREB). GSK3 also appears to play a role, albeit tissue specific, in regulating cellular apoptosis. The role of GSK3 in modulating cellular apoptosis, via a pro-apoptotic mechanism, may be of particular relevance to medical conditions in which neuronal apoptosis can occur. Examples of these are head trauma, stroke, epilepsy, Alzheimer's and motor neuron diseases, progressive supranuclear palsy, corticobasal degeneration, and Pick's disease. In vitro it has been shown that GSK3 is able to hyper-phosphorylate the microtubule associated protein Tau. Hyperphosphorylation of Tau disrupts its normal binding to microtubules and may also lead to the formation of intra-cellular Tau filaments. It is believed that the progressive accumulation of these filaments leads to eventual neuronal dysfunction and degeneration. Inhbition of Tau phosphorylation, through inhibition of GSK3, may thus provide a means of limiting and/or preventing neurodegenerative effects.

WO 02/34721 from Du Pont discloses a class of indeno [1,2-c]pyrazol-4-ones as inhibitors of cyclin dependent kinases.

WO 01/81348 from Bristol Myers Squibb describes the use of 5-thio-, sulphinyl- and sulphonylpyrazolo[3,4-b]-pyridines as cyclin dependent kinase inhibitors.

WO 00/62778 also from Bristol Myers Squibb discloses a class of protein tyrosine kinase inhibitors.

WO 01/72745A1 from Cyclacel describes 2-substituted 4-heteroaryl-pyrimidines and their preparation, pharmaceutical compositions containing them and their use as inhibitors of cyclin-dependant kinases (CDKs) and hence their use in the treatment of proliferative disorders such as cancer, leukaemia, psoriasis and the like.

WO 99/21845 from Agouron describes 4-aminothiazole derivatives for inhibiting cyclin-dependent kinases (CDKs), such as CDK1, CDK2, CDK4, and CDK6. The invention is also directed to the therapeutic or prophylactic use of pharmaceutical compositions containing such compounds and to methods of treating malignancies and other disorders by administering effective amounts of such compounds.

WO 01/53274 from Agouron discloses as CDK kinase inhibitors a class of compounds which can comprise an amide-substituted benzene ring linked to an N-containing heterocyclic group.

WO 01/98290 (Pharmacia & Upjohn) discloses a class of 3-aminocarbonyl-2-carboxamido thiophene derivatives as protein kinase inhibitors.

WO 01/53268 and WO 01/02369 from Agouron disclose compounds that mediate or inhibit cell proliferation through the inhibition of protein kinases such as cyclin dependent kinase or tyrosine kinase. The Agouron compounds have an aryl or heteroaryl ring attached directly or though a CH═CH or CH═N group to the 3-position of an indazole ring.

WO 00/39108 and WO 02/00651 (both to Du Pont Pharmaceuticals) describe heterocyclic compounds that are inhibitors of trypsin-like serine protease enzymes, especially factor Xa and thrombin. The compounds are stated to be useful as anticoagulants or for the prevention of thromboembolic disorders.

US 2002/0091116 (Zhu et al.), WO 01/19798 and WO 01/64642 each disclose diverse groups of heterocyclic compounds as inhibitors of Factor Xa. Some 1-substituted pyrazole carboxamides are disclosed and exemplified.

U.S. Pat. No. 6,127,382, WO 01/70668, WO 00/68191, WO 97/48672, WO 97/19052 and WO 97/19062 (all to Allergan) each describe compounds having retinoid-like activity for use in the treatment of various hyperproliferative diseases including cancers.

WO 02/070510 (Bayer) describes a class of amino-dicarboxylic acid compounds for use in the treatment of cardiovascular diseases. Although pyrazoles are mentioned generically, there are no specific examples of pyrazoles in this document.

WO 97/03071 (Knoll AG) discloses a class of heterocyclyl-carboxamide derivatives for use in the treatment of central nervous system disorders. Pyrazoles are mentioned generally as examples of heterocyclic groups but no specific pyrazole compounds are disclosed or exemplified.

WO 97/40017 (Novo Nordisk) describes compounds that are modulators of protein tyrosine phosphatases.

WO 03/020217 (Univ. Connecticut) discloses a class of pyrazole 3-carboxamides as cannabinoid receptor modulators for treating neurological conditions. It is stated (page 15) that the compounds can be used in cancer chemotherapy but it is not made clear whether the compounds are active as anti-cancer agents or whether they are administered for other purposes.

WO 01/58869 (Bristol Myers Squibb) discloses cannabinoid receptor modulators that can be used inter alia to treat a variety of diseases. The main use envisaged is the treatment of respiratory diseases, although reference is made to the treatment of cancer.

WO 01/02385 (Aventis Crop Science) discloses 1-(quinoline-4-yl)-1H-pyrazole derivatives as fungicides. 1-Unsubsituted pyrazoles are disclosed as synthetic intermediates.

WO 2004/039795 (Fujisawa) discloses amides containing a 1-substituted pyrazole group as inhibitors of apolipoprotein B secretion. The compounds are stated to be useful in treating such conditions as hyperlipidemia.

WO 2004/000318 (Cellular Genomics) discloses various amino-substituted monocycles as kinase modulators. None of the exemplified compounds are pyrazoles.

SUMMARY OF THE INVENTION

The invention provides compounds that have cyclin dependent kinase inhibiting or modulating activity, and which it is envisaged will be useful in preventing or treating disease states or conditions mediated by the kinases.

Thus, for example, it is envisaged that the compounds of the invention will be useful in alleviating or reducing the incidence of cancer.

Accordingly, in one aspect, the invention provides the use of a compound for the manufacture of a medicament for the prophylaxis or treatment of a disease state or condition mediated by a cyclin dependent kinase, the compound having the formula (0):

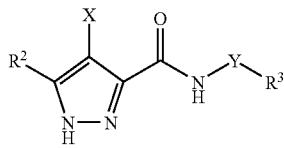

(0)

or salts or tautomers or N-oxides or solvates thereof;
  wherein
    X is a group $R^1$-A-$NR^4$— or a 5- or 6-membered carbocyclic or heterocyclic ring;
    A is a bond, $SO_2$, C=O, $NR^g$(C=O) or O(C=O) wherein $R^g$ is hydrogen or $C_{1-4}$ hydrocarbyl optionally substituted by hydroxy or $C_{1-4}$ alkoxy;
    Y is a bond or an alkylene chain of 1, 2 or 3 carbon atoms in length;
    $R^1$ is hydrogen; a carbocyclic or heterocyclic group having from 3 to 12 ring members; or a $C_{1-8}$ hydrocarbyl group optionally substituted by one or more substituents selected from halogen (e.g. fluorine), hydroxy, $C_{1-4}$ hydrocarbyloxy, amino, mono- or di-$C_{1-4}$ hydrocarbylamino, and carbocyclic or heterocyclic groups having from 3 to 12 ring members, and wherein 1 or 2 of the carbon atoms of the hydrocarbyl group may optionally be replaced by an atom or group selected from O, S, NH, SO, $SO_2$;
    $R^2$ is hydrogen; halogen; $C_{1-4}$ alkoxy (e.g. methoxy); or a $C_{1-4}$ hydrocarbyl group optionally substituted by halogen (e.g. fluorine), hydroxyl or $C_{1-4}$ alkoxy (e.g. methoxy);
    $R^3$ is selected from hydrogen and carbocyclic and heterocyclic groups having from 3 to 12 ring members; and
    $R^4$ is hydrogen or a $C_{1-4}$ hydrocarbyl group optionally substituted by halogen (e.g. fluorine), hydroxyl or $C_{1-4}$ alkoxy (e.g. methoxy).

In one embodiment, the invention provides the use of a compound for the manufacture of a medicament for the prophylaxis or treatment of a disease state or condition mediated by a cyclin dependent kinase, the compound having the formula ($I^0$):

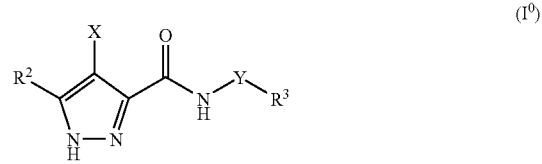

($I^0$)

or salts or tautomers or N-oxides or solvates thereof;
  wherein
    X is a group $R^1$-A-$NR^4$— or a 5- or 6-membered carbocyclic or heterocyclic ring;
    A is a bond, C=O, NR9(C=O) or O(C=O) wherein $R^g$ is hydrogen or $C_{1-4}$ hydrocarbyl optionally substituted by hydroxy or $C_{1-4}$ alkoxy;
    Y is a bond or an alkylene chain of 1, 2 or 3 carbon atoms in length;
    $R^1$ is hydrogen; a carbocyclic or heterocyclic group having from 3 to 12 ring members; or a $C_{1-8}$ hydrocarbyl group optionally substituted by one or more substituents selected from halogen (e.g. fluorine), hydroxy, $C_{1-4}$ hydrocarbyloxy, amino, mono- or di-$C_{1-4}$ hydrocarbylamino, and carbocyclic or heterocyclic groups having from 3 to 12 ring members, and wherein 1 or 2 of the carbon atoms of the hydrocarbyl group may optionally be replaced by an atom or group selected from O, S, NH, SO, $SO_2$;
    $R^2$ is hydrogen; halogen; $C_{1-4}$ alkoxy (e.g. methoxy); or a $C_{1-4}$ hydrocarbyl group optionally substituted by halogen (e.g. fluorine), hydroxyl or $C_{1-4}$ alkoxy (e.g. methoxy);
    $R^3$ is selected from hydrogen and carbocyclic and heterocyclic groups having from 3 to 12 ring members; and
    $R^4$ is hydrogen or a $C_{1-4}$ hydrocarbyl group optionally substituted by halogen (e.g. fluorine), hydroxyl or $C_{1-4}$ alkoxy (e.g. methoxy).

The invention also provides the use of a compound for the manufacture of a medicament for the prophylaxis or treatment of a disease state or condition mediated by a cyclin dependent kinase, the compound having the formula (1):

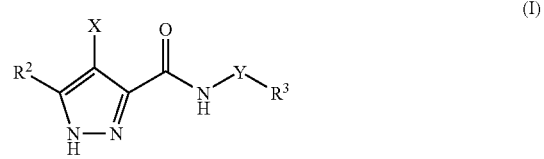

(I)

or salts or tautomers or N-oxides or solvates thereof;
  wherein
    X is a group $R^1$-A-$NR^4$—;
    A is a bond, C=O, $NR^g$(C=O) or O(C=O) wherein $R^g$ is hydrogen or $C_{1-4}$ hydrocarbyl optionally substituted by hydroxy or $C_{1-4}$ alkoxy;
    Y is a bond or an alkylene chain of 1, 2 or 3 carbon atoms in length;
    $R^1$ is hydrogen; a carbocyclic or heterocyclic group having from 3 to 12 ring members; or a $C_{1-8}$ hydrocarbyl group optionally substituted by one or more substituents selected from halogen (e.g. fluorine), hydroxy, $C_{1-4}$ hydrocarbyloxy, amino, mono- or di-$C_{1-4}$ hydrocarbylamino, and carbocyclic or heterocyclic groups having from 3 to 12 ring members, and wherein 1 or 2 of the carbon atoms of the hydrocarbyl group may optionally be replaced by an atom or group selected from O, S, NH, SO, SO$_2$;

R$^2$ is hydrogen; halogen; C$_{1-4}$ alkoxy (e.g. methoxy); or a C$_{1-4}$ hydrocarbyl group optionally substituted by halogen (e.g. fluorine), hydroxyl or C$_{1-4}$ alkoxy (e.g. methoxy);

R$^3$ is selected from hydrogen and carbocyclic and heterocyclic groups having from 3 to 12 ring members; and R$^4$ is hydrogen or a C$_{1-4}$ hydrocarbyl group optionally substituted by halogen (e.g. fluorine), hydroxyl or C$_{1-4}$ alkoxy (e.g. methoxy).

Any one or more of the following optional provisos, in any combination, may apply to the compounds of formulae (0), (I$^0$), (I) and sub-groups thereof:

(a-i) When A is a bond and Y-R$^3$ is an alkyl, cycloalkyl, optionally substituted phenyl or optionally substituted phenylalkyl, then R$^1$ is other than a substituted or unsubstituted dihydronaphthalene, dihydrochroman, dihydrothiochroman, tetrahydroquinoline or tetrahydrobenzfuranyl group.

(a-ii) X and R$^3$ are each other than a moiety containing a maleimide group wherein the maleimide group has nitrogen atoms attached to the 3- and 4-positions thereof.

(a-iii) R$^1$ is other than a moiety containing a purine nucleoside group.

(a-iv) X and R$^3$ are each other than a moiety containing a cyclobutene-1,2-dione group wherein the cyclobutene-1,2-dione group has nitrogen atoms attached to the 3- and 4-positions thereof.

(a-v) R$^3$ is other than a moiety containing a 4-monosubsituted or 4,5-disubstituted 2-pyridyl or 2-pyrimidinyl group or a 5-monosubstituted or 5,6-disubstituted 1,2,4-triazin-3-yl or 3-pyridazinyl group.

(a-vi) X and R$^3$ are each other than a moiety containing a substituted or unsubstituted pyrazol-3-ylamine group linked to a substituted or unsubstituted pyridine, diazine or triazine group.

(a-vii) When A is C=O and Y-R$^3$ is an alkyl, cycloalkyl, optionally substituted phenyl or optionally substituted phenylalkyl group, then R$^1$ is other than a substituted or unsubstituted tetrahydronaphthalene, tetrahydroquinolinyl, tetrahydrochromanyl or tetrahydrothiochromanyl group.

(a-viii) When R$^3$ is H and A is a bond, R$^1$ is other than a moiety containing a bis-aryl, bis-heteroaryl or aryl heteroaryl group.

(a-ix) R$^3$ is other than a moiety containing a 1,2,8,8a-tetrahydro-7-methyl-cyclopropa[c]pyrrolo[3,2,e]indole-4-(5H)-one group.

(a-x) When Y is a bond, R$^3$ is hydrogen, A is CO and R$^1$ is a substituted phenyl group, each substituent on the phenyl group is other than a group CH$_2$—P(O)R$^x$R$^y$ where R$^x$ and R$^y$ are each selected from alkoxy and phenyl groups.

(a-xi) X is other than 4-(tert-butyloxycarbonylamino)-3-methylimidazol-2-ylcarbonylamino.

In another aspect, the invention provides, for use in medicine, a sub-group of compounds of the formula (I) represented by the general formula (Ia):

wherein

X is a group R$^1$-A-NR$^4$—;

A is a bond, C=O, NR$^g$(C=O) or O(C=O) wherein R$^g$ is hydrogen or C$_{1-4}$ hydrocarbyl optionally substituted by hydroxy or C$_{1-4}$ alkoxy;

Y is a bond or an alkylene chain of 1, 2 or 3 carbon atoms in length;

R$^1$ is a carbocyclic or heterocyclic group having from 3 to 12 ring members; or a C$_{1-8}$ hydrocarbyl group optionally substituted by one or more substituents selected from fluorine, hydroxy, C$_{1-4}$ hydrocarbyloxy, amino, mono- or di-C$_{1-4}$ hydrocarbylamino, and carbocyclic or heterocyclic groups having from 3 to 12 ring members, and wherein 1 or 2 of the carbon atoms of the hydrocarbyl group may optionally be replaced by an atom or group selected from O, S, NH, SO, SO$_2$;

R$^2$ is hydrogen; halogen; C$_{1-4}$ alkoxy (e.g. methoxy); or a C$_{1-4}$ hydrocarbyl group optionally substituted by halogen (e.g. fluorine), hydroxyl or C$_{1-4}$ alkoxy (e.g. methoxy);

R$^3$ is selected from hydrogen and carbocyclic and heterocyclic groups having from 3 to 12 ring members; and R$^4$ is hydrogen or a C$_{1-4}$ hydrocarbyl group optionally substituted by halogen (e.g. fluorine), hydroxyl or C$_{1-4}$ alkoxy (e.g. methoxy).

Any one or more of the following optional provisos, in any combination, may apply to the compounds of formula (Ia) and sub-groups thereof:

Provisos (a-i) to (a-xi) above.

(b-i) R$^3$ is other than a bridged azabicyclo group.

(b-ii) When A is a bond, then R$^3$ is other than a moiety containing an unsubstituted or substituted phenyl group having attached to an ortho position thereof, a substituted or unsubstituted carbamoyl or thiocarbamoyl group.

(b-iii) When A is a bond, then R$^3$ is other than a moiety containing an isoquinoline or quinoxaline group each having attached thereto a substituted or unsubstituted piperidine or piperazine ring.

(b-iv) When A is a bond and R$^1$ is an alkyl group, then R$^3$ is other than a moiety containing a thiatriazine group.

(b-v) When R$^1$ or R$^3$ contain a moiety in which a heterocyclic ring having an S(=O)$_2$ ring member is fused to a carbocyclic ring, the said carbocyclic ring is other than a substituted or unsubstituted benzene ring (b-vi) When A is a bond, R$^1$ is other than an arylalkyl, heteroarylalkyl or piperidinylalkyl group each having attached thereto a substituent selected from cyano, and substituted or unsubstituted amino, aminoalkyl, amidine, guanidine, and carbamoyl groups.

(b-vii) When X is a group R$^1$-A-NR$^4$—, A is a bond and R$^1$ is a non-aromatic group, then R$^3$ is other than a six membered monocyclic aryl or heteroaryl group linked directly to a 5,6-fused bicyclic heteroaryl group.

In a further aspect, the invention provides a sub-group of novel compounds of the formulae (I) and (Ia) as defined herein, the novel compounds being represented by the formula (Ib):

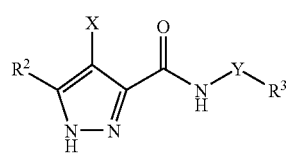

(Ia)

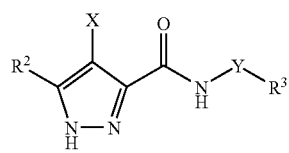

(Ib)

or salts or tautomers or N-oxides or solvates thereof;

or salts or tautomers or N-oxides or solvates thereof;

wherein

X is a group R$^1$-A-NR$^4$—;

A is a bond, C=O, NR$^g$(C=O) or O(C=O) wherein R$^g$ is hydrogen or C$_{1-4}$ hydrocarbyl optionally substituted by hydroxy or C$_{1-4}$ alkoxy;

Y is a bond or an alkylene chain of 1, 2 or 3 carbon atoms in length;

R$^1$ is a carbocyclic or heterocyclic group having from 3 to 12 ring members; or a C$_{1-8}$ hydrocarbyl group optionally substituted by one or more substituents selected from fluorine, hydroxy, C$_{1-4}$ hydrocarbyloxy, amino, mono- or di-C$_{1-4}$ hydrocarbylamino, and carbocyclic or heterocyclic groups having from 3 to 12 ring members, and wherein 1 or 2 of the carbon atoms of the hydrocarbyl group may optionally be replaced by an atom or group selected from O, S, NH, SO, SO$_2$;

R$^2$ is hydrogen; halogen; C$_{1-4}$ alkoxy (e.g. methoxy); or a C$_{1-4}$ hydrocarbyl group optionally substituted by halogen (e.g. fluorine), hydroxyl or C$_{1-4}$ alkoxy (e.g. methoxy);

R$^3$ is selected from carbocyclic and heterocyclic groups having from 3 to 12 ring members; and R$^4$ is hydrogen or a C$_{1-4}$ hydrocarbyl group optionally substituted by halogen (e.g. fluorine), hydroxyl or C$_{1-4}$ alkoxy (e.g. methoxy).

Any one or more of the following optional provisos, in any combination, may apply to the compounds of formula (Ib) and sub-groups thereof:

Provisos (a-i) to (a-vii), (a-ix) and (a-xi).

Provisos (b-i) to (b-vii).

(c-i) When A is a bond, R$^1$ is other than a substituted arylalkyl, heteroarylalkyl or piperidinylalkyl group.

(c-ii) When X is an amino or alkylamino group and Y is a bond, R$^3$ is other than a disubstituted thiazolyl group wherein one of the substituents is selected from cyano and fluoroalkyl.

The reference in proviso (a-iii) to a purine nucleoside group refers to substituted and unsubstituted purine groups having attached thereto a monosaccharide group (e.g. a pentose or hexose) or a derivative of a monosaccharide group, for example a deoxy monosaccharide group or a substituted monosaccharide group.

The reference in proviso (b-i) to a bridged azabicyclo group refers to bicycloalkane bridged ring systems in which one of the carbon atoms of the bicycloalkane has been replaced by a nitrogen atom. In bridged ring systems, two rings share more than two atoms, see for example *Advanced Organic Chemistry*, by Jerry March, 4$^{th}$ Edition, Wiley Interscience, pages 131-133, 1992.

The invention also provides the use of a compound of the formulae (Ia) or (Ib) as defined herein for the manufacture of a medicament for the prophylaxis or treatment of a disease state or condition mediated by a cyclin dependent kinase.

The provisos (a-i) to (a-x), (b-i) to (b-vii), (c-i) and (c-ii) in formulae (I), (Ia) and (Ib) above refer to the disclosures in the following prior art documents.

(a-i) US 2003/0166932, U.S. Pat. Nos. 6,127,382, 6,093,838

(a-ii) WO 03/031440

(a-iii) WO 03/014137

(a-iv) WO 02/083624

(a-v) WO 02/064586

(a-vi) WO 02/22608, WO 02/22605, WO 02/22603 & WO 02/22601

(a-vii) WO 97/48672, WO 97/19052

(a-viii) WO 00/06169

(a-ix) U.S. Pat. No. 5,502,068

(a-x) JP 07188269

(b-i) WO 03/040147

(b-ii) WO 01/70671

(b-iii) WO 01/32626

(b-iv) WO 98/08845

(b-v) WO 00/59902

(b-vi) U.S. Pat. No. 6,020,357, WO 99/32454 & WO 98/28269

(b-vii) WO 2004/012736

(c-i) U.S. Pat. No. 6,020,357, WO 99/32454 & WO 98/28269

(c-ii) US 2004/0082629

Any one or more of the foregoing optional provisos, (a-i) to (a-xi), (b-i) to (b-vii), (c-i) and (c-ii) in any combination, may also apply to the compounds of formulae (Ib), (II), (III), (IV), (IVa), (Va), (Vb), (VIa), (VIb), (VII) or (VIII) and sub-groups thereof as defined herein.

The invention also provides:

The use of a compound of the formula (Ia), (Ib), (II), (III), (IV), (IVa), (Va), (Vb), (VIa), (VIb), (VII) or (VIII) and sub-groups thereof as defined herein for manufacture of a medicament for the prophylaxis or treatment of a disease state or condition mediated by a cyclin dependent kinase.

A method for alleviating or reducing the incidence of a disease or condition comprising or arising from abnormal cell growth in a mammal, which method comprises administering to the mammal a compound of the formula (0), (I$^0$), (I), (Ia), (Ib), (II), (III), (IV), (IVa), (Va), (Vb), (VIa), (VIb), (VII) or (VIII) and sub-groups thereof as defined herein in an amount effective in inhibiting abnormal cell growth.

A method for alleviating or reducing the incidence of a disease state or condition mediated by a cyclin dependent kinase or glycogen synthase kinase-3, which method comprises administering to a subject in need thereof a compound of the formula (0), (I$^0$), (I), (Ia), (Ib), (II), (III), (IV), (IVa), (Va), (Vb), (VIa), (VIb), (VII) or (VIII) and sub-groups thereof as defined herein.

A method for the prophylaxis or treatment of a disease state or condition mediated by a cyclin dependent kinase, which method comprises administering to a subject in need thereof a compound of the formula (0), (I$^0$), (I), (Ia), (Ib), (II), (III), (IV), (IVa), (Va), (Vb), (VIa), (VIb), (VII) or (VIII) and sub-groups thereof as defined herein.

A method for treating a disease or condition comprising or arising from abnormal cell growth in a mammal, which method comprises administering to the mammal a compound of the formula (0), (I$^0$), (I), (Ia), (Ib), (II), (III), (IV), (IVa), (Va), (Vb), (VIa), (VIb), (VII) or (VIII) and sub-groups thereof as defined herein in an amount effective in inhibiting abnormal cell growth.

A method for treating a disease or condition comprising or arising from abnormal cell growth in a mammal, the method comprising administering to the mammal a compound of the formula (0), (I$^0$), (I), (Ia), (Ib), (II), (III), (IV), (IVa), (Va), (Vb), (VIa), (VIb), (VII) or (VIII) and sub-groups thereof as defined herein in an amount effective to inhibit a cyclin dependent kinase (e.g. CDK2).

A method of inhibiting a cyclin dependent kinase, which method comprises contacting the kinase with a kinase-inhibiting compound of the formula (0), (I$^0$), (I), (Ia) (Ib), (II), (III), (IV), (IVa), (Va), (Vb), (VIa), (VIb), (VII) or (VIII) and sub-groups thereof as defined herein.

A method of modulating a cellular process (for example cell division) by inhibiting the activity of a cyclin dependent kinase using a compound of the formula (0), (I$^0$), (I), (Ia), (Ib), (II), (III), (IV), (IVa), (Va), (Vb), (VIa), (VIb), (VII) or (VIII) and sub-groups thereof as defined herein.

The compounds of the invention are also considered to be inhibitors of glycogen synthase kinase-3 (GSK3) and, accordingly, the invention also provides methods and uses of kinase inhibitors or modulators of the formula (0), (I$^0$), (I), (Ia), (Ib), (II), (III), (IV), (IVa), (Va), (Vb), (VIa), (VIb), (VII) or (VIII) and sub-groups thereof as defined herein but wherein the kinase is glycogen synthase kinase-3.

In further aspects, the invention provides:

A pharmaceutical composition comprising a compound of the formula (Ia), (Ib), (II), (III), (IV), (IVa), (Va), (Vb), (VIa), (VIb), (VII) or (VIII) and sub-groups thereof as defined herein and a pharmaceutically acceptable carrier.

Compounds of the formula (Ib), (II), (III), (IV), (IVa), (Va), (Vb), (VIa), (VIb), (VII) or (VIII) and sub-groups thereof as defined herein for use in medicine.

The use of a compound of the formula (0), (I$^0$), (I), (Ia), (Ib), (II), (III), (IV), (IVa), (Va), (Vb), (VIa), (VIb), (VII) or (VIII) and sub-groups thereof as defined herein, for the manufacture of a medicament for the prophylaxis or treatment of any one of the disease states or conditions disclosed herein.

A method for the treatment or prophylaxis of any one of the disease states or conditions disclosed herein, which method comprises administering to a patient (e.g. a patient in need thereof) a compound (e.g. a therapeutically effective amount) of the formula (0), (I$^0$), (I), (Ia), (Ib), (II), (III), (IV), (IVa), (Va), (Vb), (VIa), (VIb), (VII) or (VIII) and sub-groups thereof as defined herein.

A method for alleviating or reducing the incidence of a disease state or condition disclosed herein, which method comprises administering to a patient (e,g, a patient in need thereof) a compound (e.g. a therapeutically effective amount) of the formula (0), (I$^0$), (I), (Ia), (Ib), (II), (III), (IV), (IVa), (Va), (Vb), (VIa), (VIb), (VII) or (VIII) and sub-groups thereof as defined herein.

A method for the diagnosis and treatment of a disease state or condition mediated by a cyclin dependent kinase, which method comprises (i) screening a patient to determine whether a disease or condition from which the patient is or may be suffering is one which would be susceptible to treatment with a compound having activity against cyclin dependent kinases; and (ii) where it is indicated that the disease or condition from which the patient is thus susceptible, thereafter administering to the patient a compound of the formula (0), (I$^0$), (I), (Ia), (Ib), (II), (III), (IV), (IVa), (Va), (Vb), (VIa), (VIb), (VII) or (VIII) and sub-groups thereof as defined herein.

The use of a compound of the formula (0), (I$^0$), (I), (Ia), (Ib), (II), (III), (IV), (IVa), (Va), (Vb), (VIa), (VIb), (VII) or (VIII) and sub-groups thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against cyclin dependent kinase.

In each of the foregoing uses, methods and other aspects of the invention, as well as any aspects and embodiments of the invention as set out below, references to compounds of the formulae (0), (I$^0$), (I), (Ia), (Ib), (II), (III), (IV), (IVa), (Va), (Vb), (VIa), (VIb), (VII) or (VIII) and sub-groups thereof as defined herein include within their scope the salts or solvates or tautomers or N-oxides of the compounds.

General Preferences and Definitions

The following general preferences and definitions shall apply to each of the moieties X, Y, R$^g$, R$^1$ to R$^4$ and any sub-definition, sub-group or embodiment thereof, unless the context indicates otherwise.

In this specification, references to formula (I) include formulae (0), (I$^0$), (Ia), (Ib), (II), (III), (IV), (IVa), (Va), (Vb), (VIa), (VIb), (VII) or (VIII) and sub-groups, examples or embodiments of formulae (0), (I$^0$), (Ia), (Ib), (II), (III), (IV), (IVa), (Va), (Vb), (VIa), (VIb), (VII) or (VIII) unless the context indicates otherwise.

Thus for example, references to inter alia therapeutic uses, pharmaceutical formulations and processes for making compounds, where they refer to formula (I), are also to be taken as referring to formulae (0), (I$^0$), (Ia), (Ib), (II), (III), (IV), (IVa), (Va), (Vb), (VIa), (VIb), (VII) or (VIII) and sub-groups, examples or embodiments of formulae (0), (I$^0$), (Ia), (Ib), (II), (III), (IV), (IVa), (Va), (Vb), (VIa), (VIb), (VII) or (VIII).

Similarly, where preferences, embodiments and examples are given for compounds of the formula (I), they are also applicable to formulae (0), (I$^0$), (Ia), (Ib), (II), (III), (IV), (IVa), (Va), (Vb), (VIa), (VIb), (VII) or (VIII) and sub-groups, examples or embodiments of formulae (0), (I$^0$), (Ia), (Ib), (II), (III), (IV), (IVa), (Va), (Vb), (VIa), (VIb), (VII) or (VIII) unless the context requires otherwise.

References to "carbocyclic" and "heterocyclic" groups as used herein shall, unless the context indicates otherwise, include both aromatic and non-aromatic ring systems. Thus, for example, the term "carbocyclic and heterocyclic groups" includes within its scope aromatic, non-aromatic, unsaturated, partially saturated and fully saturated carbocyclic and heterocyclic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, and preferably 5 or 6 ring members. Examples of bicyclic groups are those containing 8, 9, 10, 11 and 12 ring members, and more usually 9 or 10 ring members.

The carbocyclic or heterocyclic groups can be aryl or heteroaryl groups having from 5 to 12 ring members, more usually from 5 to 10 ring members. The term "aryl" as used herein refers to a carbocyclic group having aromatic character and the term "heteroaryl" is used herein to denote a heterocyclic group having aromatic character. The terms "aryl" and "heteroaryl" embrace polycyclic (e.g. bicyclic) ring systems wherein one or more rings are non-aromatic, provided that at least one ring is aromatic. In such polycyclic systems, the group may be attached by the aromatic ring, or by a non-aromatic ring. The aryl or heteroaryl groups can be monocyclic or bicyclic groups and can be unsubstituted or substituted with one or more substituents, for example one or more groups R$^{10}$ as defined herein.

The term "non-aromatic group" embraces unsaturated ring systems without aromatic character, partially saturated and fully saturated carbocyclic and heterocyclic ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond.

The term "fully saturated" refers to rings where there are no multiple bonds between ring atoms. Saturated carbocyclic groups include cycloalkyl groups as defined below. Partially saturated carbocyclic groups include cycloalkenyl groups as defined below, for example cyclopentenyl, cycloheptenyl and cyclooctenyl. A further example of a cycloalkenyl group is cyclohexenyl.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to about four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
  a) a benzene ring fused to a 5- or 6-membered ring containing 1, 2 or 3 ring heteroatoms;
  b) a pyridine ring fused to a 5- or 6-membered ring containing 1, 2 or 3 ring heteroatoms;
  c) a pyrimidine ring fused to a 5- or 6-membered ring containing 1 or 2 ring heteroatoms;
  d) a pyrrole ring fused to a 5- or 6-membered ring containing 1, 2 or 3 ring heteroatoms;
  e) a pyrazole ring fused to a 5- or 6-membered ring containing 1 or 2 ring heteroatoms;
  f) an imidazole ring fused to a 5- or 6-membered ring containing 1 or 2 ring heteroatoms;
  g) an oxazole ring fused to a 5- or 6-membered ring containing 1 or 2 ring heteroatoms;
  h) an isoxazole ring fused to a 5- or 6-membered ring containing 1 or 2 ring heteroatoms;
  i) a thiazole ring fused to a 5- or 6-membered ring containing 1 or 2 ring heteroatoms;
  j) an isothiazole ring fused to a 5- or 6-membered ring containing 1 or 2 ring heteroatoms;
  k) a thiophene ring fused to a 5- or 6-membered ring containing 1, 2 or 3 ring heteroatoms;
  l) a furan ring fused to a 5- or 6-membered ring containing 1, 2 or 3 ring heteroatoms;
  m) an oxazole ring fused to a 5- or 6-membered ring containing 1 or 2 ring heteroatoms;
  n) an isoxazole ring fused to a 5- or 6-membered ring containing 1 or 2 ring heteroatoms;
  o) a cyclohexyl ring fused to a 5- or 6-membered ring containing 1, 2 or 3 ring heteroatoms; and
  p) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

One sub-group of heteroaryl groups comprises pyridyl, pyrrolyl, furanyl, thienyl, imidazolyl, oxazolyl, oxadiazolyl, oxatriazolyl, isoxazolyl, thiazolyl, isothiazolyl, pyrazolyl, pyrazinyl, pyridazinyl, pyrimidinyl, triazinyl, triazolyl, tetrazolyl, quinolinyl, isoquinolinyl, benzfuranyl, benzthienyl, chromanyl, thiochromanyl, benzimidazolyl, benzoxazolyl, benzisoxazole, benzthiazolyl and benzisothiazole, isobenzofuranyl, indolyl, isoindolyl, indolizinyl, indolinyl, isoindolinyl, purinyl (e.g., adenine, guanine), indazolyl, benzodioxolyl, chromenyl, isochromenyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

Examples of polycyclic aryl and heteroaryl groups containing an aromatic ring and a non-aromatic ring include tetrahydronaphthalene, tetrahydroisoquinoline, tetrahydroquinoline, dihydrobenzthiene, dihydrobenzfuran, 2,3-dihydro-benzo[1,4]dioxine, benzo[1,3]dioxole, 4,5,6,7-tetrahydrobenzofuran, indoline and indane groups.

Examples of carbocyclic aryl groups include phenyl, naphthyl, indenyl, and tetrahydronaphthyl groups.

Examples of non-aromatic heterocyclic groups include unsubstituted or substituted (by one or more groups $R^{10}$) heterocyclic groups having from 3 to 12 ring members, typically 4 to 12 ring members, and more usually from 5 to 10 ring members. Such groups can be monocyclic or bicyclic, for example, and typically have from 1 to 5 heteroatom ring members (more usually 1,2,3 or 4 heteroatom ring members) typically selected from nitrogen, oxygen and sulphur.

When sulphur is present, it may, where the nature of the adjacent atoms and groups permits, exist as —S—, —S(O)— or —S(O)$_2$—.

The heterocylic groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ester moieties (e.g. as in butyrolactone), cyclic sulphones (e.g. as in sulpholane and sulpholene), cyclic sulphoxides, cyclic sulphonamides and combinations thereof (e.g. morpholine and thiomorpholine and its S-oxide and S,S-dioxide). Further examples of heterocyclic groups are those containing a cyclic urea moiety (e.g. as in imidazolidin-2-one), In one sub-set of heterocyclic groups, the heterocyclic groups contain cyclic ether moieties (e.g as in tetrahydrofuran and dioxane), cyclic thioether moieties (e.g. as in tetrahydrothiophene and dithiane), cyclic amine moieties (e.g. as in pyrrolidine), cyclic sulphones (e.g. as in sulpholane and sulpholene), cyclic sulphoxides, cyclic sulphonamides and combinations thereof (e.g. thiomorpholine).

Examples of monocyclic non-aromatic heterocyclic groups include 5-, 6- and 7-membered monocyclic heterocyclic groups. Particular examples include morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine.

One preferred sub-set of non-aromatic heterocyclic groups consists of saturated groups such as azetidine, pyrrolidine, piperidine, morpholine, thiomorpholine, thiomorpholine S,S-dioxide, piperazine, N-alkyl piperazines, and N-alkyl piperidines.

Another sub-set of non-aromatic heterocyclic groups consists of pyrrolidine, piperidine, morpholine, thiomorpholine, thiomorpholine S,S-dioxide, piperazine and N-alkyl piperazines such as N-methyl piperazine.

One particular sub-set of heterocyclic groups consists of pyrrolidine, piperidine, morpholine and N-alkyl piperazines (e.g. N-methyl piperazine), and optionally thiomorpholine.

Examples of non-aromatic carbocyclic groups include cycloalkane groups such as cyclohexyl and cyclopentyl, cycloalkenyl groups such as cyclopentenyl, cyclohexenyl, cycloheptenyl and cyclooctenyl, as well as cyclohexadienyl, cyclooctatetraene, tetrahydronaphthenyl and decalinyl.

Preferred non-aromatic carbocyclic groups are monocyclic rings and most preferably saturated monocyclic rings.

Typical examples are three, four, five and six membered saturated carbocyclic rings, e.g. optionally substituted cyclopentyl and cyclohexyl rings.

One sub-set of non-aromatic carboyclic groups includes unsubstituted or substituted (by one or more groups $R^{10}$) monocyclic groups and particularly saturated monocyclic groups, e.g. cycloalkyl groups. Examples of such cycloalkyl groups include cyclopropyl, cyclobutyl, cyclopentyl, cyclohexyl and cycloheptyl; more typically cyclopropyl, cyclobutyl, cyclopentyl and cyclohexyl, particularly cyclohexyl.

Further examples of non-aromatic cyclic groups include bridged ring systems such as bicycloalkanes and azabicycloalkanes although such bridged ring systems are generally less preferred. By "bridged ring systems" is meant ring systems in which two rings share more than two atoms, see for example *Advanced Organic Chemistry*, by Jerry March, $4^{th}$ Edition, Wiley Interscience, pages 131-133, 1992. Examples of bridged ring systems include bicyclo[2.2.1]heptane, aza-bicyclo[2.2.1]heptane, bicyclo[2.2.2]octane, aza-bicyclo[2.2.2]octane, bicyclo[3.2.1]octane and aza-bicyclo[3.2.1]octane. A particular example of a bridged ring system is the 1-aza-bicyclo[2.2.2]octan-3-yl group.

Where reference is made herein to carbocyclic and heterocyclic groups, the carbocyclic or heterocyclic ring can, unless the context indicates otherwise, be unsubstituted or substituted by one or more substituent groups $R^{10}$ selected from halogen, hydroxy, trifluoromethyl, cyano, nitro, carboxy, amino, mono- or di-$C_{1-4}$ hydrocarbylamino, carbocyclic and heterocyclic groups having from 3 to 12 ring members; a group $R^a$—$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, carbocyclic and heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from hydrogen and $C_{1-4}$ hydrocarbyl; and
$X^1$ is O, S or $NR^c$ and $X^2$ is =O, =S or =$NR^c$.

Where the substituent group $R^{10}$ comprises or includes a carbocyclic or heterocyclic group, the said carbocyclic or heterocyclic group may be unsubstituted or may itself be substituted with one or more further substituent groups $R^{10}$. In one sub-group of compounds of the formula (I), such further substituent groups $R^{10}$ may include carbocyclic or heterocyclic groups, which are typically not themselves further substituted. In another sub-group of compounds of the formula (I), the said further substituents do not include carbocyclic or heterocyclic groups but are otherwise selected from the groups listed above in the definition of $R^{10}$.

The substituents $R^{10}$ may be selected such that they contain no more than 20 non-hydrogen atoms, for example, no more than 15 non-hydrogen atoms, e.g. no more than 12, or 11, or 10, or 9, or 8, or 7, or 6, or 5 non-hydrogen atoms.

Where the carbocyclic and heterocyclic groups have a pair of substituents on adjacent ring atoms, the two substituents may be linked so as to form a cyclic group. Thus, two adjacent groups $R^{10}$, together with the carbon atoms or heteroatoms to which they are attached may form a 5-membered heteroaryl ring or a 5- or 6-membered non-aromatic carbocyclic or heterocyclic ring, wherein the said heteroaryl and heterocyclic groups contain up to 3 heteroatom ring members selected from N, O and S. For example, an adjacent pair of substituents on adjacent carbon atoms of a ring may be linked via one or more heteroatoms and optionally substituted alkylene groups to form a fused oxa-, dioxa-, aza-, diaza- or oxa-aza-cycloalkyl group.

Examples of such linked substituent groups include:

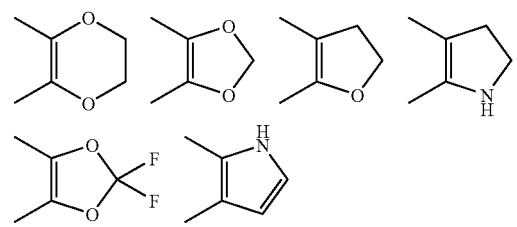

Examples of halogen substituents include fluorine, chlorine, bromine and iodine. Fluorine and chlorine are particularly preferred.

In the definition of the compounds of the formula (I) above and as used hereinafter, the term "hydrocarbyl" is a generic term encompassing aliphatic, alicyclic and aromatic groups having an all-carbon backbone and consisting of carbon and hydrogen atoms, except where otherwise stated.

In certain cases, as defined herein, one or more of the carbon atoms making up the carbon backbone may be replaced by a specified atom or group of atoms.

Examples of hydrocarbyl groups include alkyl, cycloalkyl, cycloalkenyl, carbocyclic aryl, alkenyl, alkynyl, cycloalkylalkyl, cycloalkenylalkyl, and carbocyclic aralkyl, aralkenyl and aralkynyl groups. Such groups can be unsubstituted or, where stated, substituted by one or more substituents as defined herein. The examples and preferences expressed below apply to each of the hydrocarbyl substituent groups or hydrocarbyl-containing substituent groups referred to in the various definitions of substituents for compounds of the formula (I) unless the context indicates otherwise.

Preferred non-aromatic hydrocarbyl groups are saturated groups such as alkyl and cycloalkyl groups.

Generally by way of example, the hydrocarbyl groups can have up to eight carbon atoms, unless the context requires otherwise. Within the sub-set of hydrocarbyl groups having 1 to 8 carbon atoms, particular examples are $C_{1-6}$ hydrocarbyl groups, such as $C_{1-4}$ hydrocarbyl groups (e.g. $C_{1-3}$ hydrocarbyl groups or $C_{1-2}$ hydrocarbyl groups), specific examples being any individual value or combination of values selected from $C_1$, $C_2$, $C_3$, $C_4$, $C_5$, $C_6$, $C_7$ and $C_8$ hydrocarbyl groups.

The term "alkyl" covers both straight chain and branched chain alkyl groups. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers. Within the sub-set of alkyl groups having I to 8 carbon atoms, particular examples are $C_{1-6}$ alkyl groups, such as $C_{1-4}$ alkyl groups (e.g. $C_{1-3}$ alkyl groups or $C_{1-2}$ alkyl groups).

Examples of cycloalkyl groups are those derived from cyclopropane, cyclobutane, cyclopentane, cyclohexane and cycloheptane. Within the sub-set of cycloalkyl groups the cycloalkyl group will have from 3 to 8 carbon atoms, particular examples being $C_{3-4}$ cycloalkyl groups.

Examples of alkenyl groups include, but are not limited to, ethenyl (vinyl), 1-propenyl, 2-propenyl (allyl), isopropenyl, butenyl, buta-1,4-dienyl, pentenyl, and hexenyl. Within the sub-set of alkenyl groups the alkenyl group will have 2 to 8 carbon atoms, particular examples being $C_{2-6}$ alkenyl groups, such as $C_{2-4}$ alkenyl groups.

Examples of cycloalkenyl groups include, but are not limited to, cyclopropenyl, cyclobutenyl, cyclopentenyl, cyclopentadienyl and cyclohexenyl. Within the sub-set of cycloalkenyl groups the cycloalkenyl groups have from 3 to 8 carbon atoms, and particular examples are $C_{3-6}$ cycloalkenyl groups.

Examples of alkynyl groups include, but are not limited to, ethynyl and 2-propynyl (propargyl) groups. Within the sub-set of alkynyl groups having 2 to 8 carbon atoms, particular examples are $C_{2-6}$ alkynyl groups, such as $C_{2-4}$ alkynyl groups.

Examples of carbocyclic aryl groups include substituted and unsubstituted phenyl groups.

Examples of cycloalkylalkyl, cycloalkenylalkyl, carbocyclic aralkyl, aralkenyl and aralkynyl groups include phenethyl, benzyl, styryl, phenylethynyl, cyclohexylmethyl, cyclopentylmethyl, cyclobutylmethyl, cyclopropylmethyl and cyclopentenylmethyl groups.

When present, and where stated, a hydrocarbyl group can be optionally substituted by one or more substituents selected from hydroxy, oxo, alkoxy, carboxy, halogen, cyano, nitro, amino, mono- or di-$C_{1-4}$ hydrocarbylamino, and monocyclic or bicyclic carbocyclic and heterocyclic groups having from 3 to 12 (typically 3 to 10 and more usually 5 to 10) ring members. Preferred substituents include halogen such as fluorine. Thus, for example, the substituted hydrocarbyl group can be a partially fluorinated or perfluorinated group such as difluoromethyl or trifluoromethyl. In one embodiment preferred substituents include monocyclic carbocyclic and heterocyclic groups having 3-7 ring members, more usually 3, 4, 5 or 6 ring members.

Where stated, one or more carbon atoms of a hydrocarbyl group may optionally be replaced by O, S, SO, $SO_2$, $NR^c$, $X^1C(X^2)$, $C(X^2)X^1$ or $X^1C(X^2)X^1$ (or a sub-group thereof) wherein $X^1$ and $X^2$ are as hereinbefore defined, provided that at least one carbon atom of the hydrocarbyl group remains. For example, 1, 2, 3 or 4 carbon atoms of the hydrocarbyl group may be replaced by one of the atoms or groups listed, and the replacing atoms or groups may be the same or different. In general, the number of linear or backbone carbon atoms replaced will correspond to the number of linear or backbone atoms in the group replacing them. Examples of groups in which one or more carbon atom of the hydrocarbyl group have been replaced by a replacement atom or group as defined above include ethers and thioethers (C replaced by O or S), amides, esters, thioamides and thioesters (C—C replaced by $X^1C(X^2)$ or $C(X^2)X^1$), sulphones and sulphoxides (C replaced by SO or $SO_2$), amines (C replaced by $NR^c$). Further examples include ureas, carbonates and carbamates (C—C—C replaced by $X^1C(X^2)X^1$).

Where an amino group has two hydrocarbyl substituents, they may, together with the nitrogen atom to which they are attached, and optionally with another heteroatom such as nitrogen, sulphur, or oxygen, link to form a ring structure of 4 to 7 ring members, more usually 5 to 6 ring members.

The term "aza-cycloalkyl" as used herein refers to a cycloalkyl group in which one of the carbon ring members has been replaced by a nitrogen atom. Thus examples of aza-cycloalkyl groups include piperidine and pyrrolidine. The term "oxa-cycloalkyl" as used herein refers to a cycloalkyl group in which one of the carbon ring members has been replaced by an oxygen atom. Thus examples of oxa-cycloalkyl groups include tetrahydrofuran and tetrahydropyran. In an analogous manner, the terms "diaza-cycloalkyl", "dioxa-cycloalkyl" and "aza-oxa-cycloalkyl" refer respectively to cycloalkyl groups in which two carbon ring members have been replaced by two nitrogen atoms, or by two oxygen atoms, or by one nitrogen atom and one oxygen atom.

The definition "$R^a$—$R^b$" as used herein, either with regard to substituents present on a carbocyclic or heterocyclic moiety, or with regard to other substituents present at other locations on the compounds of the formula (I), includes inter alia compounds wherein $R^a$ is selected from a bond, O, CO, OC(O), SC(O), $NR^cC(O)$, OC(S), SC(S), $NR^cC(S)$, $OC(NR^c)$, $SC(NR^c)$, $NR^cC(NR^c)$, C(O)O, C(O)S, $C(O)NR^c$, C(S)O, C(S)S, $C(S)NR^c$, $C(NR^c)O$, $C(NR^c)S$, $C(NR^c)NR^c$, OC(O)O, SC(O)O, $NR^cC(O)O$, OC(S)O, SC(S)O, $NR^cC(S)$ O, $OC(NR^c)O$, $SC(NR^c)O$, $NR^cC(NR^c)O$, OC(O)S, SC(O)S, $NR^cC(O)S$, OC(S)S, SC(S)S, $NR^cC(S)S$, $OC(NR^c)S$, $SC(N-R^c)S$, $NR^cC(NR^c)S$, $OC(O)NR^c$, $SC(O)NR^c$, $NR^cC(O)NR^c$, $OC(S)NR^c$, $SC(S)NR^c$, $NR^cC(S)NR^c$, $OC(NR^c)NR^c$, $SC(N-R^c)NR^c$, $NR^cC(NR^cNR^c$, S, SO, $SO_2$, $NR^c$, $SO_2NR^c$ and $NR^cSO_2$ wherein $R^c$ is as hereinbefore defined.

The moiety $R^b$ can be hydrogen or it can be a group selected from carbocyclic and heterocyclic groups having from 3 to 12 ring members (typically 3 to 10 and more usually from 5 to 10), and a $C_{1-8}$ hydrocarbyl group optionally substituted as hereinbefore defined. Examples of hydrocarbyl, carbocyclic and heterocyclic groups are as set out above.

When $R^a$ is O and $R^b$ is a $C_{1-8}$ hydrocarbyl group, $R^a$ and $R^b$ together form a hydrocarbyloxy group. Preferred hydrocarbyloxy groups include saturated hydrocarbyloxy such as alkoxy (e.g. $C_{1-6}$ alkoxy, more usually $C_{1-4}$ alkoxy such as ethoxy and methoxy, particularly methoxy), cycloalkoxy (e.g. $C_{3-6}$ cycloalkoxy such as cyclopropyloxy, cyclobutyloxy, cyclopentyloxy and cyclohexyloxy) and cycloalkylalkoxy (e.g. $C_{3-6}$ cycloalkyl-$C_{1-2}$ alkoxy such as cyclopropylmethoxy).

The hydrocarbyloxy groups can be substituted by various substituents as defined herein. For example, the alkoxy groups can be substituted by halogen (e.g. as in difluoromethoxy and trifluoromethoxy), hydroxy (e.g. as in hydroxyethoxy), $C_{1-2}$ alkoxy (e.g. as in methoxyethoxy), hydroxy-$C_{1-2}$ alkyl (as in hydroxyethoxyethyl) or a cyclic group (e.g. a cycloalkyl group or non-aromatic heterocyclic group as hereinbefore defined. Examples of alkoxy groups bearing a non-aromatic heterocyclic group as a substituent are those in which the heterocyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkoxy group is a $C_{1-4}$ alkoxy group, more typically a $C_{1-3}$ alkoxy group such as methoxy, ethoxy or n-propoxy.

Alkoxy groups substituted by a monocyclic group such as pyrrolidine, piperidine, morpholine and piperazine and N-substituted derivatives thereof such as N-benzyl, N—$C_{1-4}$ acyl and N—$C_{1-4}$ alkoxycarbonyl. Particular examples include pyrrolidinoethoxy, piperidinoethoxy and piperazinoethoxy.

When $R^a$ is a bond and $R^b$ is a $C_{1-8}$ hydrocarbyl group, examples of hydrocarbyl groups $R^a$—$R^b$ are as hereinbefore defined. The hydrocarbyl groups may be saturated groups such as cycloalkyl and alkyl and particular examples of such groups include methyl, ethyl and cyclopropyl. The hydrocarbyl (e.g. alkyl) groups can be substituted by various groups and atoms as defined herein. Examples of substituted alkyl groups include alkyl groups substituted by one or more halogen atoms such as fluorine and chlorine (particular examples including bromoethyl, chloroethyl and trifluoromethyl), or hydroxy (e.g. hydroxymethyl and hydroxyethyl), $C_{1-8}$ acyloxy (e.g. acetoxymethyl and benzyloxymethyl), amino and mono- and dialkylamino (e.g. aminoethyl, methylaminoethyl, dimethylaminomethyl, dimethylaminoethyl and tert-butylaminomethyl), alkoxy (e.g. $C_{1-2}$ alkoxy such as methoxy—as in methoxyethyl), and cyclic groups such as cycloalkyl groups, aryl groups, heteroaryl groups and non-aromatic heterocyclic groups as hereinbefore defined).

Particular examples of alkyl groups substituted by a cyclic group are those wherein the cyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkyl group is a $C_{1-4}$ alkyl group, more typically a $C_{1-3}$ alkyl group such as methyl, ethyl or n-propyl. Specific examples of alkyl groups substituted by a cyclic group include pyrrolidinomethyl, pyrrolidinopropyl, morpholinomethyl, morpholinoethyl, morpholinopropyl, piperidinylmethyl, piperazinomethyl and N-substituted forms thereof as defined herein.

Particular examples of alkyl groups substituted by aryl groups and heteroaryl groups include benzyl and pyridylmethyl groups.

When $R^a$ is $SO_2NR^c$, $R^b$ can be, for example, hydrogen or an optionally substituted $C_{1-8}$ hydrocarbyl group, or a carbocyclic or heterocyclic group. Examples of $R^a$—$R^b$ where $R^a$ is $SO_2NR^c$ include aminosulphonyl, $C_{1-4}$ alkylaminosulphonyl and di-$C_{1-4}$ alkylaminosulphonyl groups, and sulphonamides formed from a cyclic amino group such as piperidine, morpholine, pyrrolidine, or an optionally N-substituted piperazine such as N-methyl piperazine.

Examples of groups $R^a$—$R^b$ where $R^a$ is $SO_2$ include alkylsulphonyl, heteroarylsulphonyl and arylsulphonyl groups, particularly monocyclic aryl and heteroaryl sulphonyl groups. Particular examples include methylsulphonyl, phenylsulphonyl and toluenesulphonyl.

When $R^a$ is $NR^c$, $R^b$ can be, for example, hydrogen or an optionally substituted $C_{1-8}$ hydrocarbyl group, or a carbocyclic or heterocyclic group. Examples of $R^a$—$R^b$ where $R^a$ is $NR^c$ include amino, $C_{1-4}$ alkylamino (e.g. methylamino, ethylamino, propylamino, isopropylamino, tert-butylamino), di-$C_{1-4}$ alkylamino (e.g. dimethylamino and diethylamino) and cycloalkylamino (e.g. cyclopropylamino, cyclopentylamino and cyclohexylamino).

Specific Embodiments of and Preferences for X, Y, A, $R^g$, $R^1$ to $R^4$ and $R^{10}$

X

In formula (I), X is a group $R^1$-A-$NR^4$— or a 5- or 6-membered carbocyclic or heterocyclic ring.

In one embodiment, X is a group $R^1$-A-$NR^4$—.

In another embodiment, X is a 5- or 6-membered carbocyclic or heterocyclic ring.

A

In formula (I), A is a bond, C=O, $NR^g$(C=O) or O(C=O). It will be appreciated that the moiety $R^1$-A-$NR^4$ linked to the 4-position of the pyrazole ring can therefore take the form of an amine $R^1$—$NR^4$, an amide $R^1$—C(=O)$NR^4$, a urea $R^1$—$NR^g$C(=O)$NR^4$ or a carbamate $R^1$—OC(=O)$NR^4$.

In one preferred group of compounds of the invention, A is C=O and hence the group $R^1$-A-$NR^4$ takes the form of an amide $R^1$—C(=O)$NR^4$. In another group of compounds of the invention, A is a bond and hence the group $R^1$-A-$NR^4$ takes the form of an amine $R^1$—$NR^4$.

$R^4$ $R^4$ is hydrogen or a $C_{1-4}$ hydrocarbyl group optionally substituted by halogen (e.g. fluorine), hydroxyl or $C_{1-4}$ alkoxy (e.g. methoxy).

The number of optional subistutents on the hydrocarbyl group typically will vary according to the nature of the substituent. For example, where the substituent is halogen, there may be from one to three halogen atoms present, preferably two or three. Where the substituent is hydroxyl or an alkoxy group, typically there will be only a single such substituent present $R^4$ is preferably hydrogen or $C_{1-3}$ alkyl, more preferably hydrogen or methyl and most preferably is hydrogen.

$R^g$ $R^g$ is hydrogen or a $C_{1-4}$ hydrocarbyl group optionally substituted by hydroxyl or $C_{1-4}$ alkoxy (e.g. methoxy).

When $R^g$ is $C_{1-4}$ hydrocarbyl substituted by hydroxyl or $C_{1-4}$ alkoxy, typically there is only one such substituent present.

Preferably $R^g$ is hydrogen or $C_{1-3}$ alkyl, more preferably hydrogen or methyl and most preferably $R^g$ is hydrogen.

$R^2$ $R^2$ is hydrogen, halogen, $C_{1-4}$ alkoxy, or a $C_{1-4}$ hydrocarbyl group optionally substituted by halogen, hydroxyl or $C_{1-4}$ alkoxy.

When $R^2$ is halogen, preferably it is selected from chlorine and fluorine and more preferably it is fluorine.

When $R^2$ is $C_{1-4}$ alkoxy, it can be, for example, $C_{1-3}$ alkoxy, more preferably $C_{1-2}$ alkoxy and most preferably methoxy.

When $R^2$ is an optionally substituted $C_{1-4}$ hydrocarbyl group, the hydrocarbyl group is preferably a $C_{1-3}$ hydrocarbyl group, more preferably a $C_{1-2}$ hydrocarbyl group, for example an optionally substituted methyl group. The optional substituents for the optionally substituted hydrocarbyl group are preferably selected from fluorine, hydroxyl and methoxy.

The number of optional substituents on the hydrocarbyl group typically will vary according to the nature of the substituent. For example, where the substituent is halogen, there may be from one t6 three halogen atoms present, preferably two or three. Where the substituent is hydroxyl or methoxy, typically there will be only a single such substituent present.

The hydrocarbyl groups constituting $R^2$ are preferably saturated hydrocarbyl groups. Examples of saturated hydrocarbyl groups include methyl, ethyl, n-propyl, i-propyl and cyclopropyl.

In one embodiment, $R^2$ is hydrogen, halogen, $C_{1-4}$ alkoxy, or a $C_{1-4}$ hydrocarbyl group optionally substituted by halogen, hydroxyl or $C_{1-4}$ alkoxy.

In another embodiment, $R^2$ is hydrogen, fluorine, chlorine, methoxy, or a $C_{1-3}$ hydrocarbyl group optionally substituted by fluorine, hydroxyl or methoxy.

In a preferred embodiment, $R^2$ is hydrogen or methyl, most preferably hydrogen.

$R^1$ $R^1$ is hydrogen, a carbocyclic or heterocyclic group having from 3 to 12 ring members, or a $C_{1-8}$ hydrocarbyl group optionally substituted by one or more substituents selected from halogen (e.g. fluorine), hydroxy, $C_{1-4}$ hydrocarbyloxy, amino, mono- or di-$C_{1-4}$ hydrocarbylamino, and carbocyclic or heterocyclic groups having from 3 to 12 ring members, and wherein 1 or 2 of the carbon atoms of the hydrocarbyl group may optionally be replaced by an atom or group selected from O, S, NH, SO, $SO_2$. Examples of carbocyclic or heterocyclic groups and hydrocarbyl groups and general preferences for such groups are as set out above in the General Preferences and Definitions section, and as set out below.

In one embodiment, $R^1$ is an aryl or heteroaryl group.

When $R^1$ is a heteroaryl group, particular heteroaryl groups include monocyclic heteroaryl groups containing up to three heteroatom ring members selected from 0, S and N, and bicyclic heteroaryl groups containing up to 2 heteroatom ring members selected from O, S and N and wherein both rings are aromatic.

Examples of such groups include furanyl (e.g. 2-furanyl or 3-furanyl), indolyl (e.g. 3-indolyl, 6-indolyl), 2,3-dihydro-benzo[1,4]dioxinyl (e.g. 2,3-dihydro-benzo[1,4]dioxin-5-yl), pyrazolyl (e.g. pyrazole-5-yl), pyrazolo[1,5-a]pyridinyl (e.g. pyrazolo[1,5-a]pyridine-3-yl), oxazolyl (e.g.), isoxazolyl (e.g. isoxazol-4-yl), pyridyl (e.g. 2-pyridyl, 3-pyridyl, 4-pyridyl), quinolinyl (e.g. 2-quinolinyl), pyrrolyl (e.g. 3-pyrrolyl), imidazolyl and thienyl (e.g. 2-thienyl, 3-thienyl).

One sub-group of heteroaryl groups $R^1$ consists of furanyl (e.g. 2-furanyl or 3-furanyl), indolyl, oxazolyl, isoxazolyl, pyridyl, quinolinyl, pyrrolyl, imidazolyl and thienyl.

A preferred sub-set of $R^1$ heteroaryl groups includes 2-furanyl, 3-furanyl, pyrrolyl, imidazolyl and thienyl.

Preferred aryl groups $R^1$ are phenyl groups.

The group $R^1$ can be an unsubstituted or substituted carbocylic or heterocyclic group in which one or more substituents can be selected from the group $R^{10}$ as hereinbefore defined. In one embodiment, the substituents on $R^1$ may be selected from the group $R^{10a}$ consisting of halogen, hydroxy, trifluoromethyl, cyano, nitro, carboxy, a group $R^a$—$R^b$ wherein $R^a$ is a bond, O, CO, $X^3C(X^4)$, $C(X^4)X^3$, $X^3C(X^4)$ $X^3$, S, SO, or $SO_2$, and $R^b$ is selected from hydrogen and a $C_{1-8}$ hydrocarbyl group optionally substituted by one or more substituents selected from hydroxy, oxo, halogen, cyano, nitro, carboxy and monocyclic non-aromatic carbocyclic or heterocyclic groups having from 3 to 6 ring members; wherein one or more carbon atoms of the $C_{1-8}$ hydrocarbyl group may optionally be replaced by O, S, SO, $SO_2$, $X^3C(X^4)$, $C(X^4)X^3$ or $X^3C(X^4)X^3$; $X^3$ is O or S; and $X^4$ is =O or =S.

Where the carbocyclic and heterocyclic groups have a pair of substituents on adjacent ring atoms, the two substituents may be linked so as to form a cyclic group. Thus, two adjacent groups $R^{10}$, together with the carbon atoms or heteroatoms to which they are attached may form a 5-membered heteroaryl ring or a 5- or 6-membered non-aromatic carbocyclic or heterocyclic ring, wherein the said heteroaryl and heterocyclic groups contain up to 3 heteroatom ring members selected from N, O and S. In particular the two adjacent groups $R^{10}$, together with the carbon atoms or heteroatoms to which they are attached, may form a 6-membered non-aromatic heterocyclic ring, containing up to 3, in particular 2, heteroatom ring members selected from N, O and S. More particularly the two adjacent groups $R^{10}$ may form a 6-membered non-aromatic heterocyclic ring, containing 2 heteroatom ring members selected from N, or O, such as dioxan e.g. [1,4 dioxan]. In one embodiment $R^1$ is a carbocyclic group e.g. phenyl having a pair of substituents on adjacent ring atoms linked so as to form a cyclic group e.g. to form 2,3-dihydro-benzo[1,4]dioxine.

More particularly, the substituents on $R^1$ may be selected from halogen, hydroxy, trifluoromethyl, a group $R^a$—$R^b$ wherein $R^a$ is a bond or O, and $R^b$ is selected from hydrogen and a $C_{1-4}$ hydrocarbyl group optionally substituted by one or more substituents selected from hydroxyl, halogen (preferably fluorine) and 5 and 6 membered saturated carbocyclic and heterocyclic groups (for example groups containing up to two heteroatoms selected from O, S and N, such as unsubstituted piperidine, pyrrolidino, morpholino, piperazino and N-methyl piperazino).

The group $R^1$ may be substituted by more than one substituent. Thus, for example, there may be 1 or 2 or 3 or 4 substituents. In one embodiment, where $R^1$ is a six membered ring (e.g. a carbocyclic ring such as a phenyl ring), there may be one, two or three substituents and these may be located at the 2-, 3-, 4- or 6-positions around the ring. By way of example, a phenyl group $R^1$ may be 2-monosubstituted, 3-monosubstituted, 2,6-disubstituted, 2,3-disubstituted, 2,4-disubstituted 2,5-disubstituted, 2,3,6-trisubstituted or 2,4,6-trisubstituted. More particularly, a phenyl group $R^1$ may be monosubstituted at the 2-position or disubstituted at positions 2- and 6-with substituents selected from fluorine, chlorine and $R^a$—$R^b$, where $R^a$ is O and $R^b$ is $C_{1-4}$ alkyl (e.g. methyl or ethyl). In one embodiment, fluorine is a preferred substituent. In another embodiment, preferred substituents are selected from fluorine, chlorine and methoxy.

Particular examples of non-aromatic groups $R^1$ include unsubstituted or substituted (by one or more groups $R^{10}$) monocyclic cycloalkyl groups. Examples of such cycloalkyl groups include cyclopropyl, cyclobutyl, cyclopentyl, cyclohexyl and cycloheptyl; more typically cyclopropyl, cyclobutyl, cyclopentyl and cyclohexyl, particularly cyclohexyl.

Further examples of non-aromatic groups $R^1$ include unsubstituted or substituted (by one or more groups $R^{10}$) heterocyclic groups having from 3 to 12 ring members, typically 4 to 12 ring members, and more usually from 5 to 10 ring members. Such groups can be monocyclic or bicyclic, for example, and typically have from 1 to 5 heteroatom ring members (more usually 1,2,3 or 4 heteroatom ring members) typically selected from nitrogen, oxygen and sulphur.

When sulphur is present, it may, where the nature of the adjacent atoms and groups permits, exist as —S—, —S(O)— or —S(O)$_2$—.

The heterocylic groups can contain, for example, cyclic ether moieties (e.g as in tetrahydrofuran and dioxane), cyclic thioether moieties (e.g. as in tetrahydrothiophene and dithiane), cyclic amine moieties (e.g. as in pyrrolidine), cyclic amides (e.g. as in pyrrolidone), cyclic esters (e.g. as in butyrolactone), cyclic thioamides and thioesters, cyclic sulphones (e.g. as in sulpholane and sulpholene), cyclic sulphoxides, cyclic sulphonamides and combinations thereof (e.g. morpholine and thiomorpholine and its S-oxide and S,S-dioxide).

In one sub-set of heterocyclic groups $R^1$, the heterocyclic groups contain cyclic ether moieties (e.g as in tetrahydrofuran and dioxane), cyclic thioether moieties (e.g. as in tetrahydrothiophene and dithiane), cyclic amine moieties (e.g. as in pyrrolidine), cyclic sulphones (e.g. as in sulpholane and sulpholene), cyclic sulphoxides, cyclic sulphonamides and combinations thereof (e.g. thiomorpholine).

Examples of monocyclic non-aromatic heterocyclic groups $R^1$ include 5-, 6- and 7-membered monocyclic heterocyclic groups such as morpholine, piperidine (e.g. 1-piperidinyl, 2-piperidinyl 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include N-alkyl piperidines such as N-methyl piperidine.

One sub-group of non-aromatic heterocyclic groups $R^1$ includes unsubstituted or substituted (by one or more groups $R^{10}$) 5-, 6- and 7-membered monocyclic heterocyclic groups such as morpholine, piperidine (e.g. 1-piperidinyl, 2-piperidinyl 3-piperidinyl and 4-piperidinyl), pyrrolidine (e.g. 1-pyrrolidinyl, 2-pyrrolidinyl and 3-pyrrolidinyl), pyrrolidone, piperazine, and N-alkyl piperazines such as N-methyl piperazine, wherein a particular sub-set consists of pyrrolidine, piperidine, morpholine, thiomorpholine and N-methyl piperazine.

In general, preferred non-aromatic heterocyclic groups include pyrrolidine, piperidine, morpholine, thiomorpholine, thiomorpholine S,S-dioxide, piperazine, N-alkyl piperazines, and N-alkyl piperidines.

Another particular sub-set of heterocyclic groups consists of pyrrolidine, piperidine, morpholine and N-alkyl piperazines, and optionally, N-methyl piperazine and thiomorpholine.

When $R^1$ is a $C_{1-8}$ hydrocarbyl group substituted by a carbocyclic or heterocyclic group, the carbocyclic and heterocyclic groups can be aromatic or non-aromatic and can be selected from the examples of such groups set out hereinabove. The substituted hydrocarbyl group is typically a saturated $C_{1-4}$ hydrocarbyl group such as an alkyl group, preferably a $CH_2$ or $CH_2CH_2$ group. Where the substituted hydrocarbyl group is a $C_{2-4}$ hydrocarbyl group, one of the carbon atoms and its associated hydrogen atoms may be replaced by a sulphonyl group, for example as in the moiety $SO_2CH_2$.

When the carbocyclic or heterocyclic group attached to the a $C_{1-8}$ hydrocarbyl group is aromatic, examples of such groups include monocyclic aryl groups and monocyclic heteroaryl groups containing up to four heteroatom ring members selected from O, S and N, and bicyclic heteroaryl groups containing up to 2 heteroatom ring members selected from O, S and N and wherein both rings are aromatic.

Examples of such groups are set out in the "General Preferences and Definitions" section above.

Particular examples of such groups include furanyl (e.g. 2-furanyl or 3-furanyl), indolyl, oxazolyl, isoxazolyl, pyridyl, quinolinyl, pyrrolyl, imidazolyl and thienyl. Particular examples of aryl and heteroaryl groups as substituents for a $C_{1-8}$ hydrocarbyl group include phenyl, imidazolyl, tetrazolyl, triazolyl, indolyl, 2-furanyl, 3-furanyl, pyrrolyl and thienyl. Such groups may be substituted by one or more substituents $R^{10}$ or $R^{10a}$ as defined herein.

When $R^1$ is a $C_{1-8}$ hydrocarbyl group substituted by a non-aromatic carbocyclic or heterocyclic group, the non-aromatic or heterocyclic group may be a group selected from the lists of such groups set out hereinabove. For example, the non-aromatic group can be a monocyclic group having from 4 to 7 ring members, e.g. 5 to 7 ring members, and typically containing from 0 to 3, more typically 0, 1 or 2, heteroatom ring members selected from O, S and N. When the cyclic group is a carbocyclic group, it may additionally be selected from monocyclic groups having 3 ring members. Particular examples include monocyclic cycloalkyl groups such as cyclopropyl, cyclobutyl, cyclopentyl, cyclohexyl and cycloheptyl, and 5-, 6- and 7-membered monocyclic heterocyclic groups such as morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, piperazine, and N-alkyl piperazines such as N-methyl piperazine. In general, preferred non-aromatic heterocyclic groups include pyrrolidine, piperidine, morpholine, thiomorpholine and N-methyl piperazine.

When $R^1$ is an optionally substituted $C_{1-8}$ hydrocarbyl group, the hydrocarbyl group may be as hereinbefore defined, and is preferably up to four carbon atoms in length, more usually up to three carbon atoms in length for example one or two carbon atoms in length.

In one embodiment, the hydrocarbyl group is saturated and may be acyclic or cyclic, for example acyclic. An acyclic saturated hydrocarbyl group (i.e. an alkyl group) may be a straight chain or branched alkyl group.

Examples of straight chain alkyl groups $R^1$ include methyl, ethyl, propyl and butyl.

Examples of branched chain alkyl groups $R^1$ include isopropyl, isobutyl, tert-butyl and 2,2-dimethylpropyl.

In one embodiment, the hydrocarbyl group is a linear saturated group having from 1-6 carbon atoms, more usually 1-4 carbon atoms, for example 1-3 carbon atoms, e.g. 1, 2 or 3 carbon atoms. When the hydrocarbyl group is substituted, particular examples of such groups are substituted (e.g. by a carbocyclic or heterocyclic group) methyl and ethyl groups.

A $C_{1-8}$ hydrocarbyl group $R^1$ can be optionally substituted by one or more substituents selected from halogen (e.g. fluorine), hydroxy, $C_{1-4}$ hydrocarbyloxy, amino, mono- or di-$C_{1-4}$ hydrocarbylamino, and carbocyclic or heterocyclic groups having from 3 to 12 ring members, and wherein 1 or 2 of the carbon atoms of the hydrocarbyl group may optionally be replaced by an atom or group selected from O, S, NH, SO, $SO_2$. Particular substituents for the hydrocarbyl group include hydroxy, chlorine, fluorine (e.g. as in trifluoromethyl), methoxy, ethoxy, amino, methylamino and dimethylamino, preferred substituents being hydroxy and fluorine.

When A is C=O, particular groups $R^1$—CO are the groups set out in Table 1 below.

In Table 1, the point of attachment of the group to the nitrogen atom of the pyrazole-4-amino group is represented by the terminal single bond extending from the carbonyl group. Thus, by way of illustration, group B in the table is the trifluoroacetyl group, group D in the table is the phenylacetyl group and group I in the table is the 3-(4-chlorophenyl)propionyl group.

TABLE 1
| Examples of the group R¹—CO |
|---|
| 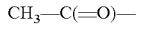<br>A |
| 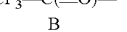<br>B |
| 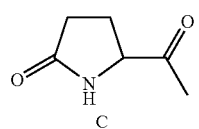<br>C |
| 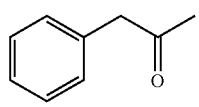<br>D |
| 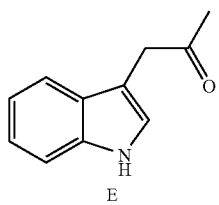<br>E |
| 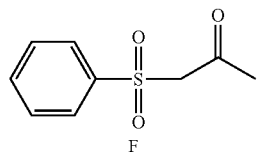<br>F |
| 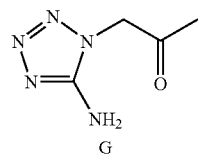<br>G |
| <br>H |
| 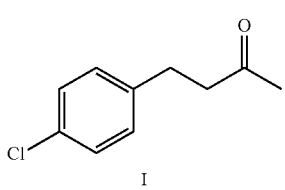<br>I |
| 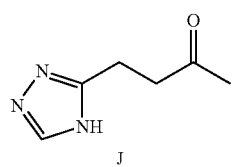<br>J |
TABLE 1-continued
| Examples of the group R¹—CO |
|---|
| <br>K |
| 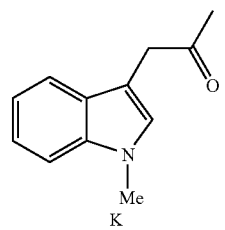<br>L |
| 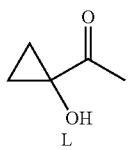<br>M |
| 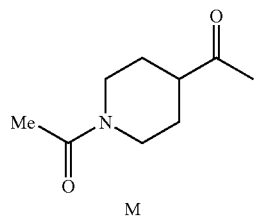<br>N |
| 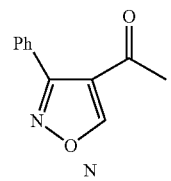<br>O |
| 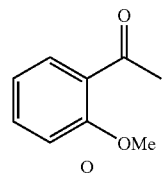<br>P |
| 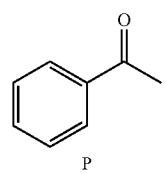<br>Q |
| 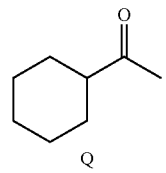<br>R |

TABLE 1-continued
Examples of the group R¹—CO
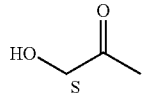
S
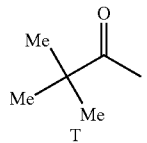
T
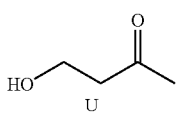
U
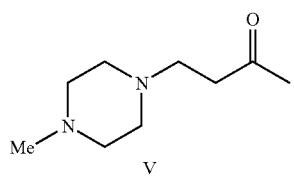
V
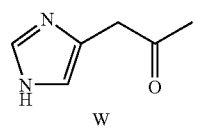
W
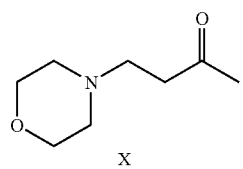
X
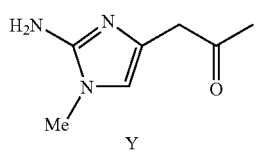
Y
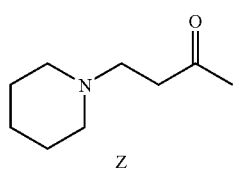
Z
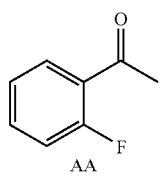
AA
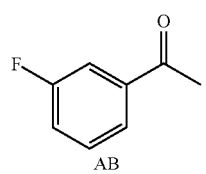
AB
TABLE 1-continued
Examples of the group R¹—CO
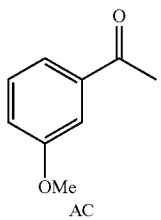
AC
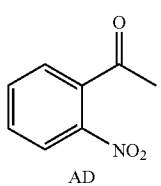
AD
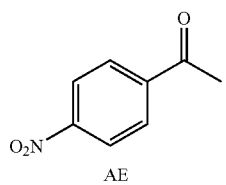
AE
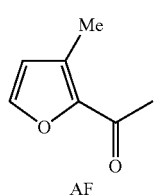
AF
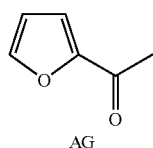
AG
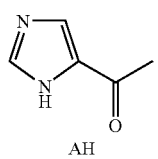
AH
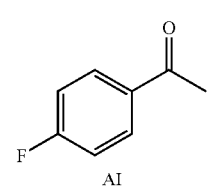
AI
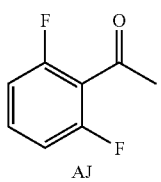
AJ TABLE 1-continued
Examples of the group R¹—CO
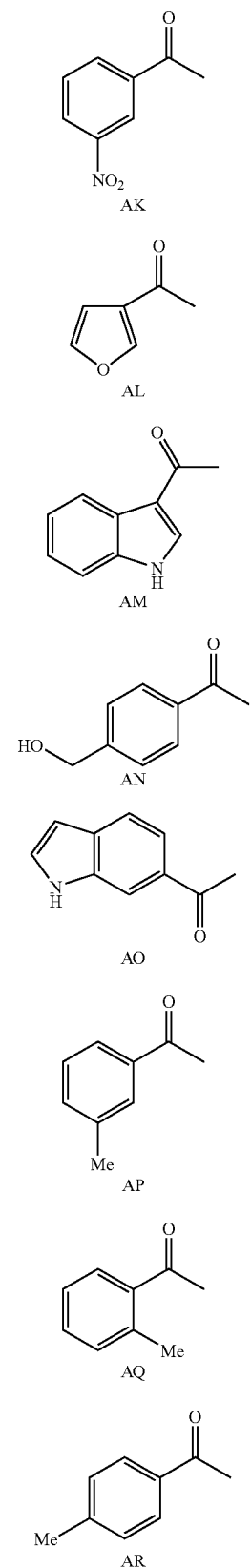
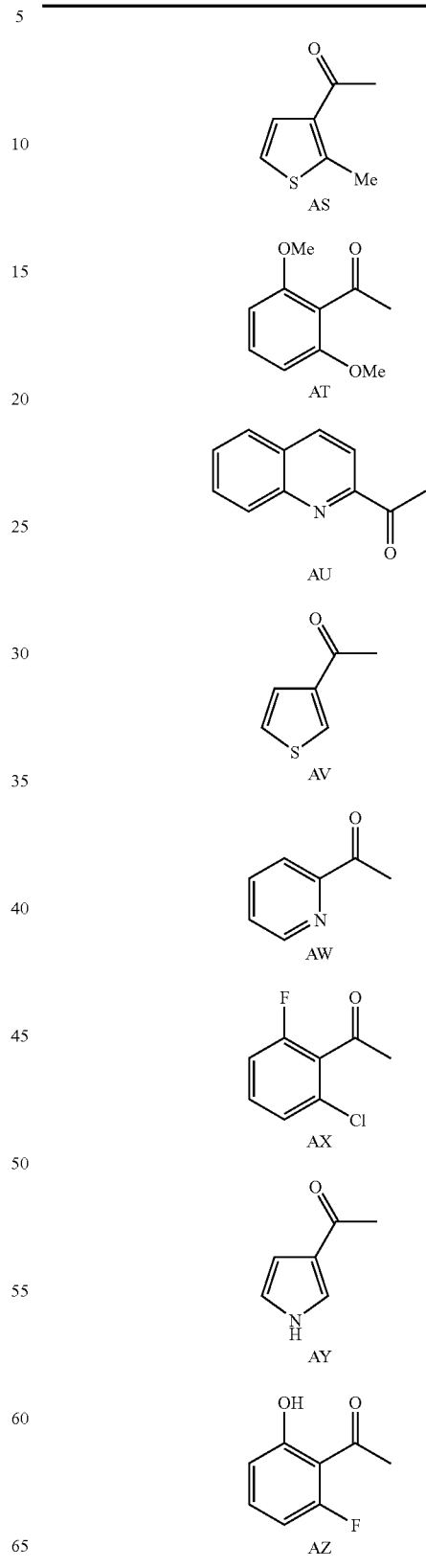

TABLE 1-continued
Examples of the group R¹—CO
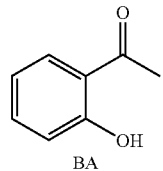
BA
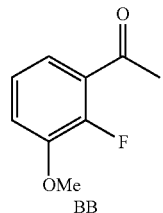
BB
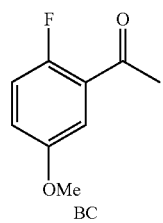
BC
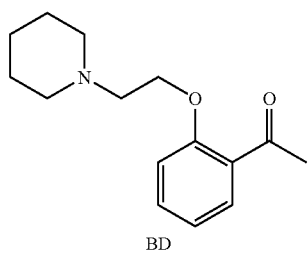
BD
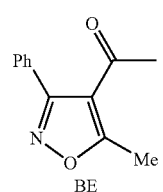
BE
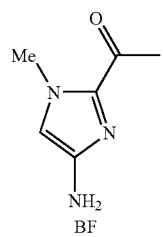
BF
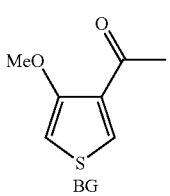
BG
TABLE 1-continued
Examples of the group R¹—CO
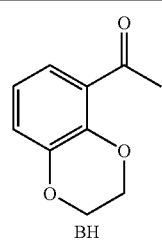
BH
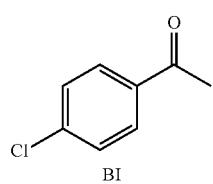
BI
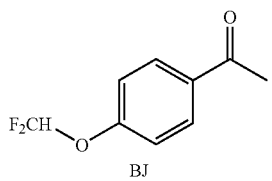
BJ
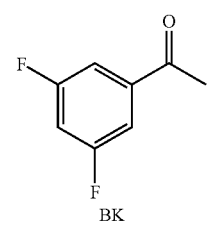
BK
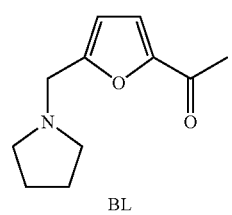
BL
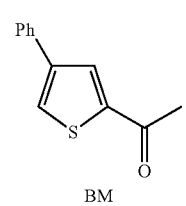
BM
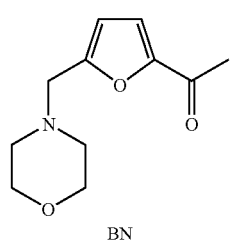
BN

TABLE 1-continued
Examples of the group R¹—CO
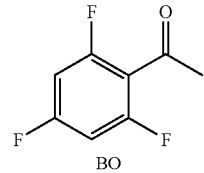
BO
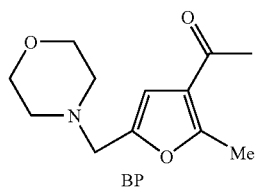
BP
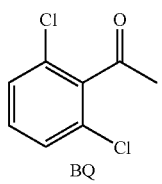
BQ
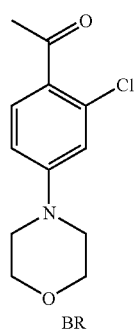
BR
BS
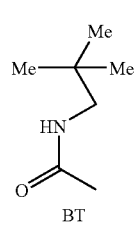
BT
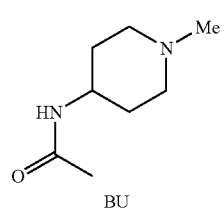
BU
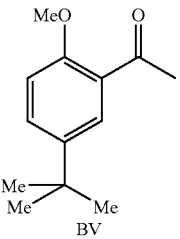
BV
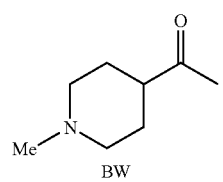
BW
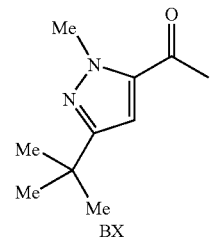
BX
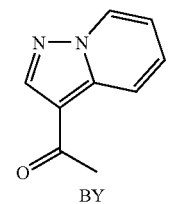
BY
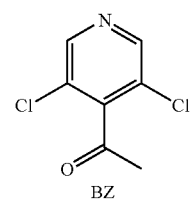
BZ
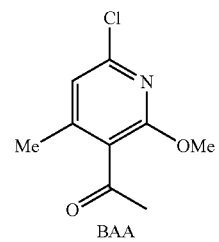
BAA
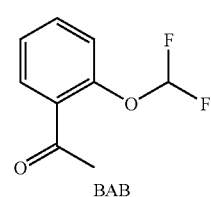
BAB TABLE 1-continued Examples of the group R¹—CO

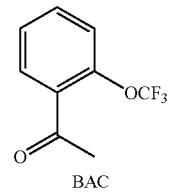
BAC

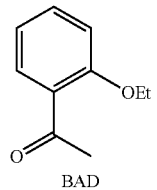
BAD

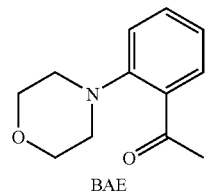
BAE

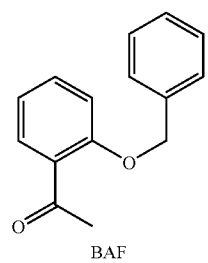
BAF

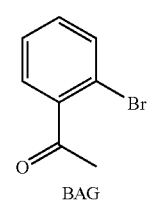
BAG

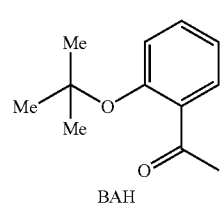
BAH

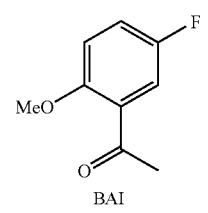
BAI

TABLE 1-continued

Examples of the group R¹—CO

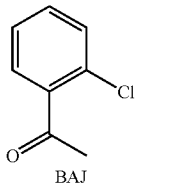
BAJ

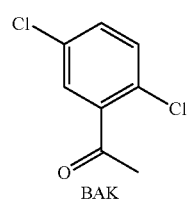
BAK

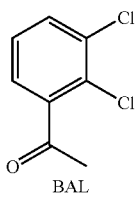
BAL

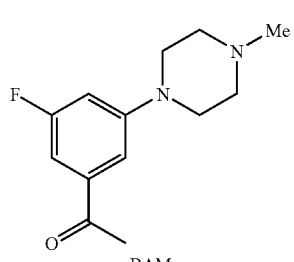
BAM

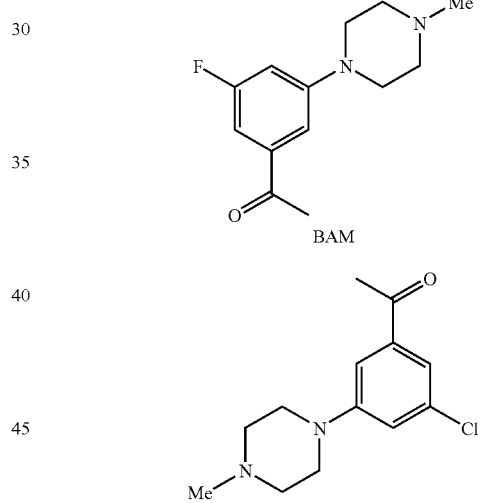
BAN

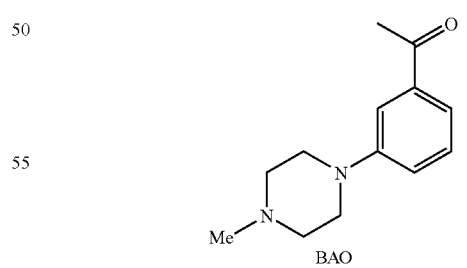
BAO

One sub-group of groups R¹—CO consists of groups A to BF in Table 1 above.

Another sub-group of groups R¹—CO consists of groups A to BS in Table 1 above.

One set of preferred groups R¹—CO consists of the groups J, AB, AH, AJ, AL, AS, AX, AY, AZ, BA, BB, BD, BH, BL, BQ, BS and BAI Another set of preferred groups R¹—CO consists of the groups J, AB, AH, AJ, AL, AS, AX, AY, AZ, BA, BB, BD, BH, BL, BQ and BS.

More preferred groups R¹—CO— are AJ, AX, BQ, BS and BAI.

One particularly preferred sub-set of groups R¹—CO— consists of AJ, BQ and BS.

Another particularly preferred sub-set of groups R¹—CO— consists of AJ and BQ.

When X is R¹-A-NR⁴ and A is C=O, and R¹ is a phenyl ring bearing a substituent at the 4-position, the substituent at the 4-position is preferably other than a phenyl group having a group $SO_2NH_2$ or $SO_2Me$ at the ortho-position.

In one general embodiment, R¹ may be other than a substituted or unsubstituted tetrahydroquinoline, chroman, chromene, thiochroman, thiochromene, dihydro-naphthalene or tetrahydronaphthalene group. More particularly, R¹ may be other than a substituted or unsubstituted tetrahydroquinoline, chroman, chromene, thiochroman, thiochromene, dihydro-naphthalene or tetrahydronaphthalene group linked by its aromatic ring to the moiety A-NR⁴—.

In another general embodiment, when R¹ is a substituted or unsubstituted phenyl group, the moiety Y-R³ may be other than hydrogen, unsubstituted $C_{1-10}$ alkyl, unsubstituted $C_{5-10}$ cycloalkyl, unsubstituted phenyl, unsubstituted $C_{1-10}$ alkylphenyl or unsubstituted phenyl-$C_{1-10}$ alkyl.

In the context of the group R¹-A-NR⁴—, when R¹ is an optionally substituted hydrocarbyl group and the hydrocarbyl group comprises or contains a substituted or unsubstituted alkene group, it is preferred that the carbon-carbon double bond of the alkene group is not directly bonded to the group A.

Also in the context of the group R¹-A-NR⁴—, when R¹ is an optionally substituted hydrocarbyl group, the hydrocarbyl group may be other than an alkene group.

In another general embodiment, when Y is a bond, R³ is hydrogen, A is CO and R¹ is a substituted phenyl group, each substituent on the phenyl group may be other than a group $CH^2$—$P(O)R^xR^y$ where $R^x$ and $R^y$ are each selected from alkoxy and phenyl groups.

Y

In the compounds of the formula (I), Y is a bond or an alkylene chain of 1, 2 or 3 carbon atoms in length.

The term "alkylene" has its usual meaning and refers to a divalent saturated acyclic hydrocarbon chain. The hydrocarbon chain may be branched or unbranched. Where an alkylene chain is branched, it may have one or more methyl group side chains. Examples of alkylene groups include —$CH_2$—, —$CH_2$—$CH_2$—, —$CH_2$—$CH_2$—$CH_2$—, $CH(CH_3)$—, —$C(CH_3)_2$—, —$CH_2$—$CH(CH_3)$—, —$CH_2$—$C(CH_3)_2$— and —$CH(CH_3)$—$CH(CH_3)$—.

In one embodiment, Y is a bond.

In another embodiment, Y is an alkylene chain.

When Y is an alkylene chain, preferably it is unbranched and more particularly contains 1 or 2 carbon atoms, preferably 1 carbon atom. Thus preferred groups Y are —$CH_2$— and —$CH_2$—$CH_2$—, a most preferred group being ($CH_2$)—.

Where Y is a branched chain, preferably it has no more than two methyl side chains. For example, it may have a single methyl side chain. In one embodiment, Y is a group —CH(Me)—.

In one sub-group of compounds, Y is a bond, $CH_2$, $CH_2CH_2$ or $CH_2CH(CH_3)$.

R³

The group R³ is selected from hydrogen and carbocyclic and heterocyclic groups having from 3 to 12 ring members.

In one sub-group of compounds, Y is a bond and R³ is hydrogen.

In another sub-group of compounds Y is an alkylene chain as hereinbefore defined and R³ is hydrogen.

In a another sub-group of compounds, Y is a bond or an alkylene chain (e.g. a group —($CH_2$)—) and R³ is a carbocyclic or heterocyclic group.

In a further sub-group of compounds, Y is a bond and R³ is a carbocyclic or heterocyclic group.

In a still further sub-group of compounds, Y is an alkylene chain (e.g. a group —($CH_2$)—) and R³ is a carbocyclic or heterocyclic group.

The carbocyclic and heterocyclic groups R³ can be aryl, heteroaryl, non-aromatic carbocyclic or non-aromatic heterocyclic and examples of such groups are as set out in detail above in the General Preferences and Definitions section, and as set out below.

Preferred aryl groups R³ are unsubstituted and substituted phenyl groups.

Examples of heteroaryl groups R³ include monocyclic heteroaryl groups containing up to three (and more preferably up to two) heteroatom ring members selected from O, S and N. Preferred heteroaryl groups include five membered rings containing one or two heteroatom ring members and six membered rings containing a single heteroatom ring member, most preferably nitrogen. Particular examples of heteroaryl groups include unsubstituted or substituted pyridyl, imidazole, pyrazole, thiazole, isothiazole, isoxazole, oxazole, furyl and thiophene groups.

Particular heteroaryl groups are unsubstituted and substituted pyridyl groups, e.g. 2-pyridyl, 3-pyridyl and 4-pyridyl groups, especially 3- and 4-pyridyl groups. When the pyridyl groups are substituted, they can bear one or more substituents, typically no more than two, and more usually one substituent selected, for example, from $C_{1-4}$ alkyl (e.g. methyl), halogen (e.g. fluorine or chlorine, preferably chlorine), and $C_{1-4}$ alkoxy (e.g. methoxy). Substituents on the pyridyl group may further be selected from amino, mono-$C_{1-4}$ alkylamino and di-$C_{1-4}$ alkylamino, particularly amino.

In one embodiment, when R³ is an aryl (e.g. phenyl) or heteroaryl group, the substituents on the carbocyclic or heterocyclic group may be selected from the group $R^{10a}$ consisting of halogen, hydroxy, trifluoromethyl, cyano, monocyclic carbocyclic and heterocyclic groups having from 3 to 7 (typically 5 or 6) ring members, and a group $R^a$—$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, a carbocyclic or heterocyclic group with 3-7 ring members and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, a carbocyclic or heterocyclic group with 3-7 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$; and $R^c$, $X^1$ and $X^2$ are as hereinbefore defined.

Examples of non-aromatic groups R³ include optionally substituted (by $R^{10}$ or $R^{10a}$) cycloalkyl, oxa-cycloalkyl, aza-cycloalkyl, diaza-cycloalkyl, dioxa-cycloalkyl and oxa-oxa-cycloalkyl groups. Further examples include $C_{7-10}$ aza-bicycloalkyl groups such as 1-aza-bicyclo[2.2.2]octan-3-yl.

Particular examples of such groups include unsubstituted or substituted cyclopropyl, cyclobutyl, cyclopentyl, cyclohexyl, tetrahydropyran, morpholine, tetrahydrofuran, piperidine and pyrrolidine groups.

One sub-set of non-aromatic groups $R^3$ consists of cyclopropyl, cyclobutyl, cyclopentyl, cyclohexyl, tetrahydropyran, tetrahydrofuran, piperidine and pyrrolidine groups.

Preferred non-aromatic groups $R^3$ include unsubstituted or substituted cyclopentyl, cyclohexyl, tetrahydropyran, tetrahydrofuran, piperidine and pyrrolidine groups, The non-aromatic groups may be unsubstituted or substituted with one or more groups $R^{10}$ or $R^{10a}$ as hereinbefore defined.

Particular substituents for $R^3$ (e.g. (i) when $R^3$ is an aryl or heteroaryl group or (ii) when $R^3$ is a non-aromatic group) are selected from the group $R^{10a}$ consisting of halogen; hydroxy; monocyclic carbocyclic and heterocyclic groups having from 3 to 6 ring members and containing up to 2 heteroatom ring members selected from O, N and S; and a group $R^a$—$R^b$ wherein $R^a$ is a bond, O, CO, $CO_2$, $SO_2$, NH, $SO_2NH$ or $NHSO_2$; and $R^b$ is selected from hydrogen, a carbocyclic or heterocyclic group with 3-6 ring members and containing up to 2 heteroatom ring members selected from O, N and S; and a $C_{1-6}$ hydrocarbyl group optionally substituted by one or more substituents selected from hydroxy, oxo, halogen, carboxy, amino, mono- or di-$C_{1-4}$ hydrocarbylamino, a carbocyclic or heterocyclic group with 3-6 ring members and containing up to 2 heteroatom ring members selected from O, N and S; and wherein one or two carbon atoms of the $C_{1-6}$ hydrocarbyl group may optionally be replaced by O, S, SO, $SO_2$ or NH.

In one embodiment, preferred $R^{10a}$ substituent groups on $R^3$ (e.g. (i) when $R^3$ is an aryl or heteroaryl group or (ii) when $R^3$ is a non-aromatic group) include halogen, a group $R^a$—$R^b$ wherein $R^a$ is a bond, O, CO, $C(X^2)X^1$, and $R^b$ is selected from hydrogen, heterocyclic groups having 3-7 ring members and a $C_{1-4}$ hydrocarbyl group optionally substituted by one or more substituents selected from hydroxy, carboxy, amino, mono- or di-$C_{1-4}$ hydrocarbylamino, and heterocyclic groups having 3-7 ring members.

Particularly preferred substituent groups $R^{10a}$ on $R^3$ (e.g. (i) when $R^3$ is an aryl or heteroaryl group or (ii) when $R^3$ is a non-aromatic group) include halogen, especially fluorine, $C_{1-3}$ alkoxy such as methoxy, and $C_{1-3}$ hydrocarbyl optionally substituted by fluorine, hydroxy (e.g. hydroxymethyl), $C_{1-2}$ alkoxy or a 5- or 6-membered saturated heterocyclic ring such as piperidino, morpholino, piperazino and N-methylpiperazino.

In another embodiment, the substituents for $R^3$ (whether aromatic or non-aromatic) are selected from:

halogen (e.g. fluorine and chlorine)

$C_{1-4}$ alkoxy (e.g. methoxy and ethoxy) optionally substituted by one or substituents selected from halogen, hydroxy, $C_{1-2}$ alkoxy and five and six membered saturated heterocyclic rings containing 1 or 2 heteroatoms selected from O, N and S, the heterocyclic rings being optionally further substituted by one or more $C_{1-4}$ groups (e.g. methyl) and wherein the S, when present, may be present as S, SO or $SO_2$;

$C_{1-4}$ alkyl optionally substituted by one or substituents selected from halogen, hydroxy, $C_{1-4}$ alkoxy, amino, $C_{1-4}$ alkylsulphonylamino, 3 to 6 membered cycloalkyl groups (e.g. cyclopropyl), phenyl (optionally substituted by one or more substituents selected from halogen, methyl, methoxy and amino) and five and six membered saturated heterocyclic rings containing 1 or 2 heteroatoms selected from O, N and S, the heterocyclic rings being optionally further substituted by one or more $C_{1-4}$ groups (e.g. methyl) and wherein the S, when present, may be present as S, SO or $SO_2$;

hydroxy;

amino, mono-$C_{1-4}$ alkylamino, di-$C_{1-4}$ alkylamino, benzyloxycarbonylamino and $C_{1-4}$ alkoxycarbonylamino;

carboxy and $C_{1-4}$ alkoxycarbonyl;

$C_{1-4}$ alkylaminosulphonyl and $C_{1-4}$ alkylsulphonylamino;

$C_{1-4}$ alkylsulphonyl;

a group O-Het$^s$ or NH-Het$^s$ where Het$^s$ is a five or six membered saturated heterocyclic ring containing 1 or 2 heteroatoms selected from O, N and S, the heterocyclic rings being optionally further substituted by one or more $C_{1-4}$ groups (e.g. methyl) and wherein the S, when present, may be present as S, SO or $SO_2$;

five and six membered saturated heterocyclic rings containing 1 or 2 heteroatoms selected from O, N and S, the heterocyclic rings being optionally further substituted by one or more $C_{1-4}$ groups (e.g. methyl) and wherein the S, when present, may be present as S, SO or $SO_2$;

oxo; and six membered aryl and heteroaryl rings containing up to two nitrogen ring members and being optionally substituted by one or substituents selected from halogen, methyl and methoxy.

In one preferred sub-group of compounds, $R^3$ is a carbocyclic or heterocyclic group $R^{3a}$ selected from phenyl; $C_{3-6}$ cycloalkyl; five and six membered saturated non-aromatic heterocyclic rings containing up to two heteroatom ring members selected from N, O, S and $SO_2$; six membered heteroaryl rings containing one, two or three nitrogen ring members; and five membered heteroaryl rings having up to three heteroatom ring members selected from N, O and S;

wherein each carbocyclic or heterocyclic group $R^{3a}$ is optionally substituted by up to four, preferably up to three, and more preferably up to two (e.g. one) substituents selected from amino; hydroxy; oxo; fluorine; chlorine; $C_{1-4}$ alkyl-(O)$_q$— wherein q is 0 or 1 and the $C_{1-4}$ alkyl moiety is optionally substituted by fluorine, hydroxy or $C_{1-2}$ alkoxy; mono-$C_{1-4}$ alkylamino; di-$C_{1-4}$ alkylamino; $C_{1-4}$ alkoxycarbonyl; carboxy; a group $R^e$—$R^{16}$ where $R^e$ is a bond or a $C_{1-3}$ alkylene chain and $R^{16}$ is selected from $C_{1-4}$ alkylsulphonyl; $C_{1-4}$ alkylaminosulphonyl; $C_{1-4}$ alkylsulphonylamino-; amino; mono-$C_{1-4}$ alkylamino; di-$C_{1-4}$ alkylamino; $C_{1-7}$-hydrocarbyloxycarbonylamino; six membered aromatic groups containing up to three nitrogen ring members; $C_{3-6}$ cycloalkyl; five or six membered saturated non-aromatic heterocyclic groups containing one or two heteroatom ring members selected from N, O, S and $SO_2$, the group $R^{16}$ when a saturated non-aromatic group being optionally substituted by one or more methyl groups, and the group $R^{16}$ when aromatic being optionally substituted by one or more groups selected from fluorine, chlorine, hydroxy, $C_{1-2}$ alkoxy and $C_{1-2}$ alkyl.

In a further embodiment, $R^3$ is selected from:

monocyclic aryl groups optionally substituted by 1-4 (for example 1-2, e.g. 1) substituents $R^{10}$ or $R^{10a}$;

$C_3$-$C_7$ cycloalkyl groups optionally substituted by 1-4 (for example 1-2, e.g. 1) substituents $R^{10}$ or $R^{10a}$;

saturated five membered heterocyclic rings containing 1 ring heteroatom selected from O, N and S and being optionally substituted by an oxo group and/or by 1-4 (for example 1-2, e.g. 1) substituents $R^{10}$ or $R^{10a}$;

saturated six membered heterocyclic rings containing 1 or 2 ring heteroatoms selected from O, N and S and being optionally substituted by an oxo group and/or by 1-4 (for example 1-2, e.g. 1) substituents $R^{10}$ or $R^{10a}$;

five membered heteroaryl rings containing 1 or 2 ring heteroatoms selected from O, N and S and being optionally substituted by 1-4 (for example 1-2, e.g. 1) substituents $R^{10}$ or $R^{10a}$;

six membered heteroaryl rings containing 1 or 2 nitrogen ring members (preferably 1 nitrogen ring member) and being optionally substituted by 1-4 (for example 1-2, e.g. 1) substituents $R^{10}$ or $R^{10a}$;

mono-azabicycloalkyl and diazabicycloalkyl groups each having 7 to 9 ring members and being optionally substituted by 1-4 (for example 1-2, e.g. 1) substituents $R^{10}$ or $R^{10a}$.

Specific examples of the group Y-$R^3$ are set out in Table 2. In Table 2, the point of attachment of the group to the nitrogen atom of the pyrazole-3-carboxamide group is represented by the terminal single bond extending from the group. Thus, by way of illustration, group CA in the table is the 4-fluorophenyl, group CB in the table is the 4-methoxybenzyl group and group CC in the table is the 4-(4-methylpiperazino)-phenylmethyl group.

TABLE 2

Examples of the Group Y-$R^3$

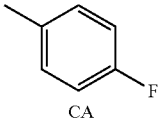
CA

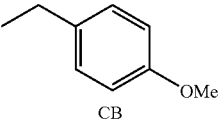
CB

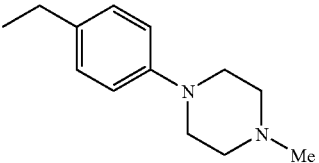
CC

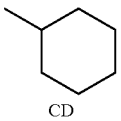
CD

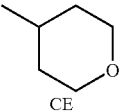
CE

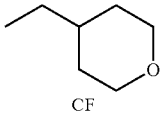
CF

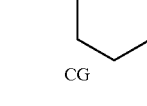
CG

CH

TABLE 2-continued

Examples of the Group Y-$R^3$

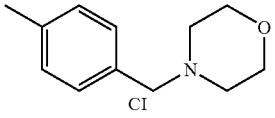
CI

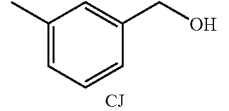
CJ

CK

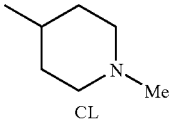
CL

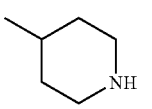
CM

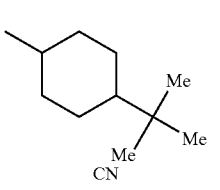
CN

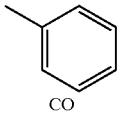
CO

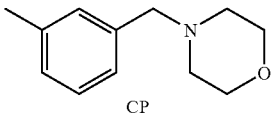
CP

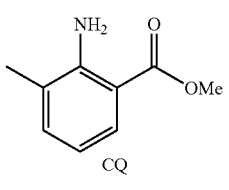
CQ

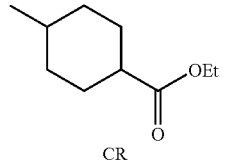
CR

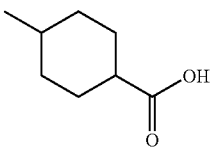

TABLE 2-continued
Examples of the Group Y-R³
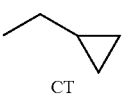
CT
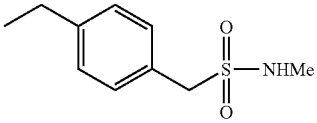
CU
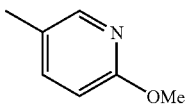
CV
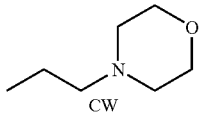
CW
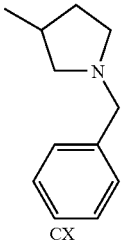
CX
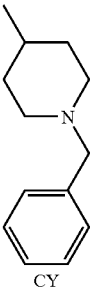
CY
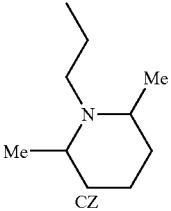
CZ
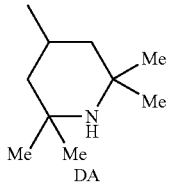
DA
TABLE 2-continued
Examples of the Group Y-R³
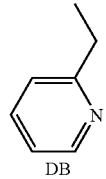
DB
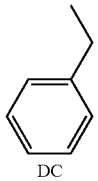
DC
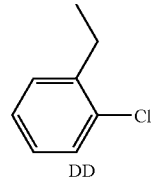
DD
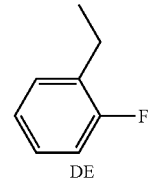
DE
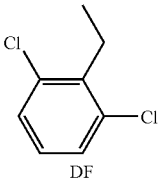
DF
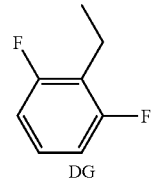
DG
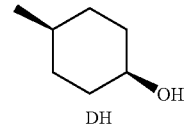
DH
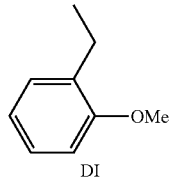
DI TABLE 2-continued
Examples of the Group Y-R³
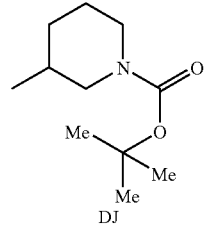
DJ
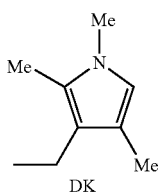
DK
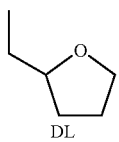
DL
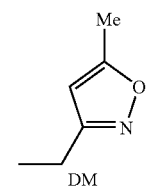
DM
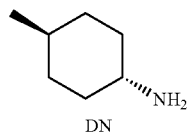
DN
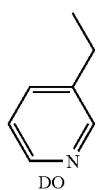
DO
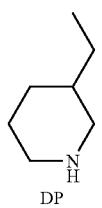
DP
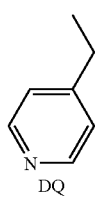
DQ
TABLE 2-continued
Examples of the Group Y-R³
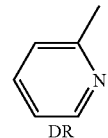
DR
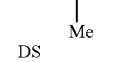
DS
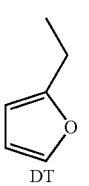
DT
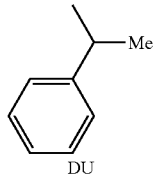
DU
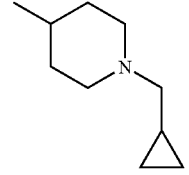
DV
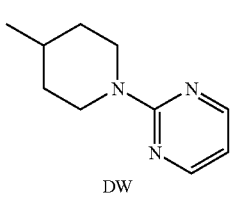
DW
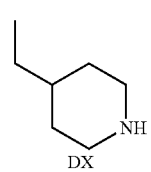
DX
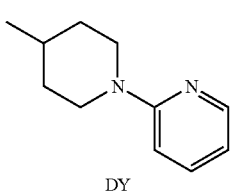
DY
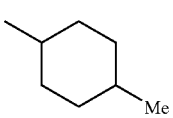

TABLE 2-continued
Examples of the Group Y-R³
DZ
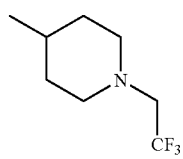
EA
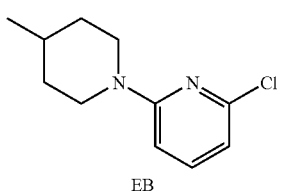
EB
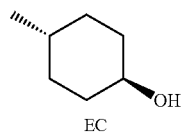
EC
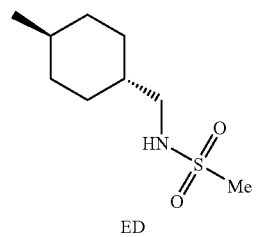
ED
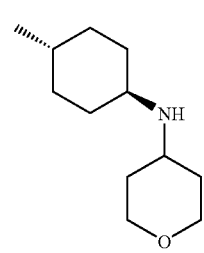
EE
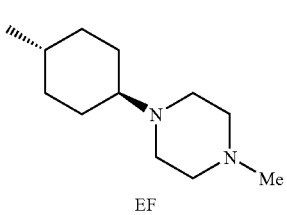
EF
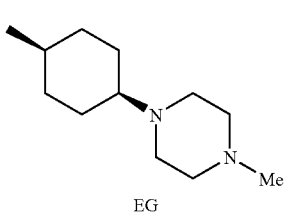
EG
TABLE 2-continued
Examples of the Group Y-R³
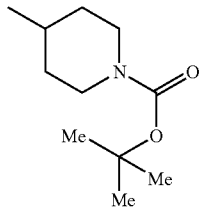
EH
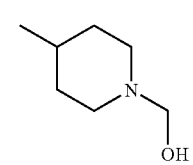
EI
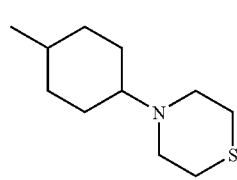
EJ
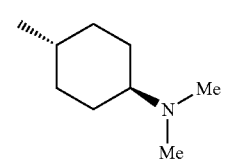
EK
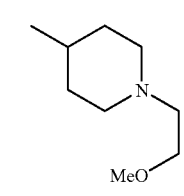
EL
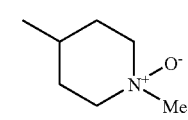
EM
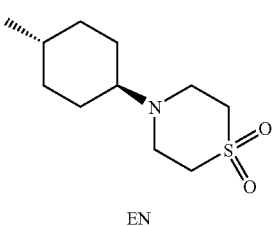
EN TABLE 2-continued
Examples of the Group Y-R³
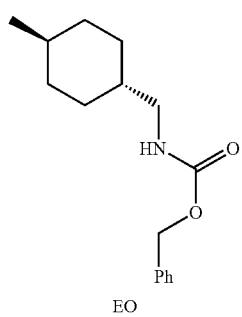
EO
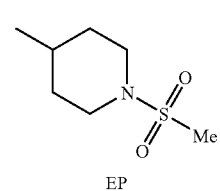
EP
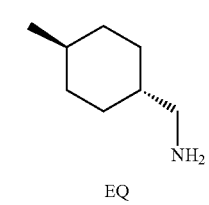
EQ
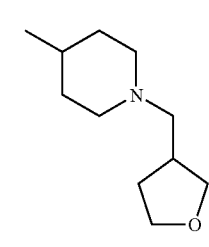
ER
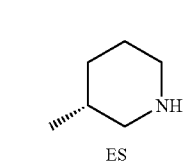
ES
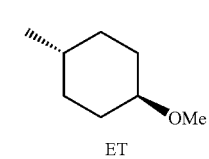
ET
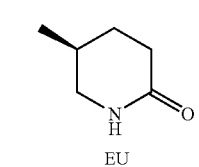
EU
TABLE 2-continued
Examples of the Group Y-R³
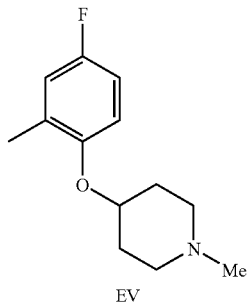
EV
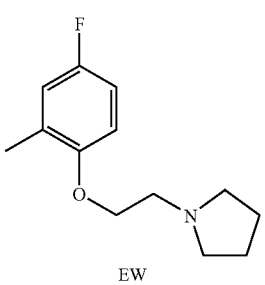
EW
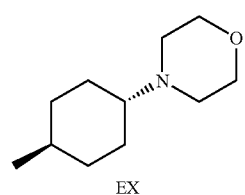
EX
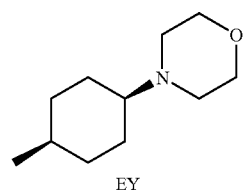
EY
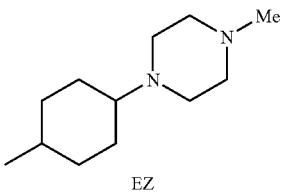
EZ
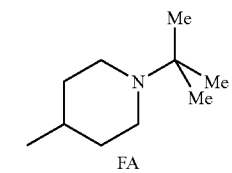
FA
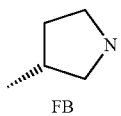
FB TABLE 2-continued Examples of the Group Y-R³

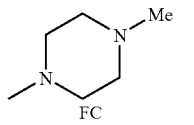
FC

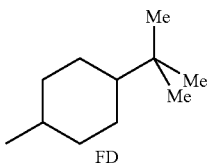
FD

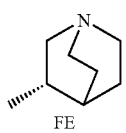
FE

FF

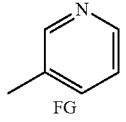
FG

FH

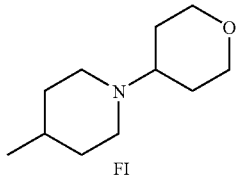
FI

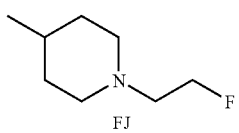
FJ

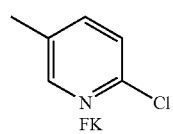
FK

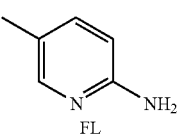
FL

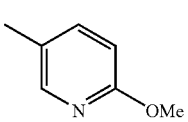

TABLE 2-continued

Examples of the Group Y-R³

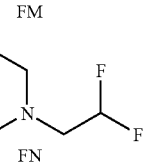
FM

FN

One sub-set of groups selected from table 2 consists of groups CA to EU.

Another sub-set of groups selected from table 2 consists of groups CA to CV.

Preferred groups selected from Table 2 include groups CL, CM, ES, ET, FC, FG and FH.

Particularly preferred groups selected from Table 2 include groups CL, CM and ES, and most preferably CL and CM.

In another general embodiment, when $R^3$ is an aza-cycloalkyl group, the group X in the compound of the formula (I) is preferably $R^1$-A-$NR^4$ wherein A is CO, $NR^g(C=O)$ or $O(C=O)$. Additionally, or alternatively, when $R^3$ is an aza-cycloalkyl group, the nitrogen atom of the aza-cycloalkyl group is preferably not substituted with an alkylene chain linked to a 2,3-dihydro-benzo[1,4]dioxine or tetrahydronaphthalene group.

In another general embodiment, when Y is an alkylene chain of 1 carbon atom in length, $R^3$ is other than an optionally substituted phenyl group bearing a substituted or unsubstituted cyclohexyloxy or cyclohexylthio group.

In another general embodiment, $R^3$ is other than a moiety containing a five membered heteroaryl ring linked directly by a single bond to a monocyclic or bicyclic aryl group or $R^3$ is other than a moiety containing a bis heteroaryl group comprising two five membered heteroaryl rings linked together by a single bond.

In a further general embodiment, $R^1$ is other than a moiety containing a five membered heteroaryl ring linked directly by a single bond to a monocyclic or bicyclic aryl group or $R^1$ is other than a moiety containing a bis heteroaryl group comprising two five membered heteroaryl rings linked together by a single bond.

In another general embodiment, $R^1$-A-$NR^4$ is other than an optionally substituted nicotinoyl-amino or benzoyl-amino group when Y-$R^3$ is an alkyl, cycloalkyl, optionally substituted phenyl or optionally substituted phenylalkyl group.

When A is a bond (and optionally when A is CO, $NR^g$ (C=O) or O(C=O)), Y-$R^3$ may be other than a cycloalkyl group substituted at the 1-position with a hydrocarbon chain simultaneously bearing an oxy substituent such as hydroxy, an aryl substituent and a diazole or triazole substituent.

Preferably, $R^1$ or $R^3$ each are other than a moiety containing a substituted phenyl group having thio and/or oxy substituents such as hydroxy, alkoxy and alkylthio at both the 3- and 4-positions of the phenyl ring.

In a further general embodiment, when Y-$R^3$ is unsubstituted or substituted benzyl or phenethyl or naphthylmethyl, X may be other than $C_{1-5}$ alkylamino or $C_{1-7}$ acylamino.

The group Y-$R^3$ preferably does not include a benzo-fused lactam group having attached thereto an unsubstituted or substituted imidazole group.

The group Y-$R^3$ preferably does not include the moiety —CH=C($CO_2R^q$)—S— where $R^q$ is hydrogen or alkyl.

In another general embodiment, neither $R^1$ nor $R^3$ contain a moiety in which a five membered nitrogen-containing heteroaryl group is linked directly or via an alkylene, oxa-alkylene, thia-alkylene or aza-alkylene group to an unsubstituted pyridyl group or to a substituted aryl, heteroaryl or piperidine ring, each said ring having attached thereto a subsitutent selected from cyano, and substituted or unsubstituted amino, aminoalkyl, amidine, guanidine, and carbamoyl groups.

In a further general embodiment, $R^1$ and $R^3$ are each other than an unsaturated nitrogen-containing heterocyclic group or a nitrogen-containing heteroaryl group, or a benzfuran or benzthiophene group wherein the said nitrogen-containing heterocyclic group, nitrogen-containing heteroaryl group, bicyclic benzfuran or benzthiophene group are linked directly by a single bond to a substituted pyridyl or phenyl group.

In another general embodiment, neither $R^1$ nor $R^3$ contain a moiety in which a five membered nitrogen-containing heteroaryl group is linked directly or via an alkylene, oxa-alkylene, thia-alkylene or aza-alkylene group to a substituted aryl, heteroaryl or piperidine group or to an unsubstituted pyridyl group.

In general, it is preferred that the compounds of the invention, where they contain a carboxylic acid group, contain no more than one such group.

Particular and Preferred Sub-groups of the formulae (I), (Ia) and (Ib)

One particular group of compounds of the invention is represented by the formula (II):

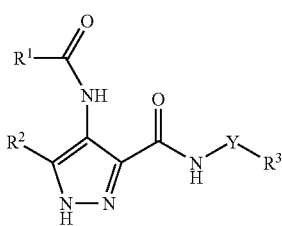

(II)

or salts or tautomers or N-oxides or solvates thereof;

wherein $R^1$, $R^2$, $R^3$ and Y are each independently selected from $R^1$, $R^2$, $R^3$ and Y as defined herein.

Within formula (II), it is preferred that $R^2$ is hydrogen or $C_{1-4}$ alkyl (e.g. $C_{1-3}$ alkyl), and more preferably $R^2$ is hydrogen.

In one sub-group of compounds of the formula (II), $R^1$ is:

(i) phenyl optionally substituted by one or more substituents (e.g. 1, 2 or 3) selected from fluorine; chlorine; hydroxy; 5- and 6-membered saturated heterocyclic groups containing 1 or 2 heteroatoms selected from O, N and S, the heterocyclic groups being optionally substituted by one or more $C_{1-4}$ alkyl groups; $C_{1-4}$ hydrocarbyloxy; and $C_{1-4}$ hydrocarbyl; wherein the $C_{1-4}$ hydrocarbyl and $C_{1-4}$ hydrocarbyloxy groups are optionally substituted by one or more substituents chosen from hydroxy, fluorine, $C_{1-2}$ alkoxy, amino, mono and di-$C_{1-4}$ alkylamino, phenyl, halophenyl, saturated carbocyclic groups having 3 to 7 ring members (more preferably 4, 5 or 6 ring members, e.g. 5 or 6 ring members) or saturated heterocyclic groups of 5 or 6 ring members and containing up to 2 heteroatoms selected from O, S and N; or 2, 3-dihydro-benzo[1,4]dioxine; or (ii) a monocyclic heteroaryl group containing one or two heteroatoms selected from O, S and N; or a bicyclic heteroaryl group containing a single heteroatom selected from O, S and N; the monocyclic and bicyclic heteroaryl groups each being optionally substituted by one or more substituents selected from fluorine; chlorine; $C_{1-3}$ hydrocarbyloxy; and $C_{1-3}$ hydrocarbyl optionally substituted by hydroxy, fluorine, methoxy or a five or six membered saturated carbocyclic or heterocyclic group containing up to two heteroatoms selected from O, S and N; or (iii) a substituted or unsubstituted cycloalkyl group having from 3 to 6 ring members; or (iv) a $C_{1-4}$ hydrocarbyl group optionally substituted by one or more substituents selected from fluorine; hydroxy; $C_{1-4}$ hydrocarbyloxy; amino; mono- or di-$C_{1-4}$ hydrocarbylamino; and carbocyclic or heterocyclic groups having from 3 to 12 ring members, and wherein one of the carbon atoms of the hydrocarbyl group may optionally be replaced by an atom or group selected from O, NH, SO and $SO_2$.

Within group (i), a sub-group of groups $R^1$ consists of phenyl optionally substituted by one or more substituents selected from fluorine; chlorine; hydroxy; $C_{1-3}$ hydrocarbyloxy; and $C_{1-3}$ hydrocarbyl wherein the $C_{1-3}$ hydrocarbyl group is optionally substituted by one or more substituents chosen from hydroxy, fluorine, $C_{1-2}$ alkoxy, amino, mono and di-$C_{1-4}$ alkylamino, saturated carbocyclic groups having 3 to 7 ring members (more preferably 4, 5 or 6 ring members, e.g. 5 or 6 ring members) or saturated heterocyclic groups of 5 or 6 ring members and containing up to 2 heteroatoms selected from O, S and N.

In another sub-group of compounds of the formula (II), $R^1$ is selected from (i) and (iii) above and additionally from a sub-set (aii) where sub-set (aii) consists of 2-furanyl, 3-furanyl, imidazolyl, 2-pyridyl, indolyl, 2-thienyl and 3-thienyl, each optionally substituted by one or more substituents selected from fluorine, chlorine, $C_{1-3}$ hydrocarbyloxy, and $C_{1-3}$ hydrocarbyl optionally substituted by hydroxy, fluorine or methoxy.

Within the group of compounds defined by the formula (II), where $R^1$ is (i) an optionally substituted phenyl group, it may be, for example, an unsubstituted phenyl group or a 2-monosubstituted, 3-monosubstituted, 2,3 disubstituted, 2,5 disubstituted or 2,6 disubstituted phenyl group or 2,3-dihydro-benzo[1,4]dioxine, where the substituents are selected from halogen; hydroxyl; $C_{1-3}$ alkoxy; and $C_{1-3}$ alkyl groups wherein the $C_{1-3}$ alkyl group is optionally substituted by hydroxy, fluorine, $C_{1-2}$ alkoxy, amino, mono and di-$C_{1-4}$ alkylamino, or saturated carbocyclic groups having 3 to 6 ring members and/or saturated heterocyclic groups of 5 or 6 ring members and containing 1 or 2 heteroatoms selected from N and O.

In one embodiment, $R^1$ is selected from unsubstituted phenyl, 2-fluorophenyl, 2-hydroxyphenyl, 2-methoxyphenyl, 2-methylphenyl, 2-(2-(pyrrolidin-1-yl)ethoxy)-phenyl, 3-fluorophenyl, 3-methoxyphenyl, 2,6-difluorophenyl, 2-fluoro-6-hydroxyphenyl, 2-fluoro-3-methoxyphenyl, 2-fluoro-5-methoxyphenyl, 2-chloro-6-methoxyphenyl, 2-fluoro-6-methoxyphenyl, 2,6-dichlorophenyl and 2-chloro-6-fluorophenyl, and is optionally further selected from 5-fluoro-2-methoxyphenyl.

In another embodiment, $R^1$ is selected from unsubstituted phenyl, 2-fluorophenyl, 2-hydroxyphenyl, 2-methoxyphenyl, 2-methylphenyl, 2-(2-(pyrrolidin-1-yl)ethoxy)-phenyl, 3-fluorophenyl, 3-methoxyphenyl, 2,6-difluorophenyl, 2-fluoro-6-hydroxyphenyl, 2-fluoro-3-methoxyphenyl and 2-fluoro-5-methoxyphenyl.

Particular groups $R^1$ are 2,6-difluorophenyl, 2-fluoro-6-methoxyphenyl and 2,6-dichlorophenyl. One particularly preferred group $R^1$ is 2,6-difluorophenyl.

Another particularly preferred group $R^1$ is 2,6-dichlorophenyl.

When R¹ is (ii) a monocyclic heteroaryl group containing one or two heteroatoms selected from O, S and N or a bicyclic heteroaryl group containing a single heteroatom, examples of monocyclic and bicyclic heteroaryl groups include furanyl (e.g. 2-furanyl and 3-furanyl), imidazolyl, pyridyl (e.g. 2-pyridyl), indolyl, thienyl (e.g. 2-thienyl and 3-thienyl) groups. The optional substituents for such groups can include chlorine, fluorine, methyl, methoxy, hydroxymethyl, methoxymethyl, morpholinomethyl, piperazinomethyl, N-methylpiperazinomethyl and piperidinylmethyl groups. Particular examples of groups (ii) include unsubstituted 2-furanyl, 3-methyl-2-furanyl, unsubstituted 4-(1H)-imidazolyl, unsubstituted 5-(1H)-imidazolyl, unsubstituted 3-furanyl, unsubstituted 3-thienyl, 2-methyl-3-thienyl and unsubstituted 3-pyrrolyl, and further examples include 4-methoxy-3-thienyl, 5-(1-pyrrolidinyl)methyl-2-furyl and 5-(4-morpholino)methyl-2-furyl groups.

When R¹ is (iii) an optionally substituted cycloalkyl group, it can be for example a substituted or unsubstituted cyclopropyl, cyclobutyl, cyclopentyl or cyclohexyl group. When the cycloalkyl group is substituted, preferred substituents include methyl, fluorine and hydroxyl. Particular examples of cycloalkyl groups include 1-methylcyclopropyl, 1-hydroxycyclopropyl, and unsubstituted cyclohexyl, cyclopentyl and cyclobutyl.

In the context of formula (II) and the group R¹, examples of optionally substituted hydrocarbyl groups are optionally substituted methyl, ethyl and propyl groups wherein one of the carbon atoms of the hydrocarbyl group is optionally replaced by O, NH, SO or $SO_2$. Particular examples of such groups include methyl, ethyl, trifluoromethyl, methyl and ethyl substituted with a carbocyclic or heterocyclic group having from 3 to 12 ring members, sulphonylmethyl substituted with a carbocyclic or heterocyclic group having from 3 to 12 ring members, hydroxymethyl, hydroxyethyl, 3-hydroxy-2-propyl, propyl, isopropyl, butyl and tertiary butyl. Examples of hydrocarbyl groups and carbocylic and heteroacyclic groups are as set out above in the general definitions of such groups. Particular carbocyclic and heterocyclic groups include unsubstituted or substituted phenyl, indolyl, tetrazolyl, triazolyl, piperidinyl, morpholinyl, piperazinyl, N-methylpiperazinyl, imidazolyl wherein the optional substituents may be selected from the group $R^{10}$, and sub-groups thereof, as defined herein.

In another sub-group of compounds of the formula (II), R¹ is a $C_{1-4}$ hydrocarbyl group optionally substituted by one or more substituents selected from fluorine, hydroxy, $C_{1-4}$ hydrocarbyloxy, amino, mono- or di-$C_{1-4}$ hydrocarbylamino, and carbocyclic or heterocyclic groups having from 3 to 12 ring members, and wherein 1 of the carbon atoms of the hydrocarbyl group may optionally be replaced by an atom or group selected from O, NH, SO and $SO_2$.

In one embodiment, R¹ is a group $R^{1a}$—$(V)_n$— where:
n is 0 or 1;
V is selected from $CH_2$, $CH_2CH_2$ and $SO_2CH_2$; and
$R^{1a}$ is a carbocyclic or heterocyclic group selected from phenyl;
five membered heteroaryl rings having up to 4 heteroatom ring members selected from N, O and S;
six membered heteroaryl rings containing one or two nitrogen ring members;
five or six membered saturated non-aromatic heterocyclic rings containing one or two heteroatom ring members selected from N, O, S and $SO_2$;
$C_{3-6}$ cycloalkyl groups; indole; and quinoline;
wherein each of the carbocyclic and heterocyclic groups $R^{1a}$ can be optionally substituted by one or more substituents selected from five or six membered saturated non-aromatic carbocyclic and heterocyclic groups containing up to two heteroatom ring members selected from N, O, S and $SO_2$; hydroxy; amino; oxo; mono-$C_{1-4}$ alkylamino; di-$C_{1-4}$ alkylamino; fluorine; chlorine; nitro; $C_{1-4}$ alkyl-$(O)_q$— wherein q is 0 or 1 and the $C_{1-4}$ alkyl moiety is optionally substituted by fluorine, hydroxy, $C_{1-2}$ alkoxy or a five or six membered saturated non-aromatic carbocyclic or heterocyclic group containing up to two heteroatom ring members selected from N, O, S and $SO_2$; phenyl and $C_{1-2}$-alkylene dioxy.

Specific examples of groups R¹—CO— in formula (II) are set out in Table 1 above.

One sub-group of preferred groups R¹—CO consists of the groups J, AB, AH, AJ, AL, AS, AX, AY, AZ, BA, BB, BD, BH, BL, BQ and BS.

Another sub-group of groups R¹—CO consists of the groups A to BF.

A further sub-group of groups R¹—CO consists of the groups A to BS.

Particularly preferred groups are the groups AJ, BQ and BS in Table 1, e.g. the sub-set consisting of AJ and BQ.

Another group of compounds of the invention is represented by the formula (III):

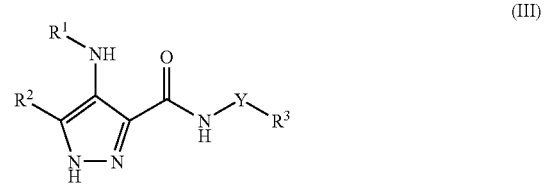

(III)

or salts or tautomers or N-oxides or solvates thereof;
wherein R¹, R², R³ and Y are as defined herein.

Examples of, and preferences, for the groups R¹, R², R³ and Y are as set out above for compounds of the formulae (0), (1⁰), (I), (Ia), (Ib) and (II) unless the context indicates otherwise.

Particular sub-groups of compounds of the formula (III) include:
(i) compounds wherein R¹ is a heteroaryl group containing 1, 2 or 3 heteroatom ring members selected from N, O and S;
(ii) compounds wherein R¹ is a $C_{1-6}$ hydrocarbyl group optionally substituted by one or more substituents selected from fluorine, hydroxy, $C_{1-4}$ hydrocarbyloxy, amino, mono- or di-$C_{1-4}$ hydrocarbylamino, and carbocyclic or heterocyclic groups having from 3 to 12 ring members, and wherein 1 of the carbon atoms of the hydrocarbyl group may optionally be replaced by an atom or group selected from O, NH, SO and $SO_2$; and
(iii) compounds wherein R¹ is a non-aromatic carbocyclic or heterocyclic group having from 3 to 12 ring members.

Examples of compounds of the formula (III) wherein R¹ is (i) a heteroaryl group include 5- and 6-membered monocyclic heteroaryl groups, e.g. containing 1 or 2 heteroatom ring members selected from O, N and S. In one embodiment, the heteroaryl group is a monocyclic group containing 1 or 2 nitrogen ring members. In another embodiment, the heteroaryl groups are selected from 6-membered rings containing 1 or 2 nitrogen ring members, for example pyridine, pyrimidine, pyrazine and pridazine groups, one particular sub-group consisting of pyrazinyl and pyridyl.

The heteroaryl groups can be unsubstituted or substituted by one or more groups $R^{10}$ as defined herein.

Examples of compounds of the formula (III) wherein $R^1$ is (ii) an optionally substituted $C_{1-6}$ hydrocarbyl group include those in which the hydrocarbyl group is unsubstituted hydrocarbyl, for example unsubstituted alkyl such as methyl, ethyl, propyl, isopropyl, butyl, isobutyl, t-butyl, 1-pentyl, 2-pentyl and 3-pentyl.

Examples of compounds wherein $R^1$ is a non-aromatic carbocyclic or heterocyclic group include those wherein the carbocyclic or heterocyclic group is monocyclic and contains up to 2 heteroatoms selected from oxygen and nitrogen. Particular examples of such groups are cyclohexyl and piperidino.

Another sub-group of compounds of the formula (I) can be represented by the formula (IV):

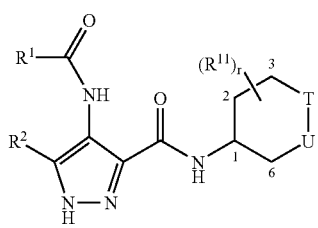

(IV)

or salts or tautomers or N-oxides or solvates thereof;
wherein $R^1$ and $R^2$ are as defined herein;
an optional second bond may be present between carbon atoms numbered 1 and 2;
one of U and T is selected from $CH_2$, $CHR^{13}$, $CR^{11}R^{13}$, $NR^{14}$, $N(O)R^{15}$, O and $S(O)_t$; and the other of U and T is selected from, $NR^{14}$, O, $CH_2$, $CHR^{11}$, $C(R^{11})_2$, and C=O; r is 0, 1, 2, 3 or 4; t is 0, 1 or 2;
$R^{11}$ is selected from hydrogen, halogen (particularly fluorine), $C_{1-3}$ alkyl (e.g. methyl) and $C_{1-3}$ alkoxy (e.g. methoxy);
$R^{13}$ is selected from hydrogen, $NHR^{14}$, NOH, $NOR^{14}$ and $R^a$—$R^b$;
$R^{14}$ is selected from hydrogen and $R^d$—$R^b$;
$R^d$ is selected from a bond, CO, $C(X^2)X^1$, $SO_2$ and $SO_2NR^c$;
$R^a$, $R^b$ and $R^c$ are as hereinbefore defined; and
$R^{15}$ is selected from $C_{1-4}$ saturated hydrocarbyl optionally substituted by hydroxy, $C_{1-2}$ alkoxy, halogen or a monocyclic 5- or 6-membered carbocyclic or heterocyclic group, provided that U and T cannot be O simultaneously.

Examples of, and preferences, for the groups $R^1$ and $R^2$ are as set out above for compounds of the formulae (I), (Ia), (Ib) and (II) unless the context indicates otherwise.

Within formula (IV), r can be 0, 1, 2, 3 or 4. In one embodiment, r is 0. In another embodiment, r is 2, and in a further embodiment r is 4.

Within formula (IV), one sub-set of preferred compounds is the set of compounds where there is only a single bond between the carbon atoms numbered 1 and 2.

However, in another sub-set of compounds, there is a double bond between the carbon atoms numbered 1 and 2.

Another sub-set of compounds is characterised by gem disubstitution at the 2-carbon (when there is a single bond between carbon atoms numbers 1 and 2) and/or the 6-carbon. Preferred gem disubstituents include difluoro and dimethyl.

A further sub-set of compounds is characterised by the presence of an alkoxy group, for example a methoxy group at the carbon atom numbered 3, i.e. at a position a with respect to the group T.

Within formula (IV) are compounds wherein, for example, $R^3$ is selected from any of the following ring systems:

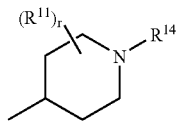

G1

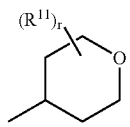

G2

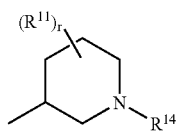

G3

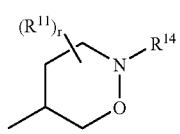

G4

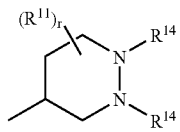

G5

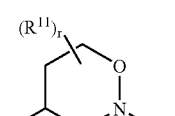

G6

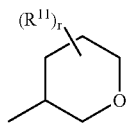

G7

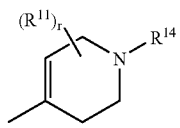

G8

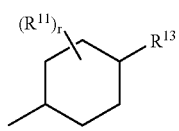

G9

Preferred ring systems include G1 and G3.

A preferred sub-group of compounds within formula (IV) can be represented by the formula (IVa):

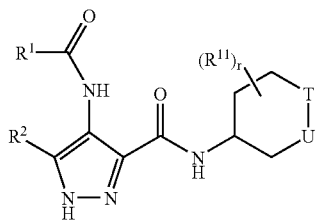

(IVa)

or salts or tautomers or N-oxides or solvates thereof;

wherein $R^1$ and $R^2$ are as hereinbefore defined;

one of U and T is selected from $CH_2$, $CHR^{13}$, $CR^{11}R^{13}$, $NR^{14}$, $N(O)R^{15}$, O and $S(O)_t$; and the other of U and T is selected from $CH_2$, $CHR^{11}$, $C(R^{11})_2$, and C=O; r is 0, 1 or 2; t is 0, 1 or 2;

$R^{11}$ is selected from hydrogen and $C_{1-3}$ alkyl;

$R^{13}$ is selected from hydrogen and $R^a$—$R^b$;

$R^{14}$ is selected from hydrogen and $R^d$—$R^b$;

$R^d$ is selected from a bond, CO, $C(X^2)X^1$, $SO_2$ and $SO_2NR^c$;

$R^a$, $R^b$ and $R^c$ are as hereinbefore defined; and $R^{15}$ is selected from $C_{1-4}$ saturated hydrocarbyl optionally substituted by hydroxy, $C_{1-2}$ alkoxy, halogen or a monocyclic 5- or 6-membered carbocyclic or heterocyclic group.

Examples of, and preferences, for the groups $R^1$ and $R^2$ are as set out above for compounds of the formulae (0), ($I^0$), (I), (Ia), (Ib) and (II) unless the context indicates otherwise.

In formula (IVa), T is preferably selected from $CH_2$, $CHR^{13}$, $CR^{11}R^{13}$, $NR^{14}$, $N(O)R^{15}$, O and $S(O)_t$; and U is preferably selected from $CH_2$, $CHR^{11}$, $C(R^{11})_2$, and C=O.

In the definitions for substituents $R^{11}$ and $R^{14}$, $R^b$ is preferably selected from hydrogen; monocyclic carbocyclic and heterocyclic groups having from 3 to 7 ring members; and $C_{1-4}$ hydrocarbyl (more preferably acyclic saturated $C_{1-4}$ groups) optionally substituted by one or more substituents selected from hydroxy, oxo, halogen, amino, mono- or di-$C_{1-4}$ hydrocarbylamino, and monocyclic carbocyclic and heterocyclic groups having from 3 to 7 ring members (more preferably 3 to 6 ring members) and wherein one or more carbon atoms of the $C_{1-4}$ hydrocarbyl group may optionally be replaced by O, S, SO, $SO_2$, $NR^c$, $X^1C(X^2)$, $C(X^2)X^1$; $R^c$ is selected from hydrogen and $C_{1-4}$ hydrocarbyl; and $X^1$ is O, S or $NR^c$ and $X^2$ is =O, =S or =$NR^c$.

$R^{11}$ is preferably selected from hydrogen and methyl and most preferably is hydrogen.

$R^{13}$ is preferably selected from hydrogen; hydroxy; halogen; cyano; amino; mono-$C_{1-4}$ saturated hydrocarbylamino; di-$C_{1-4}$ saturated hydrocarbylamino; monocyclic 5- or 6-membered carbocyclic and heterocyclic groups; $C_{1-4}$ saturated hydrocarbyl optionally substituted by hydroxy, $C_{1-2}$ alkoxy, halogen or a monocyclic 5- or 6-membered carbocyclic or heterocyclic group.

Particular examples of $R^{13}$ are hydrogen, hydroxy, amino, $C_{1-2}$ alkylamino (e.g. methylamino) $C_{1-4}$ alkyl (e.g. methyl, ethyl, propyl and butyl), $C_{1-2}$ alkoxy (e.g. methoxy), $C_{1-2}$ alkylsulphonamido (e.g. methanesulphonamido), hydroxy-$C_{1-2}$ alkyl (e.g. hydroxymethyl), $C_{1-2}$-alkoxy-$C_{1-2}$ alkyl (e.g. methoxymethyl and methoxyethyl), carboxy, $C_{1-4}$ alkoxycarbonyl (e.g.ethoxycarbonyl) and amino-$C_{1-2}$-alkyl (e.g. aminomethyl).

Particular examples of $R^{14}$ are hydrogen; $C_{1-4}$ alkyl optionally substituted by fluoro or a five or six membered saturated heterocyclic group (e.g. a group selected from (i) methyl, ethyl, n-propyl, i-propyl, butyl, 2,2,2-trifluoroethyl and tetrahydrofuranylmethyl; and/or (ii) 2-fluoroethyl and 2,2-difluoroethyl); cyclopropylmethyl; substituted or unsubstituted pyridyl-$C_{1-2}$ alkyl (e.g. 2-pyridylmethyl); substituted or unsubstituted phenyl-$C_{1-2}$ alkyl (e.g. benzyl); $C_{1-4}$ alkoxycarbonyl (e.g.ethoxycarbonyl and t-butyloxycarbonyl); substituted and unsubstituted phenyl-$C_{1-2}$ alkoxycarbonyl (e.g. benzyloxycarbonyl); substituted and unsubstituted 5- and 6-membered heteroaryl groups such as pyridyl (e.g. 2-pyridyl and 6-chloro-2-pyridyl) and pyrimidinyl (e.g. 2-pyrimidinyl); $C_{1-2}$-alkoxy-$C_{1-2}$ alkyl (e.g. methoxymethyl and methoxyethyl); $C_{1-4}$ alkylsulphonyl (e.g. methanesulphonyl).

Preferred compounds include those in which (i) U is $CHR^{13}$ (more preferably $CH_2$) and T is $NR_{14}$, and (ii) T is $CHR^{13}$ (more preferably $CH_2$) and U is $NR^{14}$.

One particular preferred sub-group of compounds of the formula (IV) can be represented by the formula (Va):

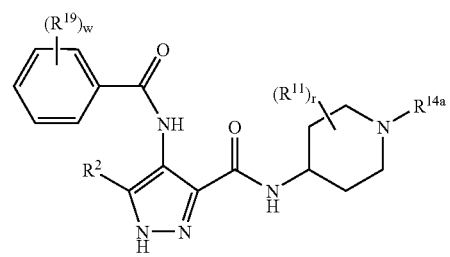

(Va)

or salts or tautomers or N-oxides or solvates thereof;

wherein $R^{14a}$ is selected from hydrogen, $C_{1-4}$ alkyl optionally substituted by fluoro (e.g. methyl, ethyl, n-propyl, i-propyl, butyl and 2,2,2-trifluoroethyl), cyclopropylmethyl, phenyl-$C_{1-2}$ alkyl (e.g. benzyl), $C_{1-4}$ alkoxycarbonyl (e.g.ethoxycarbonyl and t-butyloxycarbonyl), phenyl-$C_{1-2}$ alkoxycarbonyl (e.g. benzyloxycarbonyl), $C_{1-2}$-alkoxy-$C_{1-2}$ alkyl (e.g. methoxymethyl and methoxyethyl), and $C_{1-4}$ alkylsulphonyl (e.g.methanesulphonyl), wherein the phenyl moieties when present are optionally substituted by one to three substituents selected from fluorine, chlorine, $C_{1-4}$ alkoxy optionally substituted by fluoro or $C_{1-2}$-alkoxy, and $C_{1-4}$ alkyl optionally substituted by fluoro or $C_{1-2}$-alkoxy;

w is 0, 1, 2 or 3;

$R^2$ is hydrogen or methyl, most preferably hydrogen;

$R^{11}$ and r are as hereinbefore defined; and $R^{19}$ is selected from fluorine; chlorine; $C_{1-4}$ alkoxy optionally substituted by fluoro or $C_{1-2}$-alkoxy; and $C_{1-4}$ alkyl optionally substituted by fluoro or $C_{1-2}$-alkoxy.

Another particular preferred sub-group of compounds of the formula (IV) can be represented by the formula (Vb):

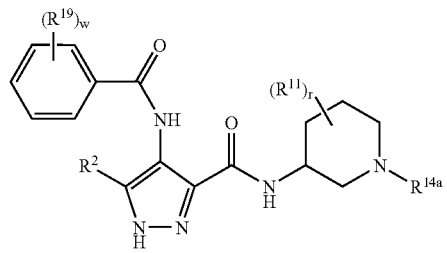

(Vb)

or salts or tautomers or N-oxides or solvates thereof;

wherein $R^{14a}$ is selected from hydrogen, $C_{1-4}$ alkyl optionally substituted by fluoro (e.g. methyl, ethyl, n-propyl, i-propyl, butyl and 2,2,2-trifluoroethyl), cyclopropylmethyl, phenyl-$C_{1-2}$ alkyl (e.g. benzyl), $C_{1-4}$ alkoxycarbonyl (e.g.ethoxycarbonyl and t-butyloxycarbonyl), phenyl-$C_{1-2}$ alkoxycarbonyl (e.g. benzyloxycarbonyl), $C_{1-2}$-alkoxy-$C_{1-2}$ alkyl (e.g. methoxymethyl and methoxyethyl), and $C_{1-4}$ alkylsulphonyl (e.g.methanesulphonyl), wherein the phenyl moieties when present are optionally substituted by one to three substituents selected from fluorine, chlorine, $C_{1-4}$ alkoxy optionally substituted by fluoro or $C_{1-2}$-alkoxy, and $C_{1-4}$ alkyl optionally substituted by fluoro or $C_{1-2}$-alkoxy;

w is 0, 1, 2 or 3;

$R^2$ is hydrogen or methyl, most preferably hydrogen;

$R^{11}$ and r are as hereinbefore defined; and $R^{19}$ is selected from fluorine; chlorine; $C_{1-4}$ alkoxy optionally substituted by fluoro or $C_{1-2}$-alkoxy; and $C_{1-4}$ alkyl optionally substituted by fluoro or $C_{1-2}$-alkoxy.

In formulae (Va) and (Vb), when w is 1, 2 or 3, it is preferred that the phenyl ring is 2-monosubstituted, 3-monosubstituted, 2,6-disubstituted, 2,3-disubstituted, 2,4-disubstituted 2,5-disubstituted, 2,3,6-trisubstituted or 2,4,6-trisubstituted. Most preferably the phenyl ring is disubstituted at positions 2- and 6- with substituents selected from fluorine, chlorine and methoxy.

$R^{11}$ is preferably hydrogen (or r is 0).

$R^{14a}$ is most preferably hydrogen or methyl.

One preferred sub-group of compounds of the formula (Va) can be represented by the formula (VIa):

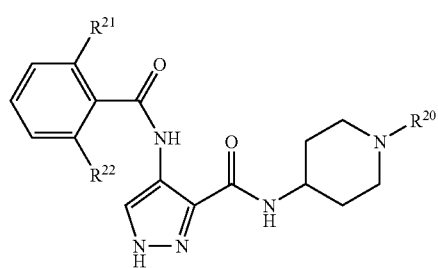

(VIa)

or salts or tautomers or N-oxides or solvates thereof;

wherein $R^{20}$ is selected from hydrogen and methyl;

$R^{21}$ is selected from fluorine and chlorine; and $R^{22}$ is selected from fluorine, chlorine and methoxy; or one of $R^{21}$ and $R^{22}$ is hydrogen and the other is selected from chlorine, methoxy, ethoxy, difluoromethoxy, trifluoromethoxy and benzyloxy.

Another preferred sub-group of compounds of the formula (Va) can be represented by the formula (VIb):

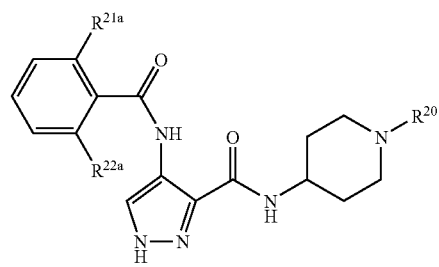

(VIb)

or salts or tautomers or N-oxides or solvates thereof;

wherein $R^{20}$ is selected from hydrogen and methyl;

$R^{21a}$ is selected from fluorine and chlorine; and $R^{22a}$ is selected from fluorine, chlorine and methoxy.

Particular compounds within formula (VIb) include:

4-(2,6-difluoro-benzoylamino)-1H-pyrazole-3-carboxylic acid piperidin-4-ylamide;

4-(2,6-difluoro-benzoylamino)-1H-pyrazole-3-carboxylic acid (1-methyl-piperidin-4-yl)-amide;

4-(2,6-dichloro-benzoylamino)-1H-pyrazole-3-carboxylic acid piperidin-4-ylamide; and 4-(2-fluoro-6-methoxy-benzoylamino)-1H-pyrazole-3-carboxylic acid piperidin-4-ylamide;

or salts or tautomers or N-oxides or solvates thereof.

A further group of compounds of the invention is represented by the formula (VII):

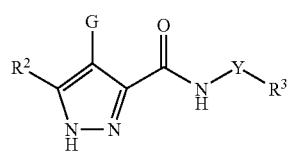

(VII)

or salts or tautomers or N-oxides or solvates thereof;

wherein $R^2$, $R^3$ and Y are as hereinbefore defined and G is a 5- or 6-membered carbocyclic or heterocyclic ring.

The group G can be an unsubstituted carbocyclic or heterocyclic ring or it can be a substituted carbocyclic or heterocyclic ring bearing one or more substituents selected from the groups $R^{10}$ and $R^{10a}$ as hereinbefore defined The carbocyclic or heterocyclic ring may be aromatic or non-aromatic and examples of such heterocyclic rings are set out above. In the context of the group G, preferred heterocyclic rings are those containing a nitrogen ring atom through which the group G is connected to the pyrazole ring. Particular heterocyclic rings are saturated heterocyclic rings containing up to 3 nitrogen atoms (more usually up to 2, for example 1) and optionally an oxygen atom. Particular examples of such rings are six membered rings such as piperidine, piperazine, N-methyl piperazine and morpholine.

When the group G is a carbocyclic group, it can be, for example a 6-membered aryl ring. For example, the group G can be an unsubstituted phenyl group or it can be a substituted phenyl group bearing one or more substituents selected from the groups $R^{10}$ and $R^{10a}$ as hereinbefore defined. The substituents, when present, are more typically small substituents such as hydroxyl, halogen (e.g. fluorine and chlorine), and $C_{1-4}$ hydrocarbyl (methyl, ethyl and cyclopropyl) optionally substituted by fluorine (e.g. trifluoromethyl) or hydroxy (e.g. hydroxymethyl).

In one general embodiment, when X is a non-aromatic heterocyclic group, then $R^3$ may be other than a six membered monocyclic aryl or heteroaryl group linked directly to a 5,6-fused bicyclic heteroaryl group.

A further group of compounds of the invention is represented by the formula (VIII):

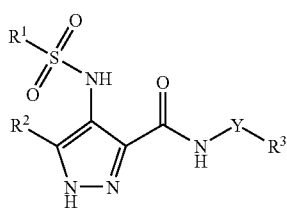

(VIII)

or salts or tautomers or N-oxides or solvates thereof;

wherein $R_1$, $R^2$, $R^3$ and Y are as defined herein.

Preferred groups $R^1$, $R^2$, Y and $R^3$ are as set out above in the section headed "General Preferences and Definitions" and in relation to compounds of the formulae (I) and (II) and subgroups thereof as defined herein.

For the avoidance of doubt, it is to be understood that each general and specific preference, embodiment and example of the groups $R^1$ may be combined with each general and specific preference, embodiment and example of the groups $R^2$ and/or $R^3$ and/or $R^4$ and/or $R^{10}$ and/or Y and/or $R^g$ and/or sub-groups thereof as defined herein and that all such combinations are embraced by this application.

The various functional groups and substituents making up the compounds of the formula (I) are typically chosen such that the molecular weight of the compound of the formula (I) does not exceed 1000. More usually, the molecular weight of the compound will be less than 750, for example less than 700, or less than 650, or less than 600, or less than 550. More preferably, the molecular weight is less than 525 and, for example, is 500 or less.

Particular compounds of the invention are as illustrated in the examples below.

Salts, Solvates, Tautomers, Isomers N-Oxides, Esters, Prodrugs and Isotopes

Unless otherwise specified, a reference to a particular compound also includes ionic, salt, solvate, and protected forms thereof, for example, as discussed below.

Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds. As in the preceding sections of this application, all references to formula (I) should be taken to refer also to formulae (0), ($I^0$), (I), (Ia), (Ib), (II), (III), (IV), (IVa), (Va), (Vb), (VIa), (VIb), (VII) or (VIII) and sub-groups thereof unless the context indicates otherwise.

Salt forms may be selected and prepared according to methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethane-sulphonic, formic, fumaric, galactaric, gentisic, glucoheptonic, D-gluconic, glucuronic (e.g. D-glucuronic), glutamic (e.g. L-glutamic), a-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-aminosalicylic, sebacic, stearic, succinic, sulphuric, tannic, (+)-L-tartaric, thiocyanic, p-toluenesulphonic, undecylenic and valeric acids, as well as acylated amino acids and cation exchange resins.

One particular group of salts consists of salts formed from hydrochloric, hydriodic, phosphoric, nitric, sulphuric, citric, lactic, succinic, maleic, malic, isethionic, fumaric, benzenesulphonic, toluenesulphonic, methanesulphonic, ethanesulphonic, naphthalenesulphonic, valeric, acetic, propanoic, butanoic, malonic, glucuronic and lactobionic acids.

One preferred group of salts consists of salts formed from hydrochloric, acetic, adipic, L-aspartic and DL-lactic acids.

Particularly preferred salts are hydrochloride salts

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth cations such as Ca²⁺ and Mg²⁺, and other cations such as Al³⁺. Examples of suitable organic cations include, but are not limited to, ammonium ion (i.e., NH₄⁺) and substituted ammonium ions (e.g., NH₃R⁺, NH₂R₂⁺, NHR₃⁺, NR₄⁺). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH₃)₄⁺.

Where the compounds of the formula (I) contain an amine function, these may form quaternary ammonium salts, for example by reaction with an alkylating agent according to methods well known to the skilled person. Such quaternary ammonium compounds are within the scope of formula (I).

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

For example, in compounds of the formula (I) the pyrazole group may take either of the following two tautomeric forms A and B. For simplicity, the general formula (I) illustrates form A but the formula is to be taken as embracing both tautomeric forms.

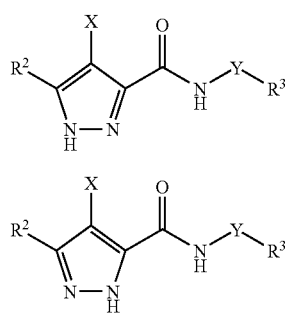

Other examples of tautomeric forms include, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

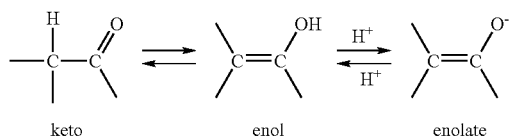

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

The compounds of the invention include compounds with one or more isotopic substitutions, and a reference to a particular element includes within its scope all isotopes of the element. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters of the compounds of formula (I) bearing a carboxylic acid group or a hydroxyl group are also embraced by Formula (I). Examples of esters are compounds containing the group —C(═O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Particular examples of ester groups include, but are not limited to, —C(═O)OCH$_3$, —C(═O)OCH$_2$CH$_3$, —C(═O)OC(CH$_3$)$_3$, and —C(═O)OPh. Examples of acyloxy (reverse ester) groups are represented by —OC(═O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(═O)CH$_3$ (acetoxy), —OC(═O)CH$_2$CH$_3$, —OC(═O)C(CH$_3$)$_3$, —OC(═O)Ph, and —OC(═O)CH$_2$Ph.

Also encompassed by formula (I) are any polymorphic forms of the compounds, solvates (e.g. hydrates), complexes (e.g. inclusion complexes or clathrates with compounds such as cyclodextrins, or complexes with metals) of the compounds, and pro-drugs of the compounds. By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:
$C_{1-7}$alkyl
  (e.g., -Me, -Et, -nPr, -iPr, -nBu, -sBu, -iBu, -tBu);
$C_{1-7}$aminoalkyl
  (e.g., aminoethyl; 2-(N,N-diethylamino)ethyl; 2-(4-morpholino)ethyl); and acyloxy-$C_{1-7}$alkyl
  (e.g., acyloxymethyl;
  acyloxyethyl;
  pivaloyloxymethyl;
  acetoxymethyl;
  1-acetoxyethyl;
  1-(1-methoxy-1-methyl)ethyl-carbonxyloxyethyl;
  1-(benzoyloxy)ethyl; isopropoxy-carbonyloxymethyl;
  1-isopropoxy-carbonyloxyethyl; cyclohexyl-carbonyloxymethyl;
  1-cyclohexyl-carbonyloxyethyl;
  cyclohexyloxy-carbonyloxymethyl;
  1-cyclohexyloxy-carbonyloxyethyl;
  (4-tetrahydropyranyloxy) carbonyloxymethyl;
  1-(4-tetrahydropyranyloxy)carbonyloxyethyl;
  (4-tetrahydropyranyl)carbonyloxymethyl; and
  1-(4-tetrahydropyranyl)carbonyloxyethyl).

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Biological Activity

The compounds of the formulae (0), (I°), (I), (Ia), (Ib), (II), (III), (IV), (IVa), (Va), (Vb), (VIa), (VIb), (VII) or (VIII) and sub-groups thereof are inhibitors of cyclin dependent kinases, and in particular cyclin dependent kinases selected from CDK1, CDK2, CDK3, CDK4, CDK5 and CDK6.

Preferred compounds are compounds that inhibit one or more CDK kinases selected from CDK1, CDK2, CDK4 and CDK5, for example CDK1 and/or CDK2.

The compounds of the invention are also considered to be inhibitors of glycogen synthase kinase-3 (GSK3).

As a consequence of their activity in modulating or inhibiting CDK kinases and glycogen synthase kinase, they are expected to be useful in providing a means of arresting, or recovering control of, the cell cycle in abnormally dividing cells. It is therefore anticipated that the compounds will prove useful in treating or preventing proliferative disorders such as cancers. It is also envisaged that the compounds of the invention will be useful in treating conditions such as viral infections, type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example. One sub-group of disease states and conditions where it is envisaged that the compounds of the invention will be useful consists of viral infections, autoimmune diseases and neurodegenerative diseases.

CDKs play a role in the regulation of the cell cycle, apoptosis, transcription, differentiation and CNS function. Therefore, CDK inhibitors could be useful in the treatment of diseases in which there is a disorder of proliferation, apoptosis or differentiation such as cancer. In particular RB+ve tumours may be particularly sensitive to CDK inhibitors. RB-ve tumours may also be sensitive to CDK inhibitors.

Examples of cancers which may be inhibited include, but are not limited to, a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, or skin, for example squamous cell carcinoma; a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example acute and chronic myelogenous leukemias, myelodysplastic syndrome, or promyelocytic leukemia; thyroid follicular cancer; a tumour of mesenchymal origin, for example fibrosarcoma or habdomyosarcoma, a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

The cancers may be cancers which are sensitive to inhibition of any one or more cyclin dependent kinases selected from CDK1, CDK2, CDK3, CDK4, CDK5 and CDK6, for example, one or more CDK kinases selected from CDK1, CDK2, CDK4 and CDK5, e.g. CDK1 and/or CDK2.

Whether or not a particular cancer is one which is sensitive to inhibition by a cyclin dependent kinase may be determined by means of a cell growth assay as set out in Example 250 below or by a method as set out in the section headed "Methods of Diagnosis".

CDKs are also known to play a role in apoptosis, proliferation, differentiation and transcription and therefore CDK inhibitors could also be useful in the treatment of the following diseases other than cancer; viral infections, for example herpes virus, pox virus, Epstein-Barr virus, Sindbis virus, adenovirus, HIV, HPV, HCV and HCMV; prevention of AIDS development in HIV-infected individuals; chronic inflammatory diseases, for example systemic lupus erythematosus, autoimmune mediated glomerulonephritis, rheumatoid arthritis, psoriasis, inflammatory bowel disease, and autoimmune diabetes mellitus; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-senstive rhinosinusitis, cystic fibrosis, multiple sclerosis, kidney diseases and cancer pain.

It has also been discovered that some cyclin-dependent kinase inhibitors can be used in combination with other anti-cancer agents. For example, the cyclin-dependent kinase inhibitor flavopiridol has been used with other anticancer agents in combination therapy.

Thus, in the pharmaceutical compositions, uses or methods of this invention for treating a disease or condition comprising abnormal cell growth, the disease or condition comprising abnormal cell growth in one embodiment is a cancer.

One group of cancers includes human breast cancers (e.g. primary breast tumours, node-negative breast cancer, invasive duct adenocarcinomas of the breast, non-endometrioid breast cancers); and mantle cell lymphomas. In addition, other cancers are colorectal and endometrial cancers.

Another sub-set of cancers includes breast cancer, ovarian cancer, colon cancer, prostate cancer, oesophageal cancer, squamous cancer and non-small cell lung carcinomas.

The activity of the compounds of the invention as inhibitors of cyclin dependent kinases and glycogen synthase kinase-3 can be measured using the assays set forth in the examples below and the level of activity exhibited by a given compound can be defined in terms of the $IC_{50}$ value. Preferred compounds of the present invention are compounds having an $IC_{50}$ value of less than 1 micromole, more preferably less than 0.1 micromole.

Methods for the Preparation of Compounds of the Invention

Compounds of the formula (I) and the various sub-groups thereof can be prepared in accordance with synthetic methods well known to the skilled person. Unless stated otherwise, $R^1$, $R^2$, $R^3$, Y, X and A are as hereinbefore defined.

In this section, as in all the other sections of this application, references to formula (I) should be taken to refer also to formulae (0), ($1^0$), (I), (Ia), (Ib), (II), (III), (IV), (IVa), (Va), (Vb), (VIa), (VIb), (VII) or (VIII) and sub-groups thereof unless the context indicates otherwise.

Compounds of the formula (I) wherein $R^1$-A-forms an acyl group $R^1$—CO— can be prepared by reacting a carboxylic acid of the formula $R^1$—$CO_2$H or an activated derivative thereof with an appropriately substituted 4-amino-pyrazole as shown in Scheme 1.

give the 4-nitro-amide (XI). The coupling reaction between the carboxylic acid (X) and the amine is preferably carried out in the presence of a reagent of the type commonly used in the formation of peptide linkages. Examples of such reagents include 1,3-dicyclohexylcarbodiimide (DCC) (Sheehan et al, *J. Amer. Chem Soc.* 1955, 77, 1067), 1-ethyl-3-(3'-dimethylaminopropyl)-carbodiimide (referred to herein either as EDC or EDAC but also known in the art as EDCI and WSCDI) (Sheehan et al, *J. Org. Chem.*, 1961, 26, 2525), uronium-based coupling agents such as O-(7-azabenzotriazol-1-yl)-N,N,N',N'-tetramethyluronium hexafluorophosphate (HATU) and phosphonium-based coupling agents such as 1-benzo-triazolyloxytris-(pyrrolidino)phosphonium hexafluorophosphate (PyBOP) (Castro et al, *Tetrahedron Letters,* 1990, 31, 205). Carbodiimide-based coupling agents are advantageously used in combination with 1-hydroxy-7-azabenzotriazole (HOAt) (L. A. Carpino, *J. Amer. Chem. Soc.,* 1993, 115, 4397) or 1-hydroxybenzotriazole (HOBt) (Konig et al, *Chem. Ber.,* 103, 708, 2024-2034). Preferred coupling reagents include EDC (EDAC) and DCC in combination with HOAt or HOBt.

The coupling reaction is typically carried out in a non-aqueous, non-protic solvent such as acetonitrile, dioxan, dimethylsulphoxide, dichloromethane, dimethylformamide or N-methylpyrrolidine, or in an aqueous solvent optionally together with one or more miscible co-solvents. The reaction can be carried out at room temperature or, where the reactants are less reactive (for example in the case of electron-poor anilines bearing electron withdrawing groups such as sulphonamide groups) at an appropriately elevated temperature. The reaction may be carried out in the presence of a non-interfering base, for example a tertiary amine such as triethylamine or N,N-diisopropylethylamine.

As an alternative, a reactive derivative of the carboxylic acid, e.g. an anhydride or acid chloride, may be used. Reaction with a reactive derivative such an anhydride is typically

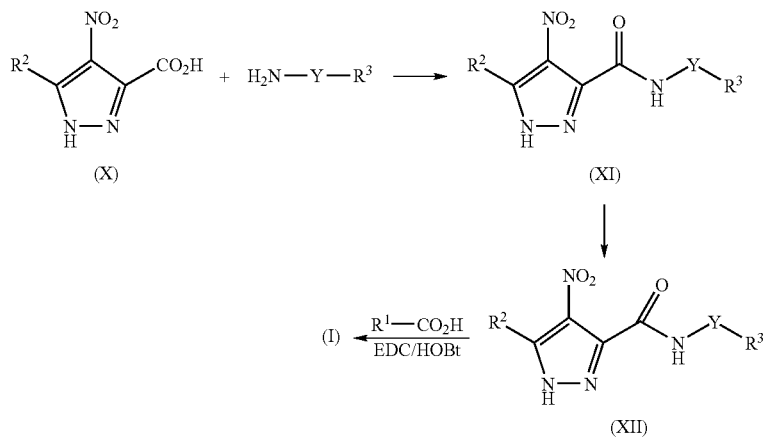

The starting material for the synthetic route shown in Scheme 1 is the 4-nitro-pyrazole-3-carboxylic acid (X) which can either be obtained commercially or can be prepared by nitration of the corresponding 4-unsubstituted pyrazole carboxy compound.

The 4-nitro-pyrazole carboxylic acid (X), or a reactive derivative thereof, is reacted with the amine $H_2N$—Y-$R^3$ to accomplished by stirring the amine and anhydride at room temperature in-the presence of a base such as pyridine.

Amines of the formula $H_2N$—Y-$R^3$ can be obtained from commercial sources or can be prepared by any of a large number of standard synthetic methods well known those skilled in the art, see for example see *Advanced Organic Chemistry* by Jerry March, $4^{th}$ Edition, John Wiley & Sons, 1992, and and *Organic Syntheses*, Volumes 1-8, John Wiley, edited by Jeremiah P. Freeman (ISBN: 0-471-31192-8), 1995, and see also the methods described in the experimental section below.

The nitro-pyrazole amide (XI) is reduced to give the corresponding 4-amino-compound of the formula (XII). The reduction may be carried out by standard methods such as catalytic hydrogenation, for example in the presence of palladium on carbon in a polar solvent such as ethanol or dimethylformamide at room temperature. As an alternative, reduction may be effected using a reducing agent such as tin (II) chloride in ethanol, typically with heating, for example to the reflux temperature of the solvent.

The 4-amino-pyrazole compound (XII) is then reacted with a carboxylic acid of the formula $R^1$—$CO_2H$, or a reactive derivative thereof, using the methods and conditions described above for the formation of the amide (XI), to give a compound of the formula (I).

Carboxylic acids of the formula $R^1$—$CO_2H$ can be obtained commercially or can be synthesised according to methods well known to the skilled person, see for example *Advanced Organic Chemistry* and *Organic Syntheses*, the details for which are given above.

Compounds of the formula (I) in which X is a group $R^1$-A-$NR^4$, where A is a bond, can be prepared from the 4-amino compounds of the formula (XII) by a number of methods. Reductive amination with an appropriately substituted aldehyde or ketone can be carried out in the presence of variety of reducing agents (see *Advanced Organic Chemistry* by Jerry March, 4$^{th}$ Edition, John Wiley & Sons, 1992, pp 898-900. For example, reductive amination can be carried out in the presence of sodium triacetoxyborohydride in the presence of an aprotic solvent such as dichloromethane at or near ambient temperatures.

Compounds in which X is a group $R^1$-A-$NR^4$ where A is a bond can also be prepared by the reaction of the 4-amino pyrazole compound (XII) with a compound of the formula $R^1$-L in a nucleophilic displacement reaction where L is a leaving group such as a halogen.

In an alternative synthetic route, compounds of the formula (I) can be prepared by reaction of a compound of the formula (XIII) with a compound of the formula $R^3$—Y—$NH_2$. The reaction can be carried out using the amide coupling conditions described above.

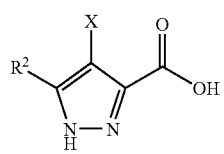

(XIII)

Compounds of the formula (I) where A is NH(C=O) can be prepared using standard methods for the synthesis of ureas. For example, such compounds can be prepared by reacting an aminopyrazole compound of the formula (XII) with a suitably substituted phenylisocyanate in a polar solvent such as DMF. The reaction is conveniently carried out at room temperature.

Compounds of the formula (I) where A is O(C=O) can be made using standard methods for the synthesis of carbamates, for example by reaction of an amino pyrazole compound of the formula (XII) with a chloroformate derivative of the formula $R^1$—O—C(O)—Cl under conditions well known to the skilled person.

Compounds of the formula (I), wherein A is $SO_2$, can be prepared from amino-compounds of the formula (XII) by standard methods for the formation of sulphonamides. For example, compounds of the formula XII) can be reacted with sulphonyl chlorides of the formula $R^1SO_2Cl$ or anhydrides of the formula $(R^1SO_2)_2O$. The reaction is typically carried out in an aprotic solvent such as acetonitrile or a chlorinated hydrocarbon (for example dichloromethane) in the presence of a non-interfering base such as a tertiary amine (e.g. triethylamine) or pyridine, or diisopropylethyl amine (Hunigs base). Alternatively, where the base is a liquid, as is the case with pyridine, the base itself may be used as the solvent for the reaction.

Compounds wherein X is a 5- or 6-membered ring containing a carbon atom ring member linked to the pyrazole group can be prepared by the sequence of reactions set out in Scheme 2.

As shown in Scheme 2, an aldehyde (XIV) (in which X is a C-linked aryl or heteroaryl group such as phenyl) is condensed with malononitrile to give the alkyne (XVI). The reaction is typically carried out in a polar solvent such as ethanol in the presence of a base such as piperidine, usually with heating. The alkyne (XVI) is then reacted with trimethylsilyldiazomethane in the presence an alkyl lithium such as butyl lithium to give the 5-trimethylsilyl pyrazole-3-nitrile (XVII). The reaction is carried out in a dry aprotic solvent such as THF under a protective atmosphere (e.g. nitrogen) at a reduced temperature (e.g. −78° C.).

The nitrile (XVII) is hydrolysed with an alkali metal hydroxide such as potassium hydroxide to give the acid (XIX) and/or the amide (XVII). Where a mixture of acid and amide are formed, they may be separated according to standard methods such as chromatography. The acid (XIX) can then be coupled with an amine of the formula $R^3$—Y—$NH_2$ under typical amide coupling conditions of the type described above to give the compound of the formula (I).

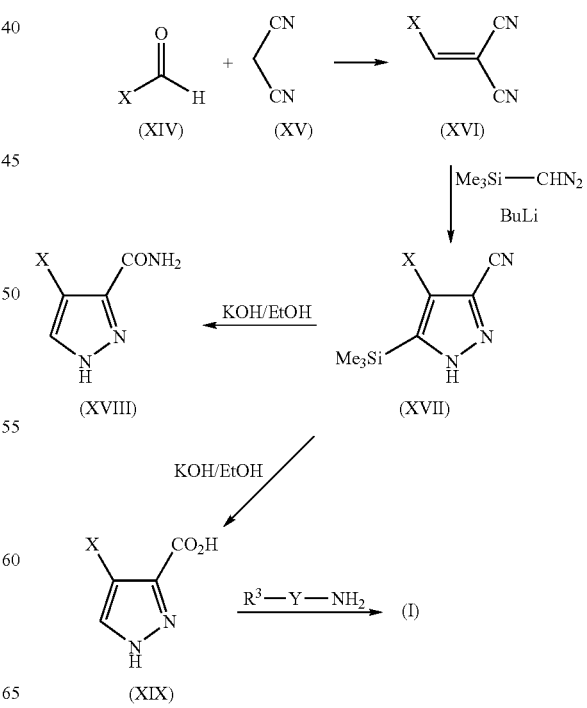

Alternatively, compounds of the formula (I) in which X is a C-linked aryl or heteroaryl group such as phenyl can be prepared from compounds of the formula (XX):

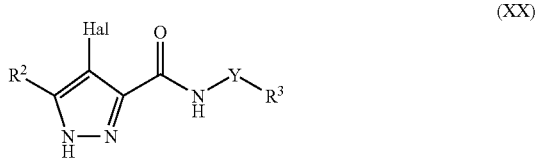

(XX)

where "Hal" is a halogen such as chlorine, bromine or iodine, by means of a Suzuki coupling reaction with the appropriate aryl or heteroaryl boronate. The reaction can be carried out under typical Suzuki Coupling conditions in the presence of a palladium catalyst such as bis(tri-t-butylphosphine)palladium and a base (e.g. a carbonate such as potassium carbonate). The reaction may be carried out in an aqueous solvent system, for example aqueous ethanol, and the reaction mixture is typically subjected to heating, for example to a temperature in excess of 100° C.

Compounds of the formula (XX) can be prepared from amino-pyrazole compounds of the formula (XII) by means of the Sandmeyer reaction (see *Advanced Organic Chemistry*, 4$^{th}$ edition, by Jerry March, John Wiley & Sons, 1992, page 723) in which the amino group is converted to a diazonium group by reaction with nitrous acid, and the diazonium compound is then reacted with a copper (I) halide such as Cu(I)Cl or Cu(I)I.

Once formed, one compound of the formula (I) may be transformed into another compound of the formula (I) using standard chemistry procedures well known in the art. For examples of functional group interconversions, see for example, *Fiesers' Reagents for Organic Synthesis*, Volumes 1-17, John Wiley, edited by Mary Fieser (ISBN: 0-471-58283-2), and *Organic Syntheses*, Volumes 1-8, John Wiley, edited by Jeremiah P. Freeman (ISBN: 0-471-31192-8), 1995.

The starting materials for the synthetic routes shown in the Schemes above, e.g. the pyrazoles of formula (X), can either be obtained commercially or can be prepared by methods known to those skilled in the art. They can be obtained using known methods e.g. from ketones, such as in a process described in EP308020 (Merck), or the methods discussed by Schmidt in *Helv. Chim. Acta.*, 1956, 39, 986-991 and *Helv. Chim. Acta.*, 1958, 41, 306-309. Alternatively they can be obtained by conversion of a commercially available pyrazole, for example those containing halogen, nitro, ester, or amide functionalities, to pyrazoles containing the desired functionality by standard methods known to a person skilled in the art. For example, in 3-carboxy-4-nitropyrazole, the nitro group can be reduced to an amine by standard methods. 4-Nitropyrazole-3-carboxylic acid (XII) can either be obtained commercially or can be prepared by nitration of the corresponding 4-unsubstituted pyrazole carboxy compound, and pyrazoles containing a halogen, may be utilized in coupling reactions with tin or palladium chemistry.

Protecting Groups

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

A hydroxy group may be protected, for example, as an ether (—OR) or an ester (—OC(=O)R), for example, as: a t-butyl ether; a tetrahydropyranyl (THP) ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

An aldehyde or ketone group may be protected, for example, as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

An amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz or NH-Z); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), or as a 2(-phenylsulphonyl)ethyloxy amide (—NH-Psec).

For example, in Scheme 1 above, when the moiety R$^3$ in the amine H$_2$N—Y-R$^3$ contains a second amino group, such as a cyclic amino group (e.g. a piperidine or pyrrolidine group), the second amino group can be protected by means of a protecting group as hereinbefore defined, one preferred group being the tert-butyloxycarbonyl (Boc) group. Where no subsequent modification of the second amino group is required, the protecting group can be carried through the reaction sequence to give an N-protected form of a compound of the formula (I) which can then be de-protected by standard methods (e.g. treatment with acid in the case of the Boc group) to give the compound of formula (I).

Other protecting groups for amines, such as cyclic amines and heterocyclic N—H groups, include toluenesulphonyl (tosyl) and methanesulphonyl (mesyl) groups, benzyl groups such as a para-methoxybenzyl (PMB) group and tetrahydropyranyl (THP) groups.

A carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$alkyl ester; or a C$_{5-20}$ aryl-C$_{1-7}$ alkyl ester (e.g., a benzyl ester; a nitrobenzyl ester); or as an amide, for example, as a methyl amide. A thiol group may be protected, for example, as a thioether (—SR), for example, as: a benzyl thioether; an acetamidomethyl ether (—S—CH$_2$NHC(=O)CH$_3$).

Isolation and Purification of the Compounds of the Invention

The compounds of the invention can be isolated and purified according to standard techniques well known to the person skilled in the art. One technique of particular usefulness in purifying the compounds is preparative liquid chromatography using mass spectrometry as a means of detecting the purified compounds emerging from the chromatography column.

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.*; 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.*; 2003; 5(3); 322-9.

An example of such a system for purifying compounds via preparative LC-MS is described below in the Examples section of this application (under the heading "Mass Directed Purification LC-MS System"). However, it will be appreciated that alternative systems and methods to those described could be used. In particular, normal-phase preparative LC based methods might be used in place of the reverse phase methods described here. Most preparative LC-MS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described below could alternatively be used to purify the compounds.

Pharmaceutical Formulations

While it is possible for the active compound to be administered alone, it is preferable to present it as a pharmaceutical composition (e.g. formulation) comprising at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Accordingly, in a further aspect, the invention provides compounds of the formula (0) and sub-groups thereof such as formulae (I⁰), (I), (Ia), (Ib), (II), (III), (IV), (IVa), (Va), (Vb), (VIa), (VIb), (VII) or (VIII) and sub-groups thereof as defined herein in the form of pharmaceutical compositions.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery.

In one preferred embodiment of the invention, the pharmaceutical composition is in a form suitable for i.v. administration, for example by injection or infusion.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formula (I) can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the inventions will generally be presented in unit dosage form and, as such, will typically contain sufficient compound to provide a desired level of biological activity. For example, a formulation intended for oral administration may contain from 0.1 milligrams to 2 grams of active ingredient, more usually from 10 milligrams to 1 gram, for example, 50 milligrams to 500 milligrams.

The active compound will be administered to a patient in need thereof (for example a human or animal patient) in an amount sufficient to achieve the desired therapeutic effect.

Methods of Treatment

It is envisaged that the compounds of the formula (0) and sub-groups thereof such as formulae (I$^0$), (I), (Ia), (Ib), (II), (III), (IV), (IVa), (Va), (Vb), (VIa), (VIb), (VII) or (VIII) and sub-groups thereof as defined herein will be useful in the prophylaxis or treatment of a range of disease states or conditions mediated by cyclin dependent kinases. Examples of such disease states and conditions are set out above.

The compounds are generally administered to a subject in need of such administration, for example a human or animal patient, preferably a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a pulsatile or continuous manner.

A typical daily dose of the compound can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams) per kilogram of bodyweight although higher or lower doses may be administered where required. Ultimately, the quantity of compound administered and the type of composition used will be commensurate with the nature of the disease or physiological condition being treated and will be at the discretion of the physician.

The compounds of the formula (I) can be administered as the sole therapeutic agent or they can be administered in combination therapy with one of more other compounds for treatment of a particular disease state, for example a neoplastic disease such as a cancer as hereinbefore defined. Examples of other therapeutic agents that may be administered together (whether concurrently or at different time intervals) with the compounds of the formula (I) include but are not limited to topoisomerase inhibitors, alkylating agents, antimetabolites, DNA binders and microtubule inhibitors (tubulin targeting agents), such as cisplatin, cyclophosphamide, doxorubicin, irinotecan, fludarabine, 5FU, taxanes, mitomycin C, or radiotherapy. Alternatively, the compounds of the formula (I) can be administered in a combination therapy with monoclonal antibodies or signal transduction inhibitors. For the case of CDK inhibitors combined with other therapies, the two or more treatments may be given in individually varying dose schedules and via different routes.

Where the compound of the formula (I) is administered in combination therapy with one, two, three, four or more other therapeutic agents (preferably one or two, more preferably one), the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery and controlled diets.

For use in combination therapy with another chemotherapeutic agent, the compound of the formula (I) and one, two, three, four or more other therapeutic agents can be, for example, formulated together in a dosage form containing two, three, four or more therapeutic agents. In an alternative, the individual therapeutic agents may be formulated separately and presented together in the form of a kit, optionally with instructions for their use.

A person skilled in the art would know through their common general knowledge the dosing regimes and combination therapies to use.

Methods of Diagnosis

Prior to administration of a compound of the formula (I), a patient may be screened to determine whether a disease or condition from which the patient is or may be suffering is one which would be susceptible to treatment with a compound having activity against cyclin dependent kinases.

For example, a biological sample taken from a patient may be analysed to determine whether a condition or disease, such as cancer, that the patient is or may be suffering from is one which is characterised by a genetic abnormality or abnormal protein expression which leads to over-activation of CDKs or to sensitisation of a pathway to normal CDK activity. Examples of such abnormalities that result in activation or sensitisation of the CDK2 signal include up-regulation of cyclin E, (Harwell R M, Mull B B, Porter D C, Keyomarsi K.; J Biol Chem. Mar. 26, 2004;279(13):12695-705) or loss of p21 or p27, or presence of CDC4 variants (Rajagopalan H, Jallepalli P V, Rago C, Velculescu V E, Kinzler K W, Vogelstein B, Lengauer C.; Nature. Mar. 4, 2004;428(6978):77-81). The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of cyclin E, or loss of p21 or p27, or presence of CDC4 variants. The term diagnosis includes screening. By marker we include genetic markers including, for example, the measurement of DNA composition to identify mutations of CDC4. The term marker also includes markers which are characteristic of up regulation of cyclin E, including enzyme activity, enzyme levels, enzyme state (e.g. phosphorylated or not) and mRNA levels of the aforementioned proteins.

Tumours with upregulation of cyclin E, or loss of p21 or p27 may be particularly sensitive to CDK inhibitors. Tumours may preferentially be screened for upregulation of cyclin E, or loss of p21 or p27 prior to treatment. Thus, the patient may be subjected to a diagnostic test to detect a marker characteristic of up-regulation of cyclin E, or loss of p21 or p27. The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, or urine.

It has been found, Rajagopalan et al (Nature. Mar. 4, 2004; 428(6978):77-81), that there were mutations present in CDC4 (also known as Fbw7 or Archipelago) in human colorectal cancers and endometrial cancers (Spruck et al, Cancer Res. Aug. 15, 2002;62(16):4535-9). Identification of individual carrying a mutation in CDC4 may mean that the patient would be particularly suitable for treatment with a CDK inhibitor. Tumours may preferentially be screened for presence of a CDC4 variant prior to treatment. The screening process will typically involve direct sequencing, oligonucleotide microarray analysis, or a mutant specific antibody.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridisation.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, 3$^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of cyclin E, or loss of p21 or p27, or detection of CDC4 variants could be applicable in the present case.

Therefore all of these techniques could also be used to identify tumours particularly suitable for treatment with CDK inhibitors. Patients with mantle cell lymphoma (MCL) could be selected for treatment with a CDK inhibitor using diagnostic tests outlined herein. MCL is a distinct clinicopathologic entity of non-Hodgkin's lymphoma, characterized by proliferation of small to medium-sized lymphocytes with co-expression of CD5 and CD20, an aggressive and incurable clinical course, and frequent t(11;14)(q13;q32) translocation. Over-expression of cyclin D1 mRNA, found in mantle cell lymphoma (MCL), is a critical diagnostic marker. Yatabe et al (Blood. Apr. 1, 2000; 95(7):2253-61) proposed that cyclin D1-positivity should be included as one of the standard criteria for MCL, and that innovative therapies for this incurable disease should be explored on the basis of the new criteria. Jones et al (J Mol Diagn. 2004 May; 6(2):84-9) developed a real-time, quantitative, reverse transcription PCR assay for cyclin D1 (CCND1) expression to aid in the diagnosis of mantle cell lymphoma (MCL). Howe et al (Clin Chem. 2004 January; 50(1):80-7) used real-time quantitative RT-PCR to evaluate cyclin D1 mRNA expression and found that quantitative RT-PCR for cyclin D1 mRNA normalized to CD19 mRNA can be used in the diagnosis of MCL in blood, marrow, and tissue.

Alternatively, patients with breast cancer could be selected for treatment with a CDK inhibitor using diagnostic tests outline above. Tumour cells commonly overexpress cyclin E and it has been shown that cyclin E is over-expressed in breast cancer (Harwell et al, Cancer Res, 2000, 60, 481-489). Therefore breast cancer may in particular be treated with a CDK inhibitor.

Antifungal Use

In a further aspect, the invention provides the use of the compounds of the formulae (0), (I$^0$), (I), (Ia), (Ib), (II), (III), (IV), (IVa), (Va), (Vb), (VIa), (VIb), (VII) or (VIII) and sub-groups thereof as defined herein as antifungal agents.

The compounds may be used in animal medicine (for example in the treatment of mammals such as humans), or in the treatment of plants (e.g. in agriculture and horticulture), or as general antifungal agents, for example as preservatives and disinfectants.

In one embodiment, the invention provides a compound of the formula (0) and sub-groups thereof such as formulae (I$^0$), (I), (Ia), (Ib), (II), (III), (IV), (IVa), (Va), (Vb), (VIa), (VIb), (VII) or (VIII) and sub-groups thereof as defined herein for use in the prophylaxis or treatment of a fungal infection in a mammal such as a human.

Also provided is the use of a compound of the formula (0) and sub-groups thereof such as formulae ($I^0$), (I), (Ia), (Ib), (II), (III), (IV), (IVa), (Va), (Vb), (VIa), (VIb), (VII) or (VIII) and sub-groups thereof as defined herein for the manufacture of a medicament for use in the prophylaxis or treatment of a fungal infection in a mammal such as a human.

For example, compounds of the invention may be administered to human patients suffering from, or at risk of infection by, topical fungal infections caused by among other organisms, species of *Candida, Trichophyton, Microsporum* or *Epidermophyton*, or in mucosal infections caused by *Candida albicans* (e.g. thrush and vaginal candidiasis). The compounds of the invention can also be administered for the treatment or prophylaxis of systemic fungal infections caused by, for example, *Candida albicans, Cryptococcus neoformans, Aspergillus flavus, Aspergillus fumigatus, Coccidiodies, Paracoccidioides, Histoplasma* or *Blastomyces*.

In another aspect, the invention provides an antifungal composition for agricultural (including horticultural) use, comprising a compound of the formula ($I^0$) and sub-groups thereof such as formulae (I), (Ia), (Ib), (II), (III), (IV), (V), (VI) and (VII) as hereinbefore defined together with an agriculturally acceptable diluent or carrier.

The invention further provides a method of treating an animal (including a mammal such as a human), plant or seed having a fungal infection, which comprises treating said animal, plant or seed, or the locus of said plant or seed, with an effective amount of a compound of the formula ($I^0$) and sub-groups thereof such as formulae (I), (Ia), (Ib), (II), (III), (IV), (V), (VI) and (VII) as hereinbefore defined.

The invention also provides a method of treating a fungal infection in a plant or seed which comprises treating the plant or seed with an antifungally effective amount of a fungicidal composition as hereinbefore defined.

Differential screening assays may be used to select for those compounds of the present invention with specificity for non-human CDK enzymes. Compounds which act specifically on the CDK enzymes of eukaryotic pathogens can be used as anti-fungal or anti-parasitic agents. Inhibitors of the Candida CDK kinase, CKSI, can be used in the treatment of candidiasis. Antifungal agents can be used against infections of the type hereinbefore defined, or opportunistic infections that commonly occur in debilitated and immunosuppressed patients such as patients with leukemias and lymphomas, people who are receiving immunosuppressive therapy, and patients with predisposing conditions such as diabetes mellitus or AIDS, as well as for non-immunosuppressed patients.

Assays described in the art can be used to screen for agents which may be useful for inhibiting at least one fungus implicated in mycosis such as candidiasis, aspergillosis, mucormycosis, blastomycosis, geotrichosis, cryptococcosis, chromoblastomycosis, coccidiodomycosis, conidiosporosis, histoplasmosis, maduromycosis, rhinosporidosis, nocaidiosis, para-actinomycosis, penicilliosis, monoliasis, or sporotrichosis. The differential screening assays can be used to identify anti-fungal agents which may have therapeutic value in the treatment of aspergillosis by making use of the CDK genes cloned from yeast such as *Aspergillus fumigatus, Aspergillus flavus, Aspergillus niger, Aspergillus nidulans*, or *Aspergillus terreus*, or where the mycotic infection is muconnycosis, the CDK assay can be derived from yeast such as *Rhizopus arrhizus, Rhizopus oryzae, Absidia corymbifera, Absidia ramosa*, or *Mucorpusillus*. Sources of other CDK enzymes include the pathogen *Pneumocystis carinii*.

By way of example, in vitro evaluation of the antifungal activity of the compounds can be performed by determining the minimum inhibitory concentration (M.I.C.) which is the concentration of the test compounds, in a suitable medium, at which growth of the particular microorganism fails to occur. In practice, a series of agar plates, each having the test compound incorporated at a particular concentration is inoculated with a standard culture of, for example, Candida albicans and each plate is then incubated for an appropriate period at 37° C. The plates are then examined for the presence or absence of growth of the fungus and the appropriate M.I.C. value is noted The in vivo evaluation of the compounds can be carried out at a series of dose levels by intraperitoneal or intravenous injection or by oral administration, to mice that have been inoculated with a fungus, e.g., a strain of *Candida albicans* or *Aspergillus flavus*. The activity of the compounds can be assessed on the basis of the survival of a treated group of mice after the death of an untreated group of mice. The activity may be measured in terms of the dose level at which the compound provides 50% protection against the lethal effect of the infection ($PD_{50}$).

For human antifungal use, the compounds can be administered alone or in admixture with a pharmaceutical carrier selected in accordance with the intended route of administration and standard pharmaceutical practice. Thus, for example, they may be administered orally, parenterally, intravenously, intramuscularly or subcutaneously by means of the formulations described above in the section headed "Pharmaceutical Formulations".

For oral and parenteral administration to human patients, the daily dosage level of the antifungal compounds of the invention can be from 0.01 to 10 mg/kg (in divided doses), depending on inter alia the potency of the compounds when administered by either the oral or parenteral route. Tablets or capsules of the compounds may contain, for example, from 5 mg. to 0.5 g of active compound for administration singly or two or more at a time as appropriate. The physician in any event will determine the actual dosage (effective amount) which will be most suitable for an individual patient and it will vary with the age, weight and response of the particular patient.

Alternatively, the antifungal compounds can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

In addition to the therapeutic uses described above, antifungal agents developed with such differential screening assays can be used, for example, as preservatives in foodstuff, feed supplement for promoting weight gain in livestock, or in disinfectant formulations for treatment of non-living matter, e.g., for decontaminating hospital equipment and rooms. In similar fashion, side by side comparison of inhibition of a mammalian CDK and an insect CDK, such as the Drosophilia CDK5 gene (Hellmich et al. (1994) FEBS Lett 356:317-21), will permit selection amongst the compounds herein of inhibitors which discriminate between the human/mammalian and insect enzymes. Accordingly, the present invention expressly contemplates the use and formulations of the compounds of the invention in insecticides, such as for use in management of insects like the fruit fly.

In yet another embodiment, certain of the subject CDK inhibitors can be selected on the basis of inhibitory specificity for plant CDK's relative to the mammalian enzyme. For example, a plant CDK can be disposed in a differential screen with one or more of the human enzymes to select those compounds of greatest selectivity for inhibiting the plant enzyme. Thus, the present invention specifically contemplates formulations of the subject CDK inhibitors for agricultural applications, such as in the form of a defoliant or the like.

For agricultural and horticultural purposes the compounds of the invention may be used in the form of a composition formulated as appropriate to the particular use and intended purpose. Thus the compounds may be applied in the form of dusting powders, or granules, seed dressings, aqueous solutions, dispersions or emulsions, dips, sprays, aerosols or smokes. Compositions may also be supplied in the form of dispersible powders, granules or grains, or concentrates for dilution prior to use. Such compositions may contain such conventional carriers, diluents or adjuvants as are known and acceptable in agriculture and horticulture and they are manufactured in accordance with conventional procedures. The compositions may also incorporate other active ingredients, for example, compounds having herbicidal or insecticidal activity or a further fungicide. The compounds and compositions can be applied in a number of ways, for example they can be applied directly to the plant foliage, stems, branches, seeds or roots or to the soil or other growing medium, and they may be used not only to eradicate disease, but also prophylactically to protect the plants or seeds from attack. By way of example, the compositions may contain from 0.01 to 1 wt. % of the active ingredient. For field use, likely application rates of the active ingredient may be from 50 to 5000 g/hectare.

The invention also contemplates the use of the compounds of the formula (0) and sub-groups thereof such as formulae (I$^0$), (I), (Ia), (Ib), (II), (III), (IV), (IVa), (Va), (Vb), (VIa), (VIb), (VII) or (VIII) and sub-groups thereof as defined herein in the control of wood decaying fungi and in the treatment of soil where plants grow, paddy fields for seedlings, or water for perfusion. Also contemplated by the invention is the use of the compounds of the formula (0) and sub-groups thereof such as formulae (I$^0$), (I), (Ia), (Ib), (II), (III), (IV), (IVa), (Va), (Vb), (VIa), (VIb), (VII) or (VIII) and sub-groups thereof as defined herein to protect stored grain and other non-plant loci from fungal infestation.

EXAMPLES

The invention will now be illustrated, but not limited, by reference to the specific embodiments described in the following examples.

In the examples, the compounds prepared were characterised by liquid chromatography and mass spectroscopy (LC-MS) using the system and operating conditions set out below. Where chlorine is present and a single mass is quoted, the mass quoted for the compound is for $^{35}$Cl. The two systems were equipped with identical chromatography columns and were set up to run under the same operating conditions. The operating conditions used are also described below. In the examples, the retention times are given in minutes.

Platform System

| | |
|---|---|
| System: | Waters 2790/Platform LC |
| Mass Spec Detector: | Micromass Platform LC |
| PDA Detector: | Waters 996 PDA |
| Analytical conditions: | |
| Eluent A: | 5% CH3CN in 95% H$_2$O (0.1% Formic Acid) |
| Eluent B: | CH$_3$CN (0.1% Formic Acid) |
| Gradient: | 10-95% eluent B |
| Flow: | 1.2 ml/min |
| Column: | Synergi 4 μm Max-RP C$_{12}$, 80A, 50 × 4.6 mm (Phenomenex) |
| MS conditions: | |
| Capillary voltage: | 3.5 kV |
| Cone voltage: | 30 V |
| Source Temperature: | 120° C. |

FractionLynx System

| | |
|---|---|
| System: | Waters FractionLynx (dual analytical/prep) |
| Mass Spec Detector: | Waters-Micromass ZQ |
| PDA Detector: | Waters 2996 PDA |
| Analytical conditions: | |
| Eluent A: | H$_2$O (0.1% Formic Acid) |
| Eluent B: | CH$_3$CN (0.1% Formic Acid) |
| Gradient: | 5-95% eluent B |
| Flow: | 1.5 ml/min |
| Column: | Synergi 4 μm Max-RP C$_{12}$, 80A, 50 × 4.6 mm (Phenomenex) |
| MS conditions: | |
| Capillary voltage: | 3.5 kV |
| Cone voltage: | 30 V |
| Source Temperature: | 120° C. |
| Desolvation Temperature: | 300° C. |

Analytical LC-MS System

Several systems were used, as described below, and these were equipped with were set up to run under closely similar operating conditions. The operating conditions used are also described below.

| | |
|---|---|
| HPLC System: | Waters 2795 |
| Mass Spec Detector: | Micromass Platform LC |
| PDA Detector: | Waters 2996 PDA |
| Acidic Analytical conditions: | |
| Eluent A: | H$_2$O (0.1% Formic Acid) |
| Eluent B: | CH$_3$CN (0.1% Formic Acid) |
| Gradient: | 5-95% eluent B over 3.5 minutes |
| Flow: | 0.8 ml/min |
| Column: | Phenomenex Synergi 4μ MAX-RP 80A, 2.0 × 50 mm |
| Basic Analytical conditions: | |
| Eluent A: | H$_2$O (10 mM NH$_4$HCO$_3$ buffer adjusted to pH = 9.5 with NH$_4$OH) |
| Eluent B: | CH$_3$CN |
| Gradient: | 05-95% eluent B over 3.5 minutes |
| Flow: | 0.8 ml/min |
| Column: | Thermo Hypersil-Keystone BetaBasic-18 5 μm 2.1 × 50 mm |
| or | |
| Column: | Phenomenex Luna C18(2) 5 μm 2.0 × 50 mm |
| Polar Analytical conditions: | |
| Eluent A: | H$_2$O (0.1% Formic Acid) |
| Eluent B: | CH$_3$CN (0.1% Formic Acid) |
| Gradient: | 00-50% eluent B over 3 minutes |
| Flow: | 0.8 ml/min |
| Column: | Thermo Hypersil-Keystone HyPurity Aquastar, 5μ, 2.1 × 50 mm |
| or | |

-continued

| | |
|---|---|
| HPLC System: | Waters 2795 |
| Mass Spec Detector: | Micromass Platform LC |
| PDA Detector: | Waters 2996 PDA |
| Column: | Phenomenex Synergi 4μ MAX-RP 80A, 2.0 × 50 mm or |
| Longer Analytical conditions: | |
| Eluent A: | H₂O (0.1% Formic Acid) |
| Eluent B: | CH₃CN (0.1% Formic Acid) |
| Gradient: | 05-95% eluent B over 15 minutes |
| Flow: | 0.4 ml/min |
| Column: | Phenomenex Synergi 4μ MAX-RP 80A, 2.0 × 150 mm |
| MS conditions: | |
| Capillary voltage: | 3.6 kV |
| Cone voltage: | 30 V |
| Source Temperature: | 120° C. |
| Scan Range: | 165-700 amu |
| Ionisation Mode: | ElectroSpray Positive or ElectroSpray Negative or ElectroSpray Positive & Negative |

Mass Directed Purification LC-MS System

The following preparative chromatography systems can be used to purify the compounds of the invention.

Hardware:
 Waters Fractionlynx system:
 2767 Dual Autosampler/Fraction Collector
 2525 preparative pump
 CFO (column fluidic organiser) for column selection
 RMA (Waters reagent manager) as make up pump
 Waters ZQ Mass Spectrometer
 Waters 2996 Photo Diode Array detector Software: Masslynx 4.0

Columns:
 1. Low pH chromatography: Phenomenex Synergy MAX-RP, 10μ, 150×15 mm (alternatively used same column type with 100×21.2 mm dimensions).
 2. High pH chromatography: Phenomenex Luna C18 (2), 10 μ, 100×21.2 mm (alternatively used Thermo Hypersil Keystone BetaBasic C18, 5 μ, 100×21.2 mm)

Eluents:
 1. Low pH chromatography:
 Solvent A: H₂O+0.1% Formic Acid, pH 1.5
 Solvent B: CH₃CN+0.1% Formic Acid
 2. High pH chromatography:
 Solvent A: H₂O+10 mM NH₄HCO₃+NH₄OH, pH 9.5
 Solvent B: CH₃CN
 3. Make up solvent: MeOH+0.1% formic acid (for both chromatography type)

Methods:
 Prior to using preparative chromatography to isolate and purify the product compounds, analytical LC-MS (see above) can first be used to determine the most appropriate conditions for preparative chromatography. A typical routine is to run an analytical LC-MS using the type of chromatography (low or high pH) most suited for compound structure. Once the analytical trace shows good chromatography, a suitable preparative method of the same type can be chosen. Typical running condition for both low and high pH chromatography methods are:
 Flow rate: 24 ml/min
 Gradient: Generally all gradients have an initial 0.4 min step with 95% A+5% B. Then according to analytical trace a 3.6 min gradient is chosen in order to achieve good separation (e.g. from 5% to 50% B for early retaining compounds; from 35% to 80% B for middle retaining compounds and so on)
 Wash: 1 minute wash step is performed at the end of the gradient
 Re-equilibration: A 2.1 minute re-equilibration step is carried out to prepare the system for the next run
 Make Up flow rate: 1 ml/min
 Solvent:
 All compounds were usually dissolved in 100% MeOH or 100% DMSO
 MS Running Conditions:
 Capillary voltage: 3.2 kV
 Cone voltage: 25 V
 Source Temperature: 120° C.
 Multiplier: 500 V
 Scan Range: 125-800 amu
 Ionisation Mode: ElectroSpray Positive
 The starting materials for each of the Examples are commercially available unless otherwise specified.

Example 1

4-Amino-1H-pyrazole-3-carboxylic acid phenylamide 1A. 4-Nitro-1H-pyrazole-3-carboxylic acid phenylamide

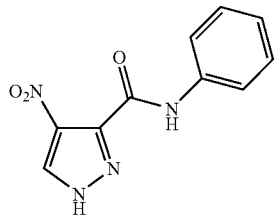

4-Nitropyrazole-3-carboxylic acid (2.5 g; 15.9 mmol) was added to a stirred solution of aniline (1.6 ml; 17.5 mmol), EDC (3.7 g; 19.1 mmol), and HOBt (2.6 g; 19.1 mmol) in N,N-dimethylformamide (DMF) (25 ml), then stirred at room temperature overnight. The solvent was removed by evaporation under reduced pressure and the residue triturated with ethyl acetate/saturated NaHCO₃ solution. The resultant solid was collected by filtration, washed with water and diethyl ether then dried under vacuum to give 2.85 g of the title compound (sodium salt) as a yellow/brown solid. (LC/MS: $R_t$ 2.78, [M+H]⁺232.95).

1B. 4-Amino-1H-pyrazole-3-carboxylic acid phenylamide

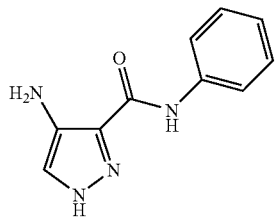

4-Nitro-1H-pyrazole-3-carboxylic acid phenylamide (100 mg; 0.43 mmol) was dissolved in ethanol (5 ml), treated with tin (II) chloride dihydrate (500 mg; 2.15 mmol) then heated at reflux overnight. The reaction mixture was cooled and evaporated. The residue was partitioned between ethyl acetate and brine, and the ethyl acetate layer was separated, dried (MgSO$_4$), filtered and evaporated. The crude product was purified by flash column chromatography eluting with 1:1 ethyl acetate /petroleum ether then 5% methanol/dichloromethane. Evaporation of product containing fractions followed by preparative LC/MS gave 15 mg of the product as an off white solid. (LC/MS: R$_t$ 1.40, [M+H]$^+$202.95).

Example 2

4-Acetylamino-1H-pyrazole-3-carboxylic acid (4-fluoro-phenyl)-amide 2A. 4-Nitro-1H-pyrazole-3-carboxylic acid (4-fluoro-phenyl)-amide

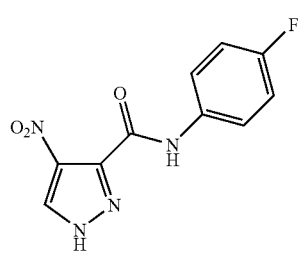

4-Nitropyrazole-3-carboxylic acid (10 g; 63.66 mmol) was added to a stirred solution of 4-fluoroaniline (6.7 ml; 70 mmol), EDC (14.6 g; 76.4 mmol), and HOBt (10.3 g; 76.4 mmol) in DMF (25 ml), then stirred at room temperature overnight. The solvent was removed by evaporation under reduced pressure and the residue triturated with ethyl acetate/saturated brine solution. The resultant yellow solid was collected by filtration, washed with 2M hydrochloric acid, then dried under vacuum to give 15.5 g of the title compound. (LC/MS: R$_t$ 2.92 [M+H]$^+$250.89).

2B. 4-Amino-1H-pyrazole-3-carboxylic acid (4-fluoro-phenyl)-amide

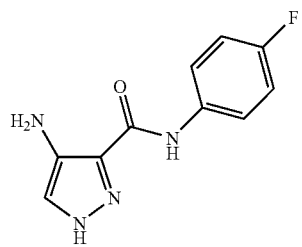

4-Nitro-1H-pyrazole-3-carboxylic acid (4-fluorophenyl)-amide (15 g) was dissolved in 200 ml of ethanol, treated with 1.5 g of 10% palladium on carbon under a nitrogen atmosphere, then hydrogenated at room temperature and pressure overnight. The catalyst was removed by filtration through Celite and the filtrate evaporated. The crude product was dissolved in acetone/water (100 ml:100 ml) and after slow evaporation of the acetone the product was collected by filtration as a brown crystalline solid (8.1 g). (LC/MS: R$_t$ 1.58, [M+H]$^+$220.95).

2C. 4-Acetylamino-1H-pyrazole-3-carboxlic acid (4-fluoro-phenyl)-amide

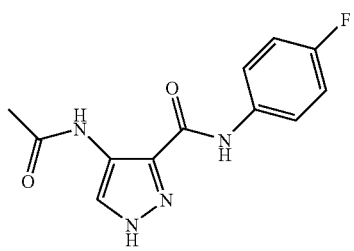

4-Amino-1H-pyrazole-3-carboxylic acid (4-fluorophenyl)-amide (500 mg; 2.27 mmol) was dissolved in 5 ml of pyridine, treated with acetic anhydride (240 μl, 2.5 mmol) then stirred at room temperature overnight. The solvent was removed by evaporation then dichloromethane (20 ml) and 2M hydrochloric acid (20 ml) were added. The undissolved solid was collected by filtration, washed with more dichloromethane and water then dried under vacuum. The product was isolated as an off white solid (275 mg). (LC/MS: R$_t$ 2.96, [M+H]$^+$262.91).

Example 3

4-(2,2,2-Trifluoro-acetylamino)-1H-pirazole-3-carboxylic acid (4-fluoro-phenyl)-amide

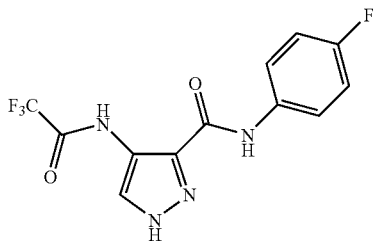

4-Amino-1H-pyrazole-3-carboxylic acid (4-fluorophenyl)-amide (Example 2B) (500 mg; 2.27 mmol) was dissolved in 5 ml of pyridine, treated with trifluoroacetic anhydride (320 μl, 2.5 mmol) then stirred at room temperature overnight. The solvent was removed by evaporation, the residue was partitioned between ethyl acetate (50 ml) and 2 M hydrochloric acid (50 ml), and the ethyl acetate layer was separated, washed with brine (50 ml), dried (MgSO$_4$), filtered and evaporated to give 560 mg of product as a brown solid. (LC/MS: [M+H]$^+$317).

Example 4

4-[(5-Oxo-pyrrolidine-2-carbonyl)-amino]-1H-pyrazole-3-carboxylic acid (4-fluoro-phenyl)-amide

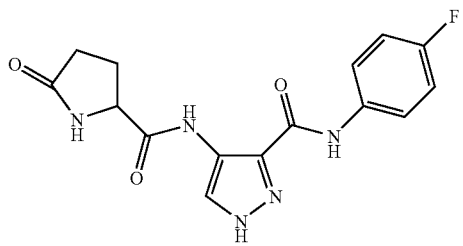

To a stirred solution of 4-amino-1H-pyrazole-3-carboxylic acid (4-fluorophenyl)-amide (Example 2B) (50 mg; 0.23 mmol), EDAC (52 mg; 0.27 mmol) and HOBt (37 mg; 0.27 mmol) in 5 ml of DMF was added 2-oxoproline (33 mg; 0.25 mmol), and the mixture was then left at room temperature overnight. The reaction mixture was evaporated and the residue purified by preparative LC/MS, to give 24 mg of the product as a white solid. (LC/MS: $R_t$ 2.27 [M+H]$^+$332).

Example 5

4-Phenylacetylamino-1H-pyrazole-3-carboxylic acid (4-fluoro-phenyl)-amide

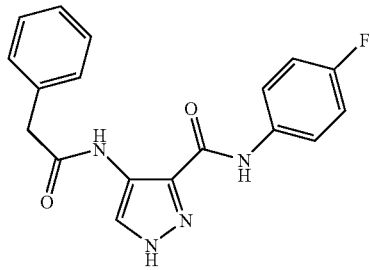

The reaction was carried out in a manner analogous to Example 4 but using phenylacetic acid (34 mg; 0.23 mmol) as the starting material. The title compound (14 mg) was isolated as a white solid. (LC/MS: $R_t$ 3.24 [M+H]$^+$339).

Example 6

4-(2-1H-Indol-3-yl-acetylamino)-1H-pyrazole-3-carboxylic acid (4-fluoro-phenyl)-amide

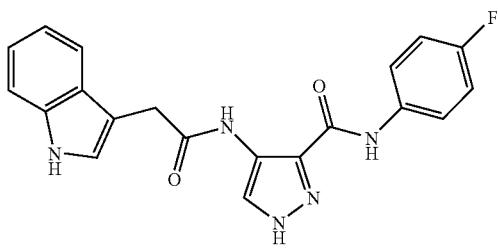

The reaction was carried out in a manner analogous to Example 4, but using indole-3-acetic acid (44 mg; 0.23 mmol) as the starting material. The title product (14 mg) was isolated as a white solid. (LC/MS: $R_t$ 3.05 [M+H]$^+$378).

Example 7

4-(2-Benzenesulphonyl-acetylamino)-1H-pyrazole-3-carboxylic acid (4-fluoro-phenyl)-amide

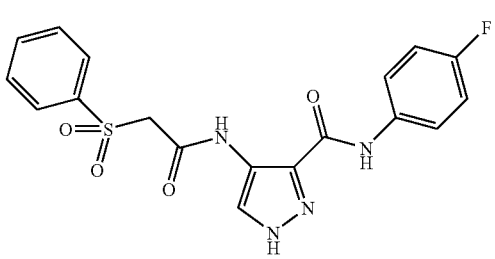

The reaction was carried out in a manner analogous to Example 4, but using 2-(phenylsulphonyl) acetic acid (50 mg; 0.23 mmol) as the starting material. The title compound (29 mg) was isolated as a white solid. (LC/MS: $R_t$ 3.00 [M+H]$^+$ 403).

Example 8

4-[2-(5-Amino-tetrazol-1-yl)-acetylamino]-1H-pyrazole-3-carboxylic acid (4-fluoro-phenyl)-amide

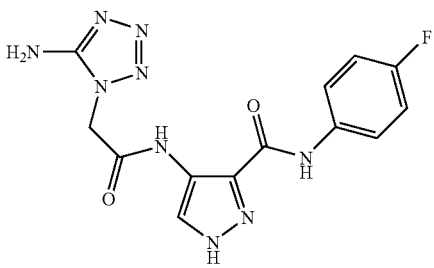

The reaction was carried out in a manner analogous to Example 4, but 5-aminotetrazole-1-acetic acid (36 mg; 0.23 mmol) was used as the starting material.

The title compound (23 mg) was isolated as a white solid. (LC/MS: $R_t$ 2.37 [M+H]$^+$346).

Example 9

N-[3-(4-Fluoro-phenylcarbamoyl)-1H-pyrazol-4-yl]-6-hydroxy-nicotinamide

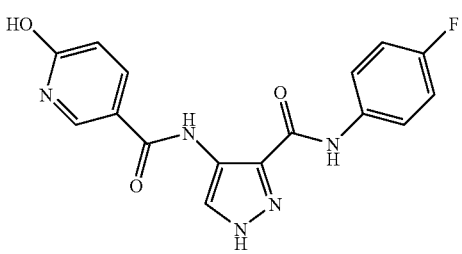

The reaction was carried out in a manner analogous to Example 4, but using 6-hydroxynicotinic acid (38 mg; 0.23 mmol) as the starting material. The title compound (17 mg) was isolated as a white solid. (LC/MS: $R_t$ 2.32 [M+H]$^+$342).

Example 10

4-[3-(4-Chloro-phenyl)-propionylamino]-1H-pyrazole-3-carboxylic acid (4-fluoro-phenyl)-amide

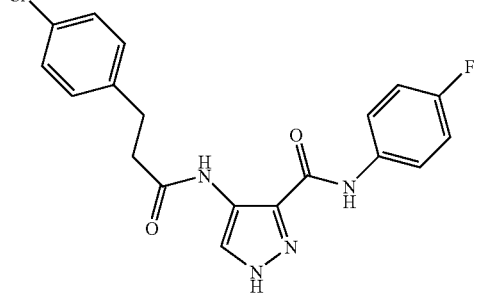

The reaction was carried out in a manner analogous to Example 4, but using 3-(4-chlorophenyl)propionic acid (46 mg; 0.23 mmol) as the starting material. The title compound (40 mg) was isolated as a white solid. (LC/MS: $R_t$ 3.60 [M+H]$^+$388).

Example 11

4-(3-4H-[1,24]Triazol-3-yl-propionylamino)-1H-pyrazole-3-carboxylic acid (4-fluoro-phenyl-amide

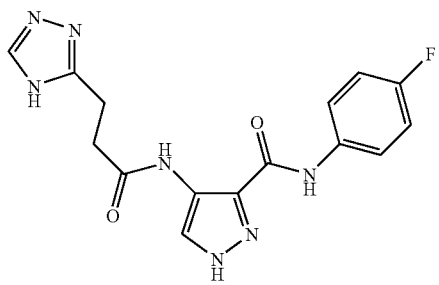

The reaction was carried out in a manner analogous to Example 4, but using 3-triazol-3-yl propionic acid (36 mg; 0.23 mmol) as the starting material. The title compound (18 mg) was isolated as a white solid. (LC/MS: $R_t$ 2.39 [M+H]$^+$ 344).

Example 12

4-[2-(1-Methyl-1H-indol-3-yl)-acetylamino]-1H-pyrazole-3-carboxylic acid (4-fluoro-phenyl)-amide

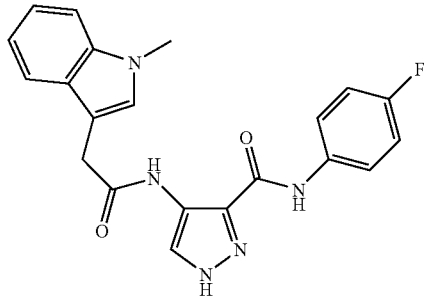

The reaction was carried out in a manner analogous to Example 4, but using N-methyl indole-3-acetic acid (48 mg; 0.23 mmol) as the starting material. The title compound (20 mg) was isolated as a white solid. (LC/MS: $R_t$ 3.34 [M+H]$^+$ 392).

Example 13

4-[(1-Hydroxy-cyclopropanecarbonyl)-amino]-1H-pyrazole-3-carboxylic acid (4-fluoro-phenyl)-amide

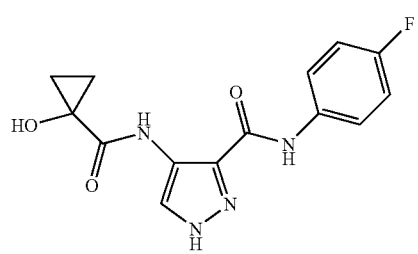

The reaction was carried out in a manner analogous to Example 4, but using 1-hydroxycyclopropane carboxylic acid (26 mg; 0.23 mmol) as the starting material. The title compound (24 mg) was isolated as a white solid. (LC/MS: $R_t$ 2.55 [M+H]$^+$305).

Example 14

1-Acetyl-piperidine-4-carboxylic acid [3-(4-fluoro-phenylcarbamoyl)-1H-pyrazol-4-yl]-amide

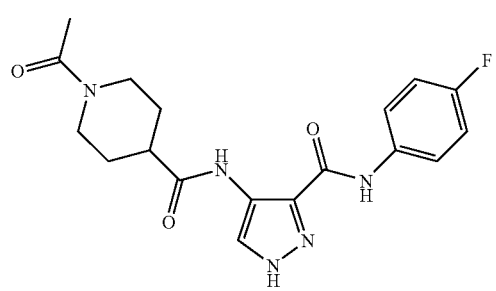

The reaction was carried out in a manner analogous to Example 4, but using N-acetylpiperidine acetic acid (43 mg; 0.23 mmol) as the starting material. The title compound (19 mg) was isolated as a white solid. (LC/MS: $R_t$ 2.49 [M+H]$^+$ 374).

Example 15

4-[3-(4-Methyl-piperazin-1-yl)-propionylamino]-1H-pyrazole-3-carboxylic acid (4-fluoro-phenyl)-amide

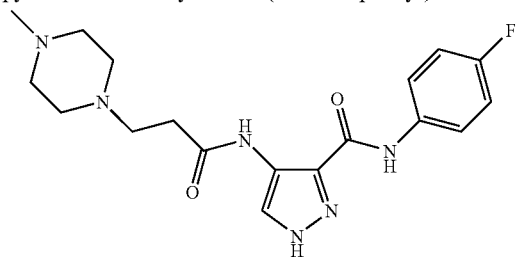

The reaction was carried out in a manner analogous to Example 4, but using 4-N-methylpiperazine-1-N-propionic acid (31 mg; 0.23 mmol) as the starting material. The title compound (19 mg) was isolated as a white solid. (LC/MS: $R_t$ 1.77 [M+H]$^+$375).

Example 16

4-(2-1H-Imidazol-4-yl-acetylamino)-1H-pyrazole-3-carboxylic acid (4-fluorophenyl)-amide

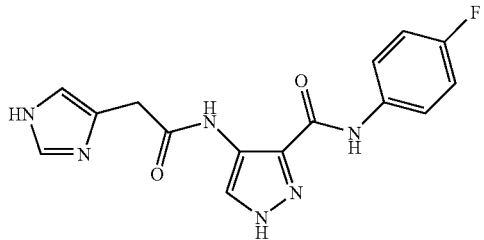

The reaction was carried out in a manner analogous to Example 4, but using imidazole-4-acetic acid (32 mg; 0.23 mmol) as the starting material. The title compound (35 mg) was isolated as a white solid. (LC/MS: $R_t$ 1.82 [M+H]$^+$329).

Example 17

4-(3-Morpholin-4-yl-propionylamino)-1H-pyrazole-3-carboxylic acid (4-fluorophenyl)-amide

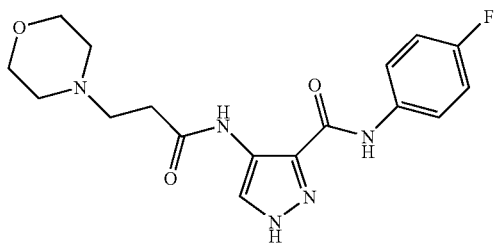

The reaction was carried out in a manner analogous to Example 4, but using 3-morpholin-4-yl-propionic acid (40 mg; 0.23 mmol) as the starting material. The title compound (15 mg) was isolated as a white solid. (LC/MS: $R_t$ 1.84 [M+H]$^+$362).

Example 18

4-(3-Piperidin-1-yl-propionylamino-1H-pyrazole-3-carboxylic acid (4-fluoro-phenyl)-amide

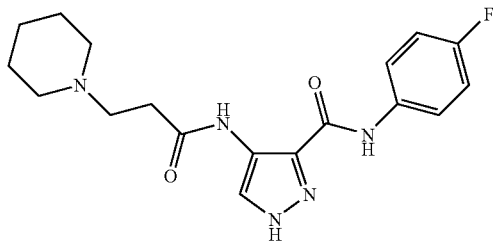

The reaction was carried out in a manner analogous to Example 4, but using 3-piperidine-4-yl-propionic acid (39 mg; 0.23 mmol) as the starting material. The title compound (19 mg) was isolated as a white solid. (LC/MS: $R_t$ 1.92 [M+H]$^+$360).

Example 19

4-Cyclohexylamino-1H-pyrazole-3-carboxylic acid (4-fluoro-phenyl)-amide

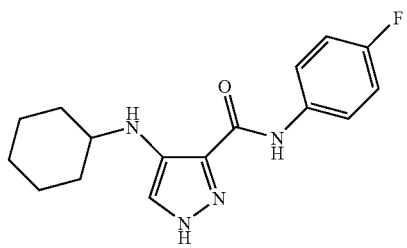

To a solution of 4-amino-1H-pyrazole-3-carboxylic acid (4-fluoro-phenyl)-amide (200 mg; 1 mmol) and cyclohexanone (107 mg; 1.1 mmol) in dichloromethane (10 ml) were added 3 Å molecular sieves (1 g) and sodium triacetoxyborohydride (315 mg; 1.5 mmol), and the mixture was then stirred at room temperature over the weekend. The reaction mixture was filtered through Celite®, diluted with ethyl acetate, washed with brine, dried (MgSO$_4$) and evaporated to give the 48 mg of the product as a grey gum. (LC/MS: $R_t$ 2.95, [M+H]$^+$ 285).

Example 20

4-Isopropylamino-1H-pyrazole-3-carboxylic acid (4-fluoro-phenyl)-amide

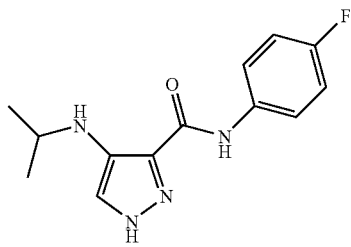

The title compound was prepared in a manner analogous to Example 19, but using acetone in place of cyclohexanone. (LC/MS: $R_t$ 2.08, [M+H]$^+$245).

Example 21

4-(2-Hydroxy-1-methyl-ethylamino)-1H-pyrazole-3-carboxylic acid (4-fluorophenyl)-amide

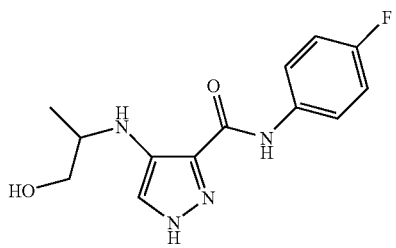

The compound was prepared in a manner analogous to Example-19, but using hydroxyacetone in place of cyclohexanone. $^1$HNMR (400 MHz, D6-DMSO): 9.9 (1H, br s), 7.8 (2H, dd), 7.3 (1H, s), 7.15 (2H, t), 5.15 (1H, d), 4.7 (1H, br s), 3.4 (2H, m), 3.2 (1H, m), 1.1 (3H, d).

Example 22

4-(1-Ethyl-propylamino)-1H-pyrazole-3-carboxylic acid (4-fluoro-phenyl)-amide

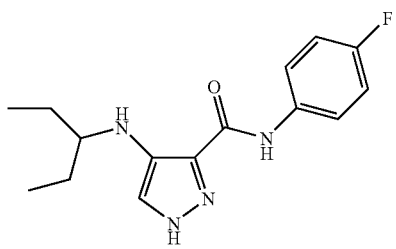

The compound was prepared in a manner analogous to Example 19, but using 3-pentanone in place of cyclohexanone. $^1$HNMR (400 MHz, D6-DMSO): 12.85 (1h,br s), 9.9 (1H, br s), 7.8 (2H, br t), 7.3 (1H, s), 7.15 (2H, t), 5.0 (1H, d), 2.9 (1H, br m), 1.5 (4H, m), 3.2 (1H, m), 0.9 (6H, t).

Example 23

4-(3-Chloro-pyrazin-2-ylamino)-1H-pyrazole-3-carboxylic acid (4-fluoro-phenyl-amide

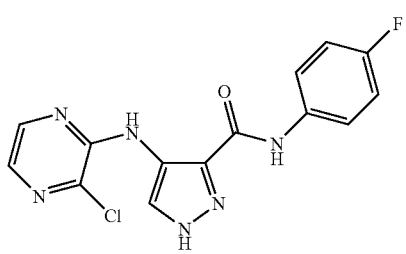

A mixture of 4-amino-1H-pyrazole-3-carboxylic acid (4-fluoro-phenyl)-amide (50 mg; 0.23 mmol) and 2,3-dichloropyrazine (140 mg; 0.92 mmol) was heated at 150° C. (50 W) for 20 minutes in a CEM Discover™ microwave synthesiser. The crude reaction mixture was purified by flash column chromatography eluting with ethyl acetate/hexane (1:3 then 1:2). Product containing fractions were combined and evaporated to give 15 mg of the title compound as a white solid. (LC/MS: $R_t$ 4.06 M+H]$^+$332).

Example 24

4-(Pyrazin-2-ylamino)-1H-pyrazole-3-carboxylic acid (4-fluoro-phenyl)-amide

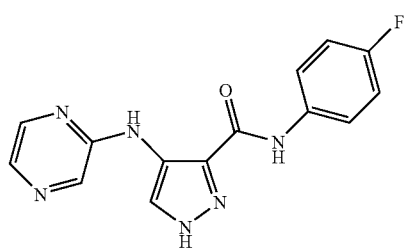

The compound was prepared in a manner analogous to Example 23, but using 2-chloropyrazine in place of 2,3-dichloropyrazine. (LC/MS: $R_t$ 3.28 [M+H]$^+$299).

Example 25

Synthesis of 4-(2-Methoxy-benzoylamino)-1H-pyrazole-3-carboxylic acid (4-fluoro-phenyl)-amide

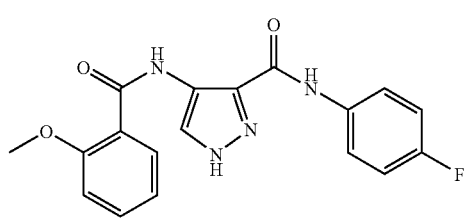

2-Methoxy-benzoic acid (38 mg, 0.25 mmol) was added to a solution of 4-amino-1H-pyrazole-3-carboxylic acid (4-fluoro-phenyl)-amide (50 mg, 0.23 mmol), EDC (53 mg, 0.27 mmol), and HOBt (37 mg, 0.27 mmol) in DMF (5 ml). The reaction mixture was stirred at room temperature for 24 hours. The solvent was removed under reduced pressure. The residue was purified by preparative LC/MS and, after evaporation of product-containing fractions, yielded the product as a pinkish solid (12 mg, 15%). (LC/MS: $R_t$ 4.00, [M+H]$^+$ 354.67).

Example 26

Synthesis of 4-Benzoylamino-1H-pyrazole-3-carboxylic acid (4-fluoro-phenyl)-amide

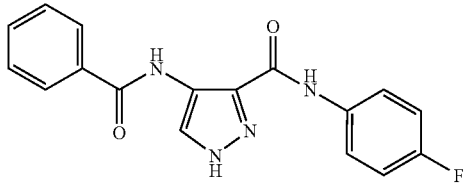

The experiment was carried out in a manner analogous to that of Example 25 using benzoic acid (31 mg, 0.25 mmol) as starting acid. The product was isolated as a pink solid (26 mg, 35%). (LC/MS: $R_t$ 3.96, [M+H]$^+$324.65).

Example 27

Synthesis of 4-(Cyclohexanecarbonyl-amino)-1H-pyrazole-3-carboxylic acid (4-fluoro-phenyl)-amide

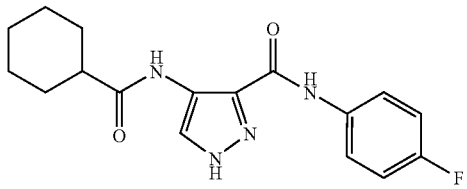

The experiment was carried out in a manner analogous to that of Example 25 using cyclohexanecarboxylic acid (32 mg, 0.25 mmol) as starting acid. The product was isolated as a pink solid (28 mg, 37%). (LC/MS: $R_t$ 4.16, [M+H]$^+$330.70).

Example 28

Synthesis of 4-[(1-Methyl-cyclopropanecarbonyl)-amino]-1H-pyrazole-3-carboxylic acid (4-fluoro-phenyl)-amide

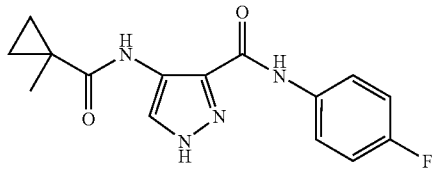

The experiment was carried out in a manner analogous to that of Example 25 using 1-methyl-cyclopropanecarboxylic acid (25 mg, 0.25 mmol) as starting acid. The product was isolated as a pink solid (24 mg, 35%). (LC/MS: $R_t$ 3.72, [M+H]$^+$302.68).

Example 29

Synthesis of 4-(2-Hydroxy-acetylamino)-1H-pyrazole-3-carboxylic acid (4-fluoro-phenyl)-amide

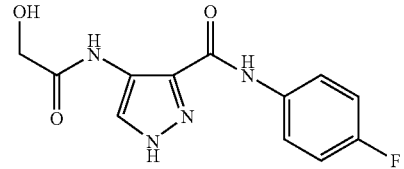

The experiment was carried out in a manner analogous to that of Example 25 using hydroxy-acetic acid (19 mg, 0.25 mmol) as starting acid. The product was isolated as a white solid (26 mg, 41%). (LC/MS: $R_t$ 2.65, [M+H]$^+$278.61).

Example 30

Synthesis of 4-(2,2-Dimethyl-propionylamino)-1H-pyrazole-3-carboxylic acid (4-fluoro-phenyl)-amide

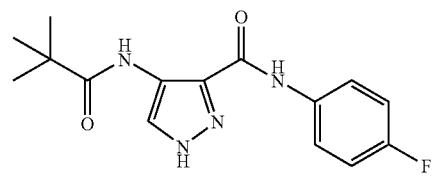

The experiment was carried out in a manner analogous to that of Example 25 using 10 2,2-dimethyl-propionic acid (26 mg, 0.25 mmol) as starting acid. The product was isolated as a pink solid (21 mg, 30%). (LC/MS: $R_t$ 3.83, [M+H]$^+$304.68).

Example 31

Synthesis of 4-(3-Hydroxy-propionylamino)-1H-pyrazole-3-carboxylic acid (4-fluoro-phenyl)-amide

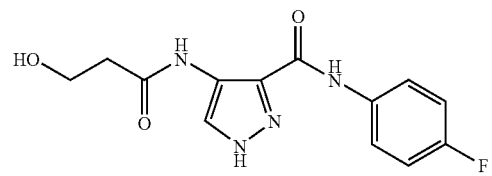

The experiment was carried out in a manner analogous to that of Example 25 using 3-hydroxy-propionic acid (75.1 mg, 0.25 mmol) as starting acid. The product was isolated as a beige solid (5 mg, 8%). (LC/MS: $R_t$ 2.58, [M+H]$^+$292.65).

Example 32

Synthesis of 4-(2-Fluoro-benzoylamino)-1H-pyrazole-3-carboxylic acid (4-fluoro-phenyl)-amide

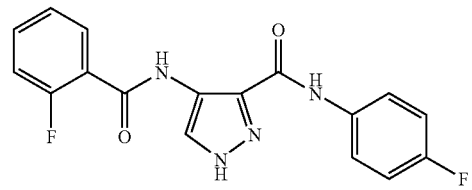

2-Fluorobenzoic acid (36 mg, 0.25 mmol) was added to a solution of 4-amino-1H-pyrazole-3-carboxylic acid (4-fluoro-phenyl)-amide (50 mg, 0.23 mmol), EDC (53 mg, 0.27 mmol) and HOBt (37 mg, 0.27 mmol) in DMSO (1 ml). The reaction mixture was stirred at room temperature for 24 hours and purified by preparative LC/MS. Evaporation of product-containing fractions yielded the product as a white solid (15 mg, 19%). (LC/MS: $R_t$ 3.91, [M+H]$^+$342.66).

Example 33

Synthesis of 4-(3-Fluoro-benzoylamino)-1H-pyrazole-3-carboxylic acid (4-fluoro-phenyl)-amide

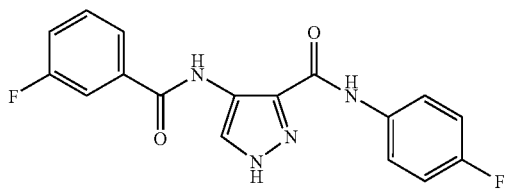

The experiment was carried out in a manner analogous to that of Example 32 using 3-fluorobenzoic acid (36 mg, 0.25 mmol) as starting acid. The product was isolated as a white solid (19 mg, 24%). (LC/MS: $R_t$ 4.03, [M+H]$^+$342.67).

Example 34

Synthesis of 4-(3-Methoxy-benzoylamino)-1H-pyrazole-3-carboxylic acid (4-fluoro-phenyl)-amide

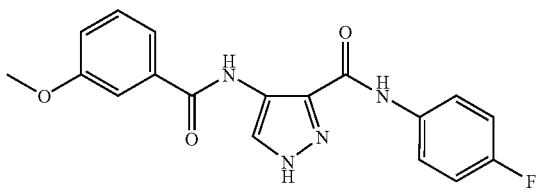

The experiment was carried out in a manner analogous to that of Example 32 using 3-methoxy-benzoic acid (39 mg, 0.25 mmol) as starting acid. The product was isolated as a white solid (20 mg, 25%). (LC/MS: $R_t$ 3.97, [M+H]$^+$354.68).

Example 35

Synthesis of 4-(2-Nitro-benzoylamino)-1H-pyrazole-3-carboxylic acid (4-fluoro-phenyl)-amide

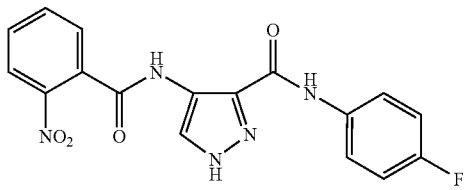

The experiment was carried out in a manner analogous to that of Example 32 using 2-nitrobenzoic acid (43 mg, 0.25 mmol) as starting acid. The product was isolated as a white solid (17 mg, 20%). (LC/MS: $R_t$ 3.67, [M+H]$^+$369.66).

Example 36

Synthesis of 4-(4-Nitro-benzoylamino)-1H-pyrazole-3-carboxylic acid (4-fluoro-phenyl)-amide

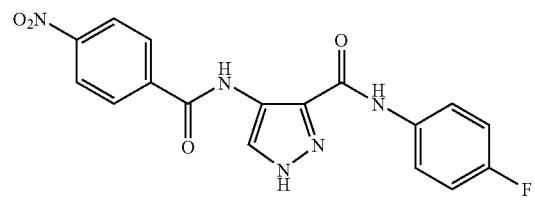

The experiment was carried out in a manner analogous to that of Example 32 using 4-nitrobenzoic acid (43 mg, 0.25 mmol) as starting acid. The product was isolated as a white solid (15 mg, 18%). (LC/MS: $R_t$ 3.98, [M+H]$^+$369.63).

Example 37

Synthesis of 4-[(3-Methyl-furan-2-carbonyl)-amino]-1H-pyrazole-3-carboxylic acid (4-fluoro-phenyl)-amide

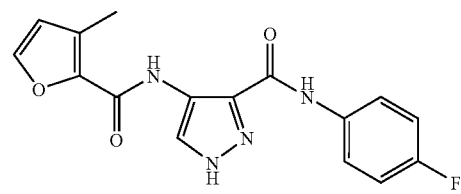

The experiment was carried out in a manner analogous to that of Example 32 using 3-methyl-2-furoic acid (32 mg, 0.25 mmol) as starting acid. The product was isolated as a white solid (15 mg, 20%). (LC/MS: $R_t$ 3.86, [M+H]$^+$328.68).

Example 38

Synthesis of 4-[(Furan-2-carbonyl)-amino]-1H-pyrazole-3-carboxylic acid (4-fluoro-phenyl)-amide

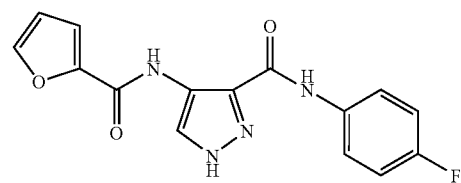

The experiment was carried out in a manner analogous to that of Example 32 using 2-furoic acid (29 mg, 0.25 mmol) as starting acid. The product was isolated as a white solid (18 mg, 25%). (LC/MS: $R_t$ 3.56, [M+H]$^+$314.64).

Example 39

Synthesis of 4-[(3H-Imidazole-4-carbonyl)-amino]-1H-pyrazole-3-carboxylic acid (4-fluoro-phenyl)-amide

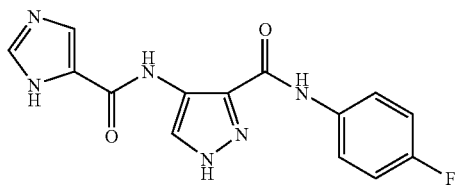

The experiment was carried out in a manner analogous to that of Example 32 using 1H-imidazole-4-carboxylic acid (29 mg, 0.25 mmol) as starting acid. The product was isolated as a white solid (16 mg, 22%). (LC/MS: $R_t$ 2.59, $[M+H]^+$ 314.65).

Example 40

Synthesis of 4-(4-Fluoro-benzoylamino)-1H-pyrazole-3-carboxylic acid (4-fluoro-phenyl)-amide

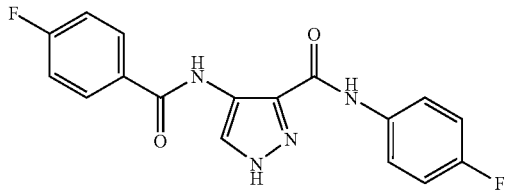

The experiment was carried out in a manner analogous to that of Example 32 using 4-fluorobenzoic acid (36 mg, 0.25 mmol) as starting acid. The product was isolated as a cream coloured solid (23 mg, 29%). (LC/MS: $R_t$ 4.00, $[M+H]^+$ 342.67).

Example 41

Synthesis of 4-(2,6-Difluoro-benzoylamino)-1H-pyrazole-3-carboxylic acid (4-fluoro-phenyl)-amide

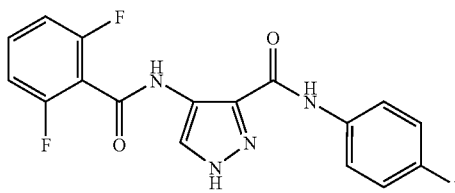

The experiment was carried out in a manner analogous to that of Example 32 using 2,6-difluorobenzoic acid (40 mg, 0.25 mmol) as starting acid. The product was isolated as a cream coloured solid (25 mg, 30%). (LC/MS: $R_t$ 3.76, $[M+H]^+$ 360.66).

Example 42

Synthesis of 4-(3-Nitro-benzoylamino)-1H-pyrazole-3-carboxylic acid (4-fluoro-phenyl)-amide

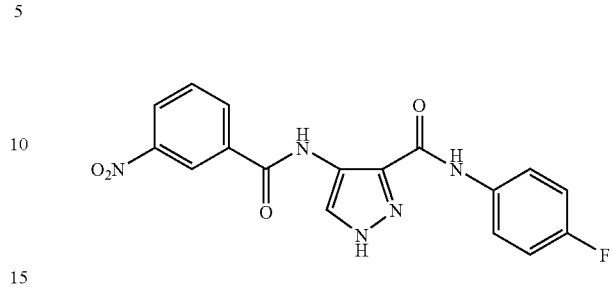

The experiment was carried out in a manner analogous to that of Example 32 using 3-nitrobenzoic acid (43 mg, 0.25 mmol) as starting acid. The product was isolated as a cream coloured solid (15 mg, 18%). (LC/MS: $R_t$ 3.94, $[M+H]^+$ 369.65).

Example 43

Synthesis of 1H-Indole-3-carboxylic acid [3-(4-fluoro-phenylcarbamoyl)-1H-pyrazol-4-yl]-amide

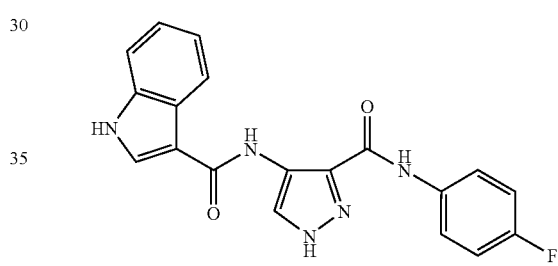

The experiment was carried out in a manner analogous to that of Example 32 using indole-3-carboxylic acid (41 mg, 0.25 mmol) as starting acid. The product was isolated as a rust coloured solid (14 mg, 17%). (LC/MS: $R_t$ 3.60, $[M+H]^+$ 363.66).

Example 44

Synthesis of 4-(4-Hydroxymethyl-benzoylamino)-1H-pyrazole-3-carboxylic acid (4-fluoro-phenyl)-amide

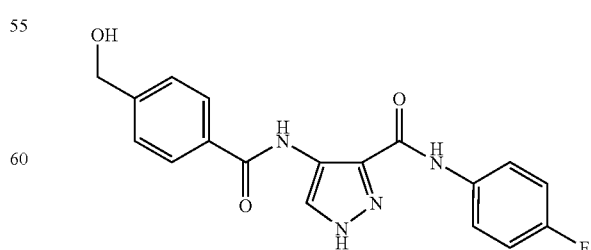

The experiment was carried out in a manner analogous to that of Example 32 using 4-hydroxymethylbenzoic acid (39 mg, 0.25 mmol) as starting acid. The product was isolated as a white solid (19 mg, 23%). (LC/MS: R$_t$ 3.12, [M+H]$^+$ 354.68).

Example 45

Synthesis of 4-(3-Methyl-benzoylamino)-1H-pyrazole-3-carboxylic acid (4-fluoro-phenyl)-amide

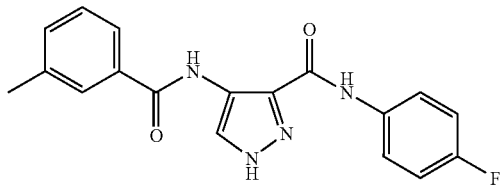

The experiment was carried out in a manner analogous to that of Example 32 using 3-methylbenzoic acid (35 mg, 0.25 mmol) as starting acid. The product was isolated as an off-white solid (21 mg, 27%). (LC/MS: R$_t$ 4.13, [M+H]$^+$338.71).

Example 46

Synthesis of 4-(2-Methyl-benzoylamino)-1H-pyrazole-3-carboxylic acid (4-fluoro-phenyl)-amide

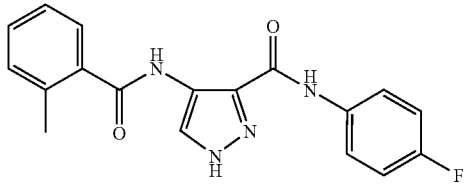

The experiment was carried out in a manner analogous to that of Example 32 using 2-methylbenzoic acid (35 mg, 0.25 mmol) as starting acid. The product was isolated as an off-white solid (20 mg, 26%). (LC/MS: R$_t$ 4.05, [M+H]$^+$338.69).

Example 47

Synthesis of 4-(4-Methyl-benzoylamino)-1H-pyrazole-3-carboxylic acid (4-fluoro-phenyl)-amide

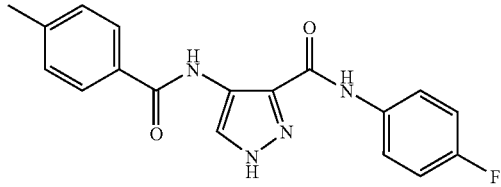

The experiment was carried out in a manner analogous to that of Example 32 using 4-methylbenzoic acid (35 mg, 0.25 mmol) as starting acid. The product was isolated as an off-white solid (19 mg, 24%). (LC/MS: R$_t$ 4.16, [M+H]$^+$338.70).

Example 48

Synthesis of 4-[(2-Methyl-thiophene-3-carbonyl)-amino]-1H-pyrazole-3-carboxylic acid (4-fluoro-phenyl)-amide

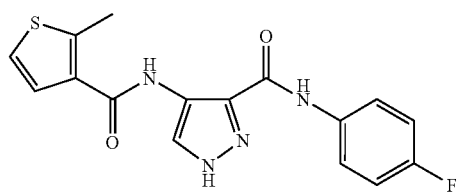

2-Methyl-3-thiophenecarboxylic acid (36 mg, 0.25 mmol) was added to a solution of 4-amino-1H-pyrazole-3-carboxylic acid (4-fluoro-phenyl)-amide (Example 2B) (50 mg, 0.23 mmol), EDC (53 mg, 0.27 mmol), and HOBt (37 mg, 0.27 mmol) in DMSO (1 ml). The reaction mixture was stirred at room temperature for 24 hours. The reaction mixture was added dropwise to water (30 ml) and the resultant solid was collected by filtration, washed with water and sucked dry. The title compound was obtained as a beige solid (15 mg, 19%). (LC/MS: R$_t$ 4.08, [M+H]$^+$344.67).

Example 49

Synthesis of Quinoline-2-carboxylic acid [3-(4-fluoro-phenylcarbamoyl)-1H-pyrazol-4-yl]-amide

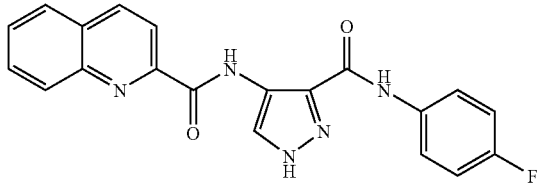

The experiment was carried out in a manner analogous to that of Example 48 using quinaldic acid (44 mg, 0.25 mmol) as starting acid. The product was isolated as a brown solid (16 mg, 19%). (LC/MS: R$_t$ 4.29, [M+H]$^+$375.66).

Example 50

Synthesis of 4-[(Thiophene-3-carbonyl)-amino]-1H-pyrazole-3-carboxylic acid (4-fluoro-phenyl)-amide

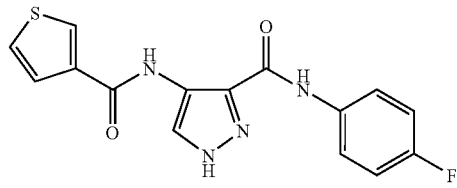

The experiment was carried out in a manner analogous to that of Example 48 using thiophene-3-carboxylic acid (33 mg, 0.25 mmol) as starting acid. The product was isolated as a beige solid (15 mg, 20%). (LC/MS: R$_t$ 3.77, [M+H]$^+$ 330.61).

Example 51

4-(2-fluoro-3-methoxy-benzoylamino)-1H-pyrazole-3-carboxylic acid (4-fluoro-phenyl)-amide

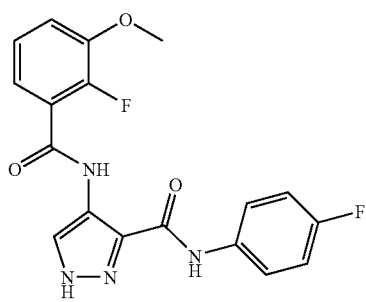

2-Fluoro-3-methoxybenzoic acid (0.047 g, 0.28 mmol), 4-amino-1H-pyrazole-3-carboxylic acid (4-fluoro-phenyl)-amide (Example 2B) (0.055 g, 0.25 mmol), EDC (0.58 g, 0.30 mmol) and HOBt (0.041 g, 0.30 mmol) were stirred at room temperature in DMSO (1.25 ml) for 5 hours. The reaction mixture was poured into water (30 ml) and the resultant solid was collected by filtration and dried in a vacuum oven to give the title compound as a grey solid (0.058 g, 63%). (LC/MS: $R_t$ 3.99, $[MH]^+$372.98).

Example 52

Synthesis of 4-[2-(2-Pyrrolidin-1-yl-ethoxy)-benzoylamino]-1H-pyrazole-3-carboxylic acid 4-fluorophenylamide

52A 2-(2-Pyrrolidin-1-yl-ethoxy)-benzoic acid methyl ester

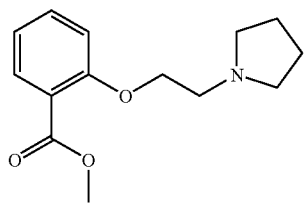

Diisopropylazodicarboxylate (0.404 g, 2 mmol) was added dropwise to a solution of triphenylphosphine (0.524 g, 2 mmol) in THF (10 ml). Methyl salicylate (0.304 g, 2 mmol) was added dropwise and the resultant mixture was stirred at room temperature for 1 hour. 1,2-Hydroxyethyl pyrrolidine (0.230 g, 2 mmol) was added dropwise and the reaction mixture was left stirring at room temperature for a further 1.5 hours. The resulting solution was reduced in vacuo and subject to flash column chromatography, eluting with hexane:ethyl acetate (5:1, 1:1) then ethyl acetate: methanol (4:1) to give the product as a clear yellow oil (0.104 g, 21%). (LC/MS: $R_t$ 0.69, 1.62, $[MH]^+$250.02).

52B. 4-[2-(2-Pyrrolidin-1-yl-ethoxy)-benzoylamino]-1H-pyrazole-3-carboxylic acid 4-fluorophenylamide

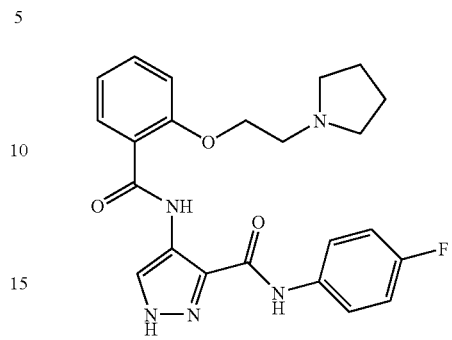

2-(2-Pyrrolidin-1-yl-ethoxy)-benzoic acid methyl ester (0.104 g, 0.42 mmol) was treated with 2 M aqueous NaOH (20 ml) and water (20 ml). The reaction mixture was stirred at room temperature for 20 hours, then reduced in vacuo and azeotroped with toluene (3×5 ml). Water (50 ml) was added and the mixture taken to pH 5 using 1M aqueous HCl. The resulting solution was reduced in vacuo and azeotroped with toluene (3×5 ml) to give a white solid, which was combined with 4-amino-1H-pyrazole-3-carboxylic acid (4-fluoro-phenyl)-amide (Example 2B) (0.055 g, 0.25 mmol), EDC (0.058 g, 0.3 mmol) and HOBt (0.041 g, 0.3 mmol) and stirred at room temperature in DMSO (3 ml) for 20 hours. The reaction mixture was poured into water (30 ml) and the resultant solid was collected by filtration and dried in a vacuum oven to give the title compound as a grey solid (0.015 g, 14%). (LC/MS: $R_t$ 2.18, $[MH]^+$438.06).

Example 53

Synthesis of 4-(2,6-Difluoro-benzoylamino)-1H-pyrazole-3-carboxylic acid (1-methyl-piperidin-4-yl)-amide

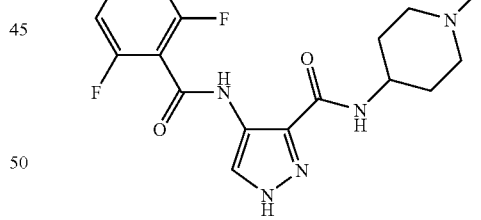

A mixture of 4-(2,6-difluoro-benzoylamino)-1H-pyrazole-3-carboxylic acid (134 mg, 0.50 mmol), 4-amino-N-methylpiperidine (50.0 µl, 0.45 mmol), EDAC (104 mg, 0.54 mmol) and HOBt (73.0 mg, 0.54 mmol) in DMF (3 ml) was stirred at ambient temperature for 16 hours. The mixture was reduced in vacuo, the residue taken up in EtOAc and washed successively with saturated aqueous sodium bicarbonate, water and brine. The organic portion was dried (MgSO$_4$) and reduced in vacuo to give 4-(2,6-difluoro-benzoylamino)-1H-pyrazole-3-carboxylic acid (1-methyl-piperidin-4-yl)-amide as a white solid (113 mg, 69%). (LC/MS: $R_t$ 2.52, $[M+H]^+$ 364.19).

Example 54

Synthesis of 4-(Cyclohexyl-methyl-amino)-1H-pyrazole-3-carboxylic acid (4-fluoro-phenyl)-amide

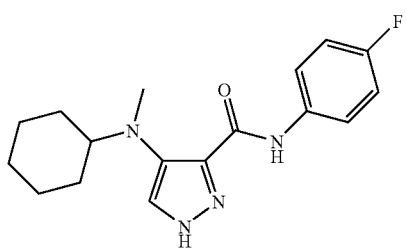

This compound was prepared in a manner analogous to the compound of Example 19 by succssive reductive alkylations using firstly cyclohexanone and then formaldehyde. (LC/MS: $R_t$ 2.77 [MH]$^+$316.71).

Example 55

4-(Pyridin-2-ylamino)-1H-pyrazole-3-carboxylic acid (4-fluoro-phenyl)-amide

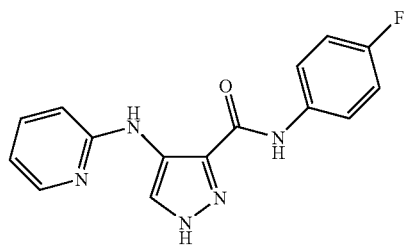

The title compound was prepared in a manner analogous to the compound of Example 23. (LC/MS: $R_t$ 2.07 [MH]$^+$ 298.03).

Examples 56-81

By following the procedures described in the foregoing examples or methods analogous thereto, or by carrying out chemical transformations using the compounds described in the above examples and synthetic methods well known to the skilled person, the compounds set out in Table 3 were prepared.

TABLE 3

| Example No. | Structure | Prepared using method analogous to Example No | Differences to Example? | LCMS |
|---|---|---|---|---|
| 56 | 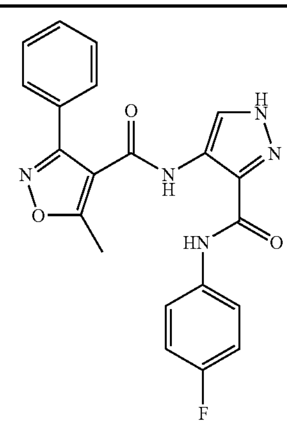 | 4 | | $R_t$ 3.20 min [M + H]$^+$ 406.07 |
| 57 | 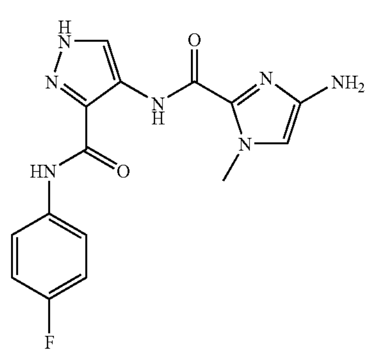 | 4 | Then removal of t-Boc protecting group with TFA as described in Example 82 | $R_t$ 2.35 min m/z 343.72 |

TABLE 3-continued

| Example No. | Structure | Prepared using method analogous to Example No | Differences to Example? | LCMS |
|---|---|---|---|---|
| 58 | 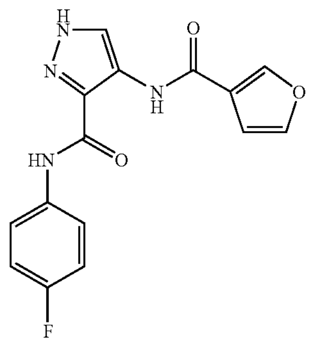 | 4 | Used DMSO instead of DMF as solvent | $R_t$ 3.51 min m/z 314.62 |
| 59 | 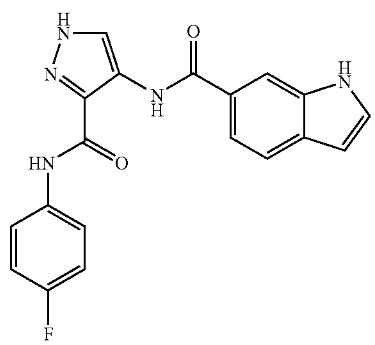 | 4 | Used DMSO instead of DMF as solvent | $R_t$ 3.79 min m/z 363.67 |
| 60 | 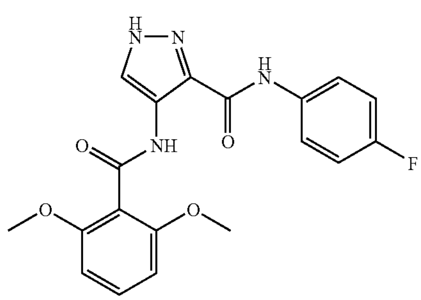 | 4 | Purified by column chromatography using EtOAC: Petroleum ether eluent | $R_t$ 3.68 min m/z 384.69 |
| 61 | 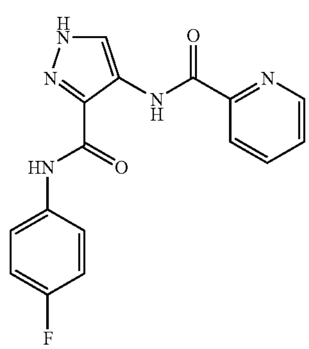 | 48 | Purified by column chromatography using EtOAC: Petroleum ether eluent | $R_t$ 3.61 min m/z 326.10 |

TABLE 3-continued

| Example No. | Structure | Prepared using method analogous to Example No | Differences to Example? | LCMS |
|---|---|---|---|---|
| 62 | 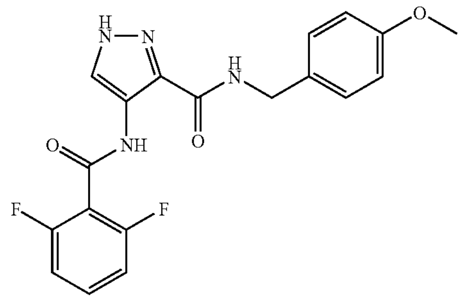 | 48 | Purified by column chromatography using EtOAC: Petroleum ether eluent | R$_t$ 3.51 min m/z 387.11 |
| 63 | 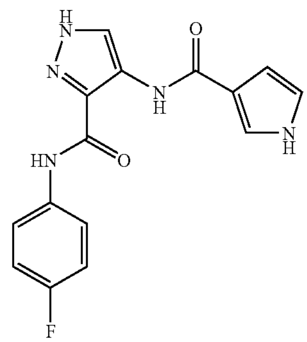 | 48 | | R$_t$ 3.11 min m/z 313.65 |
| 64 | 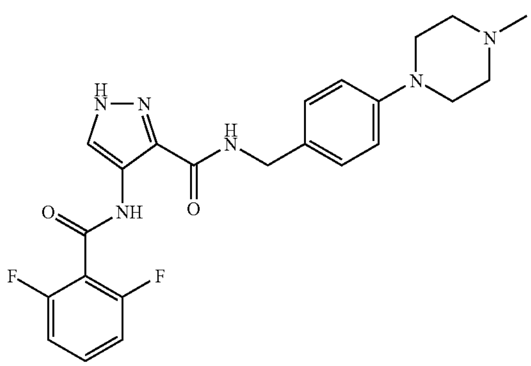 | 48 | Purified by column chromatography using EtOAC: Petroleum ether eluent | R$_t$ 2.20 min m/z 445.19 |
| 65 | 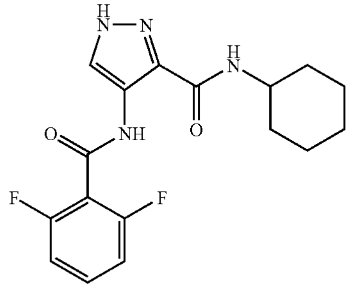 | 48 | | R$_t$ 3.95 min m/z 349.09 |

TABLE 3-continued

| Example No. | Structure | Prepared using method analogous to Example No | Differences to Example? | LCMS |
|---|---|---|---|---|
| 66 | 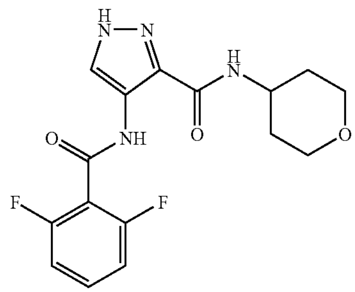 | 48 | Purified by chromatography using EtOAC: Petroleum ether eluent | $R_t$ 2.39 min m/z 351.07 |
| 67 | 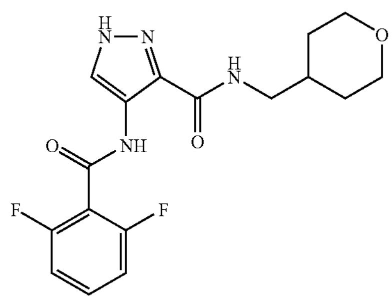 | 48 | Purified by colum chromatography using EtOAC: Petroleum ether eluent | $R_t$ 2.83 min m/z 365.13 |
| 68 | 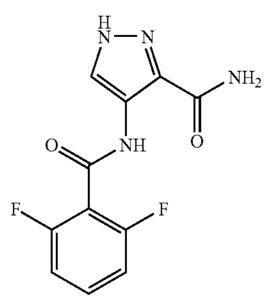 | | Removal of PMB group from the compound of Example 62 using TFA-anisole | $R_t$ 2.10 min m/z 266.97 |
| 69 | 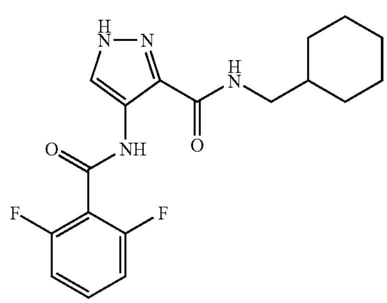 | 48 | Used DMF instead of DMSO as solvent | $R_t$ 3.22 min m/z 363.10 |
| 70 | 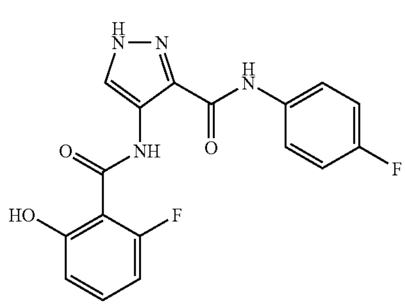 | 48 | | $R_t$ 4.48 min m/z 358.96 |

TABLE 3-continued

| Example No. | Structure | Prepared using method analogous to Example No | Differences to Example? | LCMS |
|---|---|---|---|---|
| 71 | 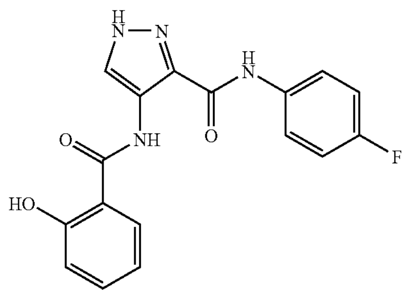 | 48 | | R$_t$ 3.93 min<br>m/z 340.96 |
| 72 | 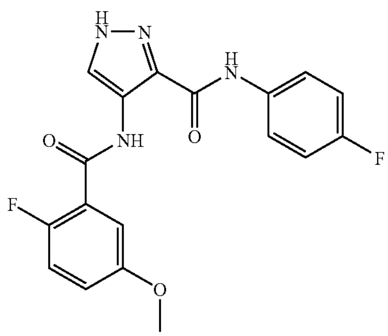 | 48 | | R$_t$ 4.11 min<br>m/z 373.01 |
| 73 | 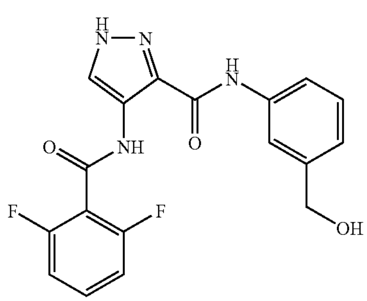 | 48 | Used DMF instead of DMSO as solvent | R$_t$ 2.56 min<br>m/z 373.05 |
| 74 | 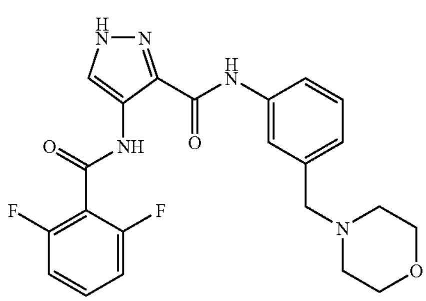 | | Obtained by oxidation and then reductive amination of Example 73 | R$_t$ 1.99 min<br>m/z 442.09 |
| 75 | 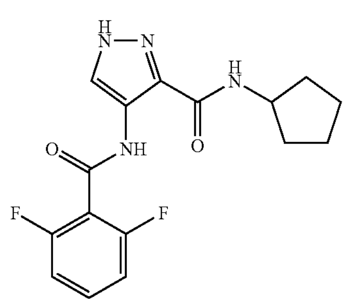 | 53 | Purified by column chromatography using DCM:MeOH (1:0 to 19:1) eluent | R$_t$ 3.65 min<br>m/z 335.03 |

TABLE 3-continued

| Example No. | Structure | Prepared using method analogous to Example No | Differences to Example? | LCMS |
|---|---|---|---|---|
| 76 | 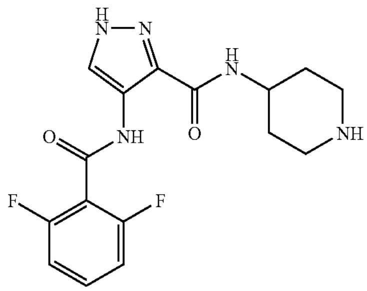 | 25 | Purified by column chromatography Then removal of t-Boc protecting group with saturated ethyl acetate/HCl | R$_t$ 1.57 min m/z 350.10 |
| 77 | 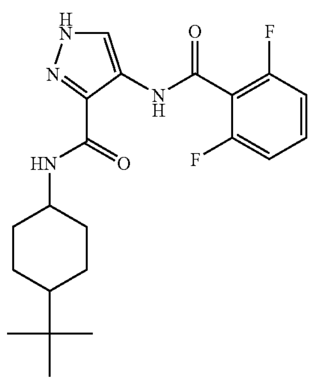 | 53 | | R$_t$ 5.05 min m/z 405.14 |
| 78 | 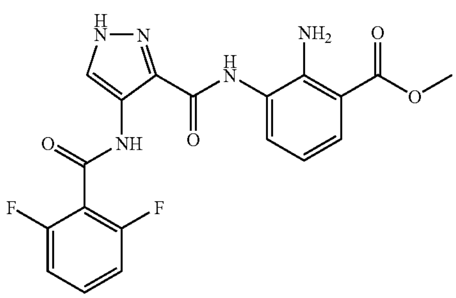 | 53 | | R$_t$ 2.87 min m/z 416.07 |
| 79 | 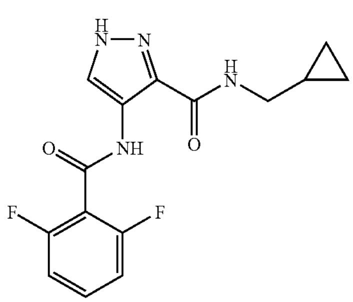 | 53 | Purified by column chromatography using EtOAC: Petroleum ether eluent (1:1) | R$_t$ 3.41 min m/z 321.03 |

TABLE 3-continued

| Example No. | Structure | Prepared using method analogous to Example No | Differences to Example? | LCMS |
|---|---|---|---|---|
| 80 | 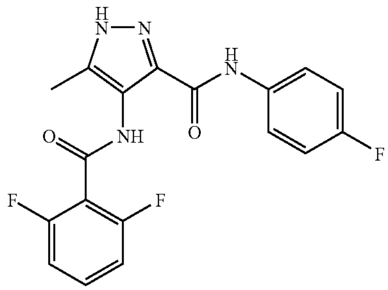 | 2A, 2B & 53 | Commercially available 5-methyl-pyrazole-1H-3-carboxylic acid used as starting material. Purified by column chromatography using EtOAc: Hexane eluent (1:3 to 1:1) | $R_t$ 3.42 min m/z 375.05 |
| 81 | 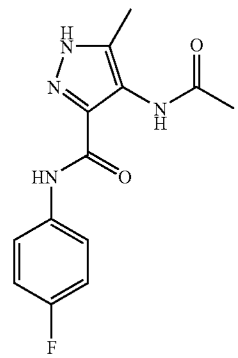 | 2C | Purified by column chromatography using EtOAC: Hexane eluent (1:1 to 1:0) | $R_t$ 2.37 min m/z 277.04 |

Example 82

4-[(4-Amino-1-methyl-1H-imidazole-2-carbonyl)-amino]-1H-pyrazole-3-carboxylic acid (4-fluoro-phenyl)-amide

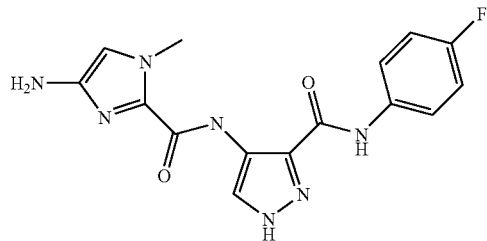

Trifluoroacetic acid (200 μl) was added to a stirred suspension of {2-[3-(4-fluoro-phenylcarbamoyl)-1H-pyrazol-4-yl-carbamoyl]-1-methyl-1H-imidazol-4-yl}-carbamic acid tert-butyl ester (30 mg) in dichloromethane (5 ml), then stirred at room temperature for 2 hours. The solvent was evaporated then re-evaporated with toluene (2×10 ml). The residue was triturated with diethyl ether and the resultant solid collected by filtration. The solid was washed with diethyl ether then dried under vacuum to give 15 mg of 4-[(4-amino-1-methyl-1H-imidazole-2-carbonyl)-amino]-1H-pyrazole-3-carboxylic acid (4-fluoro-phenyl)-amide as an off-white solid. (LC/MS: [M+H]$^+$343.72).

Example 83

Synthesis of 4-{[4-(2,6-Difluoro-benzoylamino)-1H-pyrazole-3-carbonyl]-amino}-cyclohexanecarboxylic acid 83A. 4-{[4-(2,6-difluoro-benzoylamino)-1H-pyrazole-3-carbonyl]-amino}-cyclohexanecarboxylic acid ethyl ester

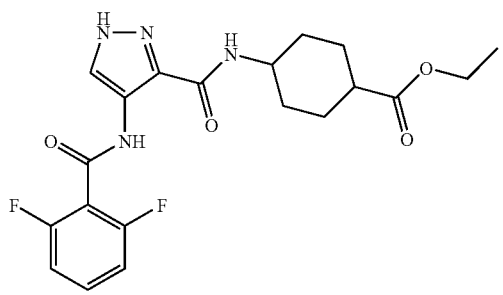

Thionyl chloride (0.32 ml, 4.40 mmol) was slowly added to a mixture of 4-aminocyclohexanecarboxylic acid (572 mg, 4.00 mmol) in EtOH (10 ml) and stirred at ambient temperature for 16 hours. The mixture was reduced in vacuo, azeotroping with toluene, to give the corresponding ethyl ester (650 mg) as a pale solid.

A mixture of the ethyl ester (103 mg, 0.60 mmol), 4-(2,6-difluoro-benzoylamino)-1H-pyrazole-3-carboxylic acid (134 mg, 0.50 mmol), EDC (115 mg, 0.60 mmol) and HOBt (81 mg, 0.60 mmol) in DMF (5 ml) was stirred at ambient temperature for 16 hours. The mixture was reduced in vacuo, the residue taken up in EtOAc and washed successively with saturated aqueous sodium bicarbonate, water and brine. The organic portion was dried (MgSO₄) and reduced in vacuo to give 4-{[4-(2,6-difluoro-benzoylamino)-1H-pyrazole-3-carbonyl]-amino}-cyclohexanecarboxylic acid ethyl ester (112 mg).

83B. 4-{[4-(2,6-difluoro-benzoylamino)-1H-pyrazole-3-carbonyl]-amino}-cyclohexanecarboxylic acid

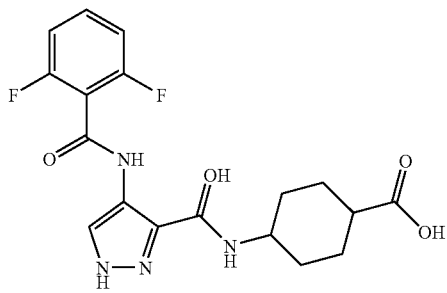

A mixture of the ester (45 mg) (from 83A) in MeOH (2.5 ml) and 2M aqueous NaOH (2.5 ml) was stirred at ambient temperature for 16 hours. The volatiles were removed in vacuo, water (10 ml) added and the mixture taken to pH 5 using 1M aqueous HCl. The precipitate formed was collected by filtration and purified by column chromatography using EtOAc/MeOH (1:0-9:1) to give 4-{[4-(2,6-difluoro-benzoylamino)-1H-pyrazole-3-carbonyl]-amino}-cyclohexanecarboxylic acid (11 mg) as a white solid and mixture of cis-/trans-isomers. (LC/MS: R$_t$ 2.78 and 2.96, [M+H]⁺393.09).

Examples 84-152

General Procedure A

Preparation of Amide from Pyrazole Carboxylic Acid

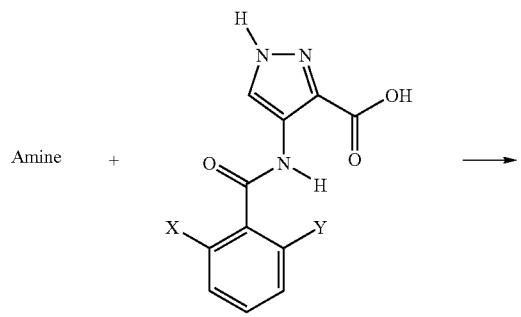

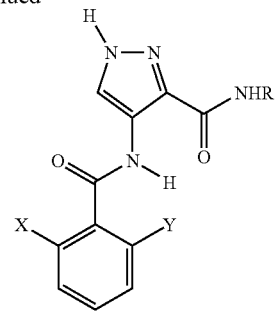

A mixture of the appropriate benzoylamino-1H-pyrazole-3-carboxylic acid (0.50 mmol), EDAC (104 mg, 0.54 mmol), HOBt (73.0 mg, 0.54 mmol) and the corresponding amine (0.45 mmol) in DMF (3 ml) was stirred at ambient temperature for 16 hours. The mixture was reduced in vacuo, the residue taken up in EtOAc and washed successively with saturated aqueous sodium bicarbonate, water and brine. The organic portion was dried (MgSO₄) and reduced in vacuo to give the desired product.

General Procedure B

Preparation of Amide from Amino-Pyrazole

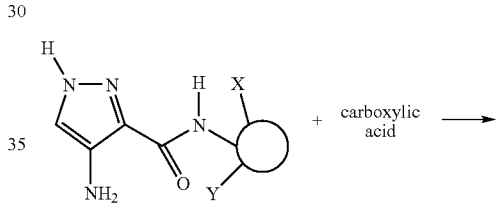

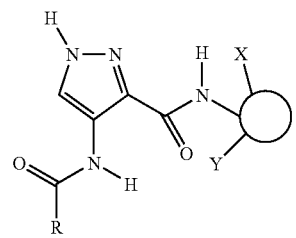

To a stirred solution of the appropriate 4-amino-1H-pyrazole-3-carboxylic acid amide (0.23 mmol), EDAC (52 mg; 0.27 mmol) and HOBt (37 mg; 0.27 mmol) in 5 ml of N,N-dimethylformamide was added the corresponding carboxylic acid (0.25 mmol), and the mixture was then left at room temperature overnight. The reaction mixture was evaporated and the residue purified by preparative LC/MS, to give the product.

General Procedure C

Deprotection of Piperidine Ring Nitrogen by Removal of tert-Butoxycarbonyl Group A product of Procedure A or Procedure B containing a piperidine group bearing an N-tert-butoxycarbonyl (t-Boc) protecting group (40 mg) was treated with saturated ethyl acetate/HCl, and stirred at room temperature for 1 hour. A solid precipitated out of the reaction mixture, which was filtered off, washed with ether, and then dried to give 25 mg product (LC/MS: [M+H]⁺364).

Procedure L

Preparation of Amine Starting Materials

The following method was used to prepare the following amines:
4-thiomorpholine-4-yl-cyclohexylamine;
4-(1,1-dioxo-thiomorpholine-4-yl)-cyclohexylamine;
N-(tetrahydro-pyran-4-yl)-cyclohexane-1,4-diamine;
4-(4-methyl-piperazin-1-yl)-cyclohexylamine;
1'-methyl-[1,4']bipiperidinyl-4-ylamine; and
4-morpholin-4-yl-cyclohexylamine.

A solution of N-4-Boc-aminocyclohexanone (0.5 g, 2.3 mmol) in THF (10 ml) was treated with the appropriate amine, e.g. thiomorpholine (0.236 g, 2.3 mmol), and sodium triacetoxyborohydride (0.715 g, 2.76 mmol) and acetic acid (0.182 ml). The reaction was stirred overnight at room temperature, then diluted with $CH_2Cl_2$ and washed with saturated sodium carbonate. The organic layer was dried over $MgSO_4$ and evaporated to give a white solid which was used without further purification in the next step. The white solid was treated with saturated HCl/EtOAc, stirred at room temperature for 1 hour, evaporated to dryness and then re-evaporated with toluene. The resulting amines were isolated as the hydrochloride salt. (LC/MS: $R_t$ 1.75, [M+H]⁺201).

By following General Procedures A, B, C and L, modified where stated, the compounds set out in Table 4 were prepared.

TABLE 4

| Example No. | | Method of Preparation | LCMS |
|---|---|---|---|
| 84 | 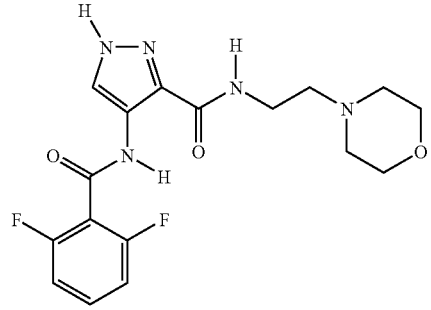 | Procedure A | [M + H]⁺ 380<br>$R_t$ 1.42 |
| 85 | 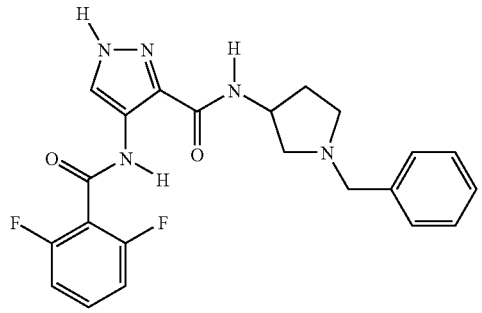 | Procedure A | [M + H]⁺ 426<br>$R_t$ 1.93 |
| 86 | 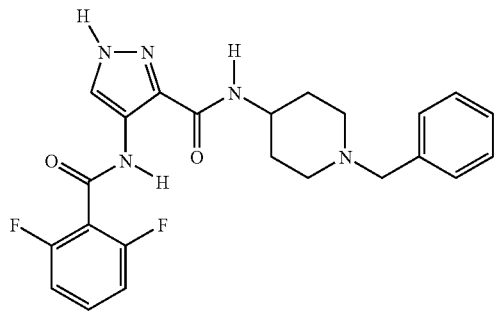 | Procedure A | [M + H]⁺ 440<br>$R_t$ 1.87 |

TABLE 4-continued

| Example No. | Structure | Method of Preparation | LCMS |
|---|---|---|---|
| 87 | | Procedure A | [M + H]+ 406<br>R$_t$ 2.78 |
| 88 | | Procedure A | [M + H]+ 406<br>R$_t$ 2.55 |
| 89 | | Procedure A<br>DMSO instead of DMF | [M + H]+ 358<br>R$_t$ 1.98 |
| 90 | | Procedure A<br>DMSO instead of DMF | [M + H]+ 357<br>R$_t$ 3.37 |

TABLE 4-continued
| Example No. | | Method of Preparation | LCMS |
|---|---|---|---|
| 91 | 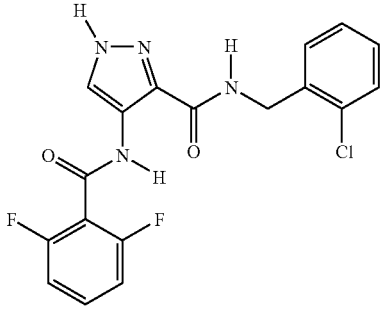 | Procedure A<br>DMSO instead of DMF | [M + H]+ 391<br>R$_t$ 3.16 |
| 92 | 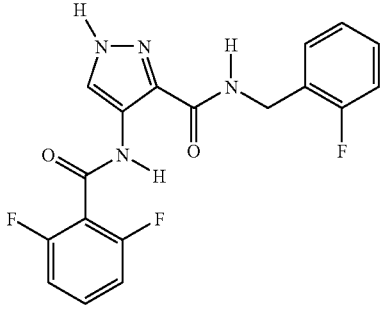 | Procedure A<br>DMSO instead of DMF | [M + H]+ 375<br>R$_t$ 3.02 |
| 93 | 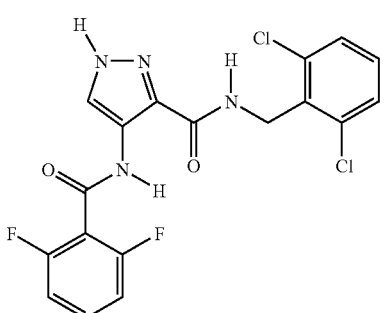 | Procedure A<br>DMSO instead of DMF | [M + H]+ 425<br>R$_t$ 3.27 |
| 94 | 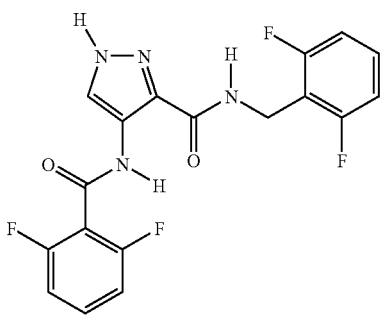 | Procedure A<br>DMSO instead of DMF | [M + H]+ 393<br>R$_t$ 3.01 |

TABLE 4-continued

| Example No. | Structure | Method of Preparation | LCMS |
|---|---|---|---|
| 95 | | Procedure A DMSO instead of DMF | [M + H]⁺ 365 R$_t$ 2.22 |
| 96 | | Procedure A DMSO instead of DMF | [M + H]⁺ 387 R$_t$ 3.05 |
| 97 | | Procedure A DMSO instead of DMF | [M + H]⁺ 464 R$_t$ 3.17 |
| 98 | | Procedure C using the product of Example 97 as starting material | [M + H]⁺ 364 R$_t$ 1.76 |

TABLE 4-continued

| Example No. | | Method of Preparation | LCMS |
|---|---|---|---|
| 99 | | Procedure A<br>DMSO instead of DMF | [M + H]+ 389<br>R$_t$ 2.36 |
| 100 | | Procedure A<br>DMSO instead of DMF | [M + H]+ 351<br>R$_t$ 2.55 |
| 101 | | Procedure A<br>DMSO instead of DMF | [M + H]+ 362<br>R$_t$ 2.63 |
| 102 | | Procedure A<br>DMSO instead of DMF<br>Starting amine prepared<br>according to Procedure L | [M + H]+ 364<br>R$_t$ 1.75 |

TABLE 4-continued
| Example No. | | Method of Preparation | LCMS |
|---|---|---|---|
| 103 | 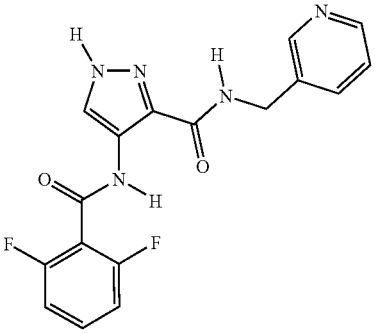 | Procedure A<br>DMSO instead of DMF | [M + H]⁺ 358<br>$R_t$ 3.2 |
| 104 | 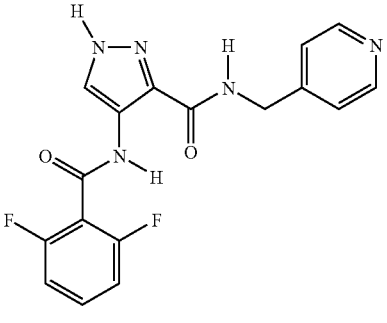 | Procedure A<br>DMSO instead of DMF | [M + H]⁺ 358<br>$R_t$ 1.77 |
| 105 | 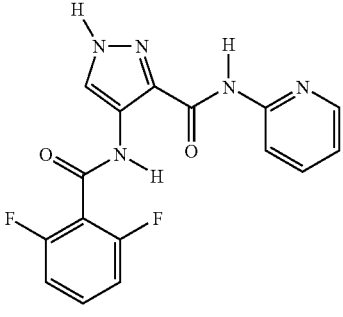 | Procedure A<br>DMSO instead of DMF | [M + H]⁺ 344<br>$R_t$ 2.71 |
| 106 | 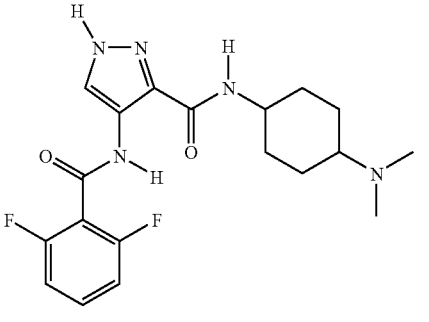 | Procedure A<br>DMSO instead of DMF | [M + H]⁺ 392<br>$R_t$ 2.57 |

TABLE 4-continued

| Example No. | Structure | Method of Preparation | LCMS |
|---|---|---|---|
| 107 | | Procedure A DMSO instead of DMF | [M + H]+ 347 R<sub>t</sub> 2.8 |
| 108 | | Procedure A DMSO instead of DMF | [M + H]+ 371 R<sub>t</sub> 3.1 |
| 109 | | Procedure A Et₃N 1 equiv., DMSO instead of DMF | [M + H]+ 404 R<sub>t</sub> 2.7 |
| 110 | | Procedure A Et₃N 2 equiv., HOAt instead of HOBt, DMSO instead of DMF | [M + H]+ 428 R<sub>t</sub> 2.63 |

TABLE 4-continued

| Example No. | | Method of Preparation | LCMS |
|---|---|---|---|
| 111 | (structure) | Procedure Procedure A followed by Procedure C Et₃N 2 equiv., HOAt instead of HOBt, DMSO instead of DMF | [M + H]⁺ 364 R_t 1.75 |
| 112 | (structure) | Procedure A Et₃N 2 equiv., HOAt instead of HOBt, DMSO instead of DMF | [M + H]⁺ 427 R_t 2.71 |
| 113 | (structure) | Procedure A HOAt instead of HOBt, DMSO instead of DMF | [M + H]⁺ 363 R_t 3.34 |
| 114 | (structure) | Procedure A Et₃N 2 equiv., HOAt instead of HOBt, DMSO instead of DMF | [M + H]⁺ 432 R_t 2.63 |

TABLE 4-continued
| Example No. | | Method of Preparation | LCMS |
|---|---|---|---|
| 115 | 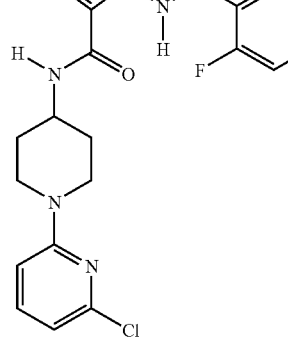 | Procedure A | [M + H]+ 461 R_t 3.3 |
| 116 | 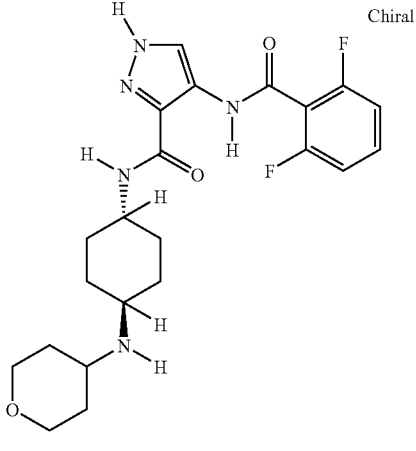 Chiral | Procedure A DMSO instead of DMF, Et_3N 2 equiv Starting amine prepared according to Procedure L | [M + H]+ 448 R_t 1.87 |
| 117 | 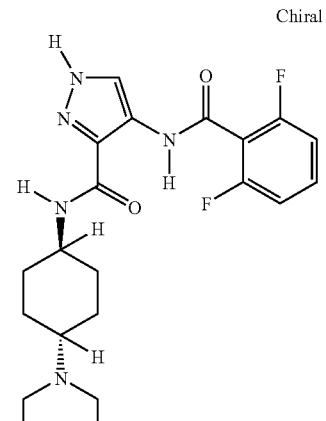 Chiral | Procedure A DMSO instead of DMF, Et_3N 2 equiv Starting amine prepared according to Procedure L | [M + H]+ 447 R_t 1.65 |

TABLE 4-continued
| Example No. | | Method of Preparation | LCMS |
|---|---|---|---|
| 118 | Chiral 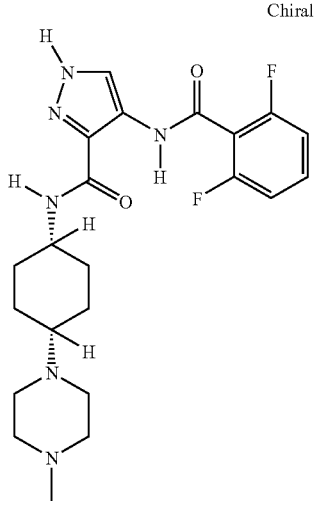 | Procedure A DMSO instead of DMF, Et₃N 2 equiv Starting amine prepared according to Procedure L | [M + H]⁺ 447 R_t 1.72 |
| 119 | 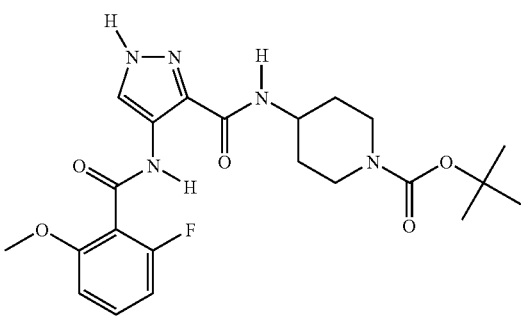 | Procedure B | [M + H]⁺ 462 R_t 2.97 |
| 120 | 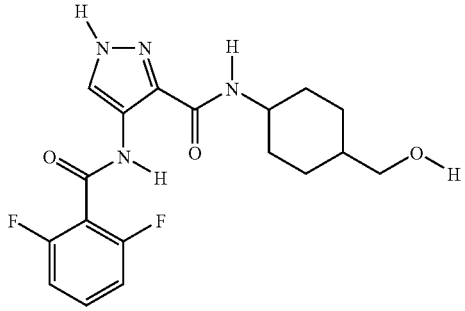 | Procedure A N-ethyl-morpholine (NEM) 2 equiv | [M + H]⁺ 379 R_t 2.45 |

TABLE 4-continued
| Example No. | | Method of Preparation | LCMS |
|---|---|---|---|
| 121 | 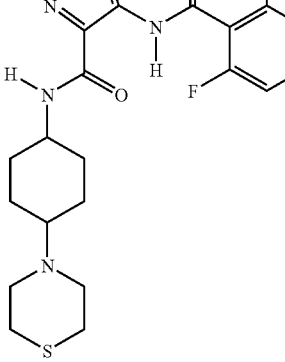 | Procedure A HOAt instead of HOBt, Et₃N 2 equiv Starting amine prepared according to Procedure L | [M + H]⁺ 450 R_t 1.97 |
| 122 | 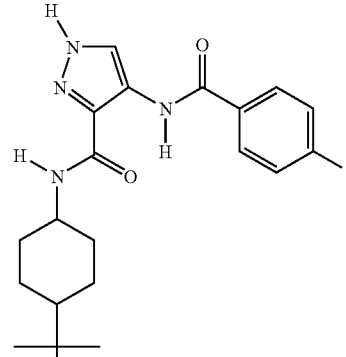 | Procedure B | [M + H]⁺ 387 R_t 3.83 |
| 123 | 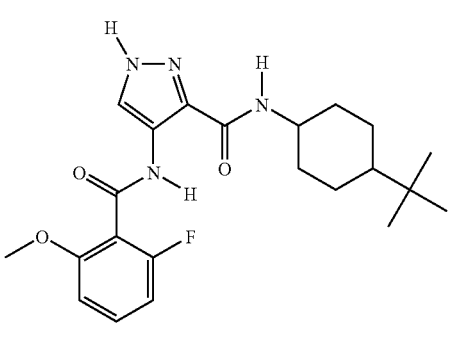 | Procedure B | [M + H]⁺ 417 R_t 3.65 |
| 124 | Chiral 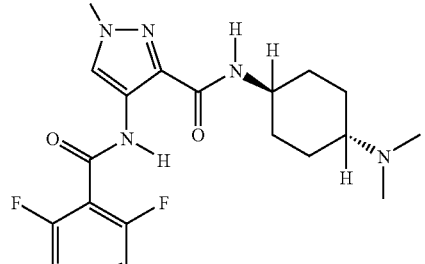 | Procedure A HOAt instead of HOBt, Et₃N 2 equiv | [M + H]⁺ 392 R_t 1.85 |

TABLE 4-continued

| Example No. | Method of Preparation | LCMS |
|---|---|---|
| 125 | Procedure A HOAt instead of HOBt, Et$_3$N 2 equiv | [M + H]$^+$ 408 R$_t$ 1.82 |
| 126 | Procedure B | [M + H]$^+$ 403 R$_t$ 4.02 |
| 127 | Procedure B | [M + H]$^+$ 369 R$_t$ 3.78 |
| 128 | Procedure B | [M + H]$^+$ 435 R$_t$ 3.83 |

TABLE 4-continued
| Example No. | | Method of Preparation | LCMS |
|---|---|---|---|
| 129 | 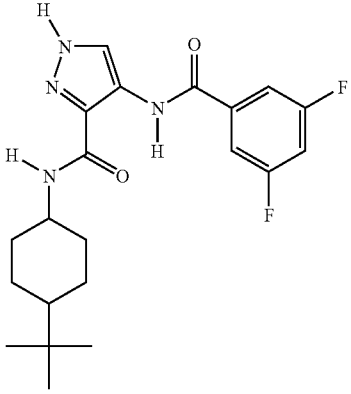 | Procedure B | [M + H]+ 405<br>R$_t$ 3.96 |
| 130 | 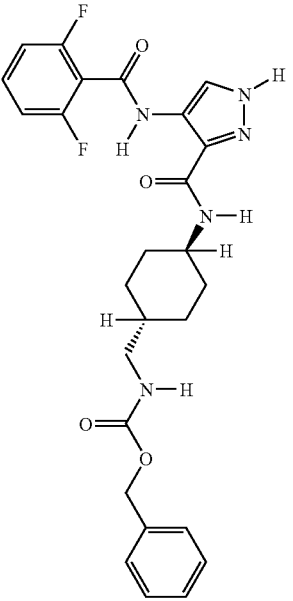<br>Chiral | Procedure A<br>HOAt instead of HOBt | [M + H]+ 512<br>R$_t$ 3.1 |
| 131 | 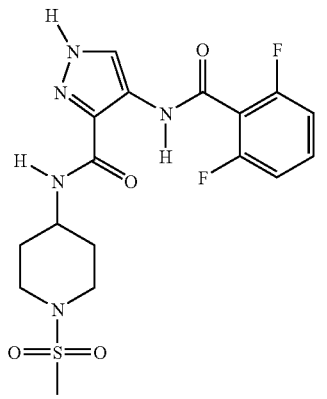 | Procedure A<br>HOAt instead of HOBt, | [M + H]+ 428<br>R$_t$ 2.45 |

TABLE 4-continued
| Example No. | | | Method of Preparation | LCMS |
|---|---|---|---|---|
| 132 | 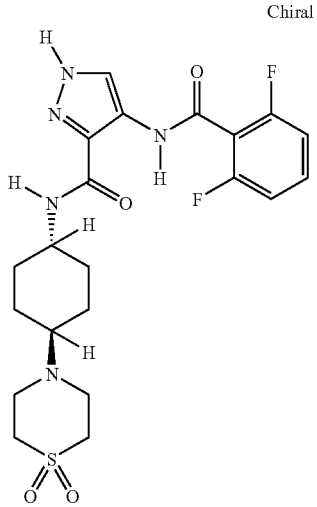 | Chiral | Procedure A<br>HOAt instead of HOBt,<br>Et₃N 2 equiv.<br>Cis and trans isomers separated<br>after amide coupling step<br>Starting amine prepared<br>according to Procedure L | [M + H]⁺ 482<br>R$_t$ 1.96 |
| 133 | 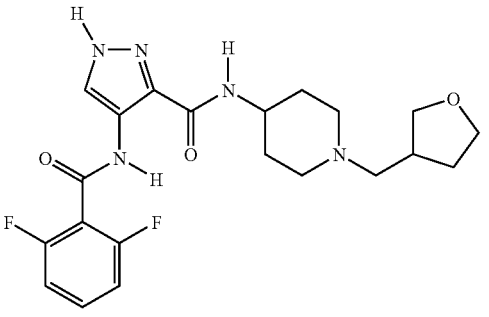 | | Procedure A<br>HOAt instead of HOBt,<br>DMSO instead of DMF | [M + H]⁺ 434<br>R$_t$ 2.3 |
| 134 | 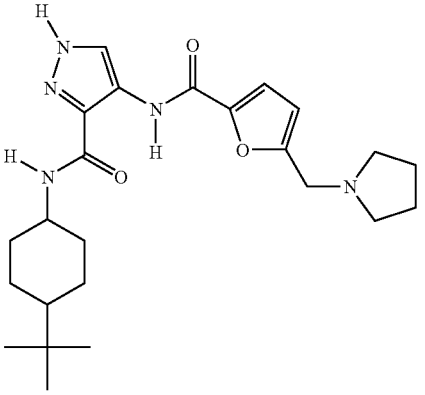 | | Procedure B | [M + H]⁺ 458<br>R$_t$ 2.26 |

TABLE 4-continued
| Example No. | | Method of Preparation | LCMS |
|---|---|---|---|
| 135 | 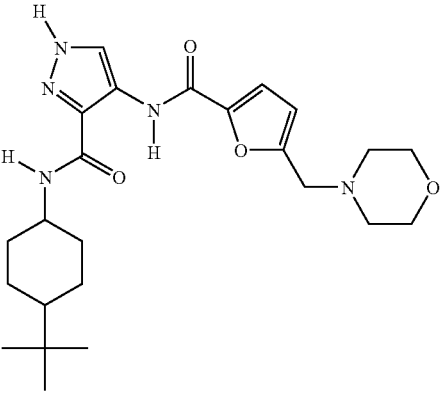 | Procedure B | [M + H]⁺ 468<br>R_t 3.07 |
| 136 | 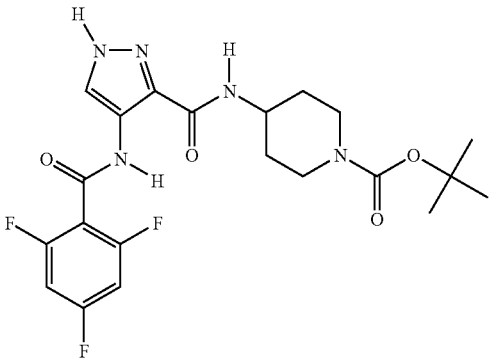 | Procedure B<br>HOAt instead of HOBt, | [M + H]⁺ 468<br>R_t 3.07 |
| 137 | 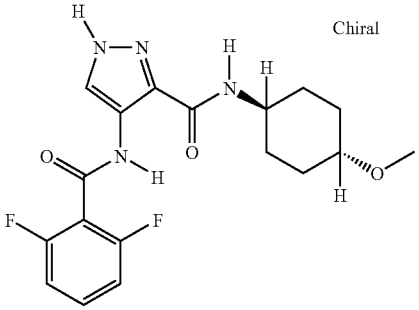 Chiral | Procedure A<br>Et₃N 2 equiv., HOAt instead of HOBt, | [M + H]⁺ 379<br>R_t 2.6 |
| 138 | 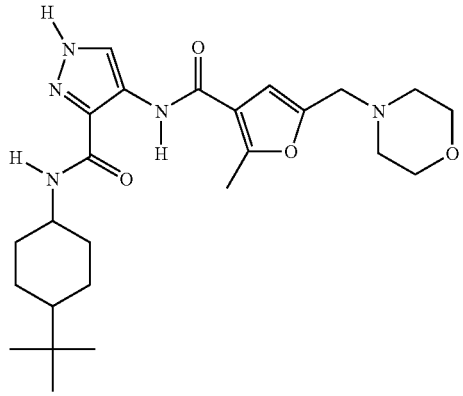 | Procedure B | [M + H]⁺ 472<br>R_t 2.40 |

TABLE 4-continued

| Example No. | | Method of Preparation | LCMS |
|---|---|---|---|
| 139 | Chiral | Procedure A Et₃N 2 equiv., HOAt instead of HOBt, DMSO instead of DMF | [M + H]⁺ 364 R$_t$ 2.1 |
| 140 | | Procedure B followed by Procedure C | [M + H]⁺ 314 R$_t$ 1.78 |
| 141 | | Procedure B followed by Procedure C | [M + H]⁺ 332 R$_t$ 1.89 |
| 142 | | Procedure B followed by Procedure C | [M + H]⁺ 362 R$_t$ 1.78 |

TABLE 4-continued

| Example No. | | Method of Preparation | LCMS |
|---|---|---|---|
| 143 | (structure) | Procedure B followed by Procedure C | [M + H]+ 348 R$_t$ 2.01 |
| 144 | (structure) | Procedure B followed by Procedure C | [M + H]+ 350 R$_t$ 1.97 |
| 145 | (structure) | Procedure B followed by Procedure C | [M + H]+ 350 R$_t$ 2.01 |
| 146 | (structure) | Procedure B followed by Procedure C | [M + H]+ 395 R$_t$ 1.94 |

TABLE 4-continued

| Example No. | Structure | Method of Preparation | LCMS |
|---|---|---|---|
| 147 | | Procedure B followed by Procedure C | [M + H]⁺ 396 R_t 2.11 |
| 148 | | Procedure B followed by Procedure C HOAt instead of HOBt | [M + H]⁺ 368 R_t 1.76 |
| 149 | | Procedure B followed by Procedure C | [M + H]⁺ 366 R_t 1.78 |
| 150 | | Procedure B followed by Procedure C | [M + H]⁺ 383 R_t 1.87 |

TABLE 4-continued

| Example No. | | Method of Preparation | LCMS |
|---|---|---|---|
| 151 | (structure) | Procedure B followed by Procedure C | [M + H]⁺ 433 R_t 1.89 |
| 152 | (structure, Chiral) | Procedure A followed by Procedure C HOAt instead of HOBt | [M + H]⁺ 350 R_t 1.76 |

Examples 153-165

General Procedure D

Preparation of Protected 4-Amino-pyrazol-3-yl carboxylic acid 4-hydroxy-cyclohexylamide

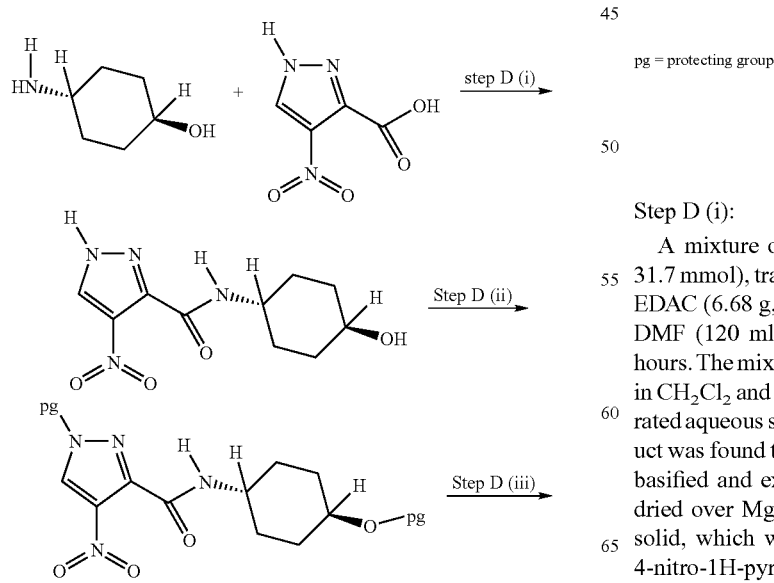

pg = protecting group

Step D (i):

A mixture of 4-nitro-3-pyrazolecarboxylic acid (4.98 g, 31.7 mmol), trans 4-aminocyclohexanol (3.65 g, 31.7 mmol), EDAC (6.68 g, 34.8 mmol) and HOBt (4.7 g, 34.8 mmol) in DMF (120 ml) was stirred at ambient temperature for 16 hours. The mixture was reduced in vacuo, the residue taken up in $CH_2Cl_2$ and washed successively with 5% citric acid, saturated aqueous sodium bicarbonate, water and brine. The product was found to be mainly in the citric acid wash, which was basified and extracted with EtOAc. The organic layer was dried over $MgSO_4$, filtered and evaporated to give a white solid, which was triturated with $CHCl_3$ to give 1.95 g of 4-nitro-1H-pyrazole-3-carboxylic acid 4-hydroxy-cyclohexylamide. (LC/MS: $R_t$ 1.62, [M+H]⁺255).

Step D (ii):

Introduction of Tetrahydro-pyran-2-yl Protecting Group

A solution of 4-nitro-1H-pyrazole-3-carboxylic acid 4-hydroxy-cyclohexylamide (1.95 g; 7.67 mmol) in a mix of THF (50 ml) and chloroform (100 ml), was treated with 3,4-dihydro-2H-pyran (1.54 ml, 15.34 mmol) and p-toluenesulphonic acid monohydrate (100 mg). The reaction mixture was stirred at room temperature overnight, and then excess pyran (0.9 ml) was added in total to bring reaction to completion. The reaction mixture was diluted with $CH_2Cl_2$ and washed successively with saturated aqueous sodium bicarbonate, water and brine. The resulting solution was reduced in vacuo and subject to Biotage column chromatography, eluting with hexane (2 column lengths) followed by 30% ethyl acetate: hexane (10 column lengths), 70% ethyl acetate: hexane (10 column lengths) to give 1.25 g of 4-nitro-1-(tetrahydro-pyran-2-yl-1H-pyrazole-3-carboxylic acid [4-(tetrahydro-pyran-2-yloxy)-cyclohexyl]-amide. (LC/MS: $R_t$ 2.97, $[M+H]^+$423).

Step D (iii):

A solution of 4-nitro-1-(tetrahydro-pyran-2-yl)-1H-pyrazole-3-carboxylic acid [4-(tetrahydro-pyran-2-yloxy)-cyclohexyl]-amide (0.3 g; 0.71 mmol) in methanol (25 ml), was treated with 10% palladium on carbon (30 mg) then hydrogenated at room temperature and pressure overnight. The catalyst was removed by filtration and washed three times with methanol. The filtrate was evaporated to give 0.264 g of the required product. (LC/MS: $R_t$ 2.39, $[M+H]^+$393).

General Procedure E

Procedure for Removal of a Tetrahydropyran-2-yl Protecting Group

To a suspension of 4-(2-methoxy-benzoylamino)-1-(tetrahydro-pyran-2-yl-1H-pyrazole-3-carboxylic acid [4-(tetrahydro-pyran-2-yloxy)-cyclohexyl]-amide (0.125 g, 0.23 mmol) in EtOH (10 ml) was added p-toluene sulphonic acid hydrate (90 mg, 0.46 mmol). The reaction mixture was heated at 70 ° C for 30 mins. The reaction was diluted with EtOAc and washed successively with saturated aqueous sodium bicarbonate, water and brine. The resulting solution was reduced in vacuo to give a white solid, which contained traces of p-toluene sulphonic acid hydrate. The solid was then taken up in EtOAc and washed with 1M NaOH and then brine. The resulting solution was reduced in vacuo and then triturated with ether/ hexane to give 10 mg of required product. (LC/MS: $R_t$ 2.29, $[M+H]^+$359)

General Procedure F

Preparation of a Urea from a 4-Amino-pyrazole-3-carboxylic acid amide

To a solution of 4-amino-1-(tetrahydro-pyran-2-yl-1H-pyrazole-3-carboxylic acid [4-(tetrahydro-pyran-2-yloxy)-cyclohexyl]-amide (80 mg, 0.2 mmol) in toluene (2 ml) was added phenyl isocyanate (929 mg, 0.24 mmol). The reaction mixture was heated at 70° C. for 1 hour. The reaction was diluted with EtOAc and washed successively with water and brine. The resulting solution was reduced in vacuo to give yellow oil. This was used without further purification. (LC/MS: $R_t$ 2.28, $[M+H]^+$344).

General Procedure G

Conversion of a 4-Amino-pyrazole group to a 4-(Morpholine-4-carbonylamino)-Pyrazole Group To a solution of 4-amino-1-(tetrahydro-pyran-2-yl-1H-pyrazole-3-carboxylic acid [4-(tetrahydro-pyran-2-yloxy)-cyclohexyl]-amide (0.1 g, 0.255 mmol) in $CH_2Cl_2$ (5 ml) at −10° C. was added in a dropwise manner a 20% solution of phosgene in toluene. The reaction mixture was stirred at −10° C. for 15 mins and then morpholine (0.765 mmol) was added. The reaction mixture was allowed to warm up to room temperature over 1 hour then stirred at room temperature overnight. The reaction was diluted with $CH_2Cl_2$ and washed successively with saturated sodium bicarbonate and brine. The resulting solution was reduced in vacuo to give a yellow oil which was used without further purification. (LC/MS: $R_t$ 1.68,$[M+H]^+$338).

General Procedure H

Preparation of N-Oxides

To a suspension of the compound of Example 53 (7.7 mg, 0.02 mmol) in $CH_2Cl_2$ (0.5 ml) was added meta-chloroperbenzoic acid (MCPBA) (3.6 mg, 0.02 mmol). The reaction mixture was stirred at room temperature overnight, and then evaporated. The residue was purified by preparative LC/MS, to give 3 mg of the required product. (LC/MS: $R_t$ 1.83, $[M+H]^+$380)

General Procedure I

Removal of a Benzyloxycarbonyl Protecting Group

A solution of the compound of Example 130 (0.2 g; 0.39 mmol) in EtOAc (40 ml) was treated with 10% palladium on carbon (20 mg) then hydrogenated at room temperature and pressure for 3 hours. The catalyst was removed by filtration and washed three times with EtOAc. The filtrate was evaporated and the residue was subjected to chromatography using 10% MeOH—$CH_2Cl_2$ then 20% MeOH—$CH_2Cl_2$ to give 80 mg of the required product. (LC/MS: $R_t$ 1.88, $[M+H]^+$378).

General Procedure J

Mesylation of an Amine

To a solution of the compound of Example 163 (20 mg, 0.05 mmol) in $CH_3CN$ (3 ml) added methane-sulphonyl chloride (0.0045 ml, 0.058 mmol) followed by Hunig's Base (0.018 ml, 0.1 mmol). The reaction mixture was stirred at room temperature for 2 hours and was then evaporated down. The residue was purified by preparative LC/MS to give 8 mg of the required product. (LC/MS: $R_t$ 2.54, $[M+H]^+$456).

By following Procedures A to L, the compounds set out in Table 5 were prepared.

TABLE 5
| Example No. | | Method of Preparation | LCMS |
|---|---|---|---|
| 153 | 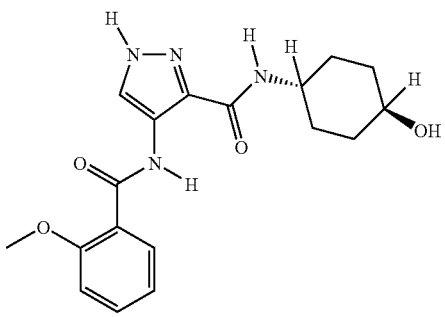 | Procedure D followed by B then E HOAt instead of HOBt, CH$_2$CL$_2$ instead of DMF | [M + H]$^+$359 R$_t$ 2.29 |
| 154 | 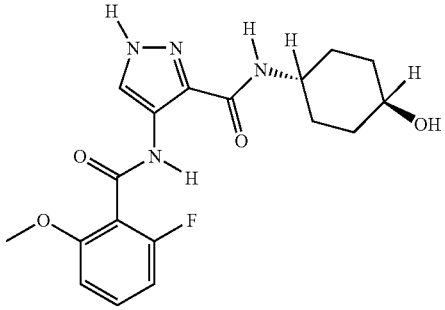 | Procedure D followed by B then E HOAt instead of HOBt, CH$_2$CL$_2$ instead of DMF | [M + H]$^+$377 R$_t$ 2.22 |
| 155 | 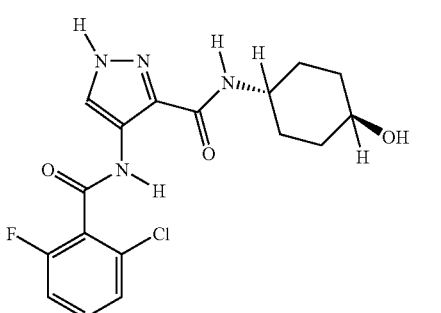 | Procedure D followed by B then E HOAt instead of HOBt, CH$_2$CL$_2$ instead of DMF | [M + H]$^+$381 R$_t$ 2.34 |
| 156 | 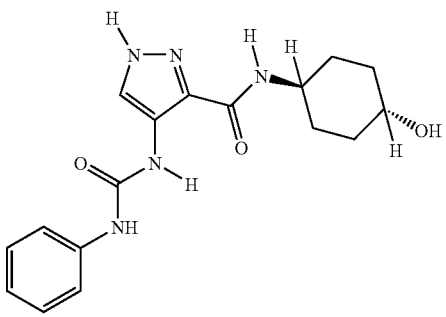 | Procedure D followed by F then E | [M + H]$^+$344 R$_t$ 2.28 |

TABLE 5-continued

| Example No. | | Method of Preparation | LCMS |
|---|---|---|---|
| 157 | (structure) | Procedure D followed by F then E | [M + H]⁺358 R_t 2.22 |
| 158 | (structure) | Procedure D followed by B then E HOAt instead of HOBt, CH₂CL₂ instead of DMF | [M + H]⁺365 R_t 2.21 |
| 159 | (structure) | Procedure D followed by B then E HOAt instead of HOBt, CH₂CL₂ instead of DMF | [M + H]⁺387 R_t 2.29 |
| 160 | (structure) | Procedure D followed by F then E | [M + H]⁺380 R_t 2.17 |

TABLE 5-continued

| Example No. | | Method of Preparation | LCMS |
|---|---|---|---|
| 161 | (structure) | Procedure D followed by G then E | [M + H]⁺ 338 R$_t$ 1.68 |
| 162 | (structure) | Procedure H | [M + H]⁺ 380 R$_t$ 1.83 |
| 163 | (structure) Chiral | Procedure A (HOAt instead of HOBt) to give the compound of Example 130 followed by Procedure I. | [M + H]⁺ 378 R$_t$ 2.58 |
| 164 | (structure) | Procedure A (HOAt instead of HOBt) and I to give the compound of Example 163 followed by Procedure J | [M + H]⁺ 358 R$_t$ 2.22 |

General Procedure M

Formation of pyrazole 4-amide group

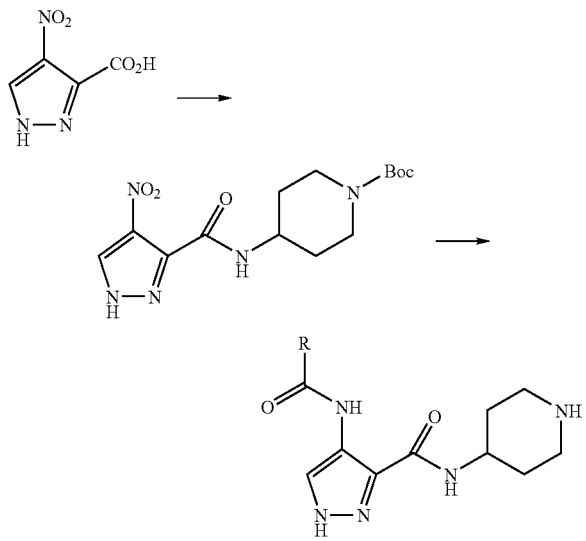

4-Nitropyrazole-3-carboxylic acid (7.3 g; 15.9 mmol) was added to a stirred solution of 4-amino-1-Boc-piperidine (10.2 mg; 51 mmol), EDC (10.7 g; 55.8 mmol), and HOAt (55.8 g; 19.1 mmol) in DMF (100 ml), and then stirred at room temperature overnight. The solvent was removed by evaporation under reduced pressure and the residue triturated with water (250 ml). The resultant cream solid was collected by filtration, washed with water then dried under vacuum to give 13.05 g of 4-[(4-nitro-1H-pyrazole-3-carbonyl)-amino]-piperidine-1-carboxylic acid tert-butyl ester (LC/MS: $R_t$ 2.50, [M+H]$^+$340).

4-[(4-Nitro-1H-pyrazole-3-carbonyl)-amino]-piperidine-1-carboxylic acid tert-butyl ester (13.05 g) was dissolved in ethanol/DMF (300 ml/75 ml), treated with 10% palladium on carbon (500 mg) then hydrogenated at room temperature and pressure overnight. The catalyst was removed by filtration through Celite and the filtrate evaporated and re-evaporated with toluene. The crude material was purified by flash column chromatography eluting with EtOAc then 2% MeOH/EtOAc then 5% MeOH/EtOAc. Product containing fractions were combined and evaporated to give 8.78 g of 4-[(4-amino-1H-pyrazole-3-carbonyl)-amino]-piperidine-1-carboxylic acid tert-butyl ester as a brown foam. (LC/MS: $R_t$ 1.91, [M+H]$^+$ 310).

To a stirred solution of 4-[(4-amino-1H-pyrazole-3-carbonyl)-amino]-piperidine-1-carboxylic acid tert-butyl ester (200 mg; 0.65 mmol), EDAC (150 mg; 0.78 mmol) and HOBt (105 mg; 0.78 mmol) in 5 ml of N,N-dimethylformamide was added the corresponding carboxylic acid (0.25 mmol), and the mixture was then left at room temperature overnight. The reaction mixture was diluted with saturated aqueous sodium bicarbonate solution and the product collected by filtration and dried under vacuum. The Boc-protected compound was dissolved in saturated HCl/EtOAc and stirred at room temperature for 3 hours. The product was collected by filtration, washed with diethyl ether and dried under vacuum.

General Procedure N

Preparation of 1-tert-Butyl-piperidin-4-ylamine

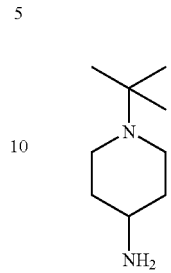

Step N (i)

To a solution of 1-ethyl-4-oxopiperidine (25 g, 0.197 mol) in acetone (250 ml) at RT in a water bath was added methyl iodide (15.5 ml, 0.25 mol) at such a rate to keep the temperature below 30° C. The mixture was filtered and the precipitate washed with acetone and dried to yield 1-ethyl-1-methyl-4-oxopiperidinium iodide (45 g) (LC/MS: $R_t$ 0.38, [M+H]$^+$ 143).

Step N (ii)

To a solution of t-butylamine (78.2 ml, 0.74 mol) in toluene (400 ml) was added a solution of 1-ethyl-1-methyl-4-oxopiperidinium iodide (40 g, 0.148 mol) and sodium bicarbonate (1.245 g, 0.014 mol) in water (60 ml). The reaction mixture was heated at 78° C. for 6 hours and then allowed to cool to ambient temperature. The layers were separated and the aqueous layer was washed with EtOAc. The organics were combined and washed with brine, dried (MgSO$_4$), filtered and reduced in vacuo to yield 1-tert-butyl-4-oxopiperidine (14 g) (LC/MS: $R_t$ 0.39, [M+H]$^+$156).

Step N (iii)

A solution of 1-tert-butyl-4-oxopiperidine (3.6 g, 23.1), benzylamine (5.1 ml, 46.8 mmol), acetic acid (1.5 ml) and sodium triacetoxyborohydride (7.38 g, 34.8 mmol) was stirred at ambient for 2 days. Reaction mixture reduced in vacuo, residue partitioned between aqueous K$_2$CO$_3$ and EtOAc. The organic portion was dried (Na$_2$SO$_4$), filtered and reduced in vacuo. The residue was subjected to chromatography using CH$_2$Cl$_2$/MeOH/NH$_4$OH (87/12/1)as the eluent to yield N-benzyl-1-tert-butylpiperidin-4-amine (1.5 g) (LC/MS: $R_t$ 0.45, [M+H]$^+$247).

Step N (iv)

A solution of N-benzyl-1-tert-butylpiperidin-4-amine (1.56 g) and 10% palladium on carbon (2 g) in MeOH (250 ml) was hydrogenated in a Parr shaker at 50 psi for 16 hours. The solution was filtered and the reaction mixture reduced in vacuo, to yield 1-tert-butylpiperidin-4-amine (0.64 g) (LC/MS: $R_t$ 02.31, no [M+H]$^+$).

Example 165

Synthesis of 4-(2,6-difluoro-benzoylamino)-1H-pyrazole-3-carboxylic acid [5-fluoro-2-(1-methyl-piperidin-4-yloxy)-phenyl]-amide

165A. Synthesis of 4-nitro-1H-pyrazole-3-carboxylic acid ethyl ester

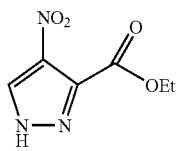

Thionyl chloride (2.90 ml, 39.8 mmol) was slowly added to a mixture of 4-nitro-3-pyrazolecarboxylic acid (5.68 g, 36.2 mmol) in EtOH (100 ml) at ambient temperature and the mixture stirred for 48 h. The mixture was reduced in vacuo and dried through azeotrope with toluene to afford 4-nitro-1H-pyrazole-3-carboxylic acid ethyl ester as a white solid (6.42 g, 96%). ($^1$H NMR (400 MHz, DMSO-$d_6$) δ 14.4 (s, 1H), 9.0 (s, 1H), 4.4 (q, 2H), 1.3 (t, 3H)).

165B. Synthesis of 4-amino-1H-pyrazole-3-carboxylic acid ethyl ester

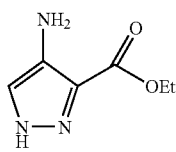

A mixture of 4-nitro-1H-pyrazole-3-carboxylic acid ethyl ester (6.40 g, 34.6 mmol) and 10% Pd/C (650 mg) in EtOH (150ml) was stirred under an atmosphere of hydrogen for 20 h. The mixture was filtered through a plug of Celite, reduced in vacuo and dried through azeotrope with toluene to afford 4-amino-1H-pyrazole-3-carboxylic acid ethyl ester as a pink solid (5.28 g, 98%). ($^1$H NMR (400 MHz, DMSO-$d_6$) δ 12.7 (s, 1H), 7.1 (s, 1H), 4.8 (s, 2H), 4.3 (q, 2H), 1.3 (t, 3H)).

165C. Synthesis of 4-(2,6-difluoro-benzoylamino)-1H-pyrazole-3-carboxylic acid ethyl ester

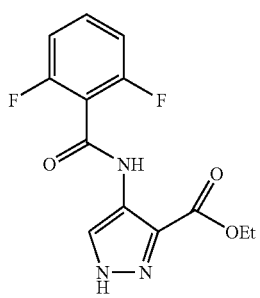

A mixture of 2,6-difluorobenzoic acid (6.32 g, 40.0 mmol), 4-amino-1H-pyrazole-3-carboxylic acid ethyl ester (5.96 g, 38.4 mmol), EDC (8.83 g, 46.1 mmol) and HOBt (6.23 g, 46.1 mmol) in DMF (100 ml) was stirred at ambient temperature for 6 h. The mixture was reduced in vacuo, water added and the solid formed collected by filtration and air-dried to give 4-(2,6-difluoro-benzoylamino)-1H-pyrazole-3-carboxylic acid ethyl ester as the major component of a mixture (15.3 g). (LC/MS: $R_t$ 3.11, [M+H]$^+$ 295.99).

165D. Synthesis of 4-(2,6-difluoro-benzoylamino)-1H-pyrazole-3-carboxylic acid

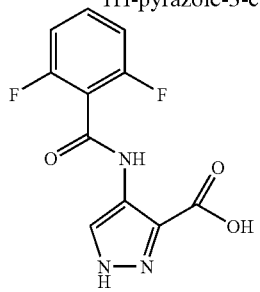

A mixture of 4-(2,6-difluoro-benzoylamino)-1H-pyrazole-3-carboxylic acid ethyl ester (10.2 g) in 2 M aqueous NaOH/MeOH (1:1, 250 ml) was stirred at ambient temperature for 14 h. Volatile materials were removed in vacuo, water (300 ml) added and the mixture taken to pH 5 using 1M aqueous HCl. The resultant precipitate was collected by filtration and dried through azeotrope with toluene to afford 4-(2,6-difluoro-benzoylamino)-1H-pyrazole-3-carboxylic acid as a pink solid (5.70 g). (LC/MS: $R_t$ 2.33, [M+H]$^+$ 267.96).

165E. Synthesis of 5-fluoro-2-(1-methyl-piperidin-4-yloxy)-phenylamine

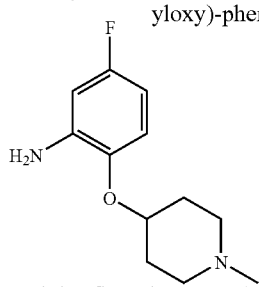

3,4-Dinitrofluorobenzene (1.86 g, 10 mmol) and 4-hydroxy-1-methylpiperidine (1.38 g, 12 mmol) were dissolved in THF (20 ml) and stirred at ambient temperature while sodium hydride (60% dispersion in mineral oil, 0.40 g, 10 mmol) was added in several small portions. The reaction mixture was stirred for one hour and then reduced in vacuo, partitioned between ethyl acetate and water, and the organic phase washed with brine, dried (MgSO$_4$) and reduced in vacuo. The resulting residue was subject to column chromatography, eluting with 5% MeOH/DCM to give a yellow solid (1.76 g, 2:1 ratio of 4-(3,4-dinitro-phenoxy)-1-methyl-piperidine and a 4-(4-fluoro-2-nitro-phenoxy)-1-methyl-piperidine).

A sample of the mixture of products obtained (0.562 g) was dissolved in DMF (10 ml) under an atmosphere of nitrogen. Palladium on carbon (10%, 0.056 g) was added and the reaction mixture was shaken under a hydrogen atmosphere for 40 hours. The solids were removed by filtration and the filtrate reduced in vacuo, taken up in ethyl acetate, washed (saturated aqueous ammonium chloride solution, then saturated aqueous brine), dried (MgSO$_4$) and reduced in vacuo to give 5-fluoro-2-(1-methyl-piperidin-4-yloxy)-phenylamine) as a brown oil (0.049 g, 7%). ($^1$H NMR (400 MHz, MeOD-$d_4$) δ 6.6 (m, 2H), 6.4 (m, 1H), 4.3 (m, 1H), 2.7 (m, 2H), 2.3 (m, 2H), 1.9 (m, 2H), 1.7 (m, 2H)).

165F. Synthesis of 4-(2,6-Difluoro-benzoylamino)-1H-pyrazole-3-carboxylic acid [5-fluoro-2-(1-methyl-piperidin-4-yloxy)-phenyl]-amide

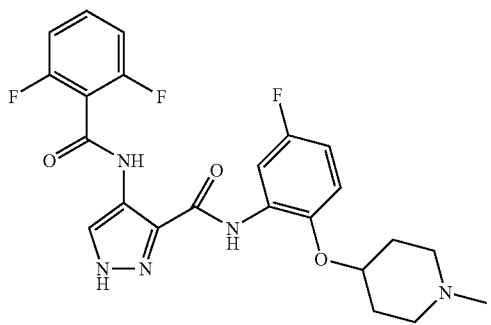

5-fluoro-2-(1-methyl-piperidin-4-yloxy)-phenylamine) (0.049 g, 0.22 mmol) was combined with 4-(2,6-difluoro-benzoylamino)-1H-pyrazole-3-carboxylic acid (0.053 g, 0.20 mmol), EDC (0.048 g, 0.25 mmol), HOBt (0.034 g, 0.25 mmol) and DMF (1 ml) and the resulting reaction mixture was stirred at ambient temperature for 18 hours. The reaction mixture was reduced in vacuo and purified by preparative LC/MS to give 4-(2,6-Difluoro-benzoylamino)-1H-pyrazole-3-carboxylic acid [5-fluoro-2-(1-methyl-piperidin-4-yloxy)-phenyl]-amide as a buff solid. (0.010 g, 11%) (LC/MS: $R_t$ 2.19, $[M+H]^+$ 474.27).

Example 166
Synthesis of 4-(2,6-Difluoro-benzoylamino)-1H-pyrazole-3-carboxylic acid [5-fluoro-2-(2-pyrrolidin-1-yl-ethoxy)-phenyl]-amide

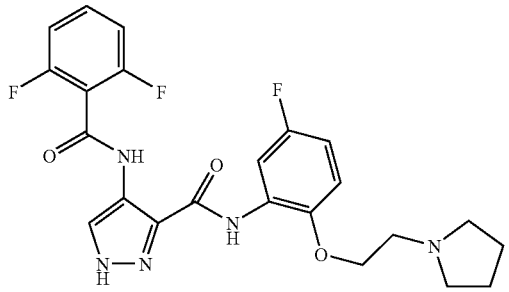

3,4-Dinitrofluorobenzene (0.93 g, 5 mmol) and 1-(2-hydroxyethylpyrrolidine) (0.69 g, 6 mmol) were dissolved in THF (10 ml) and stirred at ambient temperature while sodium hydride (60% dispersion in mineral oil, 0.24 g, 6 mmol) was added in several small portions. The reaction mixture was stirred for 5 hours, diluted with ethyl acetate and the combined organics washed with water and brine, dried ($MgSO_4$) and reduced in vacuo. The resulting residue was subject to column chromatography, eluting with 5% MeOH/DCM to give an orange oil (0.94 g, 1:1 ratio of 1-[2-(3,4-dinitro-phenoxy)-ethyl]-pyrrolidine and 1-[2-(4-Fluoro-2-nitro-phenoxy)-ethyl]-pyrrolidine.

A sample of the mixture of products obtained (0.281 g) was dissolved in DMF (5 ml) under an atmosphere of nitrogen. Palladium on carbon (10%, 0.028 g) was added and the reaction mixture was shaken under a hydrogen atmosphere for 20 hours. The solids were removed by filtration and the filtrate reduced in vacuo and combined with 4-(2,6-difluoro-benzoylamino)-1H-pyrazole-3-carboxylic acid (0.134 g, 0.50 mmol), EDC (0.116 g, 0.60 mmol), HOBt (0.081 g, 0.60 mmol) and DMF (2.5 ml) and the resulting reaction mixture was stirred at ambient temperature for 18 hours. The reaction mixture was reduced in vacuo and the residue partitioned between ethyl acetate (50 ml) and saturated aqueous sodium bicarbonate solution (50 ml). The organic layer was washed with brine, dried ($MgSO_4$) and reduced in vacuo to give the intermediate amides. Acetic acid (10 ml) was added to the crude amide and the mixture was heated at reflux for 3 hours and then reduced in vacuo. 4-(2,6-Difluoro-benzoylamino)-1H-pyrazole-3-carboxylic acid [5-fluoro-2-(2-pyrrolidin-1-yl-ethoxy)-phenyl]-amide was isolated from the residue by preparative LC/MS as an off white solid (0.040 g, 5.6%). (LC/MS: $R_t$ 2.38, $[M+H]^+$ 474.33).

Examples 167-223

By following the procedures described above, the compounds set out in Table 6 were prepared.

TABLE 6

| Example No. | Structure | Method | Differences | LCMS |
| --- | --- | --- | --- | --- |
| 167 | 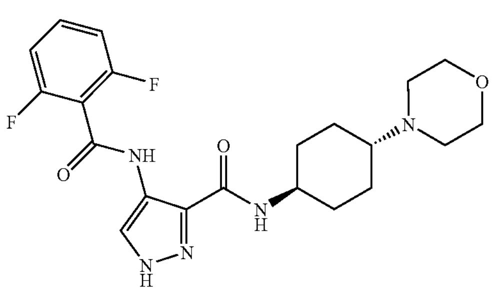 | A Starting amine prepared according to Procedure L | HOAt instead of HOBt DMSO as solvent instead of DMF Et₃N 2 eq Purified by HPLC Cis/Trans Isomers seperated after amine preparation (L) | $[M + H]^+$ 434 $R_t$ 1.97 |

TABLE 6-continued

| Example No. | Structure | Method | Differences | LCMS |
|---|---|---|---|---|
| 168 | 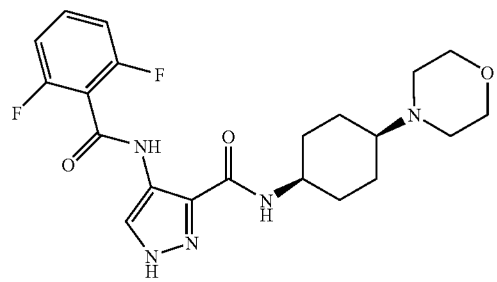 | A Starting amine prepared according to Procedure L | HOAt instead of HOBt DMSO as solvent instead of DMF Et$_3$N 2 eq Purified by chromatogrphy 10% MeOH/CH$_2$Cl$_2$ Cis/Trans Isomers seperated after amine preparation (L) | [M + H]$^+$434 R$_t$ 2.03 |
| 169 | 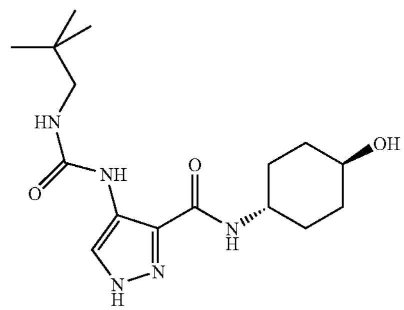 | Procedure D followed by G then E | | [M + H]$^+$338 R$_t$ 2.28 |
| 170 | 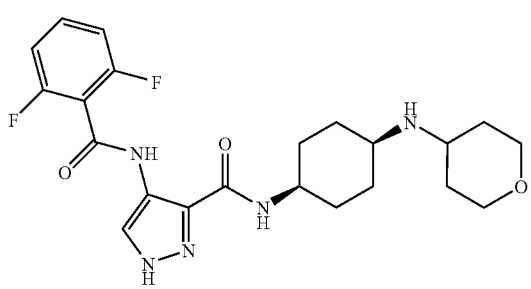 | A Starting amine prepared according to Procedure L | DMSO as solvent instead of DMF Et$_3$N eq Heated 80° C. for 4 hours then RT O/N Purified by HPLC Cis/Trans Isomers seperated after final step | [M + H]$^+$448 R$_t$ 1.97 |
| 171 | 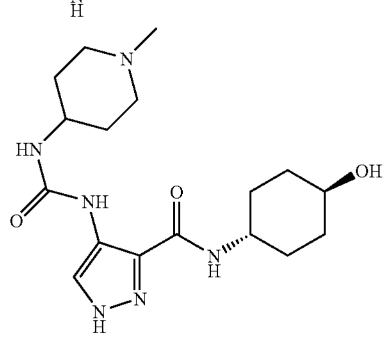 | Procedure D followed by G then E | | [M + H]$^+$365 R$_t$ 0.34 |
| 172 | 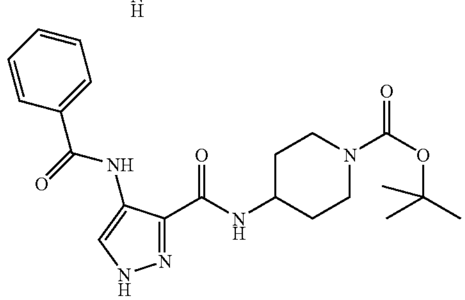 | B | Purified by column chromatography (pet. ether-EtOAc (1:1)) | [M + H]$^+$414.13 R$_t$ 3.05 |

TABLE 6-continued

| Example No. | Structure | Method | Differences | LCMS |
|---|---|---|---|---|
| 173 | (4-fluorobenzamide pyrazole carboxamide piperidine Boc) | B | Purified by column chromatography (pet. ether-EtOAc (1:1)) | [M + H]⁺432.12 R_t 3.12 |
| 174 | (4-chlorobenzamide pyrazole carboxamide piperidine Boc) | B | Purified by column chromatography (pet. ether-EtOAc (1:1)) | [M + H]⁺448.06 R_t 3.33 |
| 175 | (3,5-difluorobenzamide pyrazole carboxamide piperidine Boc) | B | Purified by column chromatography (pet. ether-EtOAc (1:1)) | [M + H]⁺450.08 R_t 3.29 |
| 176 | (4-(difluoromethoxy)benzamide pyrazole carboxamide piperidine Boc) | B | Purified by column chromatography (pet. ether-EtOAc (1:1)) | [M + H]⁺480.05 R_t 3.18 |
| 177 | (2,6-difluorobenzamide pyrazole carboxamide 4-(4-methylpiperazin-1-yl)piperidine) | A Starting amine prepared according to Procedure L | HOAt instead of HOBt DMSO as solvent instead of DMF Et₃N 2 eq Purified by HPLC and formation of HCl salt | [M + H]⁺447 R_t 2.01 |

TABLE 6-continued

| Example No. | Structure | Method | Differences | LCMS |
|---|---|---|---|---|
| 178 | 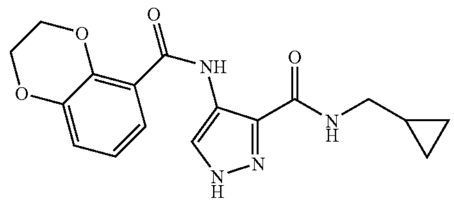 | B | | [M + H]⁺343.05 R_t 3.38 (polar method) |
| 179 | 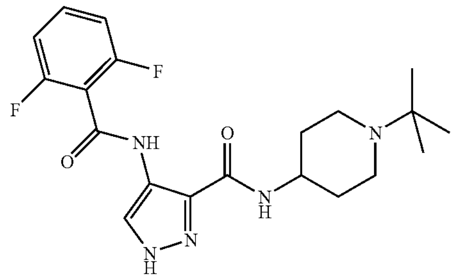 | A Butyl-piperidin-4-ylamine prepared by Procedure N | HOAt instead of HOBt Purified by trituration with MeOH | [M + H]⁺406 R_t 1.85 |
| 180 | 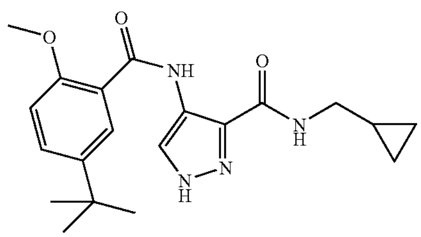 | B | | [M + H]⁺371.09 R_t 3.27 (polar method) |
| 181 | 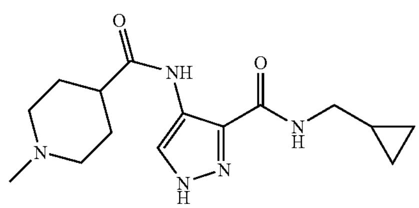 | B | | [M + H]⁺306.06 R_t 1.53 |
| 182 | 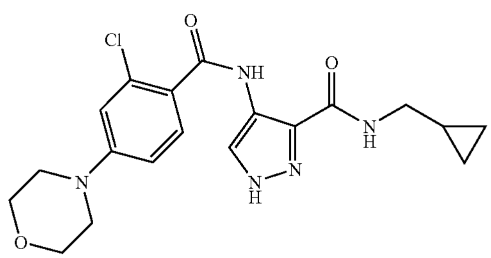 | B | | [M + H]⁺403.98 R_t 2.78 |
| 183 | 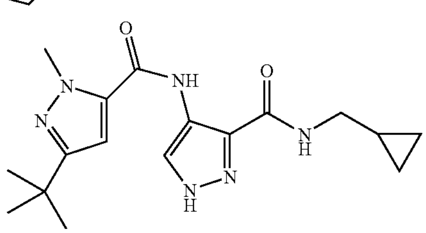 | B | | [M + H]⁺345.05 R_t 3.03 |
| 184 | 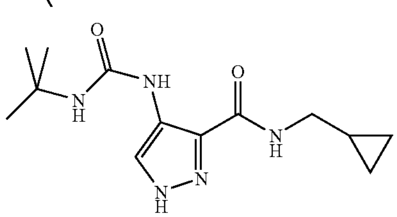 | B | | [M + H]⁺280.05 R_t 3.75 (basic method) |

TABLE 6-continued

| Example No. | Structure | Method | Differences | LCMS |
| --- | --- | --- | --- | --- |
| 185 | 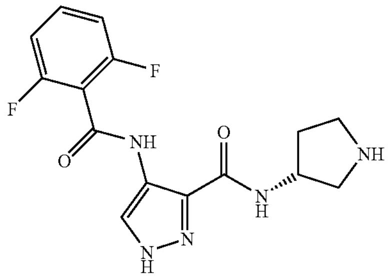 | A | HOAt instead of HOBt followed by EtOAc/HCl deprotection | [M + H]$^+$336 R$_t$ 1.67 |
| 186 | 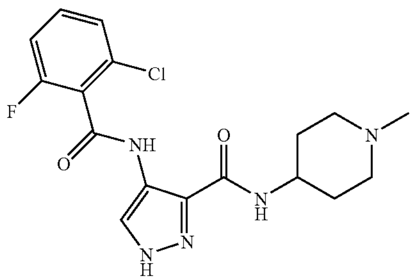 | A | | [M + H]$^+$380.05 R$_t$ 1.78 |
| 187 | 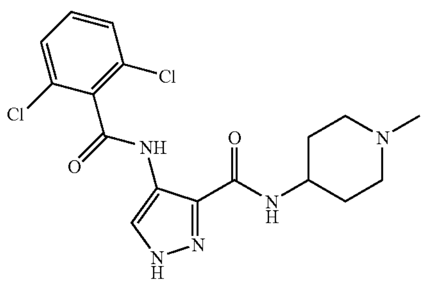 | A | | [M + H]$^+$396.02 R$_t$ 1.86 |
| 188 | 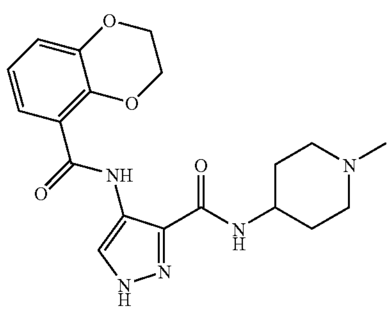 | A | | [M + H]$^+$386.10 R$_t$ 1.88 |
| 189 | 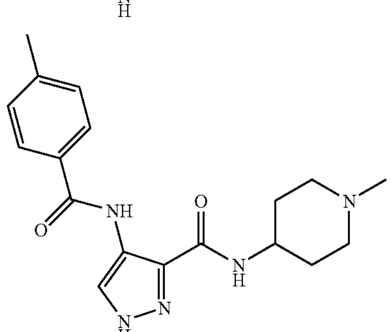 | A | | [M + H]$^+$342.10 R$_t$ 1.95 |

TABLE 6-continued

| Example No. | Structure | Method | Differences | LCMS |
| --- | --- | --- | --- | --- |
| 190 | 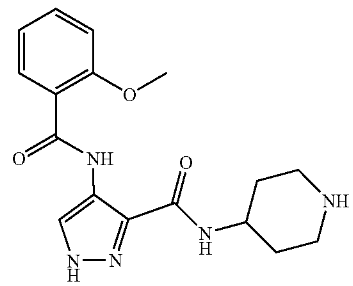 | M | | [M + H]⁺ = 344<br>R_t = 1.87 |
| 191 | 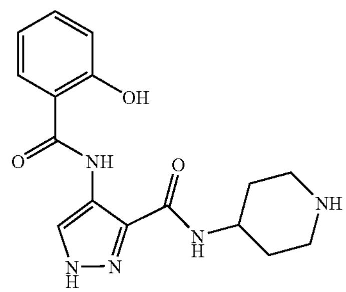 | M | | [M + H]⁺ = 330<br>R_t = 1.80 |
| 192 | 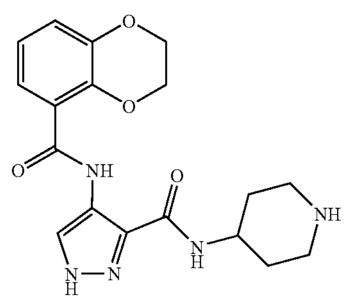 | M | | [M + H]⁺ = 372<br>R_t = 1.87 |
| 193 | 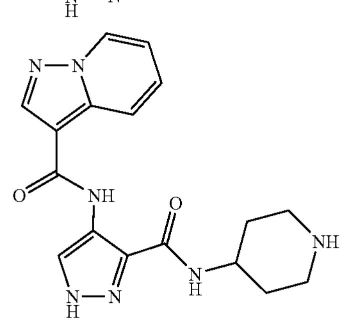 | M | | [M + H]⁺ = 354<br>R_t = 1.77 |
| 194 | 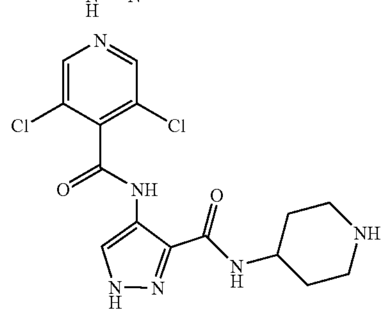 | M | Purified by flash chromatography eluting with dichloromethane 120 ml, methanol 15, acetic acid 3 ml, water 2 ml (dmaw 120) | [M + H]⁺ = 383/385<br>R_t = 1.72 |

TABLE 6-continued

| Example No. | Structure | Method | Differences | LCMS |
|---|---|---|---|---|
| 195 | 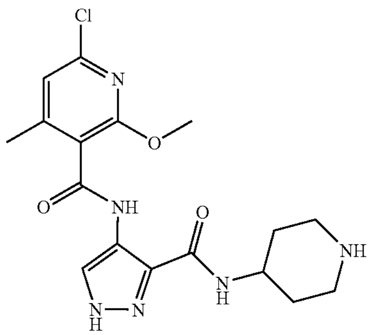 | M | Purified by flash chromatography eluting with DMAW 120 | [M + H]⁺ = 393/395<br>R$_t$ = 1.86 |
| 196 | 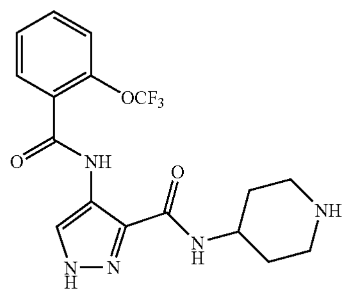 | M | | [M + H]⁺ = 398<br>R$_t$ = 1.94 |
| 197 | 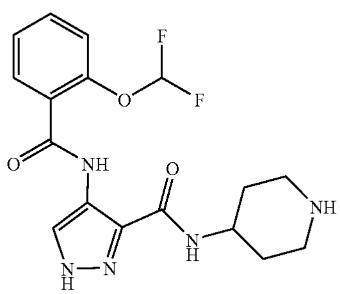 | M | | [M + H]⁺ = 330<br>R$_t$ = 1.80 |
| 198 | 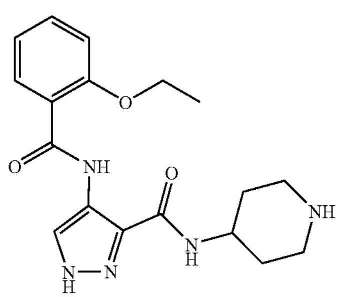 | M | | [M + H]⁺ = 358<br>R$_t$ = 1.89 |
| 199 | 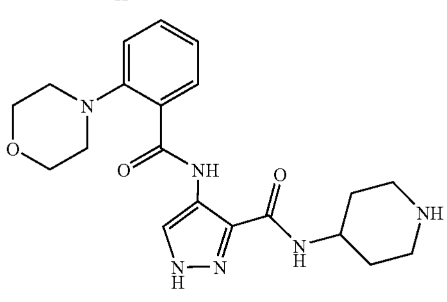 | M | | [M + H]⁺ = 399<br>R$_t$ = 1.88 |

TABLE 6-continued

| Example No. | Structure | Method | Differences | LCMS |
|---|---|---|---|---|
| 200 | 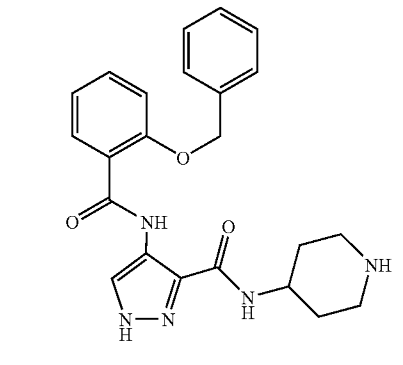 | M | | [M + H]⁺ = 420<br>R_t = 2.13 |
| 201 | 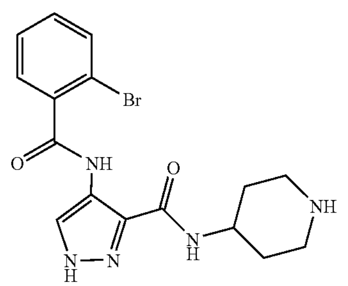 | M | | [M + H]⁺ = 392/394<br>R_t = 1.84 |
| 202 | 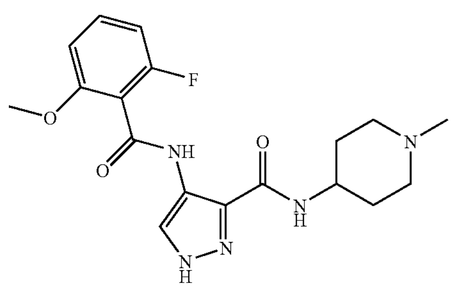 | B | Purified using flash chromatography (CH₂Cl₂–MeOH—AcOH—H₂O (90:18:3:2)) | [M + H]⁺ 376.14<br>R_t 1.78 |
| 203 | 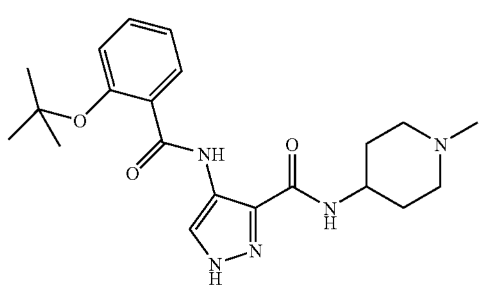 | B | Purified using flash chromatography (CH₂Cl₂–MeOH—AcOH—H₂O (90:18:3:2)) | [M + H]⁺ 400.17<br>R_t 2.08 |
| 204 | 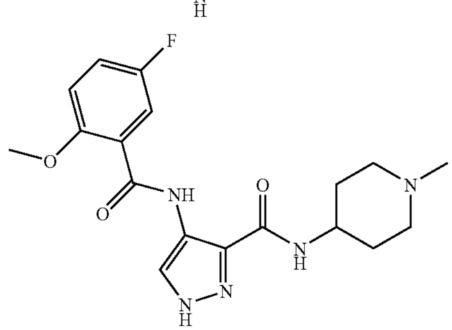 | B | Purified using flash chromatography (CH₂Cl₂–MeOH—AcOH—H₂O (90:18:3:2)) | [M + H]⁺ 376.15<br>R_t 1.92 |

TABLE 6-continued

| Example No. | Structure | Method | Differences | LCMS |
|---|---|---|---|---|
| 205 | 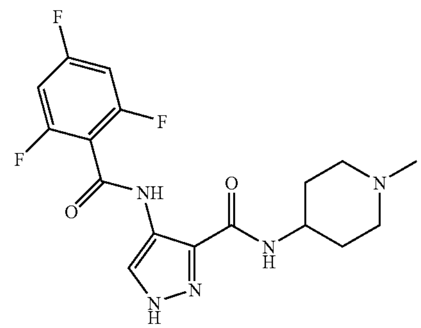 | B | Purified using column chromatography (CH₂Cl₂–MeOH—AcOH—H₂O (90:18:3:2)) | [M + H]⁺382.12 R$_t$ 1.77 |
| 206 | 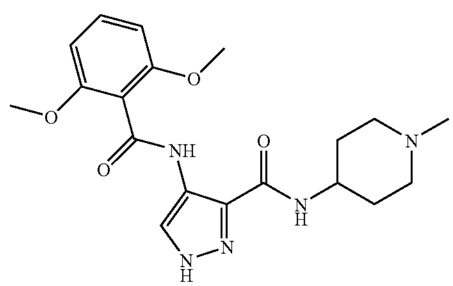 | B | Purified using column chromatography (CH₂Cl₂–MeOH—AcOH—H₂O (90:18:3:2)) | [M + H]⁺388.18 R$_t$ 1.73 |
| 207 | 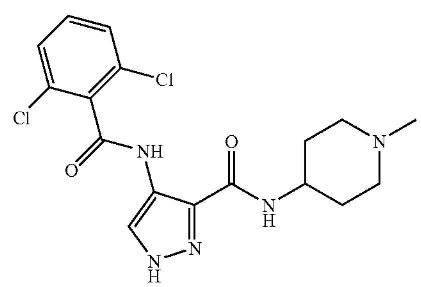 | A | Purified by flash chromatography eluting with DMAW 120 | [M + H]⁺= 397/399 R$_t$ = 1.83 |
| 208 | 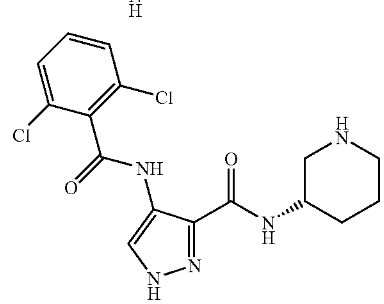 | A | Coupling using (S)-3-amino-1-N–BOC–piperidine. Deprotection as procedure M. Purified using column chromatography (CH₂Cl₂–MeOH—AcOH—H₂O (90:18:3:2)) | [M + H]⁺382.02 R$_t$ 1.82 |
| 209 | 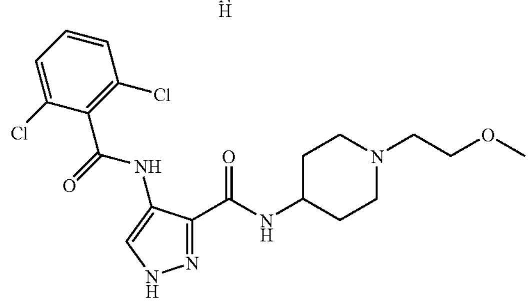 | A | | [M + H]⁺440.22 R$_t$ 1.92 |

TABLE 6-continued

| Example No. | Structure | Method | Differences | LCMS |
|---|---|---|---|---|
| 210 | 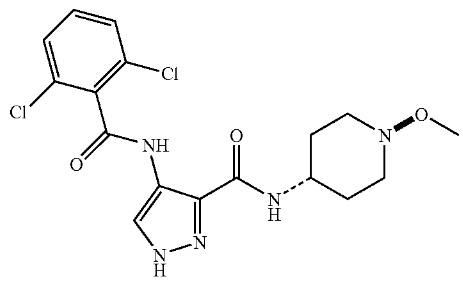 | A | | [M + H]⁺411.20<br>R$_t$ 2.97 |
| 211 | 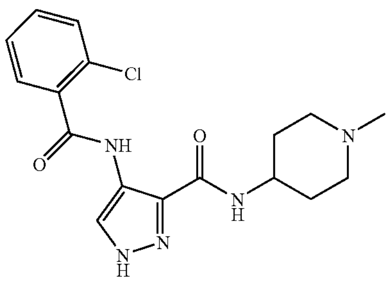 | A | Purified by prep. LCMS after work-up | [M + H]⁺362.11<br>R$_t$ 1.91 |
| 212 | 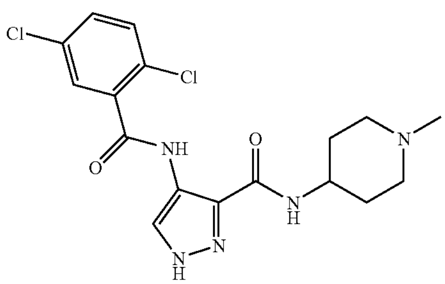 | A | Purified by prep. LCMS after work-up | [M + H]⁺396.08<br>R$_t$ 2.06 |
| 213 | 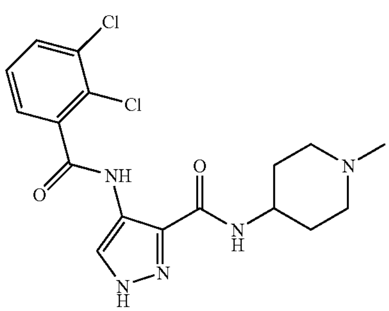 | A | Purified by prep. LCMS after work-up | [M + H]⁺396.06<br>R$_t$ 2.04 |
| 214 | 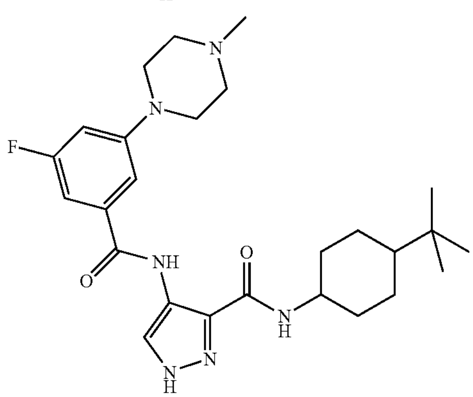 | B | The mixture was reduced in vacuo, the residue taken up in EtOAc and washed successively with saturated aqueous sodium bicarbonate, water and brine. The organic portion was dried (MgSO$_4$) and reduced in vacuo to give the desired product | [M + H]⁺485<br>R$_t$ 2.59 |

TABLE 6-continued

| Example No. | Structure | Method | Differences | LCMS |
|---|---|---|---|---|
| 215 | 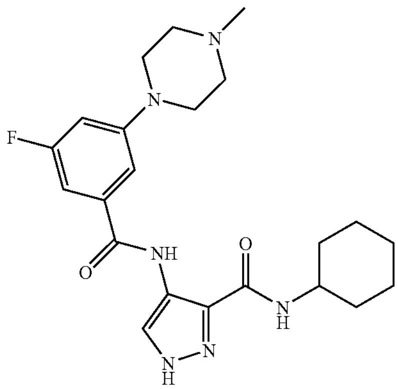 | B | The mixture was reduced in vacuo, the residue taken up in EtOAc and washed successively with saturated aqueous sodium bicarbonate, water and brine. The organic portion was dried (MgSO$_4$) and reduced in vacuo to give the desired product | [M + H]$^+$ 429<br>R$_t$ 2.25 |
| 216 | 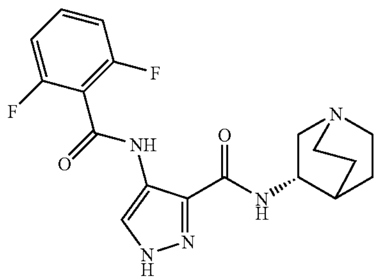 | A | Purified by flash chromatography eluting with DMAW 120 | [M + H]$^+$ = 376<br>R$_t$ = 1.85 |
| 217 | 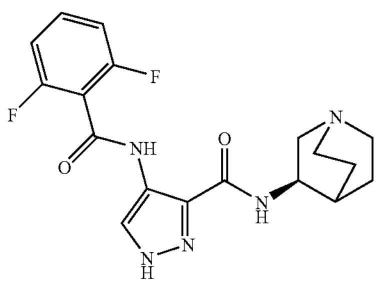 | A | Purified by flash chromatography eluting with DMAW 120 | [M + H]$^+$ = 376<br>R$_t$ = 1.87 |
| 218 | 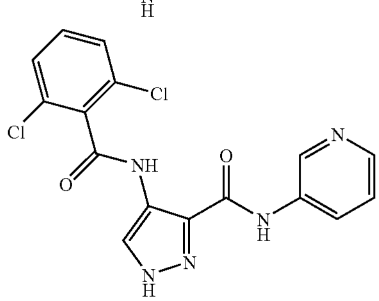 | A | Purified by flash chromatography eluting with 5% then 10% MeOH / DCM | [M + H]$^+$ = 376/ 378<br>R$_t$ = 2.23 |
| 219 | 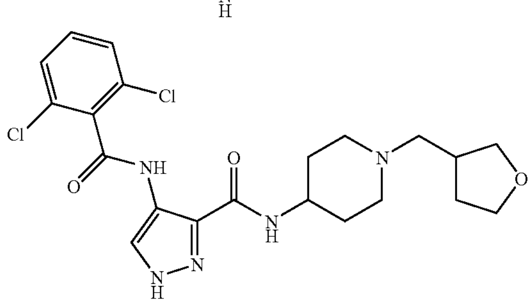 | A<br>Starting amine prepared according to Procedure L | Purified by flash chromatography eluting with DMAW 90 | [M + H]$^+$ = 466/ 468<br>R$_t$ = 1.98 |

TABLE 6-continued

| Example No. | Structure | Method | Differences | LCMS |
|---|---|---|---|---|
| 220 | 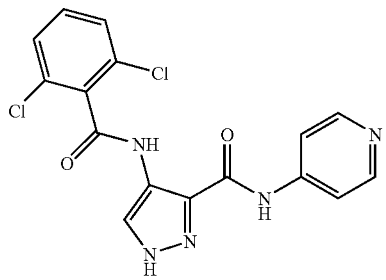 | A | Purified by flash chromatography eluting with 5% then 10% MeOH / DCM | [M + H]⁺= 376/ 378<br>R$_t$ = 2.09 |
| 221 | 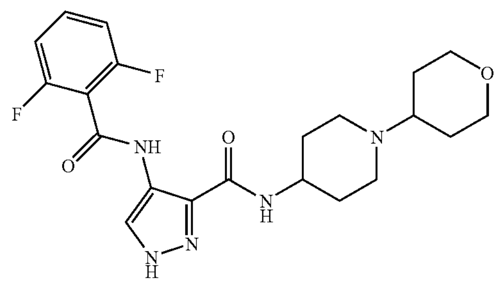 | A<br>Starting amine prepared according to Procedure L | Purified by flash chromatography eluting with DMAW 90 | [M + H]⁺= 434<br>R$_t$ = 1.82 |
| 222 | 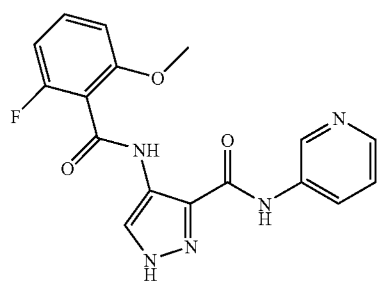 | A | Purified by flash chromatography eluting with 5% then 10% MeOH / DCM | [M + H]⁺= 356<br>R$_t$ = 2.11 |
| 223 | 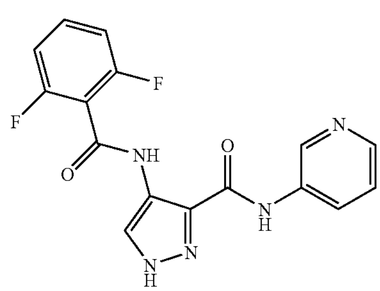 | A | Purified by flash chromatography eluting with 5% then 10% MeOH / DCM | [M + H]⁺= 344<br>R$_t$ = 2.09 |

Example 224

4-(4-Methyl-piperazin-1-yl)-1H-pyrazole-3-carboxylic acid (4-fluoro-phenyl)-amide

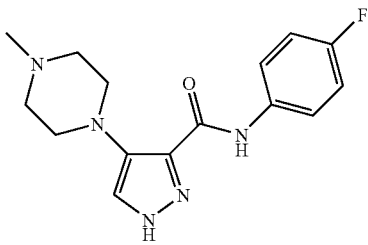

Bis(2-chloroethyl)methylamine hydrochloride (97 mg; 0.5 mmol) was added to a stirred solution of 4-amino-1H-pyrazole-3-carboxylic acid (4-fluoro-phenyl)-amide (100 mg; 0.45 mmol), tetrabutylammonium iodide (20 mg; 0.045 mmol) and diisopropyethylamine (200 ul) 1.13 mmol) in DMF (5 ml), and the resulting mixture was heated at 200° C. (100 W) for 30 minutes in a CEM Discover™ microwave synthesiser. The DMF was removed under vacuum, then purified by flash column chromatography, eluting with dichloromethane/methanol/acetic acid/water (90:18:3:2). Product containing fractions were combined and evaporated, treated with HCl in ethyl acetate and then re-evaporated with toluene (2×20 ml) to give an off white solid (27 mg). (LC/MS: $R_t$ 1.64, $[M+H]^+$ 378).

Example 225

4-Morpholin-4-yl-1H-pyrazole-3-carboxylic acid (4-fluoro-phenyl)-amide

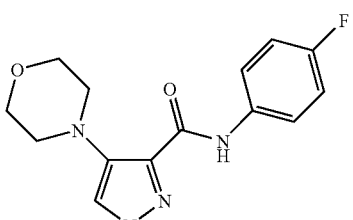

The compound was prepared in a manner analogous to Example 224, but using bis(2-chloroethyl)ether in place of bis(2-chloroethyl)methylamine hydrochloride. (LC/MS: $R_t$ 2.48 $[M+H]^+$ 291).

Example 226

4-(2,4-Dichloro-phenyl)-1H-pyrazole-3-carboxylic acid 4-(4-methyl-piperazin-1-yl)-benzylamide

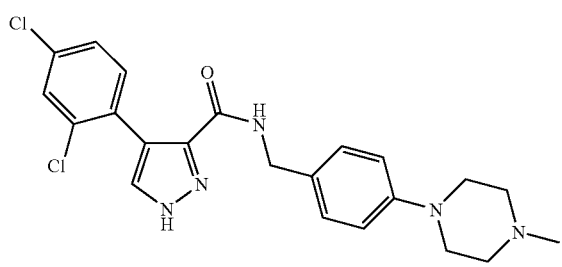

226A. Preparation of 4-(2,4-dichloro-phenyl)-1H-pyrazole-3-carboxylic acid

A solution of 4-(2,4-dichloro-phenyl)-1H-pyrazole-3-carboxylic acid ethyl ester (205 mg; 0.72 mmol) and lithium hydroxide monohydrate (125 mg; 2.9 mmol) in 1:1 THF/water (10 ml) was heated at 60° C. overnight. The THF was removed by evaporation, the aqueous phase acidified with 1 M hydrochloric acid then extracted with ethyl acetate (20 ml). The ethyl acetate layer was dried (MgSO$_4$), filtered and evaporated to give 200 mg of 4-(2,4-dichloro-phenyl)-1H-pyrazole-3-carboxylic acid. (LC/MS: $[M+H]^+$ 256.85).

226B. Preparation of 4-(2,4-dichloro-phenyl)-1H-pyrazole-3-carboxylic acid 4-(4-methyl-piperazin-1-yl)-benzylamide A solution of 4-(2,4-dichloro-phenyl)-1H-pyrazole-3-carboxylic acid (70 mg; 0.27 mmol), 4-(4-methyl-piperazin-1-yl)-benzylamine (62 mg; 0.3 mmol), EDAC (63 mg; 0.33 mmol) and HOBt (45 mg; 0.33 mmol) in 5 ml of DMF was stirred at room temperature for 48 hours. The reaction was evaporated and the residue partitioned between ethyl acetate and brine. The ethyl acetate layer was separated, dried (MgSO$_4$), filtered, evaporated then dried further under vacuum to give 34 mg of 4-(2,4-dichloro-phenyl)-1H-pyrazole-3-carboxylic acid 4-(4-methyl-piperazin-1-yl)-benzylamide. (LC/MS: $R_t$ 2.42 $[M+H]^+$ 444).

Example 227

4-(2,4-Dichloro-phenyl)-1H-pyrazole-3-carboxylic acid 4-methylsulphamoylmethyl-benzylamide

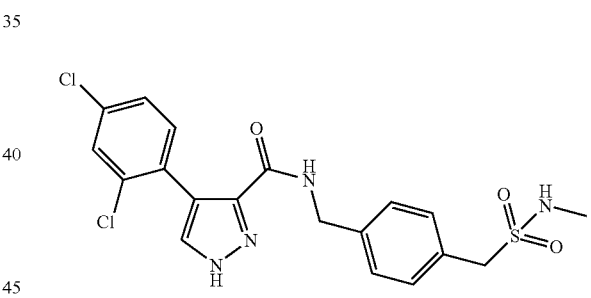

The title compound was prepared in a manner analogous to Example 226, but using (4-aminomethyl-phenyl)-N-methyl-methanesulphonamide as the starting material. 6 mg of product were isolated as a white solid. (LC/MS: $R_t$ 3.56 $[M+H]^+$ 440).

Example 228

4-Phenyl-1H-pyrazole-3-carboxylic acid amide

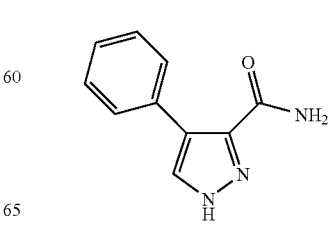

228A. 2-Benzylidene-but-3-yne nitrile

To a solution of benzaldehyde (2 g; 18.9 mmol) and malononitrile (1.37 g; 20.7 mmol) in ethanol (40 ml) was added 5 drops of piperidine and the mixture was heated at reflux overnight. The reaction was cooled, evaporated then purified by flash column chromatography eluting with 1:9 ethyl acetate/hexane and the product containing fractions combined and evaporated to give 930 mg of 2-benzylidene-but-3-yne nitrile.

228B. 4-phenyl-5-trimethylsilanyl-1H-pyrazole-3-carbonitrile n-Butyl lithium (2.7 M solution in heptane) (3.3 ml, 9 mmol) was added drop wise to a stirred solution of trimethylsilyl diazomethane (2 M solution in diethyl ether) (4.5 ml, 9 mmol) in anhydrous THF (10 ml) at −78° C. under a nitrogen atmosphere, then stirred for a further 30 minutes. To this was added drop wise a solution of 2-benzylidene-but-3-yne nitrile (920 mg; 6 mmol) in anhydrous THF (5 ml), the mixture stirred for 30 minutes at −78° C. then gradually allowed to warm to room temperature overnight. The reaction mixture was diluted with ethyl acetate (30 ml) then washed with saturated ammonium chloride solution followed by brine. The ethyl acetate layer was separated, dried (MgSO$_4$), filtered and evaporated. The crude product was purified by flash column chromatography eluting with 1:8 then 1:4 ethyl acetate/hexane and the product containing fractions combined and evaporated to give 1.0 g of 4-phenyl-5-trimethylsilanyl-1H-pyrazole-3-carbonitrile.

228C. 4-phenyl-1H-pyrazole-3-carboxylic acid amide

4-Phenyl-5-trimethylsilanyl-1H-pyrazole-3-carbonitrile (500 mg; 2.1 mmol) was dissolved in 1 ml of ethanol, treated with potassium hydroxide (600 mg) in water (3 ml) then heated at 150° C. (100 W) for 30 minutes then 170° C. (100 W) for 20 minutes in a CEM Discover™ microwave synthesiser. The reaction mixture was acidified to pH1 with concentrated hydrochloric acid, diluted with water (40 ml) then extracted with ethyl acetate (2×40 ml). The combined ethyl acetate layers were separated, dried (MgSO$_4$), filtered and evaporated to give a 3:1 mixture of 4-phenyl-1H-pyrazole-3-carboxylic acid and 4-phenyl-1H-pyrazole-3-carboxylic acid amide. A 50 mg batch of the crude material was purified by flash column chromatography eluting with 5% methanol/dichloromethane, and the product containing fractions combined and evaporated to give 15 mg of 4-phenyl-1H-pyrazole-3-carboxylic acid amide as a white solid. (LC/MS: R$_t$ 2.15 [M+H]$^+$188).

Example 229

4-phenyl-1H-pyrazole-3-carboxylic acid phenylamide

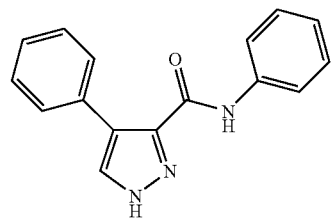

A solution of 4-phenyl-1H-pyrazole-3-carboxylic acid (75 mg; 0.4 mmol) (prepared according to Example 228C), aniline (45 µl; 0.48 mmol), EDAC (92 mg; 0.48 mmol) and HOBt (65 mg; 0.48 mmol) in 5 ml of DMF was stirred at room temperature overnight. The reaction was evaporated then purified by flash column chromatography eluting with 1:3 then 1:2 ethyl acetate/hexane. Product containing fractions were combined and evaporated to give 30 mg of 4-phenyl-1H-pyrazole-3-carboxylic acid phenylamide as a white solid. (LC/MS: R$_t$ 3.12 [M+H]$^+$264).

Example 230

4-Phenyl-1H-pyrazole-3-carboxylic acid 4-(4-methyl-piperazin-1-yl)-benzylamide

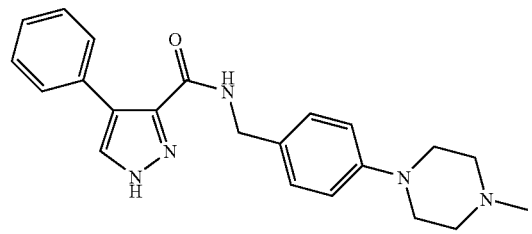

The compound was prepared in a manner analogous to Example 229, but using 4-(4-methyl-piperazin-1-yl)-benzylamine as the starting material. 6 mg of product were isolated as a white solid. (LC/MS: R$_t$ 2.05 [M+H]$^+$376).

Example 231

4-Phenyl-1H-pyrazole-3-carboxylic acid (6-methoxy-pyridin-3-yl) amide

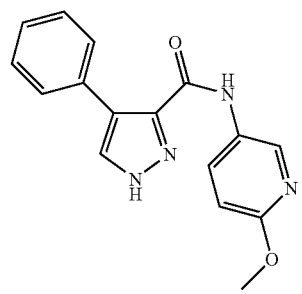

The compound was prepared in a manner analogous to Example 230, but using 3-amino-6-methoxypyridine as the amine fragment. 100 mg of product were isolated as a pale brown solid. (LC/MS: $R_t$ 3.17 [M+H]$^+$295).

Example 232

4-(3-Benzyloxy-phenyl)-1H-pyrazole-3-carboxylic acid 4-(4-methyl-piperazin-1-yl)-benzylamide

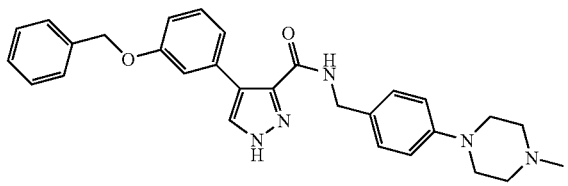

The compound was prepared in a manner analogous to Example 226. The product was isolated as a white solid. (LC/MS: $R_t$ 2.65 [M+H]$^+$482).

Example 233

4-(3-Hydroxy-phenyl)-1H-pyrazole-3-carboxylic acid 4-(4-methyl-piperazin-1-yl)-benzylamide

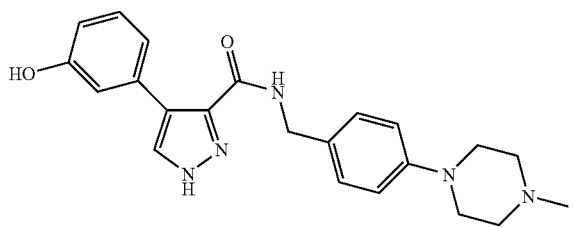

A solution of 4-(3-benzyloxy-phenyl)-1H-pyrazole-3-carboxylic acid 4-(4-methyl-piperazin-1-yl)-benzylamide (25 mg; 0.05 mmol) in methanol (5 ml), was treated with 10% palladium on carbon (10 mg) then hydrogenated at room temperature and pressure overnight. The catalyst was removed by filtration through Celite and the filtrate evaporated. Purification by preparative LC/MS gave 8 mg of the required product as a cream solid. (LC/MS: $R_t$ 1.67 [M+H]$^+$ 392).

Example 234

4-(5-Methyl-3H-imidazol-4-yl)-1H-pyrazole-3-carboxylic acid (4-fluoro-phenyl-amide

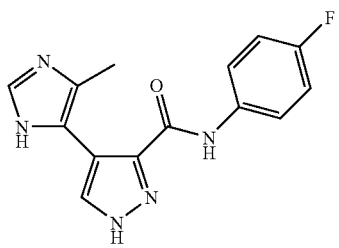

The compound was prepared in a manner analogous to Example 226, but using 4-methyl-5-formylimidazole as the starting material in the condensation step. The product (6 mg) was isolated as a white solid. (LC/MS: $R_t$ 2.00 [M+H]$^+$286).

Example 235

4-(2,5-Dimethyl-pyrrol-1-yl)-1H-pyrazole-3-carboxylic acid (4-fluoro-phenyl)-amide

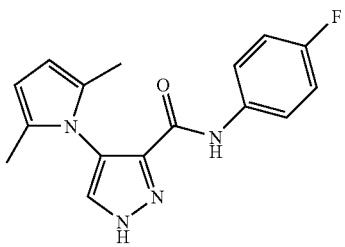

A mixture of 4-amino-1H-pyrazole-3-carboxylic acid (4-fluoro-phenyl)-amide (100 mg) and Montmorillonite KSF clay (100 mg) in acetonylacetone (1 ml) was heated at 120° C. (50 W) for 15 minutes in a CEM discover microwave synthesiser. The reaction mixture was diluted with 5% methanol/dichloromethane, filtered and evaporated. The crude product was purified by flash column chromatography eluting with 1:2 ethyl acetate/hexane, and the product containing fractions were combined and evaporated to give 65 mg of the target molecule as a pale brown solid. (LC/MS: $R_t$ 3.75 [M+H]$^+$ 299).

Example 236

4-(3-Hydroxymethyl-phenyl)-1H-pyrazole-3-carboxylic acid phenylamide

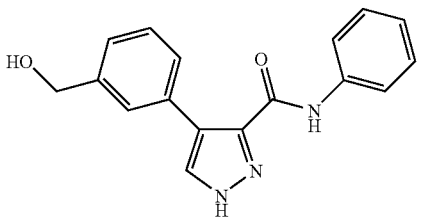

236A. 4-iodo-1H-pyrazole-3-carboxylic acid phenylamide

An aqueous solution of sodium nitrite (760 mg) in 2 ml of water was added drop wise to a stirred suspension of 4-amino-1H-pyrazole-3-carboxylic acid phenylamide (2 g; 10 mmol) in concentrated hydrochloric acid (20 ml) at 0° C., then stirred at 0° C. for a further 60 minutes. The reaction mixture was diluted with acetone (10 ml) then treated with potassium iodide (1.8 g) and copper (I) iodide (2.1 g) and stirred at room temperature for 90 minutes. The reaction mixture was diluted with brine and ethyl acetate then washed with saturated sodium thiosulphate solution. The ethyl acetate layer was separated, dried (MgSO$_4$), filtered and evaporated to give 680 mg of 4-iodo-1H-pyrazole-3-carboxylic acid phenylamide.

236B. 4-iodo-1-(4-methoxy-benzyl)-1H-pyrazole-3-carboxylic acid phenylamide

A solution of 4-iodo-1H-pyrazole-3-carboxylic acid phenylamide (670 mg; 2.14 mmol) in acetonitrile (10 ml) was treated with potassium carbonate (360 mg; 2.57 mmol)) followed by 4-methoxybenzyl chloride (320 µl; 2.35 mmol). The mixture was stirred at room temperature overnight then evaporated under reduced pressure. The residue was partitioned between ethyl acetate and brine; the ethyl acetate layer was separated, dried ($MgSO_4$), filtered and evaporated. The crude material was purified by flash column chromatography eluting with 1:3 ethyl acetate/hexane and the product containing fractions combined and evaporated to give 660 mg of 4-iodo-1-(4-methoxy-benzyl)-1H-pyrazole-3-carboxylic acid phenylamide.

236C. 4-(3-hydroxymethyl-phenyl-1-(4-methoxy-benzyl)-1H-pyrazole-3-carboxylic acid phenylamide A mixture of 4-iodo-1-(4-methoxy-benzyl)-1H-pyrazole-3-carboxylic acid phenylamide (50 mg; 0.11 mmol), bis(tri-tert-butylphosphine)palladium (12 mg), potassium carbonate (100 mg; 0.66 mmol) and 3-(hydroxmethyl)benzene boronic acid (21 mg; 0.14 mmol) in ethanol/toluene/water (4 ml:1 ml:1 ml) was heated at 120° C. (50 W) for 15 minutes in a CEM Discover microwave synthesiser. The reaction was evaporated and the residue partitioned between ethyl acetate and brine. The ethyl acetate layer was separated, dried ($MgSO_4$), filtered and evaporated and the crude material purified by flash column chromatography eluting with 1:2 then 2:1 ethyl acetate/hexane. Product containing fractions were combined and evaporated to give 60 mg of 4-(3-hydroxymethyl-phenyl)-1-(4-methoxy-benzyl)-1H-pyrazole-3-carboxylic acid phenylamide.

236D. 4-(3-Hydroxymethyl-phenyl)-1H-pyrazole-3-carboxylic acid phenylamide

A mixture of 4-(3-hydroxymethyl-phenyl)-1-(4-methoxy-benzyl)-1H-pyrazole-3-carboxylic acid phenylamide (20 mg) and anisole (20 µl) in trifluoroacetic acid (1 ml) was heated at 120° C. (50 W) for 15 minutes in a CEM Discover microwave synthesiser. The reaction was evaporated then purified by flash column chromatography eluting with 2:1 ethyl acetate/hexane. Product containing fractions were combined and evaporated to give 5 mg of product. (LC/MS: $R_t$ 2.55 [M+H]$^+$294).

Example 237

Preparation of 4-(2,6-dichloro-benzoylamino)-1H-pyrazole-3-carboxylic acid piperidin-4-ylamide hydrochloride

237A. 4-(2,6-dichloro-benzoylamino)-1H-pyrazole-3-carboxylic acid 2,6-dichlorobenzoyl chloride (8.2 g; 39.05 mmol) was added cautiously to a solution of 4-amino-1H-pyrazole-3-carboxylic acid methyl ester (prepared in a manner analogous to 165B) (5 g; 35.5 mmol) and triethylamine (5.95 ml; 42.6 mmol) in dioxan (50 ml) then stirred at room temperature for 5 hours. The reaction mixture was filtered and the filtrate treated with methanol (50 ml) and 2M sodium hydroxide solution (100 ml), heated at 50° C. for 4 hours, and then evaporated. 100 ml of water was added to the residue then acidified with concentrated hydrochloric acid. The solid was collected by filtration, washed with water (100 ml) and sucked dry to give 10.05 g of 4-(2,6-dichloro-benzoylamino)-1H-pyrazole-3-carboxylic acid as a pale violet solid.

237B. 4-{[4-(2,6-dichloro-benzoylamino)-1H-pyrazole-3-carbonyl]-amino}-piperidine-1-carboxylic acid tert-butyl ester A mixture of 4-(2,6-dichloro-benzoylamino)-1H-pyrazole-3-carboxylic acid (6.5 g, 21.6 mmol), 4-amino-1-BOC-piperidine (4.76 g, 23.8 mmol), EDC (5.0 g, 25.9 mmol) and HOBt (3.5 g, 25.9 mmol) in DMF (75 ml) was stirred at room temperature for 20 hours. The reaction mixture was reduced in vacuo and the residue partitioned between ethyl acetate (100 ml) and saturated aqueous sodium bicarbonate solution (100 ml). The organic layer was washed with brine, dried ($MgSO_4$) and reduced in vacuo. The residue was taken up in 5% MeOH-DCM (~30 ml). The insoluble material was collected by filtration and, washed with DCM and dried in vacuo to give 4-{[4-(2,6-dichloro-benzoylamino)-1H-pyrazole-3-carbonyl]-amino}-piperidine-1-carboxylic acid tert-butyl ester (5.38 g) as a white solid. The filtrate was reduced in vacuo and the residue purified by column chromatography using gradient elution 1:2 EtOAc/hexane to EtOAc to give further 4-{[4-(2,6-dichloro-benzoylamino)-1H-pyrazole-3-carbonyl]-amino}-piperidine-1-carboxylic acid tert-butyl ester (2.54 g) as a white solid.

237C. 4-(2,6-dichloro-benzoylamino)-1H-pyrazole-3-carboxylic acid piperidin-4-ylamide A solution of 4-{[4-(2,6-dichloro-benzoylamino)-1H-pyrazole-3-carbonyl]-amino}-piperidine-1-carboxylic acid tert-butyl ester (7.9 g) in MeOH (50 mL) and EtOAc (50ml) was treated with sat. HCl-EtOAc (40 mL) then stirred at r.t. overnight. The product did not crystallise due to the presence of methanol, and therefore the reaction mixture was evaporated and the residue triturated with EtOAc. The resulting off white solid was collected by filtration, washed with EtOAc and sucked dry on the sinter to give 6.3 g of 4-(2,6-dichloro-benzoylamino)-1H-pyrazole-3-carboxylic acid piperidin-4-ylamide as the hydrochloride salt. (LC/MS: $R_t$ 5.89, [M+H]$^+$ 382/384).

Example 238

4-Methanesulfonylamino-1H-pyrazole-3-carboxylic acid (4-fluoro-phenyl)-amide

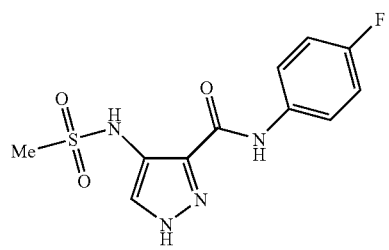

A solution of 4-amino-1H-pyrazole-3-carboxylic acid (4-fluorophenyl)-amide (50 mg) (Example 2B) and methanesulphonic anhydride (45 mg) in pyridine (1 ml) was stirred at room temperature overnight then evaporated and purified by flash column chromatography eluting with 2:1 EtOAc/hexane. Evaporation of product containing fractions gave 20 mg of the title compound. (LC/MS: Rt 2.87; [M+H+] 299).

Examples 239 to 245

The compounds of Examples 239 to 245 were prepared using the methods described above or methods closely analogous thereto.

Example 239

4-(2,6-Difluoro-benzoylamino)-1H-pyrazole-3-carboxylic acid [1-(2-fluoro-ethyl)-piperidin-4-yl]-amide

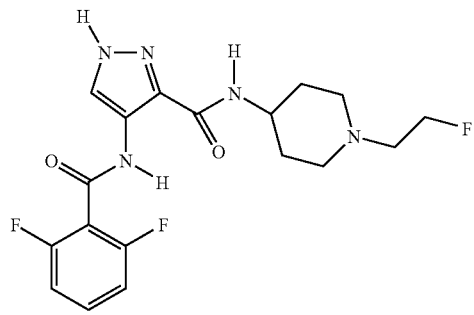

Example 240

4-(2,6-Dichloro-benzoylamino)-1H-pyrazole-3-carboxylic acid (6-chloro-pyridin-3-yl)-amide

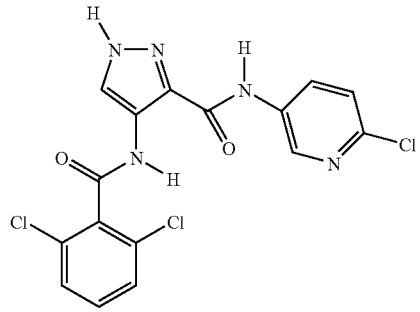

Example 241

4-(2,6-Dichloro-benzoylamino)-1H-pyrazole-3-carboxylic acid (6-amino-pyridin-3-yl)-amide

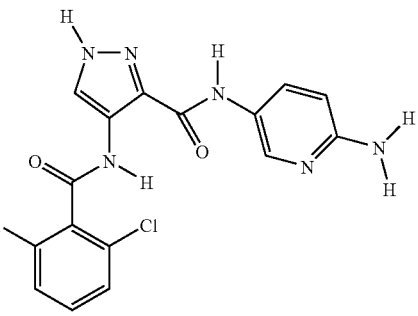

Example 242

4-(2,6-Dichloro-benzoylamino)-1H-pyrazole-3-carboxylic acid (6-methoxy-pyridin-3-yl)-amide

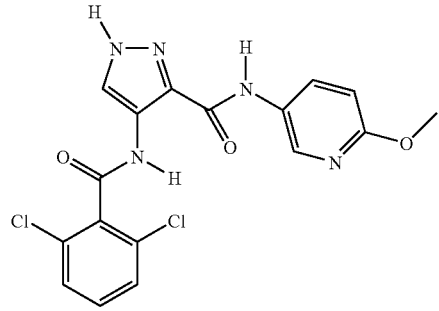

Example 243

4-[3-Chloro-5-(4-methyl-piperazin-1-yl)-benzoylamino]-1H-pyrazole-3-carboxylic acid cyclohexylamide

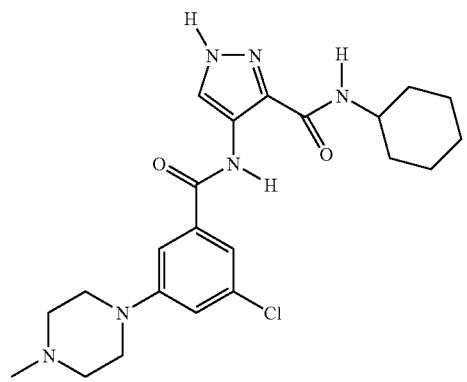

Example 244

4-(2,6-Difluoro-benzoylamino)-1H-pyrazole-3-carboxylic acid [1-(2,2-difluoro-ethyl)-piperidin-4-yl]-amide

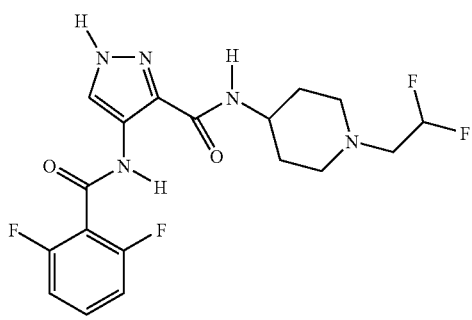

Example 245

4-[3-(4-Methyl-piperazin-1-yl)-benzoylamino]-1H-pyrazole-3-carboxylic acid cyclohexylamide

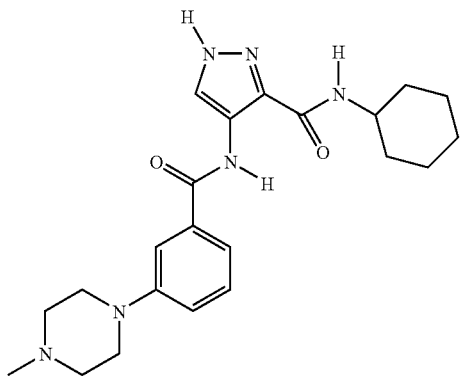

Biological Activity

Example 246

Measurement of CDK2 Kinase Inhibitory Activity ($IC_{50}$)

Compounds of the invention were tested for kinase inhibitory activity using either the following protocol or the activated CDK2/cyclin A kinase protocol described in Example 241.

1.7 µl of active CDK2/CyclinA (Upstate Biotechnology, 10U/µl) is diluted in assay buffer (250 µl of 10× strength assay buffer (200 mM MOPS pH 7.2, 250 mM β-glycerophosphate, 50 mM EDTA, 150 mM MgCl$_2$), 11.27 µl 10 mM ATP, 2.5 µl 1M DTT, 25 µl 100 mM sodium orthovanadate, 708.53 µl H$_2$O), and 10 µl mixed with 10 µl of histone substrate mix (60 µl bovine histone H1 (Upstate Biotechnology, 5 mg/ml), 940 µl H$_2$O, 35 µCi γ$^{33}$P-ATP) and added to 96 well plates along with 5 µl of various dilutions of the test compound in DMSO (up to 2.5%). The reaction is allowed to proceed for 5 hours before being stopped with an excess of ortho-phosphoric acid (30 µl at 2%).

γ$^{33}$P-ATP which remains unincorporated into the histone H1 is separated from phosphorylated histone H1 on a Millipore MAPH filter plate. The wells of the MAPH plate are wetted with 0.5% orthophosphoric acid, and then the results of the reaction are filtered with a Millipore vacuum filtration unit through the wells. Following filtration, the residue is washed twice with 200 µl of 0.5% orthophosphoric acid. Once the filters have dried, 25 µl of Microscint 20 scintillant is added, and then counted on a Packard Topcount for 30 seconds.

The % inhibition of the CDK2 activity is calculated and plotted in order to determine the concentration of test compound required to inhibit 50% of the CDK2 activity ($IC_{50}$).

By means of the protocol set out above, it was found that the compounds of Examples 2C to 87, 89-92, 94, 96-101, 104-105, 165, 166, 224, 225, 227, 229, 231, 233, 234 and 236 each have $IC_{50}$ values less than 20 µM or provide at least 50% inhibition of the CDK2 activity at a concentration of 10 µM. The compounds of Examples 88, 93, 226, 228, 230 and 235 each have $IC_{50}$ values less than 750 µM.

Example 247

CDK Selectivity Assays

Compounds of the invention are tested for kinase inhibitory activity against a number of different kinases using the general protocol described in Example 239, but modified as set out below.

Kinases are diluted to a 10× working stock in 20 mM MOPS pH 7.0, 1 mM EDTA, 0.1% γ-mercaptoethanol, 0.01% Brij-35, 5% glycerol, 1 mg/ml BSA. One unit equals the incorporation of 1 nmol of phosphate per minute into 0.1 mg/ml histone H1, or CDK7 substrate peptide at 30° C. with a final ATP concentration of 100 uM.

The substrate for all the CDK assays (except CDK7) is histone H1, diluted to 10× working stock in 20 mM MOPS pH 7.4 prior to use. The substrate for CDK7 is a specific peptide obtained from Upstate diluted to 10× working stock in deionised water.

Assay Procedure for CDK1/CyclinB CDK2/CyclinA. CDK2/CyclinE, CDK3/CyclinE, CDK5/p35, CDK6/CyclinD3:

In a final reaction volume of 25 µl, the enzyme (5-10 mU) is incubated with 8 mM MOPS pH 7.0, 0.2 mM EDTA, 0.1 mg/ml histone H1, 10 mM MgAcetate and [γ-$^{33}$P-ATP] (specific activity approx 500 cpm/pmol, concentration as required). The reaction is initiated by the addition of Mg$^{2+}$ [γ-$^{33}$P-ATP]. After incubation for 40 minutes at room temperature the reaction is stopped by the addition of 5 µl of a 3% phosphoric acid solution. 10 ml of the reaction is spotted onto a P30 filter mat and washed 3 times for 5 minutes in 75 mM phosphoric acid and once in methanol prior to drying and counting.

In the CDK3/cyclinE assay, the compound of Example 150 had an $IC_{50}$ of less than 20 µM.

In the CDK5/p35 assay, the compounds of Examples 41 and 150 had an $IC_{50}$ of less than 20 µM.

In the CDK6/cyclinD3 assay, the compound of Example 150 had an $IC_{50}$ of less than 20 µM.

Assay Procedure for CDK7/CyclinH/MAT1

In a final reaction volume of 25 µl, the enzyme (5-10 mU) is incubated with 8 mM MOPS pH 7.0, 0.2 mM EDTA, 500

μM peptide, 10 mM MgAcetate and [γ-$^{33}$P-ATP] (specific activity approx 500 cpm/pmol, concentration as required). The reaction is initiated by the addition of Mg$^{2+}$+[γ-$^{33}$P-ATP]. After incubation for 40 minutes at room temperature the reaction is stopped by the addition of 5 μl of a 3% phosphoric acid solution. 10 ml of the reaction is spotted onto a P30 filtermat and washed 3 times for 5 minutes in 75 mM phosphoric acid and once in methanol prior to drying and counting.

Example 248

A. Measurement of Activated CDK2/CyclinA Kinase Inhibitory Activity Assay (IC$_{50}$)

Compounds of the invention were tested for kinase inhibitory activity using the following protocol.

Activated CDK2/CyclinA (Brown et al, Nat. Cell Biol., 1, pp 438-443, 1999; Lowe, E. D., et al Biochemistry, 41, pp 15625-15634, 2002) is diluted to 125 pM in 2.5× strength assay buffer (50 mM MOPS pH 7.2, 62.5 mM β-glycerophosphate, 12.5 mM EDTA, 37.5 mM MgCl$_2$, 112.5 mM ATP, 2.5 mM DTT, 2.5 mM sodium orthovanadate, 0.25 mg/ml bovine serum albumin), and 10 μl mixed with 10 μl of histone substrate mix (60 μl bovine histone H1 (Upstate Biotechnology, 5 mg/ml), 940 μl H$_2$O, 35 μCi γ$^{33}$P-ATP) and added to 96 well plates along with 5 μl of various dilutions of the test compound in DMSO (up to 2.5%). The reaction is allowed to proceed for 2 to 4 hours before being stopped with an excess of ortho-phosphoric acid (5 μl at 2%).

γ$^{33}$P-ATP which remains unincorporated into the histone H1 is separated from phosphorylated histone H1 on a Millipore MAPH filter plate. The wells of the MAPH plate are wetted with 0.5% orthophosphoric acid, and then the results of the reaction are filtered with a Millipore vacuum filtration unit through the wells. Following filtration, the residue is washed twice with 200 μl of 0.5% orthophosphoric acid. Once the filters have dried, 20 μl of Microscint 20 scintillant is added, and then counted on a Packard Topcount for 30 seconds.

The % inhibition of the CDK2 activity is calculated and plotted in order to determine the concentration of test compound required to inhibit 50% of the CDK2 activity (IC$_{50}$).

By means of the foregoing protocol, it was found that the compounds of Examples 95, 96, 99-104, 106-121, 123-125, 130-137, 139, 142-145, 147-150, 152-156, 158-160, 162-164, 167-173, 177-179, 181-182, 184-190, 194, 196-204, 208-213 and 215 have IC$_{50}$ values less than 20 μM. The compounds of Examples 122, 126-129, 140, 141, 146, 157 and 161 each have IC$_{50}$ values less than than 750 μM and most have IC$_{50}$ values of less than 100 μM.

B. CDK1/CyclinB Assay.

CDK1/CyclinB assay is identical to the CDK2/CyclinA above except that CDK1/CyclinB (Upstate Discovery) is used and the enzyme is diluted to 6.25 nM.

In the CDK1 assay carried out as described above or by means of the protocol set out in Example 240, the compounds of Examples 2C, 41, 48, 53, 64, 65, 66, 73, 76, 77, 91, 95, 102, 106, 117, 123, 125, 133, 137, 142, 150, 152, 154, 167, 186, 187, 189, 190, 193, 194, 196, 199, 202-204, 207, 208-213, 215 AND 218-223 were found to have IC$_{50}$ values less than 20 μM, and the compounds of Examples 188 and 206, were found to have IC$_{50}$ values less than 100 μM.

Example 249

Assay Procedure for CDK4

Assays for CDK4 inhibitory activity were carried out by Proqinase GmbH, Freiburg, Germany using their proprietary 33PanQinase® Activity Assay. The assays were performed in 96 well FlashPlates™ (PerkinElmer). In each case, the reaction cocktail (50 μl final volume) is composed of; 20 μl assay buffer (final composition 60 mM HEPES-NaOH, pH 7.5, 3 mM MgCl$_2$, 3 μM Na-orthovanadate, 1.2 mM DTT, 50 μg/ml PEG$_{2000}$, 5 μl ATP solution (final concentration 1 μM [γ-$^{33}$P]-ATP (approx 5×10$^5$ cpm per well)), 5 μl test compound (in 10% DMSO), 10 μl substrate/10 μl enzyme solution (premixed). The final amounts of enzyme and substrate were as below.

| Kinase | Kinase ng/50 μl | Substrate | Substrate ng/50 μl |
|---|---|---|---|
| CDK4/CycD1 | 50 | Poly (Ala, Glu, Lys, Tyr) 6:2:5:1 | 500 |

The reaction cocktail was incubated at 30° C. for 80 minutes. The reaction was stopped with 50 μl of 2% H$_3$PO$_4$, plates were aspirated and washed twice with 200 μl 0.9% NaCl. Incorporation of $^{33}$P was determined with a microplate scintillation counter. Background values were subtracted from the data before calculating the residual activities for each well. IC$_{50}$s were calculated using Prism 3.03.

The compound of Example 150 has an IC50 of less than 5 μM in this assay.

Example 250

Anti-proliferative Activity

The anti-proliferative activities of compounds of the invention are determined by measuring the ability of the compounds to inhibition of cell growth in a number of cell lines. Inhibition of cell growth is measured using the Alamar Blue assay (Nociari, M. M, Shalev, A., Benias, P., Russo, C. *Journal of Immunological Methods* 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds for a further 72 hours. At the end of the incubation period 10% (v/v) Alamar Blue is added and incubated for a further 6 hours prior to determination of fluorescent product at 535 nM ex/590 nM em. In the case of the non-proliferating cell assay cells are maintained at confluence for 96 hour prior to the addition of inhibitor compounds for a further 72 hours. The number of viable cells is determined by Alamar Blue assay as before. All cell lines are obtained from ECACC (European Collection of cell Cultures).

In assays against the human colon carcinoma cell line HCT 116 (ECACC No. 91091005), the compounds of Examples 10, 25-27, 41, 44, 46, 48, 50, 52, 53, 60, 62, 64-67, 69, 73-77, 79, 80, 83A, 86, 90-93, 95-98, 100-104, 106, 107, 109-121, 123-125, 131-134, 136-143, 147-155, 158, 159, 162-164, 166, 167, 178, 179, 185-190, 192-205, 207-215 and 218-223 have IC$_{50}$ values of less than 20 μM and the compounds of Examples 2C, 3, 29, 38, 39, 49, 51, 85, 89, 99, 108, 135, 160, 182, 183, 206 and 216 have IC$_{50}$ values of less than 100 μM.

Example 251

Measurement of Inhibitory Activity Against Glycogen Synthase Kinase-3 (GSK-3)

The activities of the compounds of the invention as inhibitors of GSK-3 were determined using either Protocol A or Protocol B below.

Protocol A

GSK3-β (Upstate Discovery) is diluted to 7.5 nM in 25 mM MOPS, pH 7.00, 25 mg/ml BSA, 0.0025% Brij-35™, 1.25% glycerol, 0.5 mM EDTA, 25 mM MgCl$_2$, 0.025% β-mercaptoethanol, 37.5 mM ATP and 10 μl mixed with 10 μl of substrate mix. The substrate mix is 12.5 μM phospho-glycogen synthase peptide-2 (Upstate Discovery) in 1 ml of water with 35 μCi γ$^{33}$P-ATP. Enzyme and substrate are added to 96 well plates along with 5 μl of various dilutions of the test compound in DMSO (up to 2.5%). The reaction is allowed to proceed for 3 hours before being stopped with an excess of ortho-phosphoric acid (5 μl at 2%). The filtration procedure is as for Activated CDK2/CyclinA assay above.

Protocol B

GSK3β (human) is diluted to a 10× working stock in 50 mM Tris pH 7.5, 0.1 mM EGTA, 0.1 mM sodium vanadate, 0.1% β-mercaptoethanol, 1 mg/ml BSA. One unit equals the incorporation of 1 nmol of phosphate per minute phosphoglycogen synthase peptide 2 per minute.

In a final reaction volume of 25 μl, GSK3β (5-10 mU) is incubated with 8 mM MOPS 7.0, 0.2 mM EDTA, 20 μM YRRAAVPPSPSLSRHSSPHQS(p)EDEEE (phospho GS2 peptide), 10 mM MgAcetate and [γ-$^{33}$P-ATP] (specific activity approx 500 cpm/pmol, concentration as required). The reaction is initiated by the addition of Mg$^{2+}$+[γ-$^{33}$P-ATP]. After incubation for 40 minutes at room temperature the reaction is stopped by the addition of 5 μl of a 3% phosphoric acid solution. 10 μl of the reaction is spotted onto a P30 filter mat and washed 3 times for 5 minutes in 50 mM phosphoric acid and once in methanol prior to drying and counting.

From the results of the GSK3-B assays carried out using either of the two procols set out above, it was found that the compounds of Examples 2C, 26, 48, 53, 65, 76, 77, 84, 86, 95, 102, 106, 119, 122, 123, 126, 127, 128, 129, 131, 134, 135, 138, 140, 141, 142, 143, 144, 145, 146, 147, 149, 150 and 151 each have IC$_{50}$ values of less than 10 μM.

Pharmaceutical Formulations

Example 252

(i) Tablet Formulation

A tablet composition containing a compound of the formula (I) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (I) with 100 mg lactose and filling the resulting mixture into standard opaque hard gelatin capsules.

(iii) Injectable Formulation I

A parenteral composition for administration by injection can be prepared by dissolving a compound of the formula (I) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral compositon for injection is prepared by dissolving in water a compound of the formula (I) (e.g. in salt form) (2 mg/ml) and mannitol (50 mg/ml), sterile filtering the solution and filling into sealable 1 ml vials or ampoules.

(iv) Subcutaneous Injection Formulation

A composition for sub-cutaneous administration is prepared by mixing a compound of the formula (I) with pharmaceutical grade corn oil to give a concentration of 5 mg/ml. The composition is sterilised and filled into a suitable container.

Example 253

Determination of Antifungal Activity

The antifungal activity of the compounds of the formula (I) is determined using the following protocol.

The compounds are tested against a panel of fungi including *Candida parpsilosis, Candida tropicalis, Candida albicans*-ATCC 36082 and *Cryptococcus neoformans*. The test organisms are maintained on Sabourahd Dextrose Agar slants at 4° C. Singlet suspensions of each organism are prepared by growing the yeast overnight at 27° C. on a rotating drum in yeast-nitrogen base broth (YNB) with amino acids (Difco, Detroit, Mich.), pH 7.0 with 0.05 morpholine propanesulphonic acid (MOPS). The suspension is then centrifuged and washed twice with 0.85% NaCl before sonicating the washed cell suspension for 4 seconds (Branson Sonifier, model 350, Danbury, Conn.). The singlet blastospores are counted in a haemocytometer and adjusted to the desired concentration in 0.85% NaCl.

The activity of the test compounds is determined using a modification of a broth microdilution technique. Test compounds are diluted in DMSO to a 1.0 mg/ml ratio then diluted to 64 μg/ml in YNB broth, pH 7.0 with MOPS (Fluconazole is used as the control) to provide a working solution of each compound. Using a 96-well plate, wells 1 and 3 through 12 are prepared with YNB broth, ten fold dilutions of the compound solution are made in wells 2 to 11 (concentration ranges are 64 to 0.125 μg/ml). Well 1 serves as a sterility control and blank for the spectrophotometric assays. Well 12 serves as a growth control. The microtitre plates are inoculated with 10 μl in each of well 2 to 11 (final inoculum size is 10$^4$ organisms/ml). Inoculated plates are incubated for 48 hours at 35° C. The MIC values are determined spectrophotometrically by measuring the absorbance at 420 nm (Automatic Microplate Reader, DuPont Instruments, Wilmington, Del.) after agitation of the plates for 2 minutes with a vortex-mixer (Vorte-Genie 2 Mixer, Scientific Industries, Inc., Bolemia, N.Y.). The MIC endpoint is defined as the lowest drug concentration exhibiting approximately 50% (or more) reduction of the growth compared with the control well. With the turbidity assay this is defined as the lowest drug concentration at which turbidity in the well is <50% of the control (IC50). Minimal Cytolytic Concentrations (MCC) are determined by sub-culturing all wells from the 96-well plate onto a Sabourahd Dextrose Agar (SDA) plate, incubating for 1 to 2 days at 35° C. and then checking viability.

Example 254

Protocol for the Biological Evaluation of Control of in vivo Whole Plant Fungal Infection Compounds of the formula (I) are dissolved in acetone, with subsequent serial dilutions in acetone to obtain a range of desired concentrations. Final treatment volumes are obtained by adding 9 volumes of 0.05% aqueous Tween-20™ or 0.01% Triton X-100™, depending upon the pathogen.

The compositions are then used to test the activity of the compounds of the invention against tomato blight (Phytophthora infestans) using the following protocol. Tomatoes (cultivar Rutgers) are grown from seed in a soil-less peat-based potting mixture until the seedlings are 10-20 cm tall. The plants are then sprayed to run-off with the test compound at a rate of 100 ppm. After 24 hours the test plants are inoculated by spraying with an aqueous sporangia suspension of Phytophthora infestans, and kept in a dew chamber overnight. The plants are then transferred to the greenhouse until disease develops on the untreated control plants.

Similar protocols are also used to test the activity of the compounds of the invention in combatting Brown Rust of Wheat (*Puccinia*), Powdery Mildew of Wheat (*Ervsiphe vraminis*), Wheat (*cultivar Monon*), Leaf Blotch of Wheat (*Septoria tritici*), and Glume Blotch of Wheat (*Leptosphaeria nodorum*).

Equivalents

1. The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A compound of the formula (Va):

(Va)

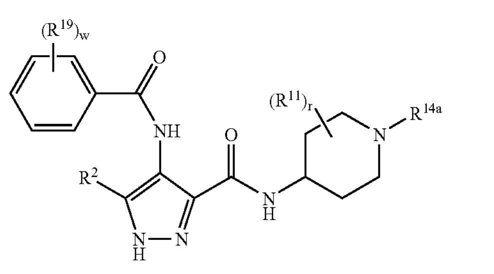

or salts or tautomers or N-oxides or solvates thereof;

wherein $R^{14a}$ is hydrogen or methyl;

w is 0, 1, 2 or 3;

r is 0, 1 or 2

$R^2$ is hydrogen or methyl;

$R^{11}$ is selected from hydrogen and $C_{1-3}$ alkyl; and $R^{19}$ is selected from fluorine; chlorine; $C_{1-4}$ alkoxy optionally substituted by fluoro or $C_{1-2}$-alkoxy; and $C_{1-4}$ alkyl optionally substituted by fluoro or $C_{1-2}$-alkoxy.

2. A compound according to claim 1, or salts or tautomers or N-oxides or solvates thereof, wherein r is 0.

3. A compound according to claim 1, or salts or tautomers or N-oxides or solvates thereof, wherein $R^2$ is hydrogen.

4. A compound according to claim 3, or salts or tautomers or N-oxides or solvates thereof, wherein r is 0.

5. A compound according to claim 1, or salts or tautomers or N-oxides or solvates thereof, wherein w is 1, 2 or 3 and the phenyl ring is 2-monosubstituted, 3-monosubstituted, 2,6-disubstituted, 2,3-disubstituted, 2,4-disubstituted 2,5-disubstituted, 2,3,6-trisubstituted or 2,4,6-trisubstituted.

6. A compound according to claim 5, or salts or tautomers or N-oxides or solvates thereof, wherein r is 0.

7. A compound according to claim 6, or salts or tautomers or N-oxides or solvates thereof, wherein $R^2$ is hydrogen.

8. A compound according to any one of claims 5, 6 or 7, or salts or tautomers or N-oxides or solvates thereof, wherein the phenyl ring is disubstituted at positions 2- and 6- with substituents selected from fluorine, chlorine and methoxy.

9. A compound according to claim 1 of the formula (VIa):

(VIa)

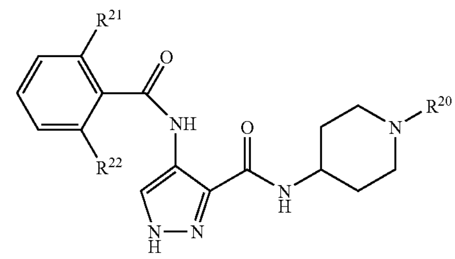

or salts or tautomers or N-oxides or solvates thereof;

wherein $R^{20}$ is selected from hydrogen and methyl;

$R^{21}$ is selected from fluorine and chlorine; and $R^{22}$ is selected from fluorine, chlorine and methoxy; or one of $R^{21}$ and $R^{22}$ is hydrogen and the other is selected from chlorine, methoxy, ethoxy, difluoromethoxy, trifluoromethoxy and benzyloxy.

10. A compound according to claim 1 of the formula (VIb):

(VIb)

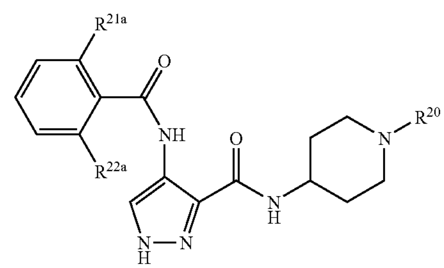

or salts or tautomers or N-oxides or solvates thereof;

wherein $R^{20}$ is selected from hydrogen and methyl;

$R^{21a}$ is selected from fluorine and chlorine; and $R^{22a}$ is selected from fluorine, chlorine and methoxy.

11. A compound according to claim 10 selected from:

4-(2,6-difluoro-benzoylamino)-1H-pyrazole-3-carboxylic acid piperidin-4-ylamide;

4-(2,6-difluoro-benzoylamino)-1H-pyrazole-3-carboxylic acid (1-methyl-piperidin-4-yl)-amide;

4-(2,6-dichloro-benzoylamino)-1H-pyrazole-3-carboxylic acid piperidin-4-ylamide; and 4-(2-fluoro-6-methoxy-benzoylamino)-1H-pyrazole-3-carboxylic acid piperidin-4-ylamide;

or salts or tautomers or N-oxides or solvates thereof.

12. A compound according to claim 1 wherein the compound is in the form of a salt.

13. A compound according to claim 11 wherein the compound is in the form of a salt.

14. A method for alleviating or reducing the incidence of carcinoma of the colon, which method comprises administering to the mammal a compound as defined in claim 1, or a salt or tautomer or N-oxide or solvate thereof, in an amount effective in inhibiting abnormal cell growth.

15. A method for alleviating or reducing the incidence of carcinoma of the colon, which method comprises administering to the mammal a compound as defined in claim 11, or a salt or tautomer or N-oxide or solvate thereof, in an amount effective in inhibiting abnormal cell growth.

16. A pharmaceutical composition comprising a compound as defined in claim 1, or a salt or tautomer or N-oxide or solvate thereof, and a pharmaceutically acceptable carrier.

17. A pharmaceutical composition comprising a compound as defined in claim 11, or a salt or tautomer or N-oxide or solvate thereof, and a pharmaceutically acceptable carrier.

18. A process for the preparation of a compound as defined in claim 1, which process comprises;

(i) the reaction of a carboxylic avid of the formula:

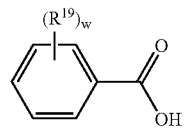

or an activated derivative thereof with a 4-amino-pyrazole of the formula:

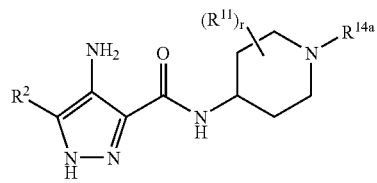

or (ii) the reaction of a compound of the formula:

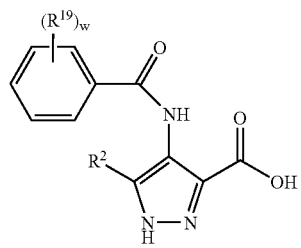

with a compound of the formula:

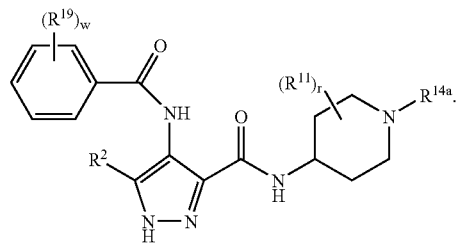

19. 4-(2,6-Dichloro-benzoylamino)-1H-pyrazole-3-carboxylic acid piperidin-4-ylamide according to claim 11.

20. A salt of 4-(2,6-dichloro-benzoylamino)-1H-pyrazole-3-carboxylic acid piperidin-4-ylamide according to claim 11.

* * * * *

UNITED STATES PATENT AND TRADEMARK OFFICE
CERTIFICATE OF CORRECTION

PATENT NO. : 7,385,059 B2
APPLICATION NO. : 11/336599
DATED : June 10, 2008
INVENTOR(S) : Berdini et al.

It is certified that error appears in the above-identified patent and that said Letters Patent is hereby corrected as shown below:

In the Claims:

Claim 18, Col. 217, Line 30: Delete "carboxylic avid" and insert
-- carboxylic acid --

Signed and Sealed this

Twenty-sixth Day of August, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,385,059 B2 |
| APPLICATION NO. | : 11/336599 |
| DATED | : June 10, 2008 |
| INVENTOR(S) | : Berdini et al. |

It is certified that error appears in the above-identified patent and that said Letters Patent is hereby corrected as shown below:

On the Title Page:

(30) Foreign Application Priority Data: please delete "Jul. 22, 2004" and insert -- Jul. 22, 2003 --

In the Claims:

Claim 5, Col. 216, line 6: please delete "2,4-disubstituted 2,5" and insert -- 2,4-disubstituted, 2,5 --

Signed and Sealed this

Seventh Day of April, 2009

JOHN DOLL
*Acting Director of the United States Patent and Trademark Office*